(12) United States Patent
Sharei et al.

(10) Patent No.: US 11,692,168 B2
(45) Date of Patent: Jul. 4, 2023

(54) DELIVERY OF BIOMOLECULES TO PBMCS TO MODIFY AN IMMUNE RESPONSE

(71) Applicant: SQZ Biotechnologies Company, Watertown, MA (US)

(72) Inventors: Armon R. Sharei, Watertown, MA (US); Howard Bernstein, Cambridge, MA (US); Scott Loughhead, Watertown, MA (US); Matthew Booty, Cambridge, MA (US); Katarina Blagovic, Cambridge, MA (US); Kelan Hlavaty, Belmont, MA (US); Defne Yarar, Watertown, MA (US); Emrah Ilker Ozay, Watertown, MA (US); Carolyne Kelly Smith, Waltham, MA (US)

(73) Assignee: SQZ Biotechnologies Company, Watertown, MA (US)

( * ) Notice: Subject to any disclaimer, the term of this patent is extended or adjusted under 35 U.S.C. 154(b) by 192 days.

(21) Appl. No.: 16/803,937

(22) Filed: Feb. 27, 2020

(65) Prior Publication Data

US 2020/0318066 A1    Oct. 8, 2020

Related U.S. Application Data

(60) Provisional application No. 62/948,732, filed on Dec. 16, 2019, provisional application No. 62/933,304, filed on Nov. 8, 2019, provisional application No. 62/886,799, filed on Aug. 14, 2019, provisional application No. 62/841,089, filed on Apr. 30, 2019, provisional application No. 62/812,225, filed on Feb. 28, 2019.

(30) Foreign Application Priority Data

Mar. 11, 2019  (EP) .................................. 19161964

(51) Int. Cl.
| | | |
|---|---|---|
| *A61K 39/12* | (2006.01) | |
| *A61K 39/39* | (2006.01) | |
| *C12N 5/078* | (2010.01) | |
| *A61K 45/06* | (2006.01) | |
| *A61K 39/00* | (2006.01) | |

(52) U.S. Cl.
CPC ............ *C12N 5/0634* (2013.01); *A61K 39/12* (2013.01); *A61K 39/39* (2013.01); *A61K 45/06* (2013.01); *A61K 2039/5154* (2013.01); *A61K 2039/55561* (2013.01)

(58) Field of Classification Search
None
See application file for complete search history.

(56) References Cited

U.S. PATENT DOCUMENTS

| | | |
|---|---|---|
| 4,055,799 A | 10/1977 | Coster |
| 4,376,634 A | 3/1983 | Prior et al. |
| 4,835,457 A | 5/1989 | Hanss |
| 5,023,054 A | 6/1991 | Sato |
| 8,147,867 B2 | 4/2012 | Hong |
| 9,192,667 B2 | 11/2015 | Hoves et al. |
| 9,364,504 B2 | 6/2016 | Godfrin |
| 9,950,049 B2 | 4/2018 | Godfrin |
| 10,124,336 B2 | 11/2018 | Sharei |
| 10,526,573 B2 | 1/2020 | Ding |
| 10,696,944 B2 | 6/2020 | Sharei |
| 10,780,151 B2 | 9/2020 | Godfrin |
| 10,870,112 B2 | 12/2020 | Sharei |
| 2004/0197898 A1 | 10/2004 | Nakatani |
| 2006/0134067 A1 | 6/2006 | Liu |
| 2006/0134772 A1 | 6/2006 | Miles |
| 2007/0243523 A1 | 10/2007 | Ionescu-zanetti |
| 2007/0249038 A1 | 10/2007 | Adamo |
| 2008/0026465 A1 | 1/2008 | Nakata |
| 2008/0241844 A1 | 10/2008 | Kellogg |
| 2008/0311140 A1 | 12/2008 | Lee |
| 2009/0280518 A1 | 11/2009 | Adamo |
| 2010/0203068 A1 | 8/2010 | Betz |
| 2010/0249621 A1 | 9/2010 | Ichitani |
| 2011/0030808 A1 | 2/2011 | Chiou |
| 2011/0300205 A1 | 12/2011 | Geall |
| 2012/0009140 A1 | 1/2012 | Godfrin |
| 2012/0207745 A1 | 8/2012 | Godfrin |
| 2014/0287509 A1 | 9/2014 | Sharei |
| 2016/0193605 A1 | 7/2016 | Sharei |
| 2016/0324946 A1 | 11/2016 | Godfrin |

(Continued)

FOREIGN PATENT DOCUMENTS

| | | |
|---|---|---|
| CN | 101031641 A | 9/2007 |
| CN | 103987836 A | 8/2014 |

(Continued)

OTHER PUBLICATIONS

Verthelyi et al., The Journal of Immunology, 2001, 166:2372-2377. (Year: 2001).*

(Continued)

*Primary Examiner* — Stacy B Chen

(74) *Attorney, Agent, or Firm* — Sterne, Kessler, Goldstein & Fox P.L.L.C.

(57) ABSTRACT

The present application provides peripheral blood mononuclear cells comprising an antigen, methods of manufacturing such PBMCs, and methods of using such PBMCs, such as for modulating an immune response in an individual. In some embodiments, the PBMCs are conditioned by incubating the PBMC in the presence of an adjuvant.

38 Claims, 78 Drawing Sheets

Specification includes a Sequence Listing.

(56) References Cited

U.S. PATENT DOCUMENTS

| | | | |
|---|---|---|---|
| 2018/0003696 | A1 | 1/2018 | Sharei |
| 2018/0016539 | A1 | 1/2018 | Ding |
| 2018/0142198 | A1 | 5/2018 | Sharei |
| 2018/0201889 | A1 | 7/2018 | Sharei |
| 2018/0245089 | A1 | 8/2018 | Sharei |
| 2018/0344822 | A1 | 12/2018 | Godfrin |
| 2019/0017072 | A1 | 1/2019 | Ditommaso |
| 2019/0030536 | A1 | 1/2019 | Sharei |
| 2019/0093073 | A1 | 3/2019 | Sharei |
| 2019/0111082 | A1 | 4/2019 | Gilbert |
| 2019/0382796 | A1 | 12/2019 | Gilbert |
| 2020/0277566 | A1 | 9/2020 | Sharei |
| 2020/0316604 | A1 | 10/2020 | Dadgar |
| 2020/0318066 | A1 | 10/2020 | Sharei |
| 2020/0332243 | A1 | 10/2020 | Dadgar et al. |
| 2021/0038709 | A1 | 2/2021 | Loughhead |
| 2021/0077602 | A1 | 3/2021 | Godfrin et al. |
| 2021/0113628 | A1 | 4/2021 | Loughhead et al. |
| 2021/0138050 | A1 | 5/2021 | Loughhead et al. |
| 2021/0170411 | A1 | 6/2021 | Sharei et al. |

FOREIGN PATENT DOCUMENTS

| | | |
|---|---|---|
| EA | 007232 B1 | 8/2006 |
| JP | H01196566 A | 8/1989 |
| JP | H03257366 A | 11/1991 |
| JP | 2010025852 A | 2/2010 |
| RU | 2424792 C2 | 7/2011 |
| RU | 2539989 C1 | 1/2015 |
| WO | 2002067863 A2 | 9/2002 |
| WO | 2003015711 A2 | 2/2003 |
| WO | 2003020039 A1 | 3/2003 |
| WO | 2003015711 A3 | 6/2004 |
| WO | 2005060993 A1 | 7/2005 |
| WO | 2006105251 A2 | 10/2006 |
| WO | 2007001677 A2 | 1/2007 |
| WO | 2007067032 A1 | 6/2007 |
| WO | 2007001677 A3 | 7/2007 |
| WO | 2007001677 A9 | 8/2007 |
| WO | 2008021465 A2 | 2/2008 |
| WO | 2009019317 A1 | 2/2009 |
| WO | 2010016800 A1 | 2/2010 |
| WO | 2011051346 A1 | 5/2011 |
| WO | 2011079217 A1 | 6/2011 |
| WO | 2011119492 A2 | 9/2011 |
| WO | 2012069568 A2 | 5/2012 |
| WO | 2013059343 A1 | 4/2013 |
| WO | 2013185032 A1 | 12/2013 |
| WO | 2014165707 A2 | 10/2014 |
| WO | 2015023982 A1 | 2/2015 |
| WO | 2016070136 A1 | 5/2016 |
| WO | 2016077761 A1 | 5/2016 |
| WO | 2016115179 A1 | 7/2016 |
| WO | 2017008063 A1 | 1/2017 |
| WO | 2017041050 A1 | 3/2017 |
| WO | 2017041051 A1 | 3/2017 |
| WO | 2017117418 A1 | 7/2017 |
| WO | 2017123663 A1 | 7/2017 |
| WO | 2017192785 A1 | 11/2017 |
| WO | 2017192786 A1 | 11/2017 |
| WO | 2018106849 A1 | 6/2018 |
| WO | 2019113125 A1 | 6/2019 |
| WO | 2019126212 A1 | 6/2019 |
| WO | 2019178005 A2 | 9/2019 |
| WO | 2019178006 A2 | 9/2019 |
| WO | 2019178005 A3 | 10/2019 |
| WO | 2020072833 A1 | 4/2020 |
| WO | 2020154696 A1 | 7/2020 |
| WO | 2020210162 A1 | 10/2020 |

OTHER PUBLICATIONS

Adamo, A. et al. (Aug. 7, 2012, e-pub. Jul. 10, 2012). "Microfluidics-Based Assessment of Cell Deformability," Anal Chem 84(15):6438-6443, 13 pages.

Bolhassani, A. et al. (Feb. 1, 2014, e-pub. Oct. 15, 2013). "Polymeric Nanoparticles, Potent Vectors for Vaccine Delivery Targeting Cancer and Infectious Diseases," Hum Vaccin & Immunother 10(2):321-332.

Chen, C. et al. (2009, e-pub. May 14, 2009). "Patch Clamping on Plane Glass-Fabrication of Hourglass Aperture and High Yield Ion Channel Recording," Lab Chip 9:2370-2380.

Chen, Xian-Zhen et al. (2010, e-pub. Jul. 4, 2009). "Toll Like Receptor Agonists Augment HPV 11 E7-Specific T Cell Responses by Modulating Monocyte-Derived Dendritic Cells", Arch Dermatol Res. 302(1):57-65.

Ding, X. et al. (Mar. 9, 2017). "High-throughput nuclear delivery and rapid expression of DNA via mechanical and electrical cellmembrane disruption," Nature Biomedical Engineering 1(3):39, 15 pages.

Hallow D.M. et al. (Mar. 1, 2008, e-pub. Sep. 18, 2007). "Shear-Induced Intracellular Loading of Cells With Molecules by Controlled Microfluidics", Biotechnology and Bioengineering 99(4):846-854.

Hillerdal, V. et al. (Jan. 18, 2014). "Systemic Treatment With CAR-engineered T Cells Against PSCA Delays Subcutaneous Tumor Growth and Prolongs Survival of Mice," BMC Cancer 14(30):1-9.

Hosokawa, M. et al. (Aug. 1, 2010). "Size-Selective Microcavity Array for Rapid and Efficient Detection of Circulating Tumor Cells", Analytical Chemistry 82(15):6629-6635.

Howarth, M. et al. (May 2008). "Monovalent, Reduced-Size Quantum Dots for Imaging Receptors on Living Cells," Nature Methods 5(5):397-399, 7 pages.

Indrova, M. et al. (Jan. 1, 2004). "Immunogenicity of Dendritic Cell-Based HPV16 E6/E7 Peptide Vaccines: CTL Activation and Protective Effects", Folia Biologica 50:184-193.

International Preliminary Report on Patentability dated Nov. 15, 2018, for Patent Application No. PCT/US2017/030933, filed May 3, 2017, 13 pages.

International Preliminary Report on Patentability dated Jun. 18, 2020, for International Patent Application No. PCT/US2018/063931, filed Dec. 4, 2018, 9 pages.

International Preliminary Report on Patentability, dated Sep. 15, 2020, for Patent Application No. PCT/US2019/021703, filed Mar. 11, 2019, 10 pages.

International Search Report and Written Opinion of the International Searching Authority dated Apr. 16, 2020, for International Patent Application No. PCT/US2020/020194, 16 pages.

International Search Report and Written Opinion of the International Searching Authority dated Feb. 25, 2013, for International Patent Application No. PCT/US12/060646, filed Oct. 17, 2012, 10 pages.

International Search Report and Written Opinion of the International Searching Authority dated Mar. 19, 2019, for International Patent Application No. PCT/US2018/063931, filed Dec. 14, 2018, 14 pages.

International Search Report and Written Opinion of the International Searching Authority dated Oct. 16, 2019 for International Patent Application No. PCT/US2019/021705, filed Mar. 11, 2019, 25 pages.

International Search Report and Written Opinion of the International Searching Authority dated Mar. 11, 2016, for International Patent Application No. PCT/US2015/058489, filed Oct. 30, 2015, 18 pages.

International Search Report and Written Opinion of the International Searching Authority dated Sep. 18, 2019, for International Patent Application No. PCT/US2019/021703, filed Mar. 11, 2019, 19 pages.

International Search Report and Written Opinion of the Searching Authority dated Feb. 12, 2020, for International Patent Application No. PCT/US2019/054586, filed Oct. 3, 2019, 27 pages.

International Search Report mailed Jul. 21, 2017, for International Patent Application No. PCT/2017030933 filed May 3, 2017, 4 pages.

(56) References Cited

OTHER PUBLICATIONS

Invitation to Pay Additional Fees dated Dec. 19, 2019, for International Patent Application No. PCT/US2019/054586, filed Oct. 3, 2019, 8 pages.
Invitation to Pay Additional Fees dated Jul. 24, 2019, for International Patent Application No. PCT/US2019/021703, filed Mar. 11, 2019, 14 pages.
Invitation to Pay Additional Fees dated Jun. 28, 2019, for International Patent Application No. PCT/US2019/021705, filed Mar. 11, 2019, 17 pages.
Kada, G. et al. (Mar. 14, 1999). "Rapid Estimation of Avidin and Streptavidin by Fluorescence Quenching or Fluorescence Polarization," Biochim. Biophys. Acta. 1427(1):44-48.
Kaka, A. S. et al. (Sep. 1, 2009). Genetic Modification of T Cells With IL-21 Enhances Antigen Presentation and Generation of Central Memory Tumor-specific Cytotoxic T-lymphocytes, Journal of Immunology 32(7):726-736.
Kenter, G. G. et al. (Nov. 5, 2009). "Vaccination against HPV-16 Oncoproteins for Vulvar Intraepithelial Neoplasia", The New England Journal of Medicine 361(19):1838-1847, 14 pages. (Including Supplemental Material).
Kim, D. et al. (2009, e-pub Apr. 13, 2009). "Microengineered Platforms for Cell Mechanobiology," Annual Review of Biomedical Engineering 11:203-233.
Lee, L. et al. (Nov. 16, 2012, e-pub. Dec. 2012). "Non-Endocytic Delivery of Functional Engineered Nanoparticles into the Cytoplasm of Live Cells Using a Novel, High-Throughput Microfluidic Device," Nano Letters 12(12):6322-6327, 34 pages. (Including Supplemental Material).
Li, J. et al. (Jun. 30, 2016, May 19, 2016). "The Combination of Pleurotus Ferulaewater Extract and CpG-ODN Enhances the Immune Responses and Antitumor Efficacy of HPV Peptides Pulsed Dendritic Cell-Based Vaccine", Vaccine 34(31):3568-3575.
Li, J. et al. (Oct. 31, 2017). "Microfluidic-Enabled Intracellular Delivery of Membrane Impermeable Inhibitors to Study Target Engagement in Human Primary Cells," ACS Chemical Biology 12(12):2970-2974.
Liang, X. et al. (Aug. 20, 2015, e-pub. May 21, 2015). "Rapid and Highly Efficient Mammalian Cell Engineering via Cas9 Protein Transfection", J. Biotech 208:44-53.
Lin, B.K. et al. (Jun. 26, 2013). "Highly selective biomechanical separation of cancer cells from leukocytes using 1-19 microfluidic ratchets and hydrodynamic concentrator," Biomicrofluidics 7(3):1-11.
Liu, W. et al. (Jan. 20, 2010). "Compact Biocompatible Quantum Dots Via RAFT-Mediated Synthesis of Imidazole-Based Random Copolymer Ligand," JACS 132(2):472-483, 27 pages.
Liu, Y. et al. (Sep. 19, 2012, e-pub. Jul. 13, 2012). "Spatially Selective Reagent Delivery Into Cancer Cells Using A Two-Layer Microfluidic Culture System," Anal Chim Acta 743(1):125-130, 20 pages. (including Supplemental Material).
Liu, Z. et al. (Jul. 28, 2014). "Molecular Imaging in Tracking Tumor Specific Cytotoxic T Lymphocytes (CTLs)," Theranostics 4(10):990-1001.
Loughhead, S.M. et al. (Dec. 1, 2018). "SQZing Cells to Rapidly Generate Antigen Presenting Cells (APC) for Solid Tumor Immune Therapies With Efficient, Scalable Manufacturing," Abstract, Annals of Oncology 29(Suppl No. 10):1page, (Abstract No. 38P).
Maratou, E. et al. (Apr. 2007). "Glucose Transporter Expression on the Plasma Membrane of Resting and Activated White Blood Cells," Eur J Clin Invest 37(4):282-290.
Matthews, B.D. et al. (2006). "Cellular Adaptation to Mechanical Stress: Role of Integrins, Rho, Cytoskeletal Tension and Mechanosensitive Ion Channels," Journal of Cell Science 119:508-518.
Moser, B. et al. (Jul. 2011, e-pub. May 15, 2011). "gamma delta T-APCs: A Novel Tool for Immunotherapy?," Cellular and Molecular Life Sciences 68(14):2443 2452.
Murphy, J.S. et al. (Sep. 1, 1956, e-pub May 2004). "Measurement of Wall Shearing Stress in the Boundary Layer by Means of an Evaporating Liquid Film," Journal of Applied Physics 27(9):1097-1103, 9 pages.
Papaioannou, N.E. et al. (2016). "Harnessing the Immune System to Improve Cancer Therapy," Annals of Translational Medicine 4(14):261, 15 pages.
Patel, K. et al. (Dec. 1, 2016). "Combination Immunotherapy with NY-ESO-1-Specific CAR+ T Cells with T-Cell Vaccine Improves Anti-Myeloma Effect," Blood Journal 128(22):3366,1 page (Poster).
Plummer, E. et al. (Mar.-Apr. 2011, e-pub. Sep. 24, 2010). "Viral Nanoparticles and Virus-Like Particles: Platforms for Contemporary Vaccine Design," Wiley Interdiscip Rev Nanomed Nanobiotechnol. 3(2):174-196.
Rughetti, A. et al. (Sep. 2000). "Transfected Human Dendritic Cells to Induce Antitumor Immunity", Gene Therapy 7(17):1458-1466.
Rutella, S. et al. (Sep. 1, 2006). "Tolerogenic Dendritic Cells: Cytokine Modulation Comes of Age", Blood 180(5):1435-1440.
Sercombe, L. et al. (2015, e-pub. Dec. 1, 2015). "Advances and Challenges of Liposome Assisted Drug Delivery," Front Pharmacol. 6:286, 13 pages.
Sharei, A. (Jun. 26, 2013). "Cell Squeezing: A Vector-Free Microfluidic Platform for Intracellular Delivery of Macromolecules," MIT Thesis (Public, located here: https://dspace.mit.edu/bitstream/handle/1721.1/81688/860804208-MIT.pdf?sequence=2) 165 pages.
Sharei, A. et al. (2015, e-pub. Apr. 13, 2015). "Ex Vivo Cytosolic Delivery of Functional Macromolecules to Immune Cells", PLoS One 10(4):e011803, 12 pages.
Sharei, A. et al. (Feb. 5, 2013, e-pub. Jan. 22, 2013). "A Vector-Free Mircrofuidic platform for Intracellular Delivery", Proc Natl Acad Sci U.S.A. 110(6):2082-2087.
Sharei, A. et al. (Nov. 7, 2013). "Cell Squeezing as a Robust, Microfluidic Intracellular Delivery Platform," Journal of Visualized Experiments (81):e50980, 9 pages.
Sharei, A. et al. (Oct. 31, 2012). "(483d) Microfluidic Cell Deformation as a Robust, Vector-Free Method for Cytosolic Delivery of Macromolecules," 12AIChE Proceedings Annual Meeting (https://www.aiche.org/conferences/aiche-annual-meeting/2012/proceeding/paper/483d-microfluidic-cell-deformation-robust-vector-free-method-cytosolic-delivery-macromolecules) last visited on Feb. 4, 2021, 8 pages.
Shelby, J.P. et al. (Dec. 9, 2003). "A Microfluidic Model for Single-Cell Capillary Obstruction by Plasmodium Falciparum-Infected Erythrocytes," PNAS 100(25):14618-14622.
Song, A.Y. et al. (2006). "Scientific Basis for the Use of Hypotonic Solutions with Ultrasonic Liposuction," Aesth. Plast. Surg. 30:233-238, 3 pages.
Steinman, R.M. et al. (Apr. 1, 2003). "Tolerogenic Dendritic Cells", Annu. Rev. Immunol. 21:685-711.
Stewart, M.P. et al. (Oct. 12, 2016). "In Vitro and Ex Vitro Strategies for Intracellular Delivery", Nature 538 (7624):183-192, 23 pages.
Suresh, T. et al. (2017). "The Emerging Role of Immunotherapy in Head and Neck Squamous Cell Cancer," in The American Journal of Hematology/Oncology 13(6):20-27, 8 pages.
Szeto, G.L. et al. (May 22, 2015). "Microfluidic Squeezing for Intracellular Antigen Loading in Polyclonal B-Cells as Cellular Vaccines," Scientific Reports 5:10276, 13 pages.
Talarico, L. et al. (Nov. 2017). "Engineered Antigen Presenting T Cells for the Treatment of Solid Tumor Cancers," EMBASE, 32nd Annual Meeting and Pre-Conference Programs of the Society for Immunotherapy of Cancer, SITC 2017, Journal for ImmunoTherapy of Cancer 5(Suppl. 2):EMB-619371158, 1 page. (Abstract).
Tsaoir, C. et al. (Jun. 2016). "Scalable Antibody Production from CHO Cell Line of Choice Using Flow Electroporation," Poster, Cell Line Development Jun. 2016, © 2016 MaxCyte, Inc., located at: https://www.maxcyte.com/wp-content/uploads/2017/10/scalable-ab-production-from-cho-cells.pdf, last retrieved on Apr. 2, 2019, 1 page. (Poster).
U.S. Appl. No. 16/098,405, filed May 3, 2017, by Loughhead et al.
U.S. Appl. No. 16/769,993, filed Dec. 4, 2018, by Sharei et al.
U.S. Appl. No. 16/954,113, filed Dec. 18, 2018, by Loughhead et al.
U.S. Appl. No. 16/980,339, filed Mar. 11, 2019, by Loughhead et al.
U.S. Appl. No. 17/000,007, filed Aug. 21, 2020, by Godfrin et al.

(56) References Cited

OTHER PUBLICATIONS

U.S. Appl. No. 17/075,116, filed Oct. 20, 2020, by Sharei et al.
U.S. Appl. No. 17/169,357, filed Feb. 5, 2021, by Godfrini et al.
Verma, R. R et al. (Nov. 2013, e-pub. Sep. 6, 2013). "E6 protein of human papillomavirus 16 (HPV16) expressed in *Escherichia coli* sans a stretch of hydrophobic amino acids, enables purification of GST-[Delta]E6 in the soluble form and retains the binding ability to p53," Protein Expression and Purification 92(1):41-47.
Wang, H.L. et al. (Jan. 2014, e-pub. Aug. 3, 2013). "In Vitro and In Vivo Evaluations of Human Papillomavirus Type 16 (HPV16)-Derived Peptide-Loaded Dendritic Cells (DCs) With A CpG oligodeoxynucleotide (CpG-ODN) Adjuvant as Tumor Vaccines for Immunotherapy of Cervical Cancer," Gynecologic Oncology 289(1):155-162.
Williams, A.R. et al. (Nov. 5, 1999). "Filtroporation: A Simple, Reliable Technique dor Transfection and Macromolecular Loading of Cells in Suspension," Biotechnology and Bioengineering 65(3):341-346.
Written Opinion of the International Searching Authority dated Jul. 21, 2017, for Patent Application No. PCT/US2017/030933, filed May 3, 2017, 11 pages.
Zarnitsyn, V.G. et al. (2008, e-pub. Nov. 10, 2007). "Electrosonic Ejector Microarray for Drug and Gene Delivery," Biomed Microdevices 10:299-308.
International Preliminary Report on Patentability dated Mar. 23, 2021, for Patent Application No. PCT/US2019/054586, filed Oct. 3, 2019, 17 pages.
International Preliminary Report on Patentability dated Aug. 25, 2021, for International Patent Appliation No. PCT/US2020/020194, filed Feb. 27, 2020, 10 pages.
Celluzzi, C.M. et al. (Jan. 1996). "Peptide-Pulsed Dendritic Cells Induce Antigen-Specific, CTL-Mediated Protective Tumor Immunity," J. Exp. Med. 183:283-287.
Diebold, S.S. et al. (2011). "MHC Class II Presentation of Endogenously Expressed Antigens by Transfected Dendritic Cells," Gene Therapy 8:487-493.

\* cited by examiner

| Day of Blood Collection | No Treatment | | | | | | | pg/mL | |
|---|---|---|---|---|---|---|---|---|---|
| | -1 | 1 | 7 | 8 | 14 | 15 | 21 | Range | Mean |
| G-CSF | | | | | | | | 359.3 - 3872.3 | 1222.6 |
| GM-CSF | | | | | | | | 4.2 - 38.2 | 20.8 |
| IFNγ | | | | | | | | 0.0 - 2.0 | 0.3 |
| IL-1α | | | | | | | | 503.1 - 3574.3 | 1671.2 |
| IL-1β | | | | | | | | 0.0 - 3.3 | 1.2 |
| IL-2 | | | | | | | | 0.0 - 4.0 | 0.9 |
| IL-4 | | | | | | | | 0.0 - 0.0 | 0.0 |
| IL-5 | | | | | | | | 4.7 - 54.8 | 21.7 |
| IL-6 | | | | | | | | 6.9 - 135.9 | 34.1 |
| IL-7 | | | | | | | | 0.0 - 1.6 | 0.5 |
| IL-9 | | | | | | | | 162.2 - 261.5 | 189.7 |
| IL-10 | | | | | | | | 3.2 - 13.2 | 10.1 |
| IL-12 p40 | | | | | | | | 7.2 - 19.4 | 12.8 |
| IL-12 p70 | | | | | | | | 2.2 - 16.7 | 7.3 |
| IL-13 | | | | | | | | 41.4 - 56.2 | 48.3 |
| IL-15 | | | | | | | | 13.7 - 47.4 | 23.4 |
| IL-17 | | | | | | | | 0.0 - 2.5 | 0.9 |
| IP-10 | | | | | | | | 74.7 - 357.9 | 213.5 |
| KC | | | | | | | | 58.5 - 374.3 | 155.1 |
| MCP-1 | | | | | | | | 18.8 - 84.7 | 49.9 |
| MIP-1α | | | | | | | | 27.2 - 68.4 | 51.4 |
| MIP-1β | | | | | | | | 4.3 - 57.8 | 38.6 |
| MIP-2 | | | | | | | | 93.8 - 230.7 | 180.3 |
| RANTES | | | | | | | | 13.4 - 32.0 | 24.1 |
| TNF | | | | | | | | 3.1 - 12.6 | 8.1 |

0          400          4000 pg/mL

| Day of Blood Collection | M-SQZ-Spleno-HPV | | | | | | | pg/mL | |
|---|---|---|---|---|---|---|---|---|---|
| | -1 | 1 | 7 | 8 | 14 | 15 | 21 | Range | Mean |
| G-CSF | | | | | | | | 291.1 - 824.5 | 596.4 |
| GM-CSF | | | | | | | | 10.9 - 31.4 | 19.1 |
| IFNγ | | | | | | | | 0.0 - 2.8 | 0.7 |
| IL-1α | | | | | | | | 374.0 - 2892.7 | 1178.1 |
| IL-1β | | | | | | | | 0.0 - 1.8 | 0.7 |
| IL-2 | | | | | | | | 0.0 - 1.7 | 0.2 |
| IL-4 | | | | | | | | 0.0 - 0.0 | 0.0 |
| IL-5 | | | | | | | | 8.8 - 18.4 | 12.8 |
| IL-6 | | | | | | | | 6.9 - 34.8 | 13.9 |
| IL-7 | | | | | | | | 0.0 - 28.4 | 5.7 |
| IL-9 | | | | | | | | 115.1 - 371.0 | 217.3 |
| IL-10 | | | | | | | | 0.0 - 15.6 | 7.2 |
| IL-12 p40 | | | | | | | | 0.0 - 25.3 | 11.1 |
| IL-12 p70 | | | | | | | | 0.0 - 14.4 | 5.9 |
| IL-13 | | | | | | | | 0.0 - 60.2 | 37.1 |
| IL-15 | | | | | | | | 7.3 - 402.8 | 102.6 |
| IL-17 | | | | | | | | 0.0 - 3.5 | 1.4 |
| IP-10 | | | | | | | | 98.5 - 312.8 | 221.9 |
| KC | | | | | | | | 54.4 - 111.2 | 74.7 |
| MCP-1 | | | | | | | | 22.0 - 43.1 | 31.5 |
| MIP-1α | | | | | | | | 34.5 - 78.2 | 59.3 |
| MIP-1β | | | | | | | | 0.0 - 43.8 | 31.6 |
| MIP-2 | | | | | | | | 63.1 - 186.3 | 138.5 |
| RANTES | | | | | | | | 9.2 - 33.8 | 23.2 |
| TNF | | | | | | | | 0.0 - 7.5 | 3.8 |

0   400   4000 pg/mL

| | M-SQZ-Spleno-HPV + 1μg Co-Injected CpG | | | | | | | pg/mL | |
|---|---|---|---|---|---|---|---|---|---|
| Day of Blood Collection | -1 | 1 | 7 | 8 | 14 | 15 | 21 | Range | Mean |
| G-CSF | | | | | | | | 365.0 - 2681.4 | 986.4 |
| GM-CSF | | | | | | | | 2.1 - 32.6 | 18.2 |
| IFNγ | | | | | | | | 0.0 - 6.9 | 1.8 |
| IL-1α | | | | | | | | 363.2 - 3172.7 | 1329.3 |
| IL-1β | | | | | | | | 0.0 - 4.0 | 0.6 |
| IL-2 | | | | | | | | 0.0 - 0.0 | 0.0 |
| IL-4 | | | | | | | | 0.0 - 1.1 | 0.2 |
| IL-5 | | | | | | | | 2.1 - 18.1 | 11.9 |
| IL-6 | | | | | | | | 2.6 - 46.5 | 21.7 |
| IL-7 | | | | | | | | 0.0 - 69.3 | 13.6 |
| IL-9 | | | | | | | | 111.0 - 294.3 | 228.9 |
| IL-10 | | | | | | | | 2.6 - 41.7 | 13.4 |
| IL-12 p40 | | | | | | | | 6.5 - 28.2 | 11.9 |
| IL-12 p70 | | | | | | | | 0.0 - 9.0 | 5.1 |
| IL-13 | | | | | | | | 16.4 - 68.0 | 42.1 |
| IL-15 | | | | | | | | 7.3 - 1339.1 | 229.7 |
| IL-17 | | | | | | | | 0.0 - 4.6 | 1.0 |
| IP-10 | | | | | | | | 112.5 - 553.3 | 293.0 |
| KC | | | | | | | | 54.8 - 152.9 | 82.4 |
| MCP-1 | | | | | | | | 26.6 - 51.4 | 39.4 |
| MIP-1α | | | | | | | | 36.3 - 136.3 | 73.3 |
| MIP-1β | | | | | | | | 0.0 - 57.7 | 21.6 |
| MIP-2 | | | | | | | | 72.5 - 258.2 | 165.7 |
| RANTES | | | | | | | | 8.8 - 45.5 | 20.8 |
| TNF | | | | | | | | 2.3 - 13.1 | 6.4 |

0    400    4000 pg/mL

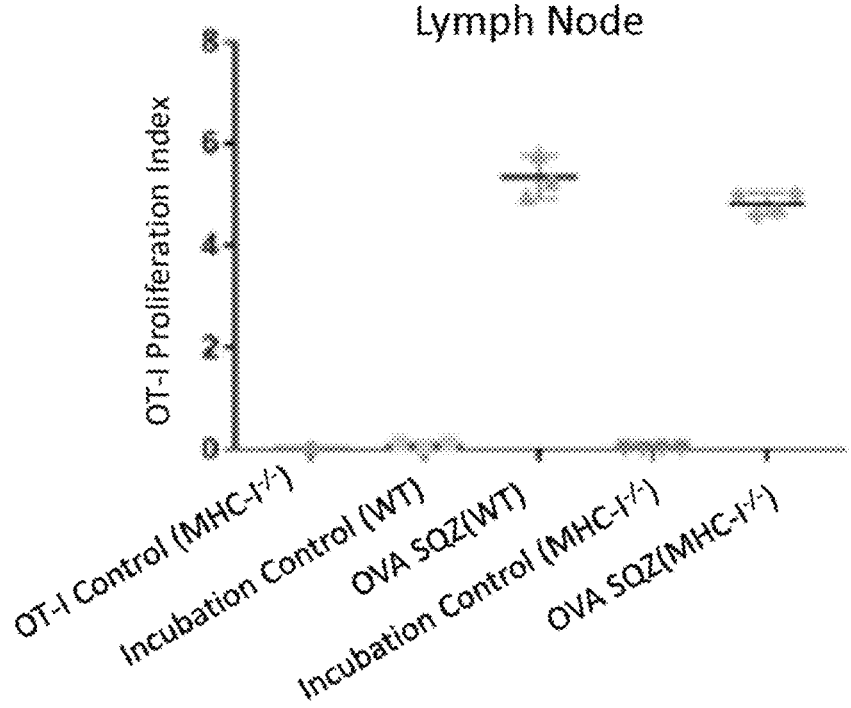
FIG. 27C  ELN102741 Lymph Node
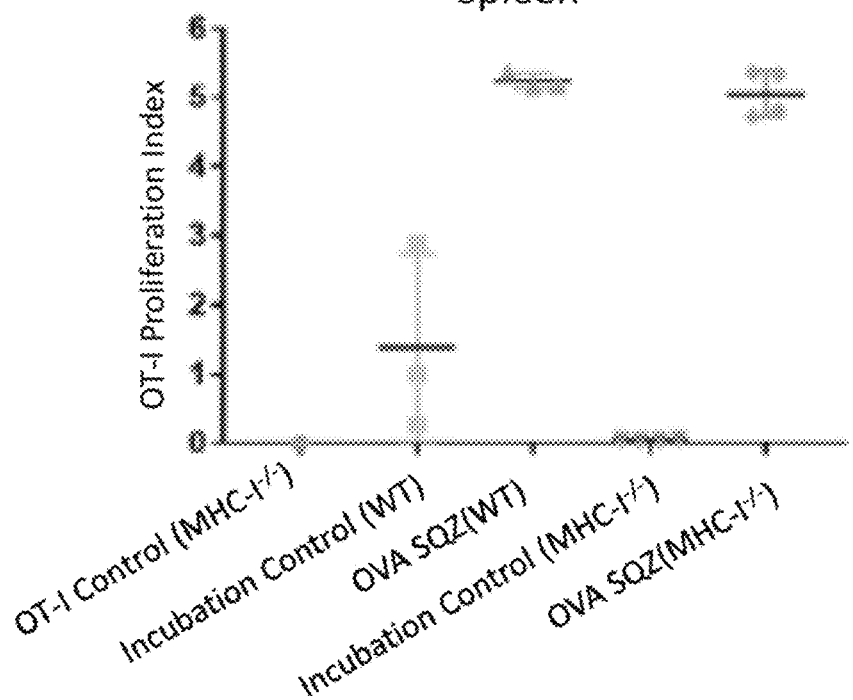
FIG. 27D  ELN102741 Spleen

| Group | M-SQZ-PBMC-HPV Dose | Cell Dose | Mice per Group |
|---|---|---|---|
| A | Untreated | -- | 10 |
| B | M-SQZ-PBMC-HPV | $1\times10^6$ cells | 10 |
| C | M-SQZ-PBMC-HPV + Sch. 1 αCTLA4 | $1\times10^6$ cells | 10 |
| D | M-SQZ-PBMC-HPV + Sch. 2 αCTLA4 | $1\times10^6$ cells | 10 |
| E | M-SQZ-PBMC-HPV + Sch.3 αCTLA4 | $1\times10^6$ cells | 10 |
| F | Sch. 1 αCTLA4 | -- | 10 |
| G | Sch. 2 αCTLA4 | -- | 10 |
| H | Sch. 3 αCTLA4 | -- | 10 | form (CRF) of the Sequence Listing (file

SEQUENCE LISTING

<160> NUMBER OF SEQ ID NOS: 55

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Thr Ile His Asp Ile Ile Leu Glu Cys Val
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Glu Val Tyr Asp Phe Ala Phe Arg Asp Leu
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Tyr Met Leu Asp Leu Gln Pro Glu Thr Thr
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct

<400> SEQUENCE: 4

Arg Ala His Tyr Asn Ile Val Thr Phe
1               5

<210> SEQ ID NO 5
<211> LENGTH: 10

```
<212> TYPE: PRT
<213> ORGANISM: Homo sapiens

<400> SEQUENCE: 5

Leu Pro Gln Leu Ser Thr Glu Leu Gln Thr
1               5                   10

<210> SEQ ID NO 6
<211> LENGTH: 8
<212> TYPE: PRT
<213> ORGANISM: Homo sapiens

<400> SEQUENCE: 6

Gln Leu Cys Thr Glu Leu Gln Thr
1               5

<210> SEQ ID NO 7
<211> LENGTH: 7
<212> TYPE: PRT
<213> ORGANISM: Mus musculus

<400> SEQUENCE: 7

Lys Gln Gln Leu Leu Arg Arg
1               5

<210> SEQ ID NO 8
<211> LENGTH: 10
<212> TYPE: PRT
<213> ORGANISM: Mus musculus

<400> SEQUENCE: 8

Val Tyr Ser Lys Gln Gln Leu Leu Arg Arg
1               5                   10

<210> SEQ ID NO 9
<211> LENGTH: 10
<212> TYPE: PRT
<213> ORGANISM: Homo sapiens

<400> SEQUENCE: 9

Met His Gly Asp Thr Pro Thr Leu His Glu
1               5                   10

<210> SEQ ID NO 10
<211> LENGTH: 6
<212> TYPE: PRT
<213> ORGANISM: Mus musculus

<400> SEQUENCE: 10

Gly Gln Ala Glu Pro Asp
1               5

<210> SEQ ID NO 11
<211> LENGTH: 16
<212> TYPE: PRT
<213> ORGANISM: Homo sapiens

<400> SEQUENCE: 11

Tyr Ser Lys Gln Gln Leu Leu Arg Arg Glu Val Tyr Asp Phe Ala Phe
1               5                   10                  15

<210> SEQ ID NO 12
<211> LENGTH: 7
<212> TYPE: PRT
<213> ORGANISM: Homo sapiens
```

```
<400> SEQUENCE: 12

Tyr Cys Lys Gln Gln Leu Leu
1               5

<210> SEQ ID NO 13
<211> LENGTH: 8
<212> TYPE: PRT
<213> ORGANISM: Mus musculus

<400> SEQUENCE: 13

Cys Ile Val Tyr Arg Asp Gly Asn
1               5

<210> SEQ ID NO 14
<211> LENGTH: 15
<212> TYPE: PRT
<213> ORGANISM: Mus musculus

<400> SEQUENCE: 14

Ser Ile Val Tyr Arg Asp Gly Asn Pro Tyr Ala Val Ser Asp Lys
1               5                   10                  15

<210> SEQ ID NO 15
<211> LENGTH: 15
<212> TYPE: PRT
<213> ORGANISM: Homo sapiens

<400> SEQUENCE: 15

Asp Leu Tyr Cys Tyr Glu Gln Leu Asn Asp Ser Ser Glu Glu Glu
1               5                   10                  15

<210> SEQ ID NO 16
<211> LENGTH: 20
<212> TYPE: PRT
<213> ORGANISM: Mus musculus

<400> SEQUENCE: 16

Cys Cys Lys Cys Asp Ser Thr Leu Arg Leu Cys Val Gln Ser Thr His
1               5                   10                  15

Val Asp Ile Arg
            20

<210> SEQ ID NO 17
<211> LENGTH: 20
<212> TYPE: PRT
<213> ORGANISM: Mus musculus

<400> SEQUENCE: 17

Ser Ser Lys Ser Asp Ser Thr Leu Arg Leu Ser Val Gln Ser Thr His
1               5                   10                  15

Val Asp Ile Arg
            20

<210> SEQ ID NO 18
<211> LENGTH: 36
<212> TYPE: PRT
<213> ORGANISM: Homo sapiens

<400> SEQUENCE: 18

Leu Pro Gln Leu Ser Thr Glu Leu Gln Thr Thr Ile His Asp Ile Ile
1               5                   10                  15

Leu Glu Cys Val Tyr Ser Lys Gln Gln Leu Leu Arg Arg Glu Val Tyr
```

```
                    20                  25                  30

Asp Phe Ala Phe
        35

<210> SEQ ID NO 19
<211> LENGTH: 25
<212> TYPE: PRT
<213> ORGANISM: Homo sapiens

<400> SEQUENCE: 19

Gln Leu Cys Thr Glu Leu Gln Thr Thr Ile His Asp Ile Ile Leu Glu
1               5                   10                  15

Cys Val Tyr Cys Lys Gln Gln Leu Leu
            20                  25

<210> SEQ ID NO 20
<211> LENGTH: 25
<212> TYPE: PRT
<213> ORGANISM: Mus musculus

<400> SEQUENCE: 20

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25

<210> SEQ ID NO 21
<211> LENGTH: 35
<212> TYPE: PRT
<213> ORGANISM: Mus musculus

<400> SEQUENCE: 21

Val Tyr Ser Lys Gln Gln Leu Leu Arg Arg Glu Val Tyr Asp Phe Ala
1               5                   10                  15

Phe Arg Asp Leu Ser Ile Val Tyr Arg Asp Gly Asn Pro Tyr Ala Val
            20                  25                  30

Ser Asp Lys
        35

<210> SEQ ID NO 22
<211> LENGTH: 35
<212> TYPE: PRT
<213> ORGANISM: Homo sapiens

<400> SEQUENCE: 22

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu
        35

<210> SEQ ID NO 23
<211> LENGTH: 25
<212> TYPE: PRT
<213> ORGANISM: Homo sapiens

<400> SEQUENCE: 23

Gln Leu Cys Thr Glu Leu Gln Thr Tyr Met Leu Asp Leu Gln Pro Glu
1               5                   10                  15

Thr Thr Tyr Cys Lys Gln Gln Leu Leu
```

<210> SEQ ID NO 24
<211> LENGTH: 35
<212> TYPE: PRT
<213> ORGANISM: Mus musculus

<400> SEQUENCE: 24

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 25
<211> LENGTH: 35
<212> TYPE: PRT
<213> ORGANISM: Mus musculus

<400> SEQUENCE: 25

Gly Gln Ala Glu Pro Asp Arg Ala His Tyr Asn Ile Val Thr Phe Ser
1               5                   10                  15

Ser Lys Ser Asp Ser Thr Leu Arg Leu Ser Val Gln Ser Thr His Val
            20                  25                  30

Asp Ile Arg
        35

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: 1, 2, (15)..(20)
<223> OTHER INFORMATION: Phosphorothioate bases
<220> FEATURE:
<221> NAME/KEY: MISC_FEATURE
<222> LOCATION: (3)..(14)
<223> OTHER INFORMATION: Phosphodiester bases

<400> SEQUENCE: 26
ggggtcaacg ttgaggggggg                                          20

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: 1, 2, (15)..(20)
<223> OTHER INFORMATION: Phosphorothioate bases
<220> FEATURE:
<221> NAME/KEY: MISC_FEATURE
<222> LOCATION: (3)..(14)
<223> OTHER INFORMATION: Phosphodiester bases

<400> SEQUENCE: 27
gggggacgat cgtcgggggg                                           20

<210> SEQ ID NO 28
<211> LENGTH: 21

```
<212> TYPE: DNA
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(3), (15)..(20)
<223> OTHER INFORMATION: Phosphorothioate bases
<220> FEATURE:
<221> NAME/KEY: MISC_FEATURE
<222> LOCATION: (4)..(14)
<223> OTHER INFORMATION: Phosphodiester bases

<400> SEQUENCE: 28
ggggacgacg tcgtgggggg g                                        21

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(20)
<223> OTHER INFORMATION: Phosphorothioate bases

<400> SEQUENCE: 29
tccatgacgt tcctgatgct                                          20

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(20)
<223> OTHER INFORMATION: Phosphorothioate bases

<400> SEQUENCE: 30
tccatgacgt tcctgacgtt                                          20

<210> SEQ ID NO 31
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(24)
<223> OTHER INFORMATION: Phosphorothioate bases

<400> SEQUENCE: 31
tcgtcgtttt gtcgttttgt cgtt                                     24

<210> SEQ ID NO 32
<211> LENGTH: 22
<212> TYPE: DNA
<213> ORGANISM: Bos taurus
<220> FEATURE:
<221> NAME/KEY: MISC_FEATURE
<222> LOCATION: (1)..(22)
<223> OTHER INFORMATION: Phosphorothioate bases

<400> SEQUENCE: 32
tcgtcgttgt cgttttgtcg tt                                       22
```

```
<210> SEQ ID NO 33
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(23)
<223> OTHER INFORMATION: Phosphorothioate bases

<400> SEQUENCE: 33
tcgacgttcg tcgttcgtcg ttc                                          23

<210> SEQ ID NO 34
<211> LENGTH: 26
<212> TYPE: DNA
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(26)
<223> OTHER INFORMATION: Phosphorothioate bases

<400> SEQUENCE: 34
tcgcgacgtt cgcccgacgt tcggta                                       26

<210> SEQ ID NO 35
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(22)
<223> OTHER INFORMATION: Phosphorothioate bases

<400> SEQUENCE: 35
tcgtcgtttt cggcgcgcgc cg                                           22

<210> SEQ ID NO 36
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(25)
<223> OTHER INFORMATION: Phosphorothioate bases

<400> SEQUENCE: 36
tcgtcgtcgt tcgaacgacg ttgat                                        25

<210> SEQ ID NO 37
<211> LENGTH: 29
<212> TYPE: DNA
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(29)
<223> OTHER INFORMATION: Phosphorothioate bases

<400> SEQUENCE: 37
tcgcgaacgt tcgccgcgtt cgaacgcgg                                    29
```

```
<210> SEQ ID NO 38
<211> LENGTH: 35
<212> TYPE: PRT
<213> ORGANISM: Artificial Sequence
<220> FEATURE:
<223> OTHER INFORMATION: Synthetic Construct

<400> SEQUENCE: 38

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu
        35

<210> SEQ ID NO 39
<211> LENGTH: 35
<212> TYPE: PRT
<213> ORGANISM: Artificial Sequence
<220> FEATURE:
<223> OTHER INFORMATION: Synthetic Construct

<400> SEQUENCE: 39

Leu Tyr Cys Tyr Glu Gln Leu Asn Asp Ser Ser Glu Glu Glu Asp Glu
1               5                   10                  15

Ile Asp Gly Pro Ala Gly Gln Ala Glu Pro Asp Arg Ala His Tyr Asn
            20                  25                  30

Ile Val Thr
        35

<210> SEQ ID NO 40
<211> LENGTH: 35
<212> TYPE: PRT
<213> ORGANISM: Artificial Sequence
<220> FEATURE:
<223> OTHER INFORMATION: Synthetic Construct

<400> SEQUENCE: 40

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 41
<211> LENGTH: 35
<212> TYPE: PRT
<213> ORGANISM: Artificial Sequence
<220> FEATURE:
<223> OTHER INFORMATION: Synthetic Construct

<400> SEQUENCE: 41

Thr Leu Arg Leu Cys Val Gln Ser Thr His Val Asp Ile Arg Thr Leu
1               5                   10                  15

Glu Asp Leu Leu Met Gly Thr Leu Gly Ile Val Cys Pro Ile Cys Ser
            20                  25                  30

Gln Lys Pro
        35

<210> SEQ ID NO 42
```

```
<211> LENGTH: 32
<212> TYPE: PRT
<213> ORGANISM: Artificial Sequence
<220> FEATURE:
<223> OTHER INFORMATION: Synthetic Construct

<400> SEQUENCE: 42

Met His Gln Lys Arg Thr Ala Met Phe Gln Asp Pro Gln Glu Arg Pro
 1               5                  10                  15

Arg Lys Leu Pro Gln Leu Cys Thr Glu Leu Gln Thr Thr Ile His Asp
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Synthetic Construct

<400> SEQUENCE: 43

Leu Pro Gln Leu Cys Thr Glu Leu Gln Thr Thr Ile His Asp Ile Ile
 1               5                  10                  15

Leu Glu Cys Val Tyr Cys Lys Gln Gln Leu Leu Arg Arg Glu Val Tyr
            20                  25                  30

<210> SEQ ID NO 44
<211> LENGTH: 25
<212> TYPE: PRT
<213> ORGANISM: Artificial Sequence
<220> FEATURE:
<223> OTHER INFORMATION: Synthetic Construct

<400> SEQUENCE: 44

Lys Gln Gln Leu Leu Arg Arg Glu Val Tyr Asp Phe Ala Phe Arg Asp
 1               5                  10                  15

Leu Cys Ile Val Tyr Arg Asp Gly Asn
            20                  25

<210> SEQ ID NO 45
<211> LENGTH: 26
<212> TYPE: PRT
<213> ORGANISM: Artificial Sequence
<220> FEATURE:
<223> OTHER INFORMATION: Synthetic Construct

<400> SEQUENCE: 45

Arg Asp Leu Cys Ile Val Tyr Arg Asp Gly Asn Pro Tyr Ala Val Cys
 1               5                  10                  15

Asp Lys Cys Leu Lys Phe Tyr Ser Lys Ile
            20                  25

<210> SEQ ID NO 46
<211> LENGTH: 25
<212> TYPE: PRT
<213> ORGANISM: Artificial Sequence
<220> FEATURE:
<223> OTHER INFORMATION: Synthetic Construct

<400> SEQUENCE: 46

Asp Lys Cys Leu Lys Phe Tyr Ser Lys Ile Ser Glu Tyr Arg His Tyr
 1               5                  10                  15

Cys Tyr Ser Leu Tyr Gly Thr Thr Leu
            20                  25
```

-continued

```
<210> SEQ ID NO 47
<211> LENGTH: 25
<212> TYPE: PRT
<213> ORGANISM: Artificial Sequence
<220> FEATURE:
<223> OTHER INFORMATION: Synthetic Construct

<400> SEQUENCE: 47

His Tyr Cys Tyr Ser Leu Tyr Gly Thr Thr Leu Glu Gln Gln Tyr Asn
1               5                   10                  15

Lys Pro Leu Cys Asp Leu Leu Ile Arg
            20                  25

<210> SEQ ID NO 48
<211> LENGTH: 32
<212> TYPE: PRT
<213> ORGANISM: Artificial Sequence
<220> FEATURE:
<223> OTHER INFORMATION: Synthetic Construct

<400> SEQUENCE: 48

Tyr Gly Thr Thr Leu Glu Gln Gln Tyr Asn Lys Pro Leu Cys Asp Leu
1               5                   10                  15

Leu Ile Arg Cys Ile Asn Cys Gln Lys Pro Leu Cys Pro Glu Glu Lys
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Synthetic Construct

<400> SEQUENCE: 49

Arg Cys Ile Asn Cys Gln Lys Pro Leu Cys Pro Glu Glu Lys Gln Arg
1               5                   10                  15

His Leu Asp Lys Lys Gln Arg Phe His Asn Ile Arg Gly Arg Trp Thr
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Synthetic Construct

<400> SEQUENCE: 50

Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
            20                  25                  30

<210> SEQ ID NO 51
<211> LENGTH: 35
<212> TYPE: PRT
<213> ORGANISM: Homo sapiens

<400> SEQUENCE: 51

Pro Pro Trp Gln Ala Gly Ile Leu Ala Arg Asn Leu Val Pro Met Val
1               5                   10                  15

Ala Thr Val Gln Gly Gln Asn Leu Lys Tyr Gln Glu Phe Phe Trp Asp
            20                  25                  30

Ala Asn Asp
            35
```

```
<210> SEQ ID NO 52
<211> LENGTH: 10
<212> TYPE: PRT
<213> ORGANISM: Homo sapiens

<400> SEQUENCE: 52

Pro Pro Trp Gln Ala Gly Ile Leu Ala Arg
1               5                   10

<210> SEQ ID NO 53
<211> LENGTH: 16
<212> TYPE: PRT
<213> ORGANISM: Homo sapiens

<400> SEQUENCE: 53

Gln Gly Gln Asn Leu Lys Tyr Gln Glu Phe Phe Trp Asp Ala Asn Asp
1               5                   10                  15

<210> SEQ ID NO 54
<211> LENGTH: 8
<212> TYPE: PRT
<213> ORGANISM: Artificial Sequence
<220> FEATURE:
<223> OTHER INFORMATION: Synthetic Construct

<400> SEQUENCE: 54

Ser Ile Ile Asn Phe Glu Lys Leu
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Construct

<400> SEQUENCE: 55

Asn Leu Val Pro Met Val Ala Thr Val
1               5
```

DELIVERY OF BIOMOLECULES TO PBMCS TO MODIFY AN IMMUNE RESPONSE

CROSS REFERENCE TO RELATED APPLICATIONS

This application claims the benefit of U.S. Provisional Application No. 62/812,225, filed on Feb. 28, 2019, European Patent Application No. 19161964.2, filed on Mar. 11, 2019, U.S. Provisional Application No. 62/841,089, filed on Apr. 30, 2019, U.S. Provisional Application No. 62/886,799, filed on Aug. 14, 2019, U.S. Provisional Application No. 62/933,304, filed on Nov. 8, 2019, and U.S. Provisional Application No. 62/948,732, filed on Dec. 16, 2019, the entire contents of each of which are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750322002200SEQLIST.TXT, date recorded: Feb. 24, 2020, size: 15 KB).

FIELD OF THE INVENTION

The present disclosure relates generally to peripheral blood mononuclear cells (PBMCs) comprising an antigen and/or an adjuvant, methods of manufacturing such PBMCs cells, and methods of using such PBMCs, such as for modulating an immune response in an individual.

BACKGROUND OF THE INVENTION

Immunotherapy can be divided into two main types of interventions, either passive or active. Passive protocols include administration of pre-activated and/or engineered cells, disease-specific therapeutic antibodies, and/or cytokines. Active immunotherapy strategies are directed at stimulating immune system effector functions in vivo. Several current active protocols include vaccination strategies with disease-associated peptides, lysates, or allogeneic whole cells, infusion of autologous DCs as vehicles for tumor antigen delivery, and infusion of immune checkpoint modulators. See Papaioannou, Nikos E., et al. *Annals of translational medicine* 4.14 (2016).

CD8$^+$ cytotoxic T lymphocytes (CTL) and CD4$^+$ helper T (Th) cells stimulated by disease-associated antigens have the potential to target and destroy diseased cells; however, current methods for inducing endogenous T cell responses have faced challenges.

All references cited herein, including patent applications and publications, are incorporated by reference in their entirety.

BRIEF SUMMARY OF THE INVENTION

The present invention provides peripheral blood mononuclear cells (PBMCs) comprising an antigen for the stimulation of immune responses in individuals. In some embodiments, antigens are delivered intracellularly using the Cell Squeeze® platform. The present inventors have unexpectedly found that mixed populations of PBMCs have greater efficacy than pure B cell and T cell populations. In addition, the invention is based at least in part on the unexpected discovery that conditioning PBMCs with an adjuvant increased activation of antigen presenting cells of the PBMCs leading to increased immunostimulation when the PBMCs are administered to an individual.

In some aspects, the invention provides a plurality of modified PBMCs comprising an antigen, wherein the antigen is exogenous to the modified PBMCs. In some embodiments, the invention provides a plurality of modified PMBCs comprising an antigen, wherein the antigen is exogenous to the modified PBMCs, wherein the antigen is a cancer antigen, an infectious disease antigen or a viral-disease associated antigen. In some aspects, the invention provides a conditioned plurality of modified PBMCs comprising an antigen, wherein the antigen is exogenous to the modified PBMCs. In some embodiments, the invention provides a conditioned plurality of modified PMBCs comprising an antigen, wherein the antigen is exogenous to the modified PBMCs, wherein the antigen is a cancer antigen, an infectious disease antigen or a viral-disease associated antigen. In some embodiments, the invention provides a conditioned plurality of modified PBMCs comprising an antigen and an adjuvant, wherein the antigen is exogenous to the modified PBMCs.

In some aspects, the invention provides a conditioned plurality of PBMCs comprising an antigen, prepared by incubating the plurality of PBMCs comprising the antigen with an adjuvant for a sufficient time for the PBMCs to condition, thereby generating the conditioned plurality of PBMCs comprising the antigen. In some embodiments, the invention provides a conditioned plurality of PBMCs comprising an antigen, prepared by incubating the plurality of PBMCs with an adjuvant for a sufficient time for the PBMCs to condition prior to introducing the antigen to the PBMCs, thereby generating the conditioned plurality of PBMCs comprising the antigen.

In some aspects, the invention provides a plurality of modified PBMCs comprising an antigen, prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen. In some embodiments, the invention provides a conditioned plurality of modified PBMCs comprising an antigen, prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the process further comprises: isolating the plurality of modified PBMCs comprising the antigen from the cell suspension before incubation with the adjuvant to condition the modified PBMCs. In some embodiments, the invention provides a plurality of modified PBMCs comprising an antigen and an adjuvant, prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen and the adjuvant to pass through to form a plurality of perturbed input PBMCs; and b) incubating the plurality of perturbed input PBMCs with the antigen and the adjuvant for a sufficient time to allow the antigen and the adjuvant to enter the perturbed input PBMCs; thereby generating the plurality of modified PBMCs comprising the antigen and adjuvant.

In some aspects, the invention provides a conditioned plurality of modified PBMCs comprising an antigen, prepared by a process comprising the steps of: a) incubating a plurality of input PBMCs with an adjuvant for a sufficient time for the input PBMCs to condition, thereby generating a conditioned plurality of input PBMCs; b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and c) incubating the conditioned plurality of perturbed input PBMCs with the antigen for a sufficient time to allow the antigen to enter the perturbed input PBMCs, thereby generating the conditioned plurality of modified PBMCs comprising the antigen. In some embodiments, the invention provides a plurality of modified PBMCs comprising an antigen and an adjuvant, prepared by a process comprising the steps of: a) passing a cell suspension comprising a plurality of input PBMCs comprising the adjuvant through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; and b) incubating the plurality of perturbed input PBMCs with the antigen for a sufficient time to allow the antigen to enter the perturbed input PBMCs, thereby generating the plurality of modified PBMCs comprising the antigen and the adjuvant. In some embodiments, the invention provides a plurality of modified PBMCs comprising an antigen and an adjuvant, prepared by a process comprising the steps of: a) passing a cell suspension comprising a plurality of input PBMCs comprising the antigen through a cell-deforming constriction, wherein a diameter of the constriction is a function of a diameter of the input PBMCs in the suspension, thereby causing perturbations of the input PBMCs large enough for the adjuvant to pass through to form a plurality of perturbed input PBMCs; and b) incubating the plurality of perturbed input PBMCs with the adjuvant for a sufficient time to allow the adjuvant to enter the perturbed input PBMCs, thereby generating the plurality of modified PBMCs comprising the antigen and the adjuvant. In some embodiments, the plurality of modified PBMCs comprising the antigen and/or the adjuvant according as described herein, wherein the process further comprises: incubating the plurality of modified PBMCs comprising the antigen and/or adjuvant with a second adjuvant for a sufficient time for the modified PBMCs comprising the antigen to condition, thereby generating the conditioned plurality of modified PBMCs comprising the antigen and/or the adjuvant. In some embodiments, the process further comprises: isolating the plurality of modified PBMCs comprising the antigen and/or the adjuvant from the cell suspension before incubation with the adjuvant to condition the modified PBMCs. In some embodiments, the process further comprises a step of incubating the input PBMCs and/or the modified PBMCs with an agent that enhances the viability and/or function of the modified PBMCs as compared to corresponding modified PBMCs prepared without the further incubation step.

In some aspects, the invention provides a composition comprising the plurality of modified PBMCs as described herein for use in a method of treatment of the human or animal body by surgery, therapy or diagnosis. In some embodiments, the invention provides a composition comprising the plurality of modified PBMCs as described herein for use in the treatment of a cancer, an infectious disease or a viral-associated disease.

In some aspects, the invention provides a composition comprising a conditioned plurality of modified PBMCs comprising an antigen for use as a medicament, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the invention provides a composition comprising a conditioned plurality of modified PBMCs comprising an antigen for use in a method of treatment of the human or animal body by surgery, therapy or diagnosis, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the invention provides a composition comprising a conditioned plurality of modified PBMCs comprising an antigen for use as a medicament, wherein the conditioned plurality of modified PBMCs is prepared by a process comprising the steps of: a) incubating a plurality of input PBMCs with an adjuvant for a sufficient time for the input PBMCs to condition, thereby generating a conditioned plurality of input PBMCs; b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and c) incubating the conditioned plurality of perturbed input PBMCs with the antigen for a sufficient time to allow the antigen to enter the perturbed input PBMCs, thereby generating the conditioned plurality of modified PBMCs comprising the antigen. In some embodiments, the invention provides composition comprising a conditioned plurality of modified PBMCs comprising an antigen for use in a method of treatment of the human or animal body, wherein the conditioned plurality of modified PBMCs is prepared by a process comprising the steps of: a) incubating a plurality of input PBMCs with an adjuvant for a sufficient time for the input PBMCs to condition, thereby generating a conditioned plurality of input PBMCs; b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and c) incubating the conditioned plurality of perturbed input PBMCs with the antigen for a sufficient time to allow the antigen to enter the perturbed input PBMCs, thereby generating the conditioned plurality of modified PBMCs comprising the antigen. In some embodiments, the invention provides a composition comprising a conditioned plurality of modified PBMCs comprising an antigen for use in a method of treating cancer an infectious disease or a viral associated disease in an individual, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the invention provides a composition comprising a conditioned plurality of modified PBMCs comprising an antigen for use in the treatment of cancer, an infectious disease or a viral associated disease in an individual, wherein the conditioned plurality of modified PBMCs is prepared by a process comprising the steps of: a) passing a cell suspension comprising a plurality of input PBMCs through a cell deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the invention provides a composition comprising a conditioned plurality of modified PBMCs comprising an antigen for use in a method of treating a HPV-associated disease in an individual, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the invention provides a composition comprising a conditioned plurality of modified PBMCs comprising an antigen for use in the treatment of a HPV-associated disease in an individual, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen.

In some aspects, the invention provides the use of a composition comprising a conditioned plurality of modified PBMCs comprising an antigen in the manufacture of a medicament for treating cancer, an infectious disease or a viral-associated disease in an individual, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the invention provides the use of a composition comprising a conditioned plurality of modified PBMCs comprising an antigen in the manufacture of a medicament for treating a HPV-associated disease, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen.

In some aspects, the invention provides a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the invention provides a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, wherein the adjuvant is CpG ODN, thereby generating the conditioned plurality of modified PBMCs comprising the antigen. In some embodiments, the invention provides a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for about 1 hour to about 24 hours for the modified PBMCs comprising the antigen to condition, thereby generating the conditioned plurality of modified PBMCs comprising the antigen. In some embodiments, the invention provides a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for about 1 hour to about 24 hours for the modified PBMCs comprising the antigen to condition, wherein the adjuvant is CpG ODN, thereby generating the conditioned plurality of modified PBMCs comprising the antigen. In a preferred embodiment, the adjuvant is CPG 7909.

In some aspects, the invention provides a conditioned plurality of modified PBMCs comprising a human papillomavirus (HPV) antigen, prepared by a process comprising the steps of: a) passing a cell suspension comprising a plurality of input PBMCs through a cell-deforming constriction, wherein a diameter of the constriction is about 3 μm to about 10 μm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; and c) incubating the plurality of modified PBMCs comprising the HPV antigen with a CpG ODN for a sufficient time for the modified PBMCs comprising the HPV antigen to condition, thereby generating the conditioned plurality of modified PBMCs comprising the HPV antigen. In some embodiments, the invention provides a conditioned plurality of modified PBMCs comprising a HPV antigen, prepared by a process comprising the steps of: a) passing a cell suspension comprising a plurality of input PBMCs through a cell-deforming constriction, wherein a diameter of the constriction is about 3 μm to about 10 μm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; and c) incubating the plurality of modified PBMCs comprising the HPV antigen with a CpG ODN for a sufficient time for the modified PBMCs comprising the HPV antigen to condition, wherein the CpG ODN is CpG 7909, thereby generating the conditioned plurality of modified PBMCs comprising the HPV antigen. In some embodiments, the invention provides a conditioned plurality of modified PBMCs comprising a HPV antigen, prepared by a process comprising the steps of: a) passing a cell suspension comprising a plurality of input PBMCs through a cell-deforming constriction, wherein a diameter of the constriction is about 3 μm to about 10 μm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; and c) incubating the plurality of modified PBMCs comprising the HPV antigen with a CpG ODN for about 1 hour to about 24 hours for the modified PBMCs comprising the HPV antigen to condition, thereby generating the conditioned plurality of modified PBMCs comprising the HPV antigen. In some embodiments, the invention provides a conditioned plurality of modified PBMCs comprising a HPV antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; and c) incubating the plurality of modified PBMCs comprising the HPV antigen with a CpG ODN for about 1 hour to about 24 hours for the modified PBMCs comprising the HPV antigen to condition, wherein the CpG ODN is CpG 7909, thereby generating the conditioned plurality of modified PBMCs comprising the HPV antigen.

In some aspects, the invention provides a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for a sufficient time for the modified PBMCs comprising the antigen to condition, thereby generating the conditioned plurality of modified PBMCs comprising the antigen. In some embodiments, the invention provides a conditioned plurality of modified PBMCs comprising an antigen, prepared by a process comprising the steps of: a) passing a cell suspension comprising a plurality of input PBMCs through a cell-deforming constriction, wherein a diameter of the constriction is about 34 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for a sufficient time for the modified PBMCs comprising the antigen to condition, wherein the CpG ODN is CpG 7909, thereby generating the conditioned plurality of modified PBMCs comprising the antigen. In some embodiments, the invention provides a conditioned plurality of modified PBMCs comprising an antigen, prepared by a process comprising the steps of: a) passing a cell suspension comprising a plurality of input PBMCs through a cell-deforming constriction, wherein a diameter of the constriction is about 34 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for about 1 hour to about 24 hours for the modified PBMCs comprising the antigen to condition, thereby generating the conditioned plurality of modified PBMCs comprising the antigen. In some embodiments, the invention provides a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for about 1 hour to about 24 hours for the modified PBMCs comprising the antigen to condition, wherein the CpG ODN is CpG 7909, thereby generating the conditioned plurality of modified PBMCs comprising the antigen.

In some aspects, the invention provides a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for a sufficient time for the modified PBMCs comprising the antigen to condition, thereby generating the conditioned plurality of modified PBMCs comprising the antigen. In some embodiments, the invention provides a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for a sufficient time for the modified PBMCs comprising the antigen to condition, wherein the CpG ODN is CpG 7909, thereby generating the conditioned plurality of modified PBMCs comprising the antigen. In some embodiments, the invention provides a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for about 1 hour to about 24 hours for the modified PBMCs comprising the antigen to condition, thereby generating the conditioned plurality of modified PBMCs comprising the antigen. In some embodiments, the invention provides a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for about 1 hour to about 24 hours for the modified PBMCs comprising the antigen to condition, wherein the CpG ODN is CpG 7909, thereby generating the conditioned plurality of modified PBMCs comprising the antigen.

In some aspects, the invention provides a method for stimulating an immune response in an individual, comprising: a) administering a plurality of modified PBMCs comprising an antigen comprising the amino acid sequence of any one of SEQ ID NOs: 18-25 to the individual; and b) administering an adjuvant to the individual.

In some aspects, the invention provides a method for stimulating an immune response in an individual, comprising: a) administering a plurality of modified PBMCs comprising an antigen comprising the amino acid sequence of SEQ ID NO: 19 to the individual; and b) administering an adjuvant to the individual. In some aspects, the invention provides a method for stimulating an immune response in an individual, comprising: a) administering a plurality of modified PBMCs comprising an antigen comprising the amino acid sequence of SEQ ID NO: 23 to the individual; and b) administering an adjuvant to the individual. In some aspects, the invention provides a method for stimulating an immune response in an individual, comprising: a) administering a plurality of modified PBMCs comprising a plurality of antigens comprising the amino acid sequences of SEQ ID NO: 19 and/or SEQ ID NO:23 to the individual; and b) administering an adjuvant to the individual. In some aspects, the invention provides a method for stimulating an immune response in an individual, comprising: a) administering a plurality of modified PBMCs comprising a plurality of antigens consisting of the amino acid sequences of SEQ ID NO: 19 and SEQ ID NO:23 to the individual; and b) administering an adjuvant to the individual. In some embodiments, the plurality of antigens is contained within a pool of non-covalently linked peptides. In some embodiments, the plurality of antigens is contained within a pool of non-covalently linked peptides, wherein each peptide comprises no more than one antigen. In some embodiments, the plurality of antigens is contained within a pool of non-covalently linked peptides, wherein the amino acid sequence of SEQ ID NO: 19 and the amino acid sequence of SEQ ID NO: 23 are contained within separate peptides.

In some aspects, the invention provides a method for stimulating an immune response in an individual, comprising: a) incubating a plurality of PBMCs comprising an antigen with an adjuvant for a sufficient time for the PBMCs to condition, thereby generating a conditioned plurality of PBMCs comprising the antigen; b) administering the conditioned plurality of PBMCs comprising the antigen to the individual. In some embodiments, the invention provides a method for stimulating an immune response in an individual, comprising: a) incubating a plurality of PBMCs with an adjuvant for a sufficient time for the PBMCs to condition, thereby generating a conditioned plurality of PBMCs comprising the antigen; b) introducing an antigen to the plurality of PBMCs; and c) administering the conditioned plurality of PBMCs comprising the antigen to the individual. In some embodiments, the invention provides a method for stimulating an immune response in an individual, comprising: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for an antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; c) incubating the plurality of modified PBMCs comprising the antigen with an adjuvant for a sufficient time for the modified PBMCs comprising the antigen to condition, thereby generating a conditioned plurality of modified PBMCs comprising the antigen; and d) administering the conditioned plurality of modified PBMCs comprising the antigen to the individual. In some embodiments, the method further comprises isolating the plurality of modified PBMCs comprising the antigen from the cell suspension before incubation with the adjuvant. In some embodiments, the invention provides a method for stimulating an immune response in an individual, comprising: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for an antigen and an adjuvant to pass through to form a plurality of perturbed input PBMCs; b) incubating the plurality of perturbed input PBMCs with the antigen and the adjuvant for a sufficient time to allow the antigen and the adjuvant to enter the perturbed input PBMCs, thereby generating a plurality of modified PBMCs comprising the antigen and adjuvant; and c) administering the plurality of modified PBMCs to the individual.

In some aspects, the invention provides a method for stimulating an immune response in an individual, comprising: a) incubating a plurality of input PBMCs with an adjuvant for a sufficient time for the input PBMCs to condition, thereby generating a conditioned plurality of input PBMCs; b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for an antigen to pass through to form a conditioned plurality of perturbed input PBMCs; c) incubating the conditioned plurality of perturbed input PBMCs with the antigen for a sufficient time to allow the antigen to enter the perturbed input PBMCs, thereby generating the conditioned plurality of modified PBMCs comprising the antigen; and d) administering the conditioned plurality of modified PBMCs to the individual. In some embodiments, the invention provides a method for stimulating an immune response in an individual, comprising: a) passing a cell suspension comprising a plurality of input PBMCs comprising an adjuvant through a cell-deforming constriction, wherein a diameter of the constriction is a function of a diameter of the input PBMCs in the suspension, thereby causing perturbations of the input PBMCs large enough for an antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen and the adjuvant; and c) administering the plurality of modified PBMCs to the individual. In some embodiments, the invention provides a method for stimulating an immune response in an individual, comprising: a) passing a cell suspension comprising an input PBMCs comprising an antigen through a cell-deforming constriction, wherein a diameter of the constriction is a function of a diameter of the input PBMCs in the suspension, thereby causing perturbations of the input PBMCs large enough for an adjuvant to pass through to form a plurality of perturbed input PBMCs; b) incubating the plurality of perturbed input PBMCs with the adjuvant for a sufficient time to allow the adjuvant to enter the perturbed input PBMCs, thereby generating a plurality of modified PBMCs comprising the antigen and the adjuvant; and c) administering the plurality of modified PBMCs to the individual. In some embodiments, the invention provides a method for stimulating an immune response in an individual, comprising: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for an antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; c) administering the plurality of modified PBMCs to the individual; and d) administering an adjuvant to the individual. In some embodiments, the invention provides a method for stimulating an immune response in an individual, comprising: a) passing a cell suspension comprising an input PBMCs comprising an antigen through a cell-deforming constriction, wherein a diameter of the constriction is a function of a diameter of the input PBMCs in the suspension, thereby causing perturbations of the input PBMCs large enough for an adjuvant to pass through to form a plurality of perturbed input PBMCs; b) incubating the plurality of perturbed input PBMCs with the adjuvant for a sufficient time to allow the adjuvant to enter the perturbed input PBMCs, thereby generating a plurality of modified PBMCs comprising the antigen and the adjuvant; and c) administering the plurality of modified PBMCs to the individual; and d) administering an adjuvant to the individual.

In some aspects, the invention provides a method for stimulating an immune response in an individual, comprising: administering to the individual a plurality of PBMCs associated with an antigen, wherein the plurality of modified PBMCs is prepared by a process comprising the steps of: a) incubating a plurality of input PBMCs with an antigen for a sufficient time to allow the antigen to associate with the cell surface of the input PBMCs, thereby generating the plurality of PBMCs associated with the antigen; and b) administering the plurality of modified PBMCs to the individual. In some embodiments, the method further comprises administering an adjuvant to the individual.

In some aspects, the invention provides a method for generating a conditioned plurality of PBMCs comprising an antigen, comprising incubating a plurality of PBMCs comprising the antigen with an adjuvant for a sufficient time for the PBMCs to condition, thereby generating the conditioned plurality of PBMCs comprising the antigen. In some embodiments, the invention provides a method for generating a conditioned plurality of modified PBMCs comprising an antigen, comprising: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the method further comprises isolating the plurality of modified PBMCs comprising the antigen from the cell suspension before incubation with the adjuvant. In some embodiments, the invention provides a method for generating a plurality of modified PBMCs comprising an antigen, comprising: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; and b) incubating the plurality of perturbed input PBMCs with the antigen for a sufficient time to allow the antigen to enter the perturbed input PBMCs, thereby generating the plurality of modified PBMCs comprising the antigen. In some embodiments, the invention provides a method for generating a plurality of modified PBMCs comprising an antigen and an adjuvant, comprising: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen and the adjuvant to pass through to form a plurality of perturbed input PBMCs; and b) incubating the plurality of perturbed input PBMCs with the antigen and the adjuvant for a sufficient time to allow the antigen and the adjuvant to enter the perturbed input PBMCs, thereby generating the plurality of modified PBMCs comprising the antigen and adjuvant. In some embodiments, the invention provides a method of generating a conditioned plurality of modified PBMCs comprising an antigen, comprising: a) incubating a plurality of input PBMCs with an adjuvant for a sufficient time for the input PBMCs to condition, thereby generating a conditioned plurality of input PBMCs; b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and c) incubating the conditioned plurality of perturbed input PBMCs with the antigen for a sufficient time to allow the antigen to enter the perturbed input PBMCs, thereby generating the conditioned plurality of modified PBMCs comprising the antigen. In some embodiments, the invention provides a method for generating a plurality of modified PBMCs comprising an antigen and an adjuvant, comprising: a) passing a cell suspension comprising a plurality of input PBMCs comprising an adjuvant through a cell-deforming constriction, wherein a diameter of the constriction is a function of a diameter of the input PBMCs in the suspension, thereby causing perturbations of the input PBMCs large enough for an antigen to pass through to form a plurality of perturbed input PBMCs; and b) incubating the plurality of perturbed input PBMCs with the antigen for a sufficient time to allow the antigen to enter the perturbed input PBMCs, thereby generating the plurality of modified PBMCs comprising the antigen and the adjuvant. In some embodiments, the invention provides a method for generating a plurality of modified PBMCs comprising an antigen and an adjuvant, comprising: a) passing a cell suspension comprising a plurality of input PBMCs comprising an antigen through a cell-deforming constriction, wherein a diameter of the constriction is a function of a diameter of the input PBMCs in the suspension, thereby causing perturbations of the input PBMCs large enough for an adjuvant to pass through to form a plurality of perturbed input PBMCs; and b) incubating the plurality of perturbed input PBMCs with the adjuvant for a sufficient time to allow the adjuvant to enter the perturbed input PBMCs, thereby generating the plurality of modified PBMCs comprising the antigen and the adjuvant. In some embodiments, the method further comprises a step of incubating the input PBMCs and/or the modified PBMCs with an agent that enhances the viability and/or function of the modified PBMCs as compared to corresponding modified PBMCs prepared without the further incubation step.

BRIEF DESCRIPTION OF THE DRAWINGS

FIG. 15 bottom panel shows the stimulation of pp65-specific responder cells (a) when co-cultured, in the presence of 1 μM CpG, with human PBMCs SQZ-loaded with pp65 or human PBMCs SQZ-loaded with pp65 and matured with adjuvant; or (b) when co-cultured with human T cell SQZ-loaded with pp65 or human T cells SQZ-loaded with pp65 and matured with adjuvant.

FIGS. 27A-27D show the amount of in vivo proliferation of OVA-specific T cell (OT-I CD8+ T cell) in WT or MHC-I −/− mice, with stimulation by crafted murine splenocytes SQZ-loaded with OVA, or by crafted murine splenocytes incubated with OVA (Incubation Control) or no stimulation (OT-I Control). FIGS. 27A and 27C show the respective OT-I proliferation in recipient lymph nodes for 2 replicate experiments. FIGS. 27B and 27D show the respective OT-I proliferation in recipient spleens for 2 replicate experiments.

Figure 29A:
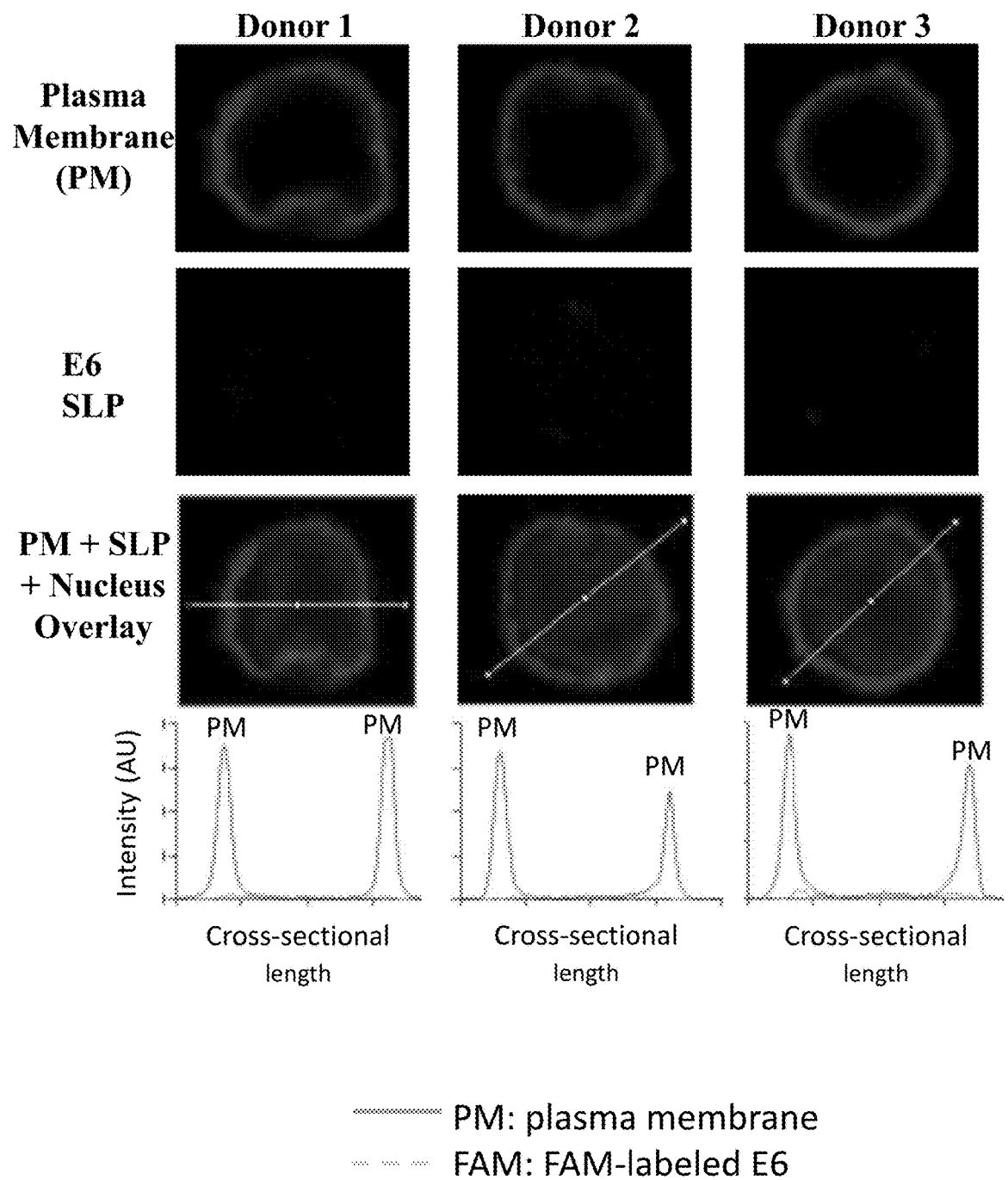
Figure 29B:
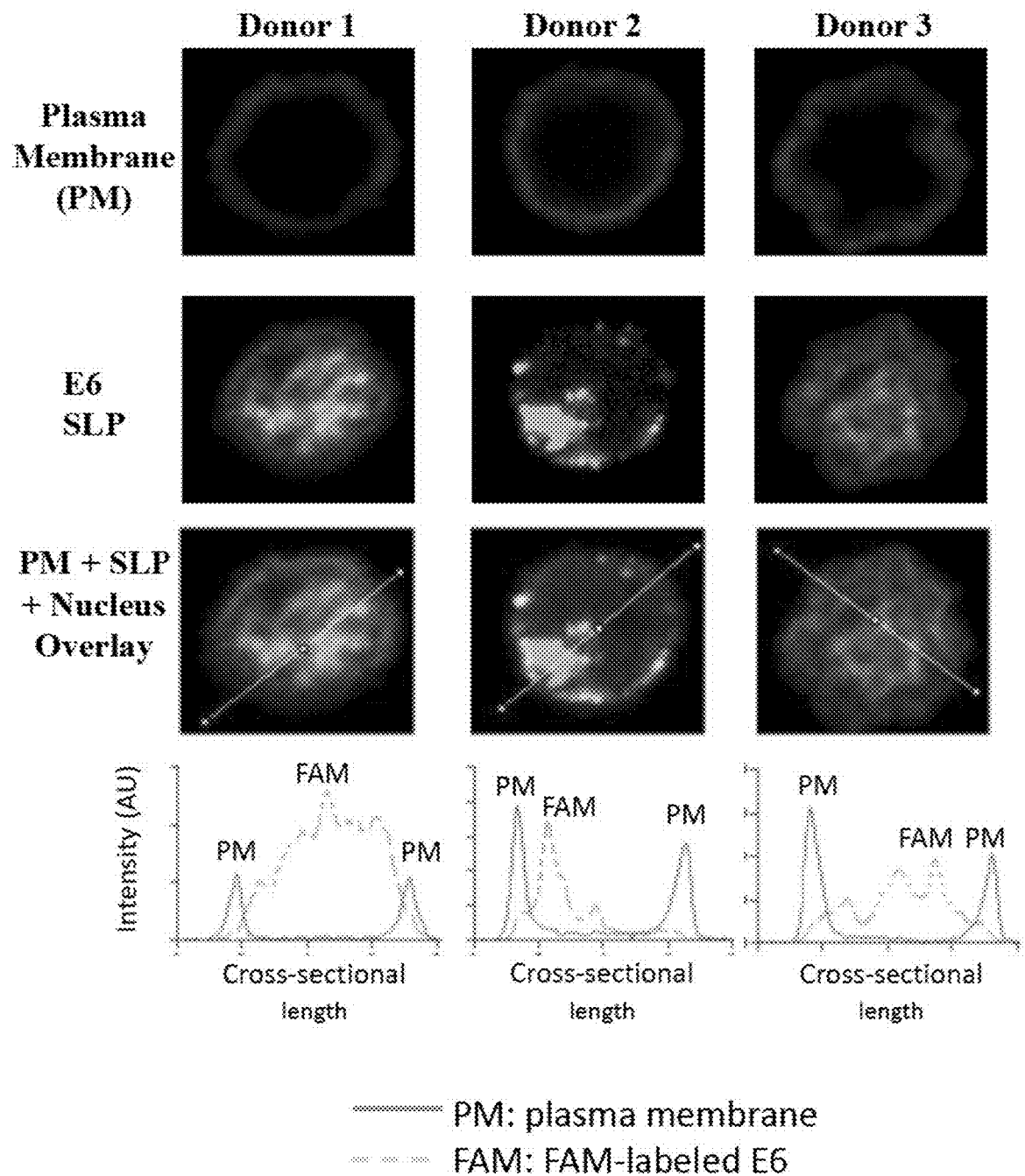
Figure 29C:
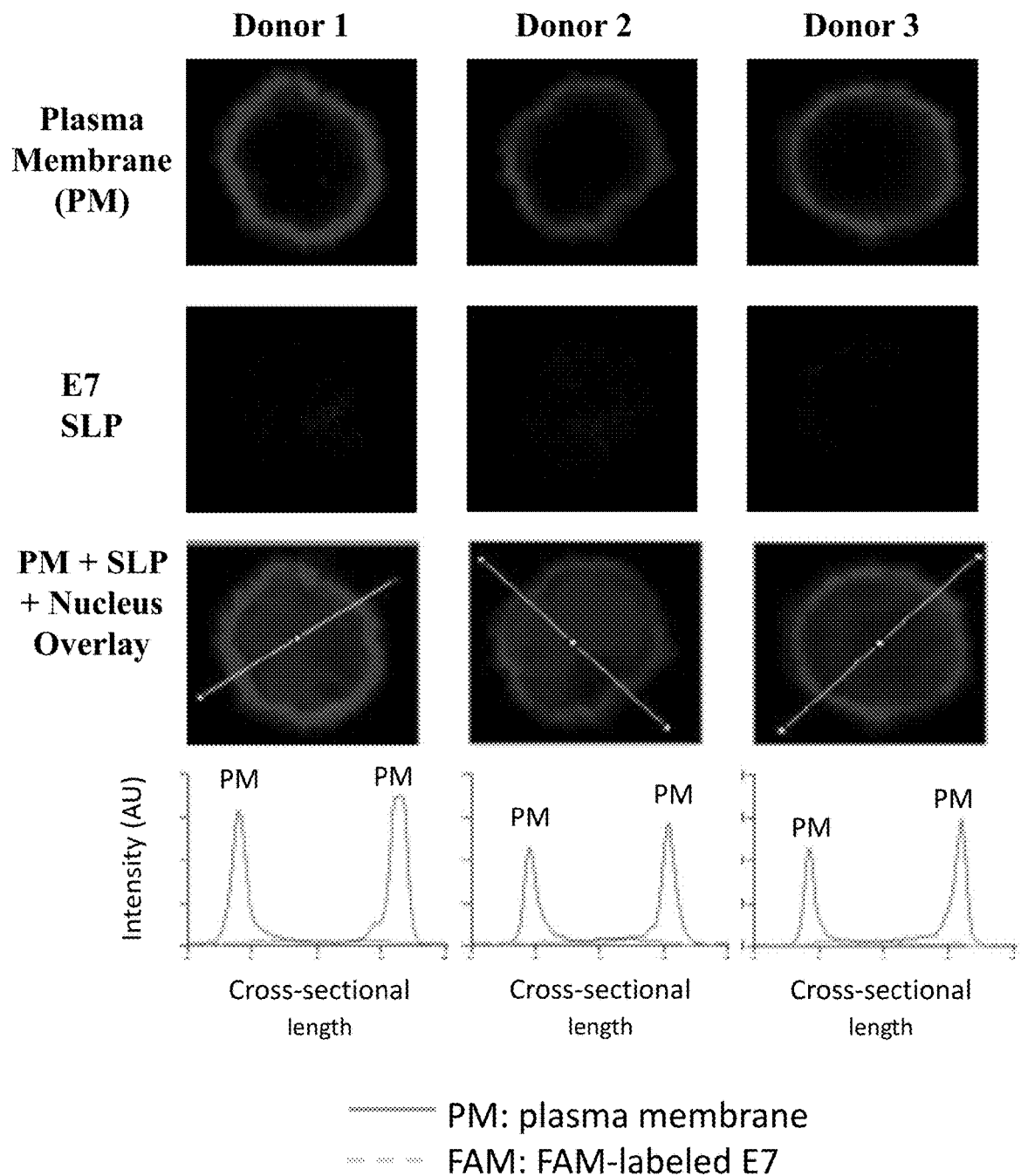
Figure 29D:
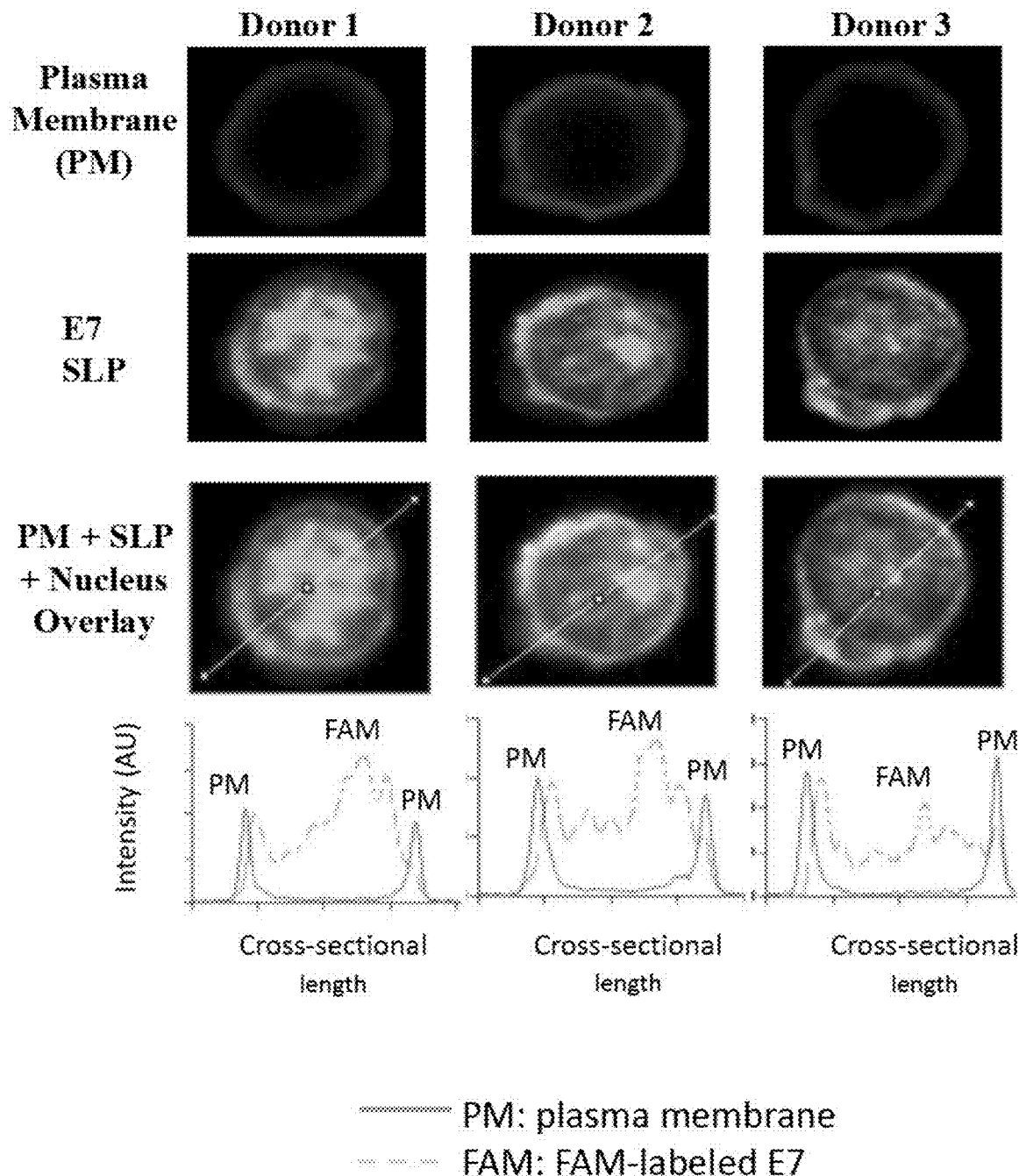
Figure 29E:
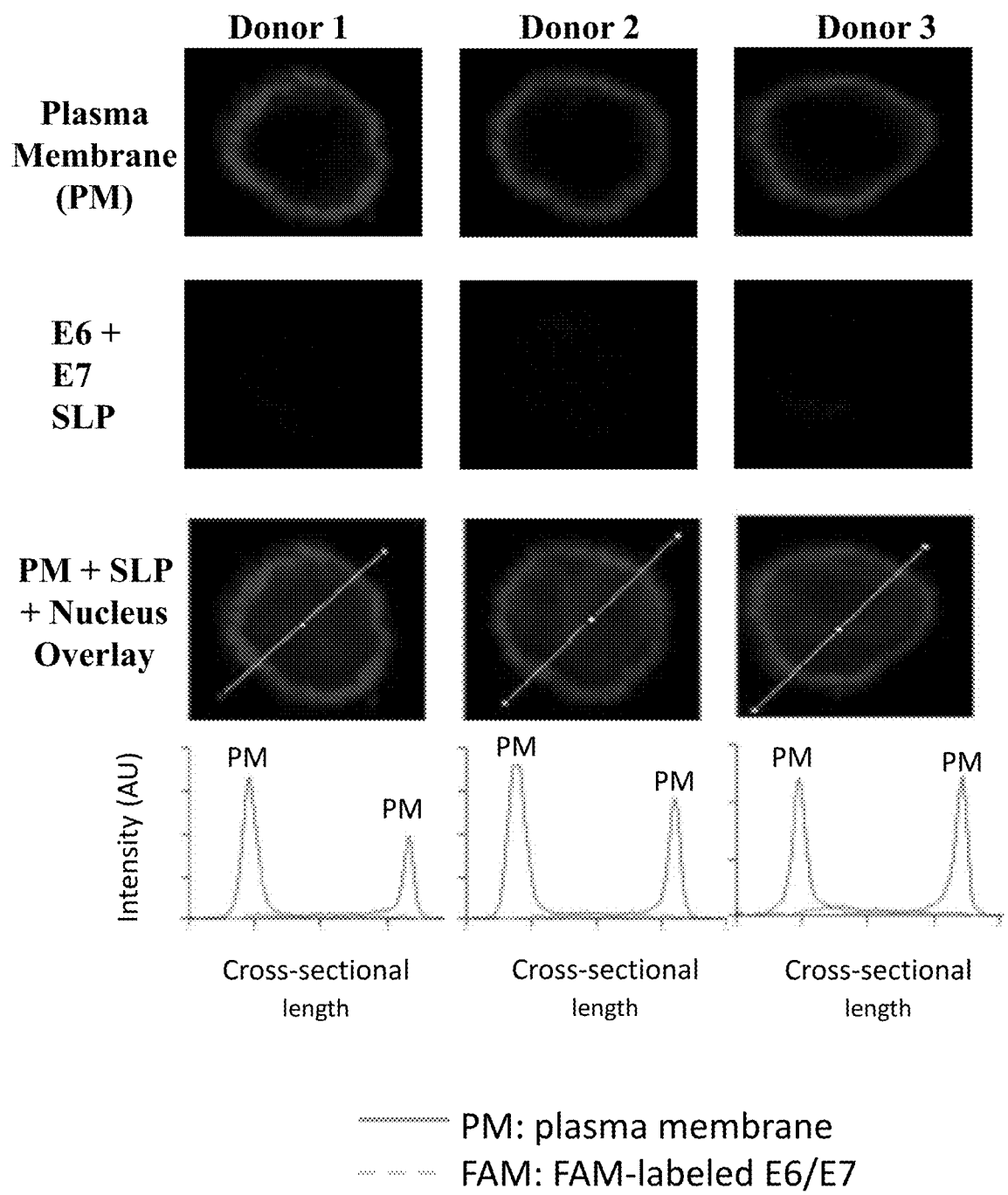
Figure 29F:
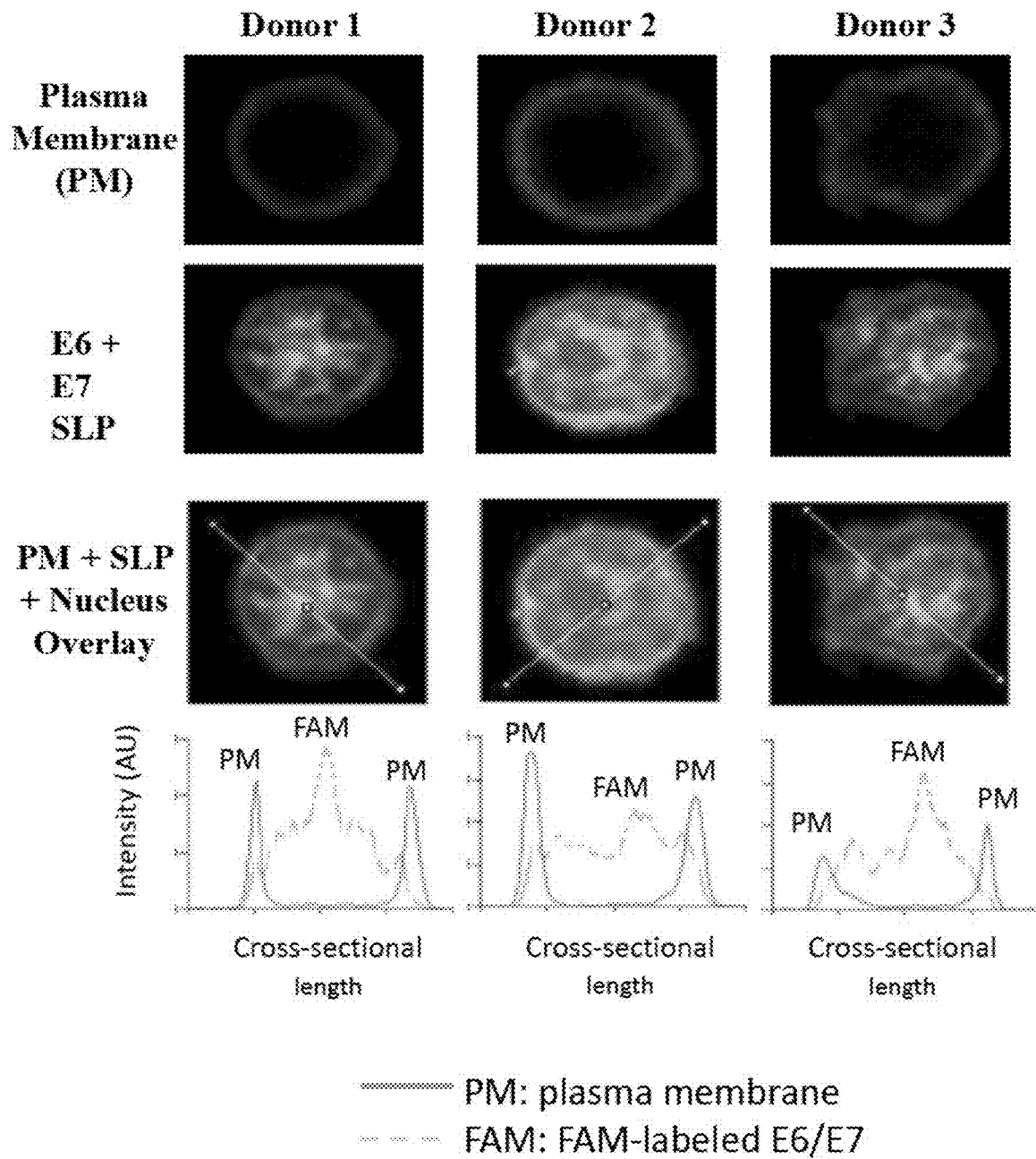

The top panels in FIGS. 29A-29F show confocal imaging from middle of a Z-stack for each sample, demonstrating localization of plasma membrane (CD45 staining, PM, top panels); the localization of FAM-labeled HPV SLPs (SLP, second panels from top); and the overlay showing their relative localization (Overlay, third panels from top), whereas the bottom panels in FIG. 29 show line traces across the center of the cell along the white lines shown in the respective overlay panels, for human PBMCs SQZ-processed in RPMI (FIG. 29A, 29C, 29E) or human PBMCs SQZ-loaded with FAM-labeled E6, E7, or E6+E7 SLPs (FIGS. 29B, 29D, 29F respectively).

Figure 30:
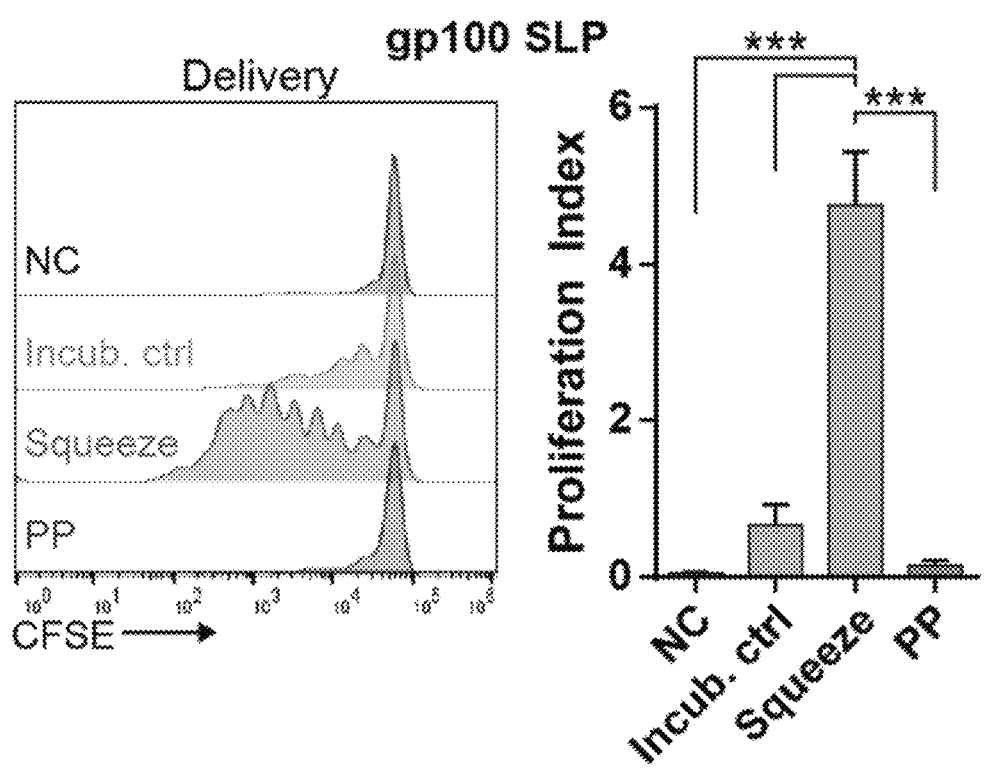

FIG. 30 shows the proliferation of gp100 specific T cells after co-injection of B cells either left untreated (NC), incubated with gp100 SLP (Incub. ctrl), SQZ-loaded with gp100 SLP (Squeeze), or pulsed with gp100 SLP (PP), as measured by CFSE dilution (left panel) and subsequent quantification (right panel).

Figure 31:
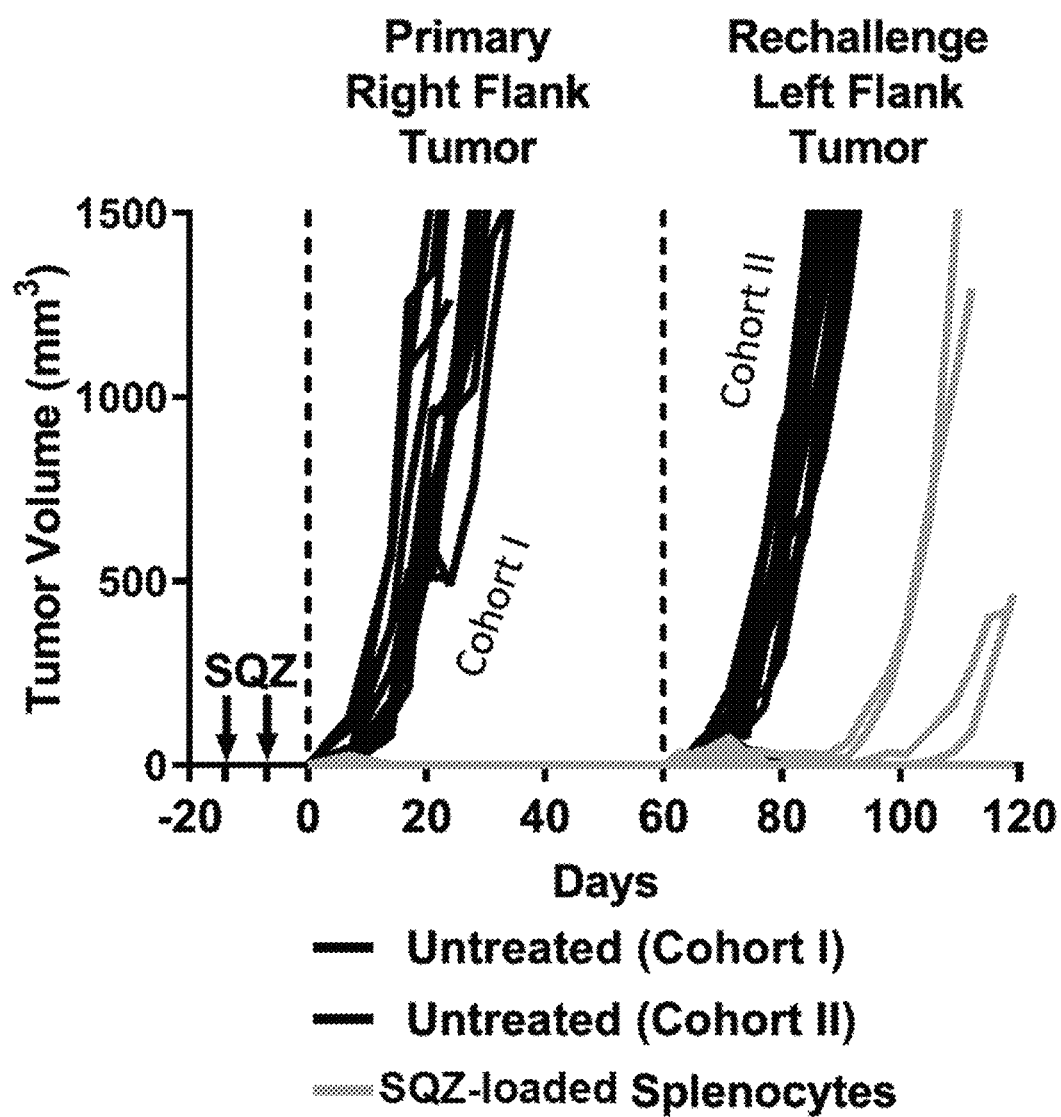

FIG. 31 shows the tumor volume change of implanted TC-1 tumors in mice that were untreated or prophylactically administered with crafted splencoytes SQZ-loaded with E7 SLP. Untreated cohort I was implanted with TC-1 tumors on Day 0. Untreated cohort II was implanted with TC-1 tumors on Day 60. Mice treated with SQZ-loaded splenocytes were implanted with TC-1 tumors on both Day 0 and Day 60.

Figure 32:
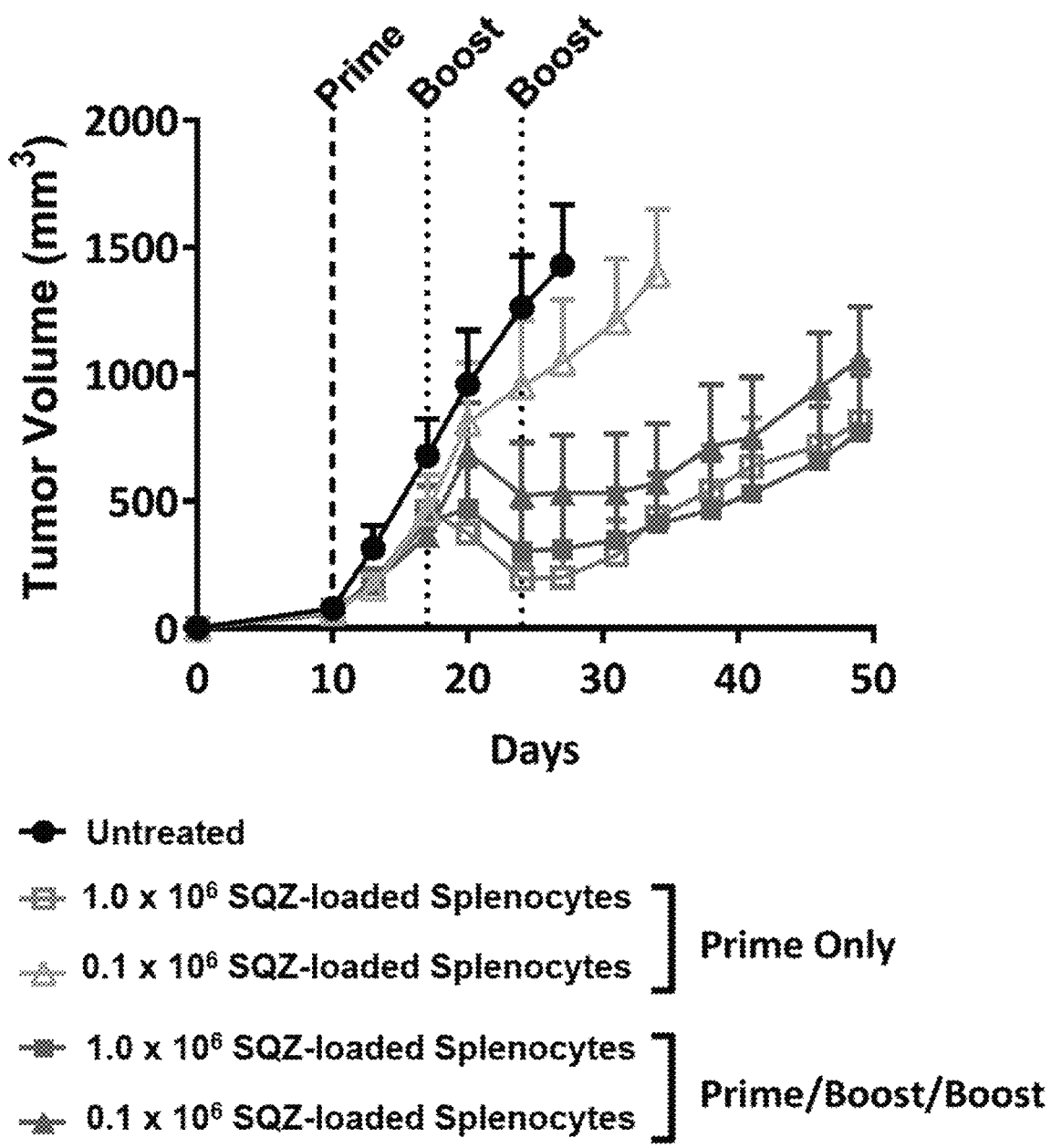

FIG. 32 shows the tumor volume changes of implanted TC-1 tumors following therapeutic treatment of crafted splenocytes SQZ-loaded with E7 SLP. Mice were treated with $0.1 \times 10^6$ or $1.0 \times 10^6$ SQZ-loaded splenocytes, administered either as a single dose of priming (on Day 10 post-implantation), or under a prime and boost regimen (Prime on Day 10, boost on Days 17 and 24 post-implantation).

Figure 33A:
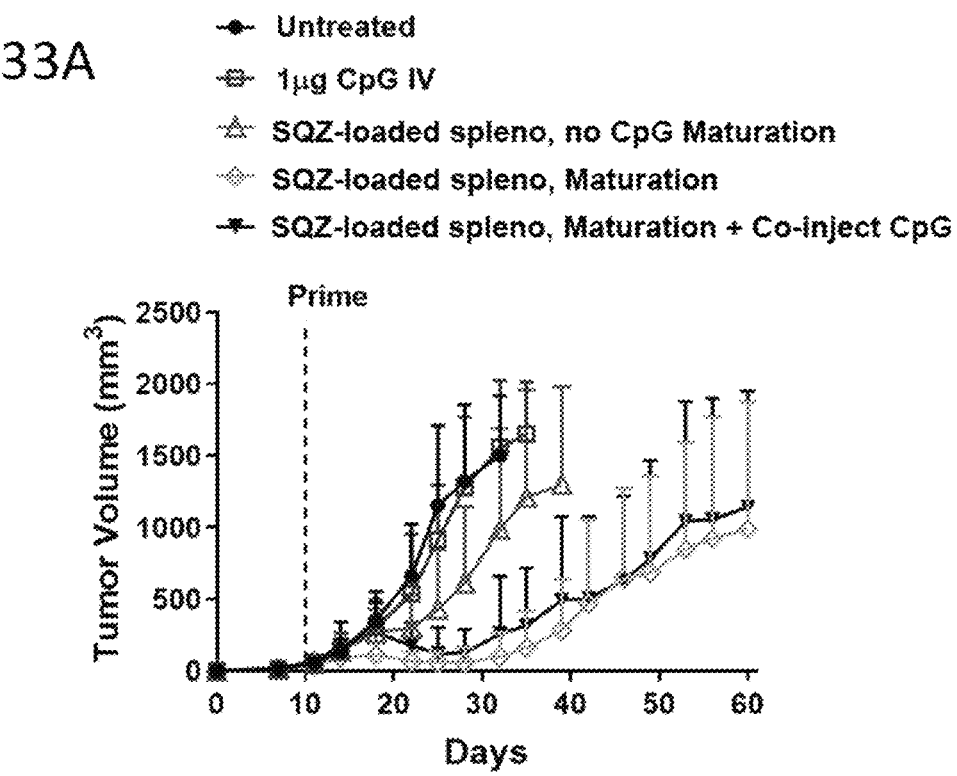
Figure 33B:
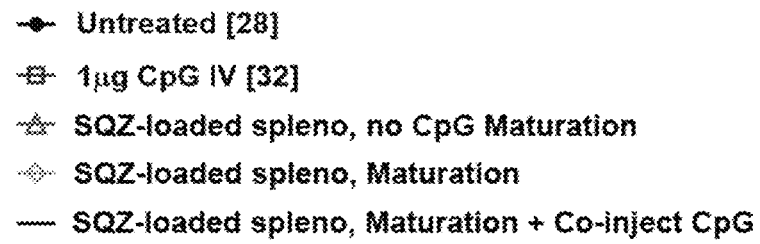
Figure 33B:
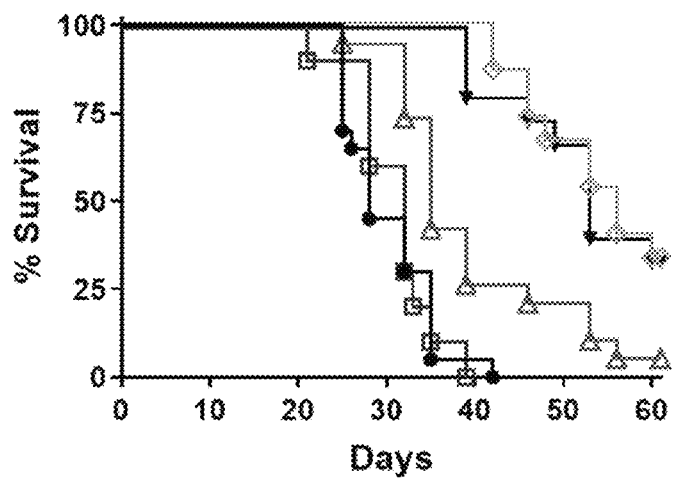

FIGS. 33A and B shows the effect of splenocyte conditioning or CpG co-administration on tumor inhibition (FIG. 33A) and survival improvement (FIG. 33B) when mice carrying an E7-expressing tumor was administered with crafted murine splenocytes SQZ-loaded with HPV E7 antigen.

Figure 34:
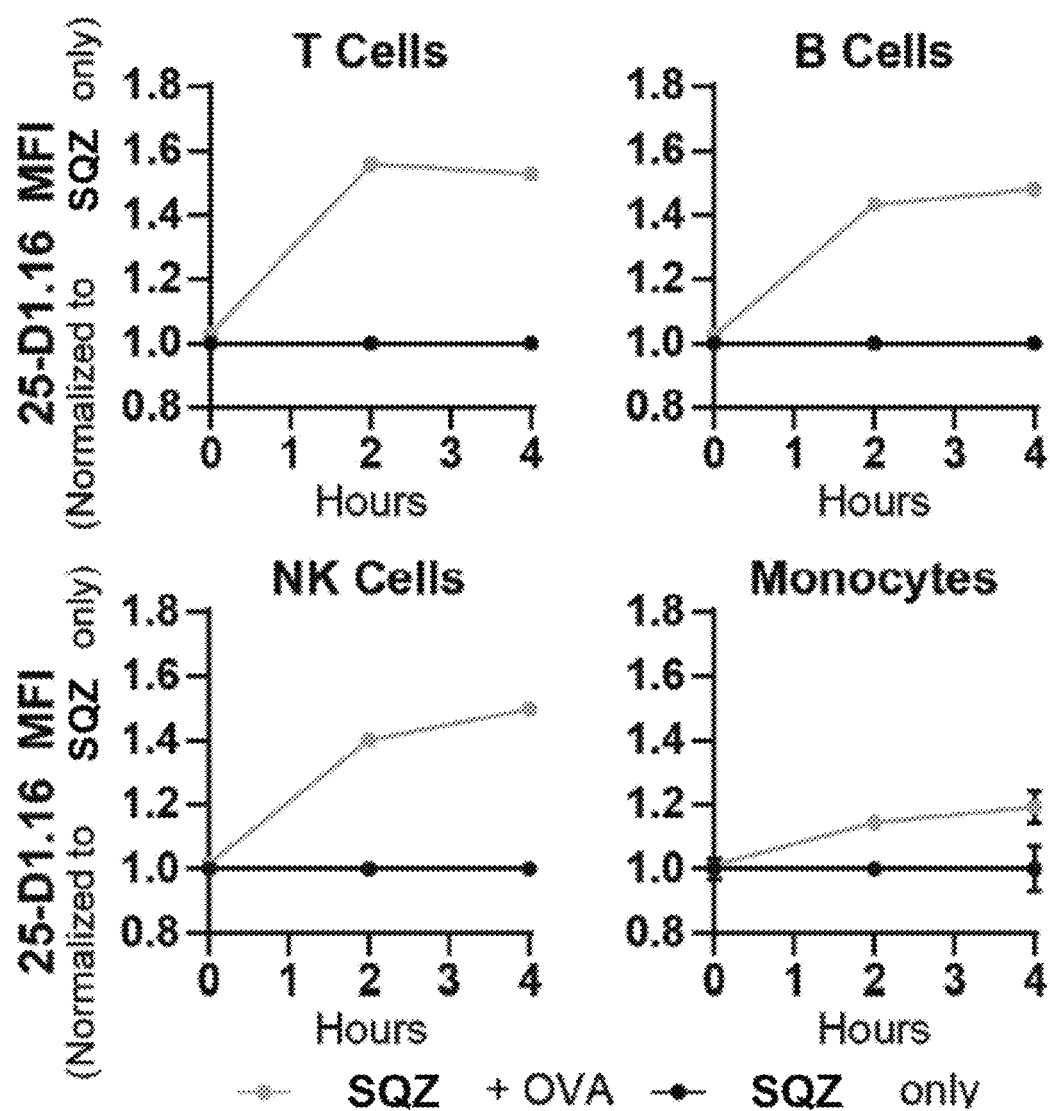

FIG. 34 shows the extent of MHC-I presentation of epitope SIINFEKL (SEQ ID NO: 54) processed from OVA in splenocyte subpopulations of T cells, B cells, NK cells and monocytes after crafted splenocytes were SQZ-processed without cargo (SQZ only) or SQZ-processed in the presence of OVA (SQZ+OVA).

Figure 35:
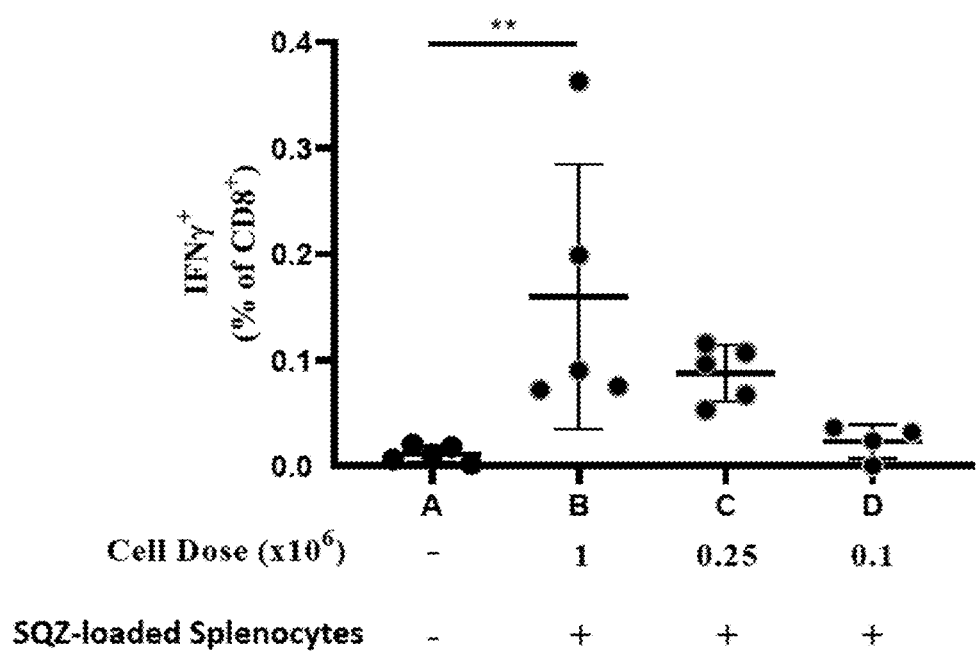

FIG. 35 shows the dose-dependent efficacy of splenocyte administration, for the antigen-specific response elicited by crafted murine splenocytes SQZ-loaded with HPV16 E7 antigen.

Figure 36A:
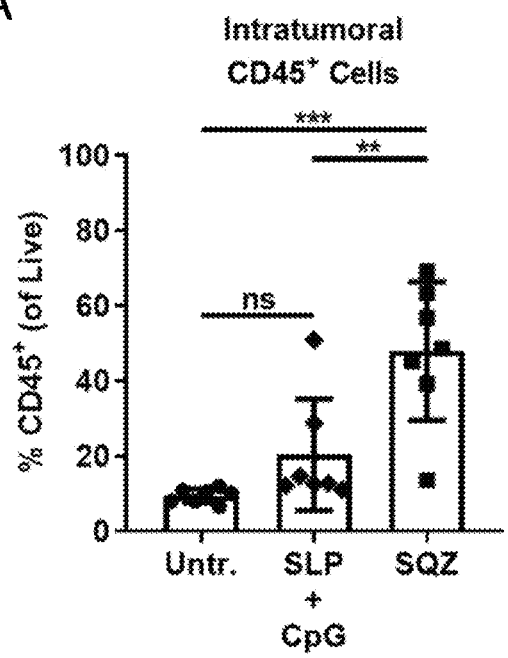
Figure 36B:
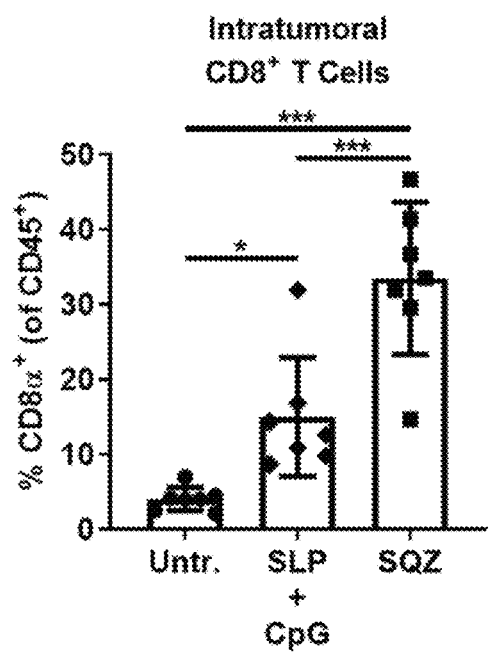
Figure 36C:
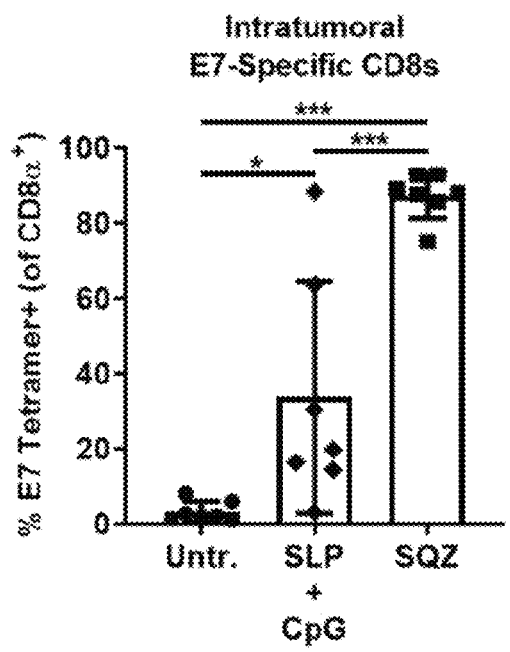
Figure 36D:
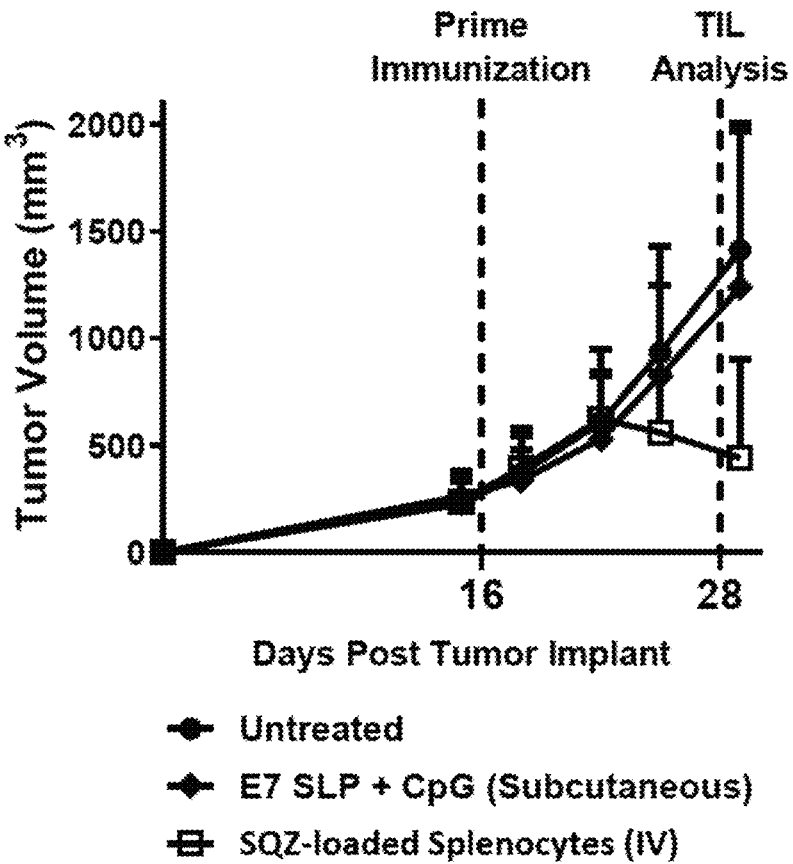

FIGS. 36A-36C show the amount of E7-specific T cell infiltration and FIG. 36D shows the tumor volume over time after immunization with crafted murine splenocytes SQZ-loaded with E7 SLP, or with a peptide vaccine, or left untreated. The percentage of CD45+ leukocytes per live cells in tumor environment, the number of CD8+ T cells out of the CD45+ cells, and the in percentage of E7-specific T cells per CD8+ T cells in tumor environment are shown in FIGS. 36A, 36B and 36C respectively.

Figure 37A:
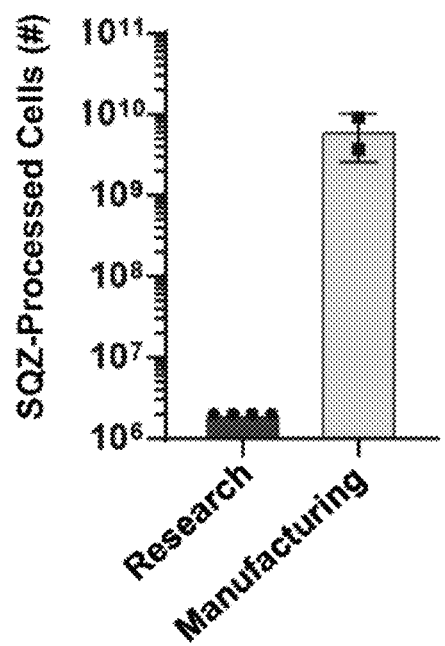
Figure 37B:
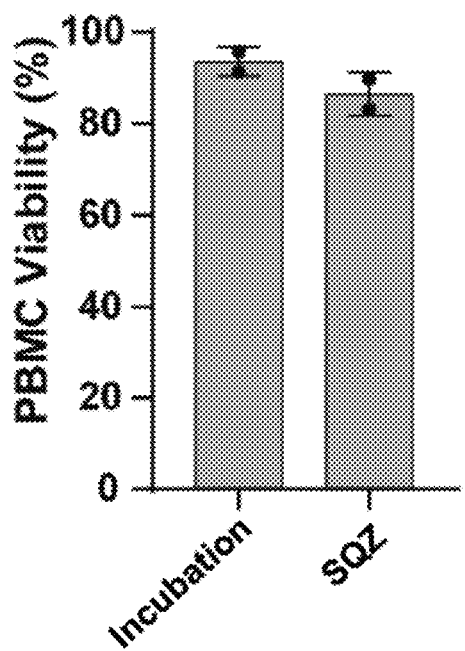
Figure 37C:
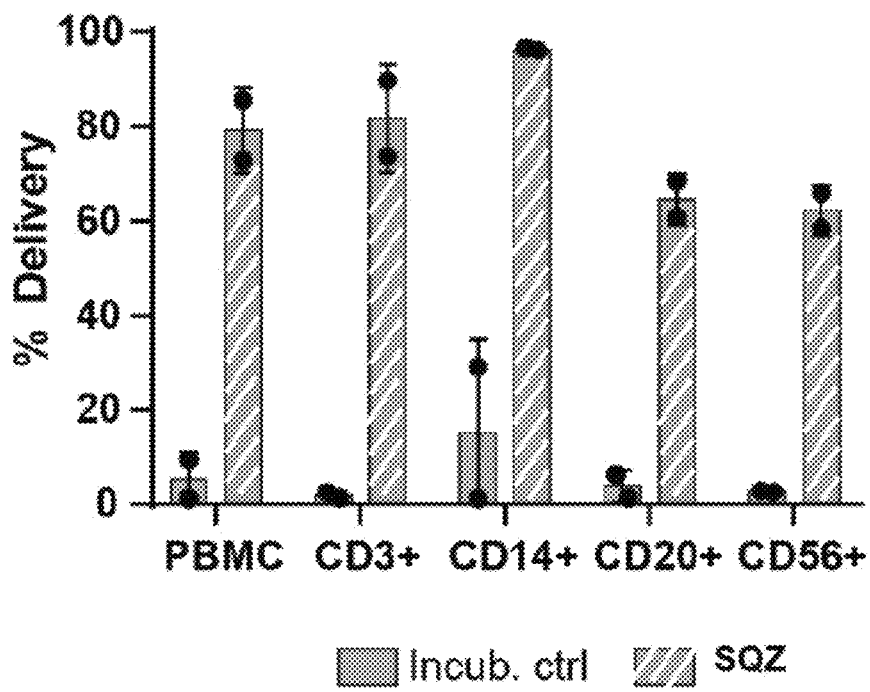

FIG. 37A shows the number of cells SQZ-processed in a typical research setting versus the number of cells SQZ-processed in a manufacturing setting. FIG. 37B shows the viability of PBMCs after incubation with Dextran, or after SQZ-processing in the presence of Dextran. FIG. 37C shows the percentage of cells positive with Dextran after incubation, or SQZ-processing with Dextran, for PBMCs as well as the component cell types of B cells (CD20+), T cells (CD3+), NK cells (CD56+) and monocytes (CD14+).

Figure 38A:
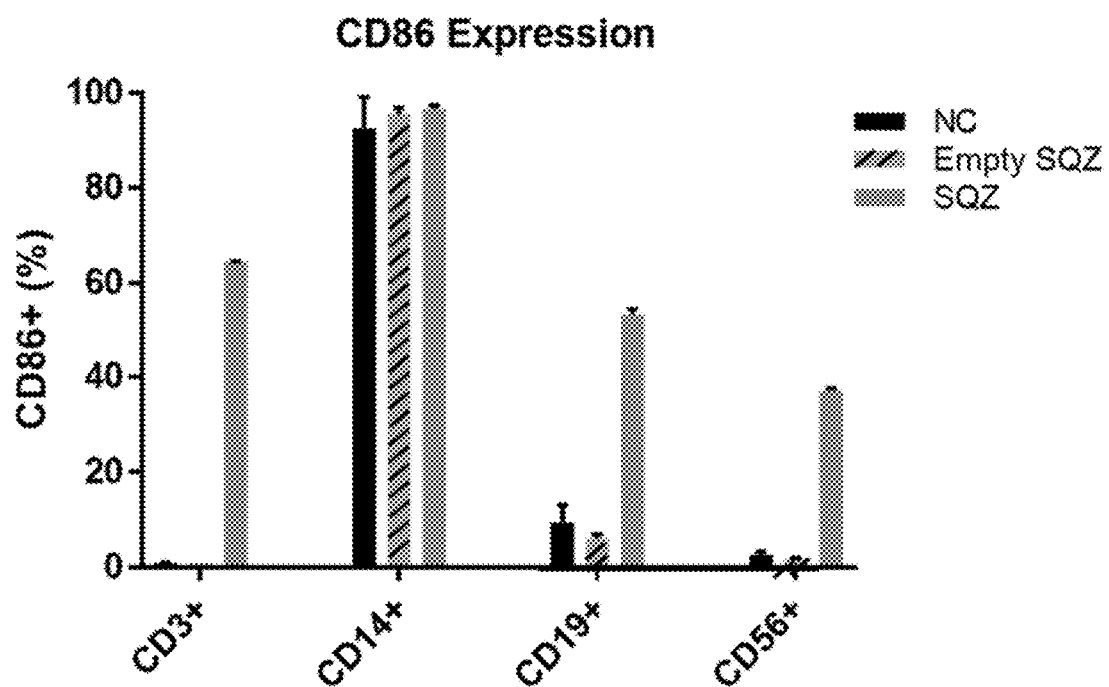
Figure 38B:
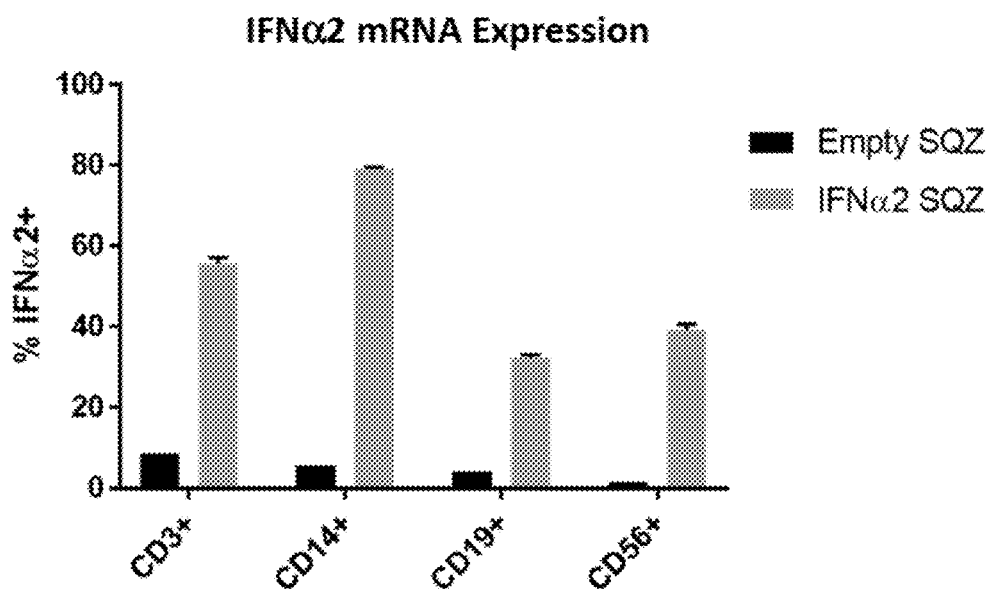

FIG. 38A shows the percentage of CD86-expressing cells within PBMC subpopulations of B cells (CD19+), T cells (CD3+), NK cells (CD56+) and monocytes (CD14+), after PBMCs were either left untreated (NC), SQZ-processed with empty payload (Empty SQZ), or SQZ-loaded with CD86-encoding mRNA (SQZ). FIG. 38B shows the percentage of IFNα2-expressing cells within PBMC subpopulations of B cells (CD19+), T cells (CD3+), NK cells (CD56+) and monocytes (CD14+), after PBMCs were either SQZ-processed with empty payload (Empty SQZ), or SQZ-loaded with IFNα2-encoding mRNA (SQZ).

Figure 39A:
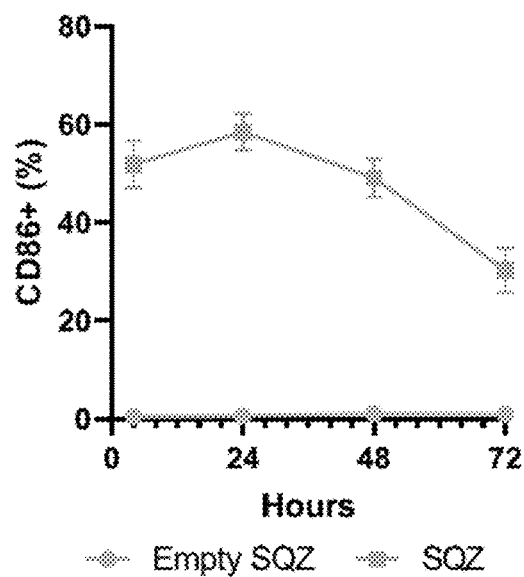
Figure 39B:
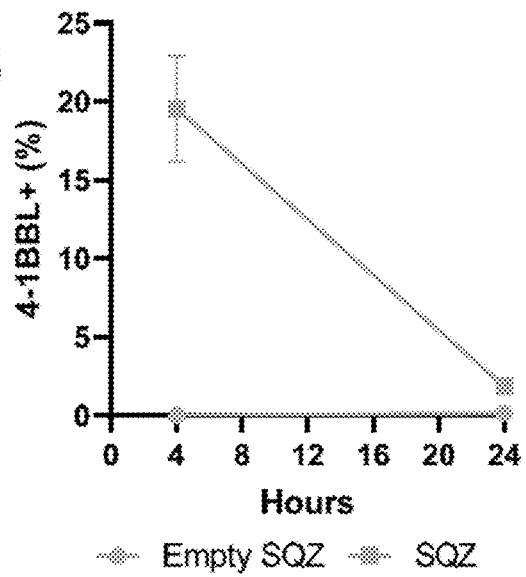

FIG. 39A shows the percentage of CD86-expressing within PBMC subpopulation of T cells (CD3+) over 72 hours, after PBMCs were either SQZ-processed with empty payload (Empty SQZ), or SQZ-loaded with CD86-encoding mRNA (SQZ. FIG. 39B shows the percentage of 4-1BBL-expressing cells within PBMC subpopulation of T cells (CD3+) over 72 hours, after PBMCs were either SQZ-processed with empty payload (Empty SQZ), or SQZ-loaded with 4-1BBL-encoding mRNA (SQZ).

Figure 40:
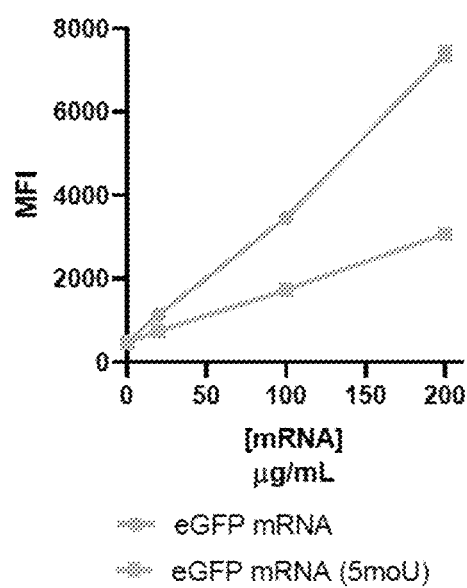

FIG. 40 shows the amount of eGFP expression within PBMC subpopulation of T cells (CD3+) after PBMCs were either SQZ-processed with an unmodified eGFP mRNA or with an eGFP mRNA carrying a 5-metoxyuridine backbone modification (5moU), at mRNA concentrations of 0 μg/mL to 200 μg/mL.

Figure 41:
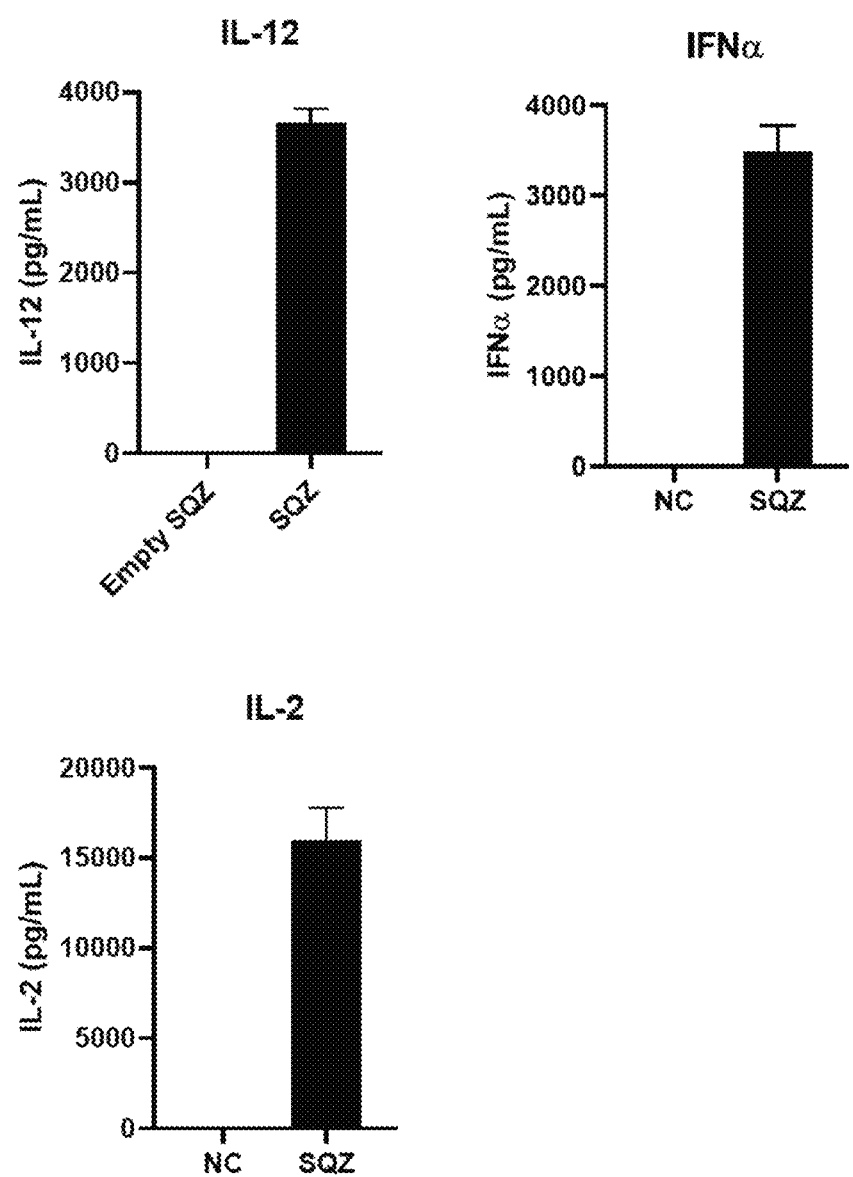

FIG. 41 shows the degree of secretion of IL-12, IFNα or IL-2 cytokine by PBMCs, after PBMCs were either left untreated (NC) or SQZ-processed with mRNA encoding IL-12, IFNα or IL-2 respectively (SQZ).

Figure 42A:
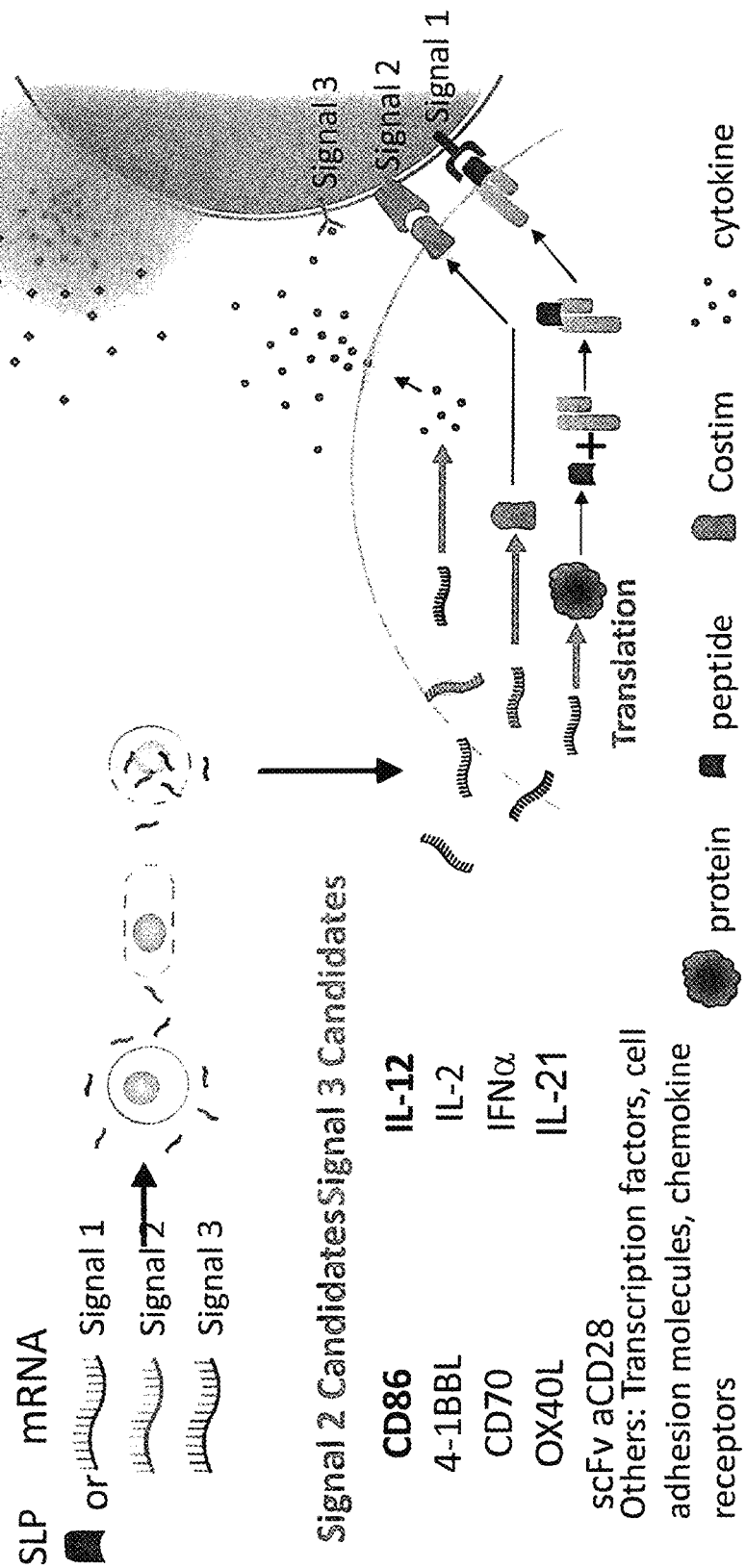
Figure 42B:
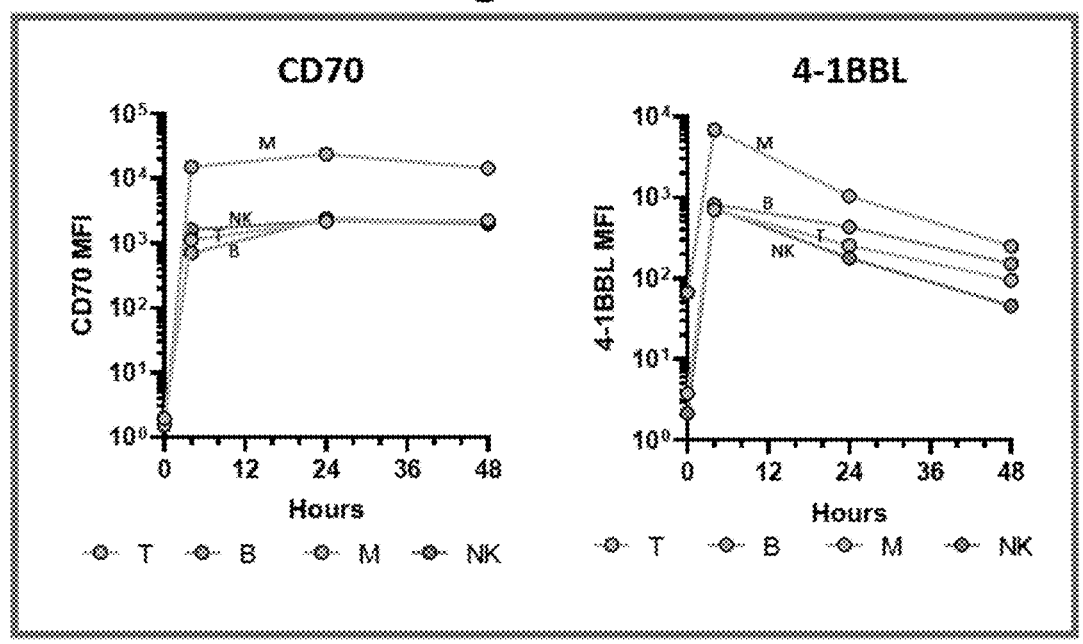
Figure 42C:
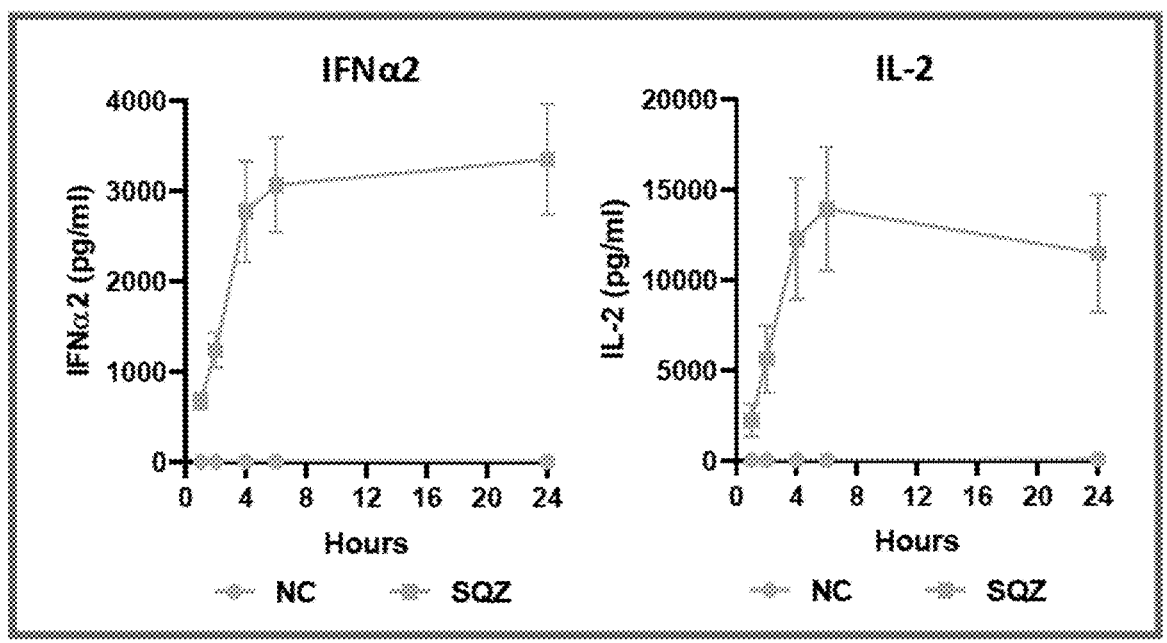

FIG. 42A shows the schematics of Signals 1, 2, 3 from an enhanced antigen presenting cell in stimulating an effector immune cell response. FIG. 42B shows the amount of Signal 2 effector expression over 48 hours within PBMC subpopulation of B cells (CD19+), T cells (CD3+), NK cells (CD56+) and monocytes (CD14+), after PBMCs were SQZ-processed with mRNA encoding CD70 or 4-1BBL respectively. FIG. 42C shows the amount of Signal 3 effector secretion by PBMCs over 24 hours, after PBMCs were SQZ-processed with mRNA encoding IFNα2 or IL-2 respectively.

Figure 43A:
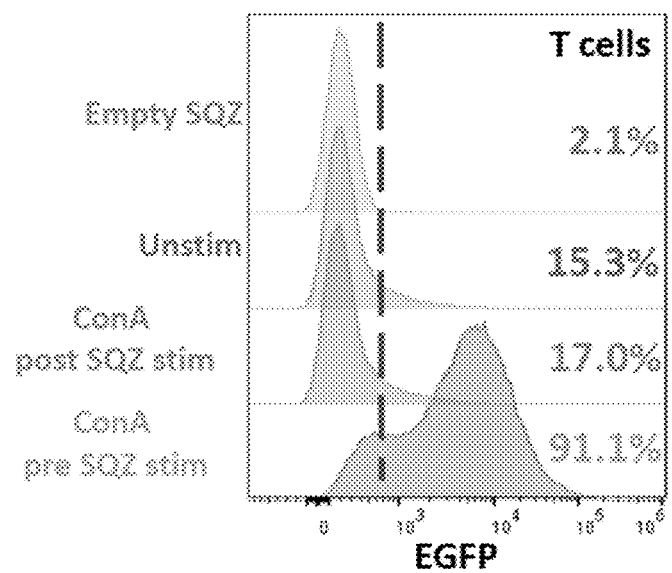
Figure 43B:
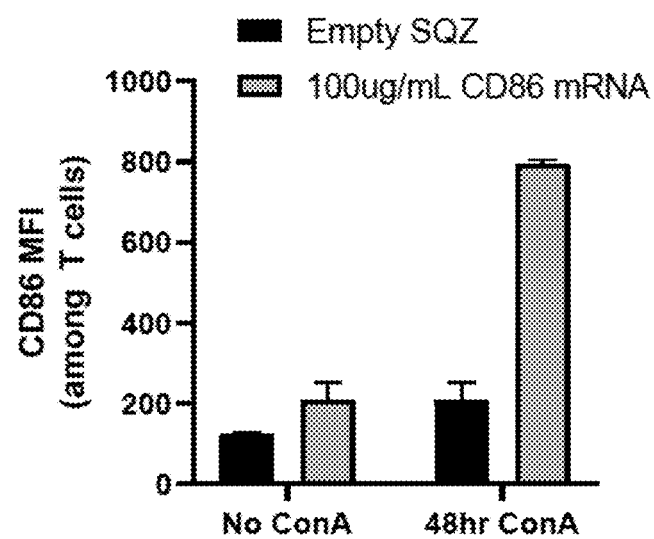
Figure 44A:
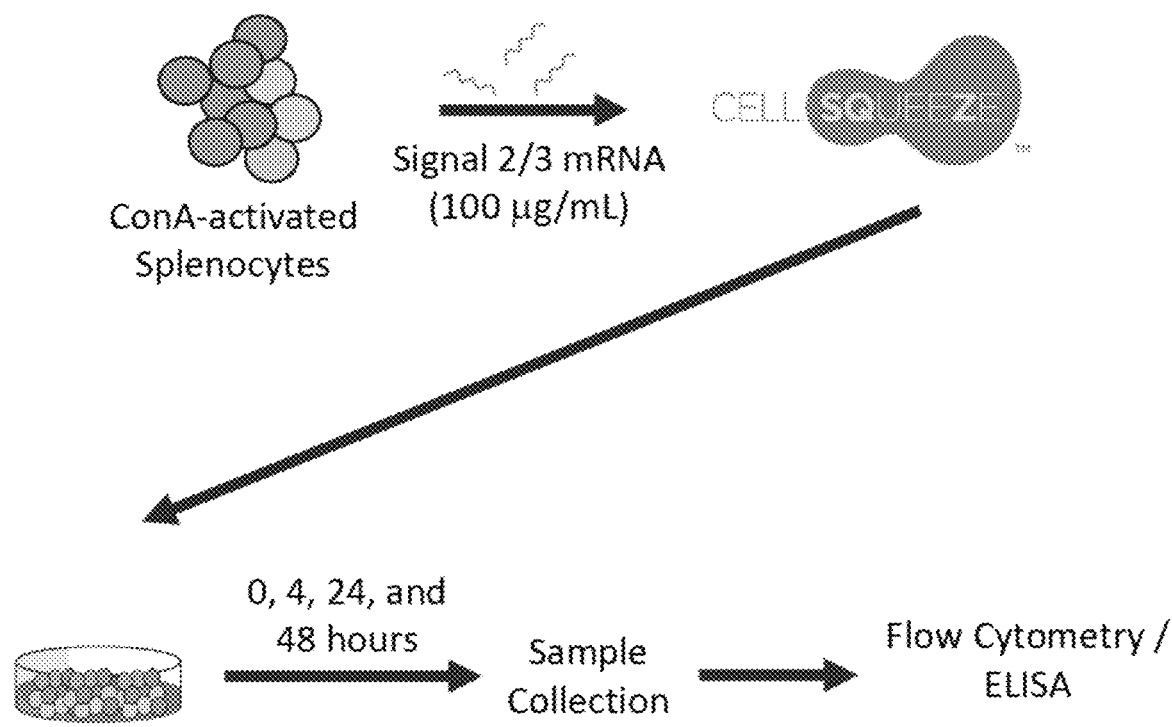
Figure 44B:
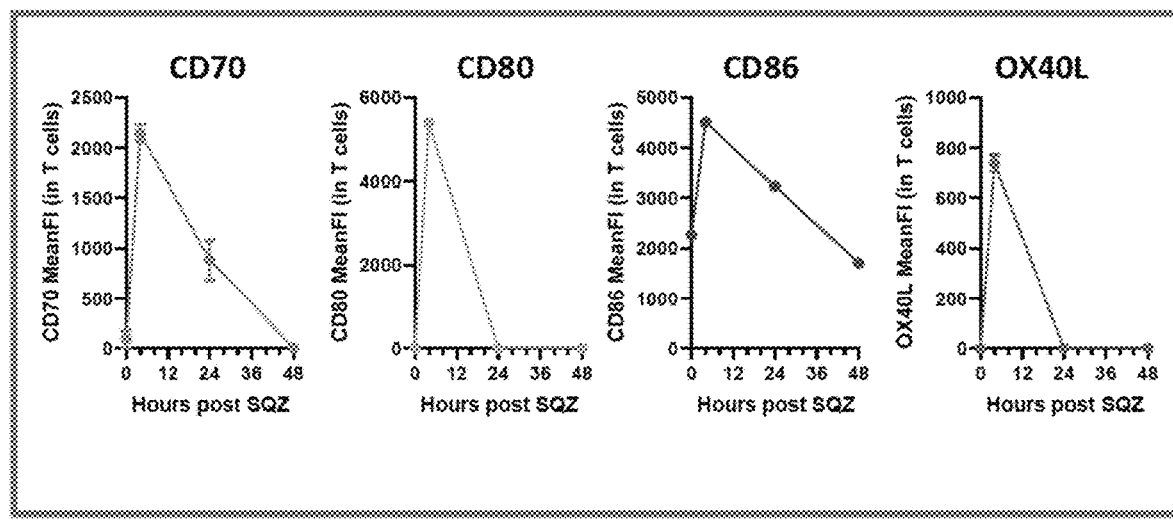
Figure 44C:
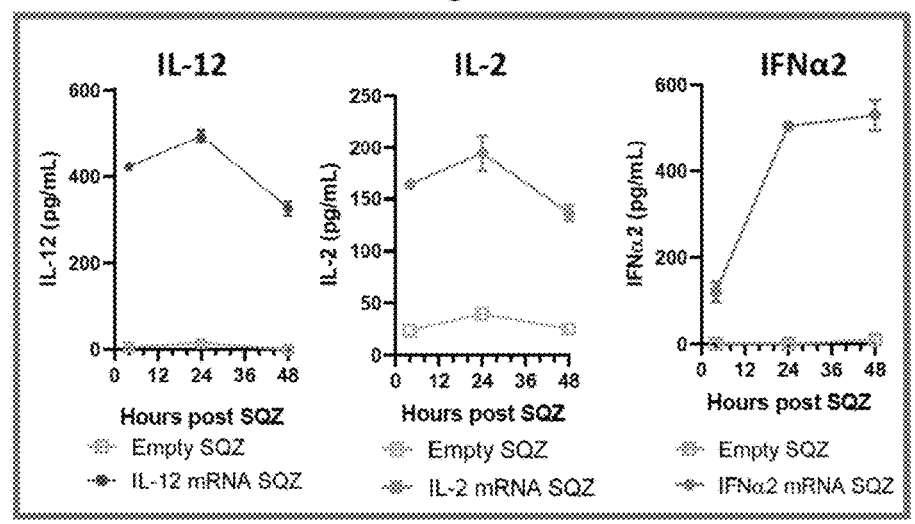

FIG. 43A shows the amount of eGFP translation and expression in PBMCs, for PBMCs that were unstimulated, stimulated with ConA before SQZ-processing, stimulated with conA after SQZ-processing, where the PBMCs were SQZ-processed in the presence of eGFP-encoding mRNA. FIG. 43B shows the amount of CD86 expression in PBMCs that were unstimulated, or stimulated with ConA before SQZ-processing, when the PBMCs were SQZ-processed in the presence of CD86-encoding mRNA FIG. 44A shows the schematics of an experiment in studying whether Signal 2 and Signal 3 Effector mRNAs were translated in crafted mouse splenocytes subsequent to SQZ-loading. FIG. 44B shows the amount of CD70, CD80, CD86 or OX40L expression in crafted murine splenocytes after the crafted splenocytes were SQZ-processed in the presence of mRNAs encoding CD70, CD80, CD86 or OX40L respectively. FIG. 44C shows the amount of IL-12, IL-2 or IFNα2 secretion by crafted murine splenocytes after the crafted splenocytes were SQZ-processed in the presence of mRNAs encoding IL-12, IL-2 or IFNα2 respectively.

Figure 45A:
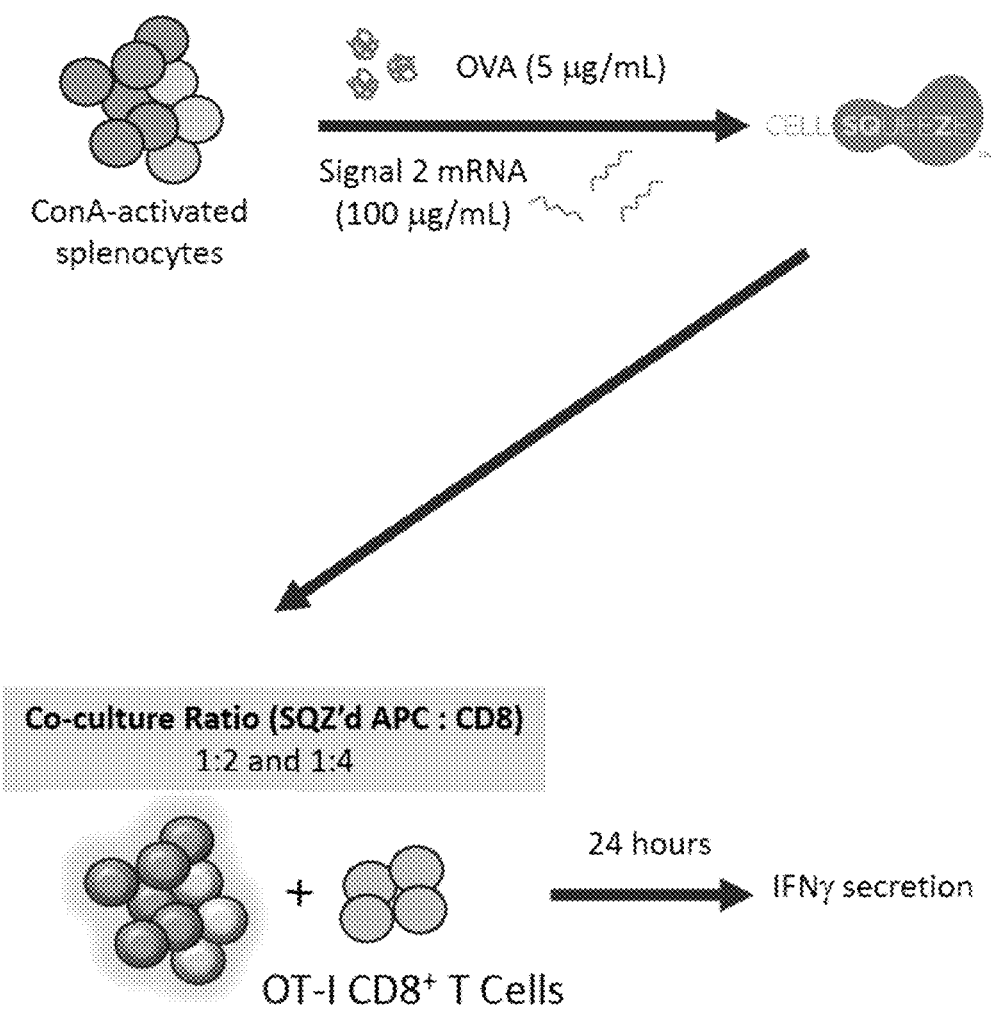
Figure 45B:
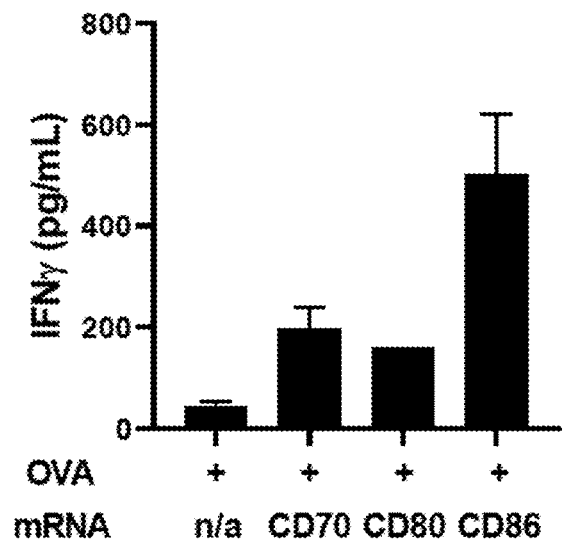
Figure 45C:
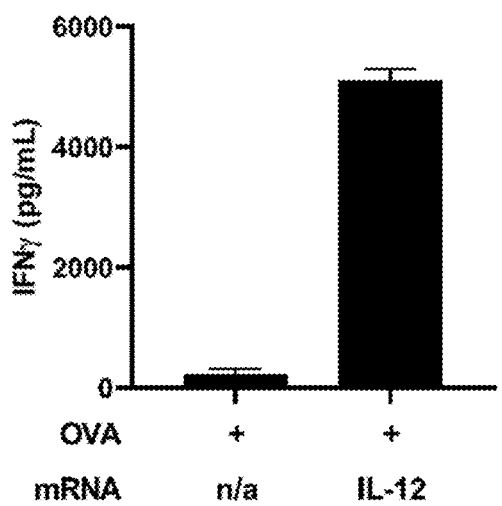

FIG. 45A shows the schematics of an experiment in studying whether SQZ-loading of Signal 2 and Signal 3 Effector mRNAs in crafted murine splenocytes could facilitate an enhanced ability to stimulate antigen-specific T cell response. FIG. 45B showed the degree of activation of OVA-specific T cells upon co-culture with crafted murine splenocytes SQZ-loaded with OVA peptide and mRNA encoding Signal 2 effectors (CD70, CD80 or CD86). FIG. 45C showed the degree of activation of OVA-specific T cells upon co-culture with crafted murine splenocytes SQZ-loaded with OVA peptide and mRNA encoding Signal 3 effector IL-2.

Figure 46A:
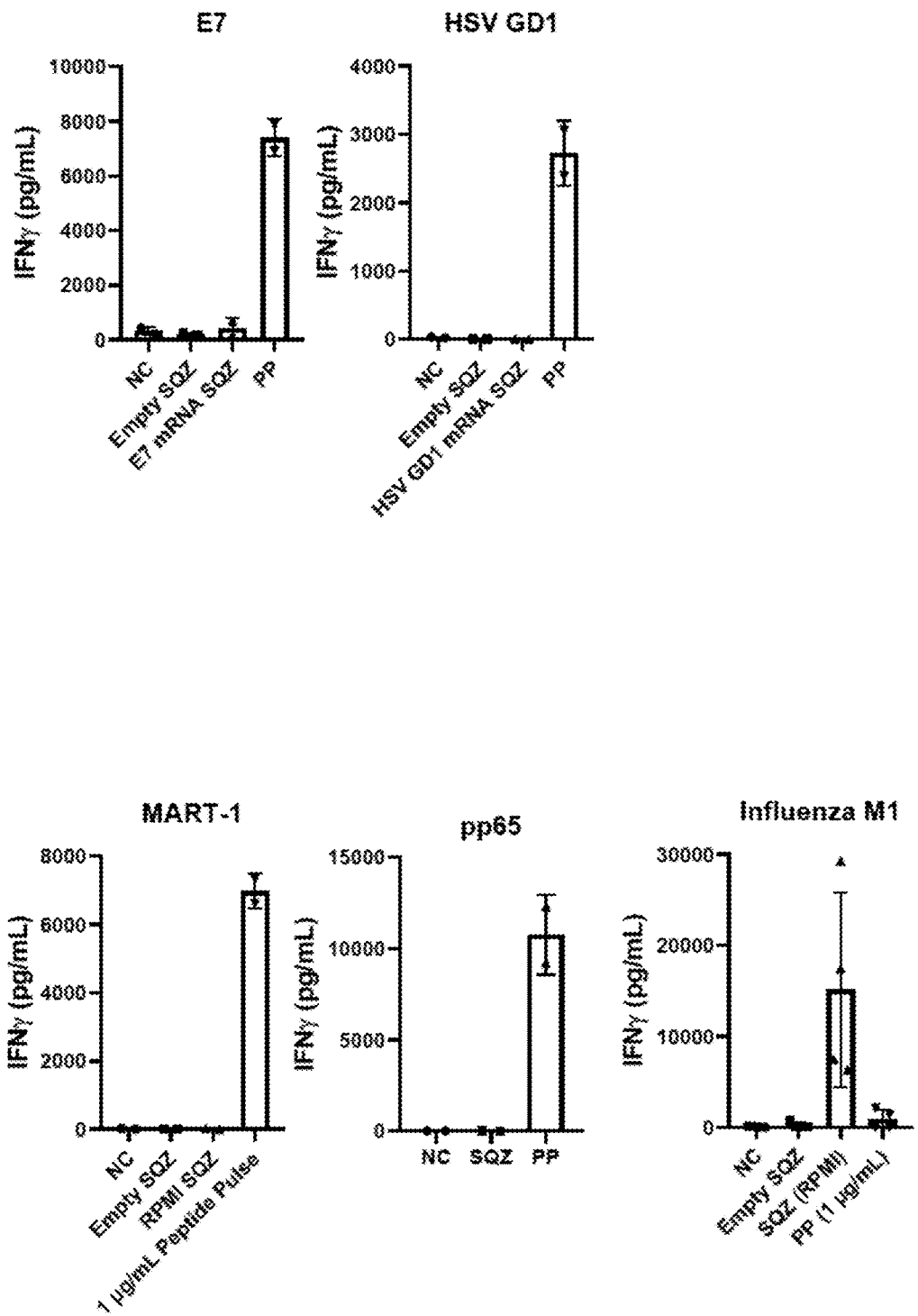
Figure 46B:
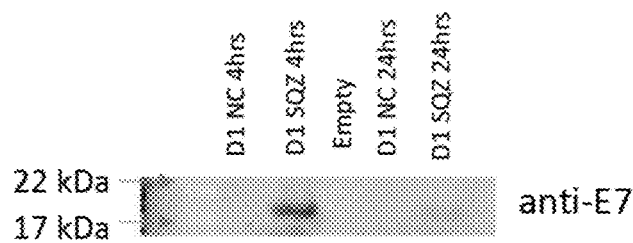
Figure 46C:
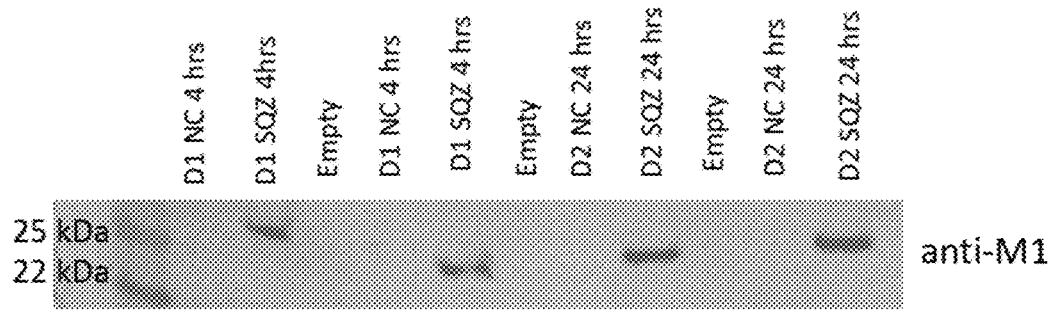

FIG. 46A shows the amount of activation of antigen-specific responder T cells upon co-culture with human PBMCs SQZ-loaded with mRNAs encoding the respective antigens (E7, HSV GD1, MART-1, pp65 or Influenza M1). FIGS. 46B and 46C shows the amount of translation and expression of E7 or M1 in PBMCs, after PBMCs were SQZ-processed in the presence of mRNAs encoding E7 or M1 respectively.

Figure 47A:
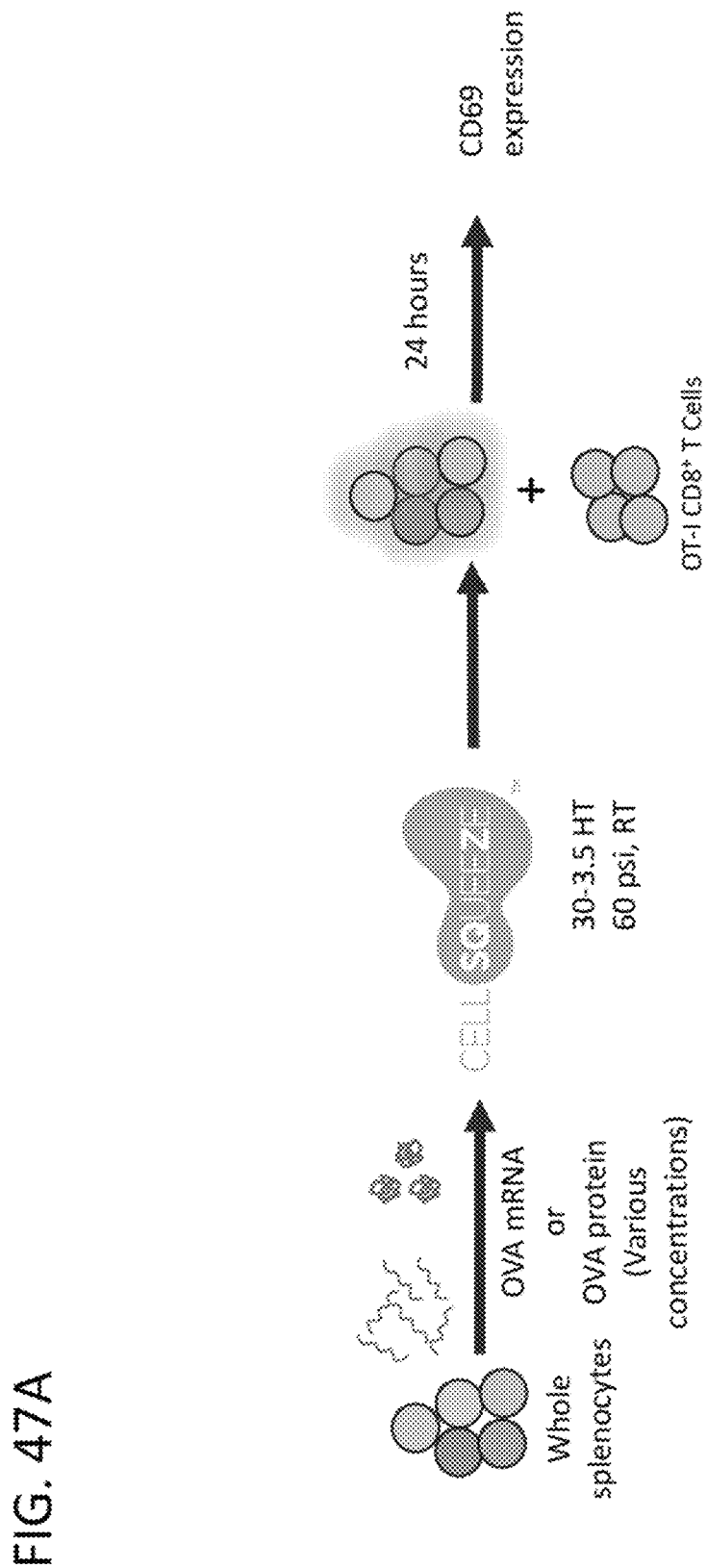
Figure 47B:
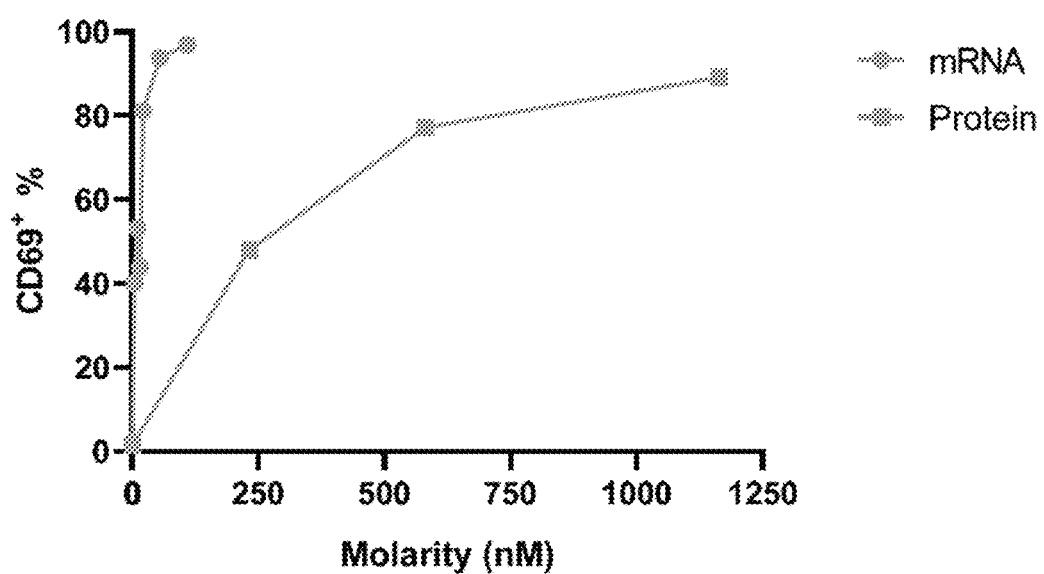

FIG. 47A shows the schematics of an experiment in comparing SQZ-loading of mRNA versus protein form of antigen with regards to potency of loaded murine splenocytes in stimulating an antigen-specific T cell response. FIG. 47B shows the amount of activated OVA-specific T cells upon co-culture with murine splenocytes SQZ-loaded with OVA protein or OVA-encoding mRNA.

Figures 48A, 48B:
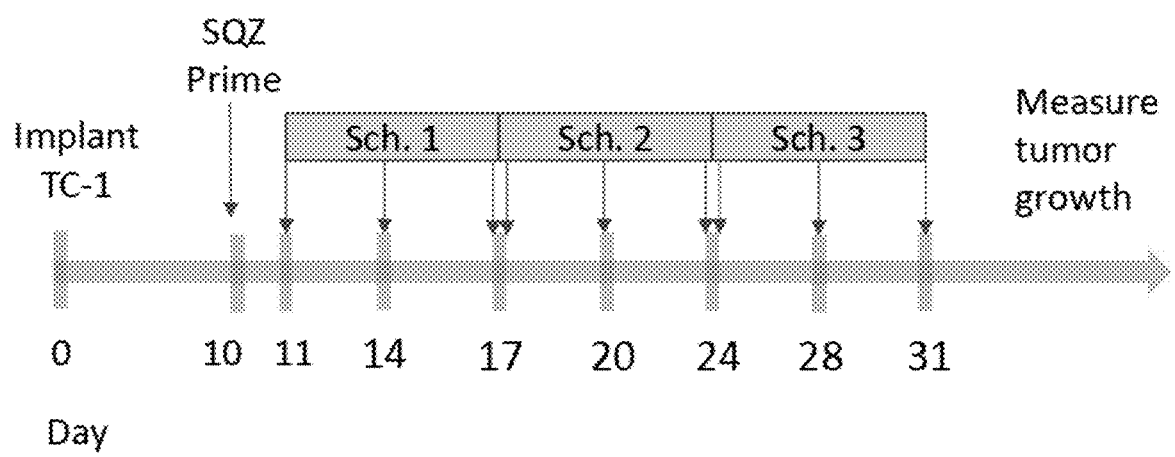

FIGS. 48A and 48B show the experimental design and schematics, respectively, of an experiment in studying whether combination of of E7-loaded crafted splenocytes and anti-CTLA4 administration will result in improved therapeutic effect against E7-carrying tumor TC1. FIGS. 48C, 48D, 48E and 48F show the additive therapeutic effect of combination of tumor antigen-loaded splenocytes and immune checkpoint inhibitor on tumor growth inhibition (FIG. 48C), delay or inhibition on tumor occurrence (FIGS. 48D and 48E) and survival improvement (FIG. 48F) when mice carrying an E7-expressing tumor was administered with crafted murine splenocytes SQZ-loaded with HPV E7 antigen with or without further administration of anti-CTLA4 antibody.

DETAILED DESCRIPTION OF THE INVENTION

Antigen presenting cells (APCs) play a key role in inducing endogenous activation of CTLs. In this work, the implementation of the Cell Squeeze® platform to engineer peripheral blood mononuclear cells (PBMCs) for use in modulating an immune response to various indications, including cancer and infectious disease, is described. By enabling efficient cytosolic delivery of target antigens and/or adjuvants to PBMCs, this platform has demonstrated the ability to induce highly effective MHC-I presentation of target antigens and stimulation of CTLs in vivo. The present inventors have unexpectedly discovered that mixed populations of PBMCs have greater efficacy that pure B cell and T cell populations alone. In addition, the inventors unexpectedly discovery that conditioning PBMCs with an adjuvant increased the activation of antigen presenting cells leading to greater immunostimulation when administered to an individual compared to non-conditioned antigen-loaded PBMCs.

The present application, in some aspects, provides modified PBMCs comprising an antigen and an adjuvant, and wherein the antigen is present intracellularly. In some embodiments, the PBMCs comprising the antigen are incubated in the presence of an adjuvant for a period of time prior to administration to an individual (i.e., the PBMCs are conditioned). In some embodiments, the PBMCs are incubated in the presence of an adjuvant for a period of time prior to introducing the antigen to the PBMCs.

In some embodiments, the modified PBMCs are prepared by a) passing an input PBMC cell suspension through a cell-deforming constriction, wherein a diameter of the constriction is a function of a diameter of the input PBMCs, thereby causing perturbations of the input PBMCs cell large enough for the antigen to pass through to form a perturbed input PBMCs; and b) incubating the perturbed input PBMCs with the antigen for a sufficient time to allow the antigen to enter the perturbed input PBMCs; thereby generating the modified PBMCs comprising the antigen. Also provided are methods of using the modified PBMCs for modulating an immune response in an individual, for example, for enhancing an immune response in the individual. In some embodiments, the enhanced immune response is directed towards the antigen. In some embodiments, the cell-deforming constriction is contained in a microfluidic channel, such as any of the microfluidic channels described herein.

General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4th ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); PCR 2: A Practical Approach (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6th ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 2011).

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

It is understood that aspects and embodiments of the invention described herein include "comprising," "consisting," and "consisting essentially of" aspects and embodiments.

The term "about" as used herein refers to the usual error range for the respective value readily known to the skilled person in this technical field. Reference to "about" a value or parameter herein includes (and describes) embodiments that are directed to that value or parameter per se.

As used herein, a "peripheral blood mononuclear cells" or "PBMCs" refers to a heterogeneous population of blood cells having a round nucleus. Examples of cells that may be found in a population of PBMCs include lymphocytes such as T cells, B cells, NK cells (including NKT cells and CIK cells) and monocytes such as macrophages and dendritic cells. A "plurality of PBMCs" as used herein refers to a preparation of PBMCs comprising cells of at least two types of blood cells. In some embodiments, a plurality of PBMCs comprises two or more of T cells, B cells, NK cells, macrophages or dendritic cells. In some embodiments, a plurality of PBMCs comprises three or more of T cells, B cells, NK cells, macrophages or dendritic cells. In some embodiments, a plurality of PBMCs comprises four or more of T cells, B cells, NK cells, macrophages or dendritic cells. In some embodiments, a plurality of PBMCs comprises T cells, B cells, NK cells, macrophages and dendritic cells.

PBMCs can be isolated by means known in the art. For example, PBMCs can be derived from peripheral blood of an individual based on density of PBMCs compared to other blood cells. In some embodiments, PBMCs are derived from peripheral blood of an individual using Ficoll (e.g., a ficoll gradient). In some embodiments, PBMCs are derived from peripheral blood of an individual using ELUTRA® cell separation system.

In some embodiments, a population of PBMCs is isolated from an individual. In some embodiments, a plurality of PBMCs is an autologous population of PBMCs where the population is derived from a particular individual, manipulated by any of the methods described herein, and returned to the particular individual. In some embodiments, a plurality of PBMCs is an allogeneic population of PBMCs where the population is derived from one individual, manipulated by any of the methods described herein, and administered to a second individual.

In some embodiments, a plurality of PBMCs is a reconstituted preparation of PBMCs. In some embodiments, the plurality of PBMCs may be generated by mixing cells typically found in a population of PBMCs; for example, by mixing populations of two or more of T cells, B cells, NK cells, or monocytes. In some embodiments, ratios of cells in a population of splenocytes are adjusted (e.g., crafted) to better reflect the population profile of human PBMCs. For example, B cells may be depleted from a population of splenocytes to better reflect a population of human PBMCs.

The term "pore" as used herein refers to an opening, including without limitation, a hole, tear, cavity, aperture, break, gap, or perforation within a material. In some examples, (where indicated) the term refers to a pore within a surface of the present disclosure. In other examples, (where indicated) a pore can refer to a pore in a cell membrane.

The term "membrane" as used herein refers to a selective barrier or sheet containing pores. The term includes a pliable sheet-like structure that acts as a boundary or lining. In some examples, the term refers to a surface or filter containing pores. This term is distinct from the term "cell membrane".

The term "filter" as used herein refers to a porous article that allows selective passage through the pores. In some examples the term refers to a surface or membrane containing pores.

The term "heterogeneous" as used herein refers to something which is mixed or not uniform in structure or composition. In some examples the term refers to pores having varied sizes, shapes or distributions within a given surface.

The term "homogeneous" as used herein refers to something which is consistent or uniform in structure or composition throughout. In some examples the term refers to pores having consistent sizes, shapes, or distribution within a given surface.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

The term "heterologous" as it relates to amino acid sequences such as peptide sequences and polypeptide sequences, denotes sequences that are not normally joined together, and/or are not normally associated with a particular cell. Thus, a "heterologous" region of a peptide sequence is a segment of amino acids within or attached to another amino acid molecule that is not found in association with the other molecule in nature. For example, a heterologous region of a peptide construct could include the amino acid sequence of the peptide flanked by sequences not found in association with the amino acid sequence of the peptide in nature. Another example of a heterologous peptide sequence is a construct where the peptide sequence itself is not found in nature (e.g., synthetic sequences having amino acids different as coded from the native gene). Similarly, a cell transformed with a vector that expresses an amino acid construct which is not normally present in the cell would be considered heterologous for purposes of this invention. Allelic variation or naturally occurring mutational events do not give rise to heterologous peptides, as used herein.

The term "exogenous" when used in reference to an agent, such as an antigen or an adjuvant, with relation to a cell refers to an agent delivered from outside the cell (that is, from outside the cell). The cell may or may not have the agent already present, and may or may not produce the agent after the exogenous agent has been delivered.

As used herein, the term "inhibit" may refer to the act of blocking, reducing, eliminating, or otherwise antagonizing the presence, or an activity of, a particular target. Inhibition may refer to partial inhibition or complete inhibition. For example, inhibiting an immune response may refer to any act leading to a blockade, reduction, elimination, or any other antagonism of an immune response. In other examples, inhibition of the expression of a nucleic acid may include, but not limited to reduction in the transcription of a nucleic acid, reduction of mRNA abundance (e.g., silencing mRNA transcription), degradation of mRNA, inhibition of mRNA translation, and so forth.

As used herein, the term "suppress" may refer to the act of decreasing, reducing, prohibiting, limiting, lessening, or otherwise diminishing the presence, or an activity of, a particular target. Suppression may refer to partial suppression or complete suppression. For example, suppressing an immune response may refer to any act leading to decreasing, reducing, prohibiting, limiting, lessening, or otherwise diminishing an immune response. In other examples, suppression of the expression of a nucleic acid may include, but not limited to reduction in the transcription of a nucleic acid, reduction of mRNA abundance (e.g., silencing mRNA transcription), degradation of mRNA, inhibition of mRNA translation, and so forth.

As used herein, the term "enhance" may refer to the act of improving, boosting, heightening, or otherwise increasing the presence, or an activity of, a particular target. For example, enhancing an immune response may refer to any act leading to improving, boosting, heightening, or otherwise increasing an immune response. In one exemplary example, enhancing an immune response may refer to employing an antigen and/or adjuvant to improve, boost, heighten, or otherwise increase an immune response. In other examples, enhancing the expression of a nucleic acid may include, but not limited to increase in the transcription of a nucleic acid, increase in mRNA abundance (e.g., increasing mRNA transcription), decrease in degradation of mRNA, increase in mRNA translation, and so forth.

As used herein, the term "modulate" may refer to the act of changing, altering, varying, or otherwise modifying the presence, or an activity of, a particular target. For example, modulating an immune response may refer to any act leading to changing, altering, varying, or otherwise modifying an immune response. In other examples, modulating the expression of a nucleic acid may include, but not limited to a change in the transcription of a nucleic acid, a change in mRNA abundance (e.g., increasing mRNA transcription), a corresponding change in degradation of mRNA, a change in mRNA translation, and so forth.

As used herein, the term "induce" may refer to the act of initiating, prompting, stimulating, establishing, or otherwise producing a result. For example, inducing an immune response may refer to any act leading to initiating, prompting, stimulating, establishing, or otherwise producing a desired immune response. In other examples, inducing the expression of a nucleic acid may include, but not limited to initiation of the transcription of a nucleic acid, initiation of mRNA translation, and so forth.

The term "homologous" as used herein refers to a molecule which is derived from the same organism. In some examples the term refers to a nucleic acid or protein which is normally found or expressed within the given organism.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and phosphorothioates, and thus can be an oligodeoxynucleoside phosphoramidate (P—NH2) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

As used herein, the term "adjuvant" refers to a substance which either directly or indirectly modulates and/or engenders an immune response. Generally, the adjuvant is administered in conjunction with an antigen to effect enhancement of an immune response to the antigen as compared to antigen alone. In some embodiments, an adjuvant is used to condition a plurality of PBMCs (e.g., as demonstrated in the Examples). Various adjuvants are described herein.

The terms "CpG oligodeoxynucleotide" and "CpG ODN" refer to DNA molecules containing a dinucleotide of cytosine and guanine separated by a phosphate (also referred to herein as a "CpG" dinucleotide, or "CpG"). The CpG ODNs of the present disclosure contain at least one unmethylated CpG dinucleotide. That is, the cytosine in the CpG dinucleotide is not methylated (i.e., is not 5-methylcytosine). CpG ODNs may have a partial or complete phosphorothioate (PS) backbone.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

For any of the structural and functional characteristics described herein, methods of determining these characteristics are known in the art.

Modified PBMCs, Compositions, and Methods of Generating Modified PBMCs

Modified PBMCs

In certain aspects, there is provided a plurality of modified PBMCs comprising an antigen, wherein the antigen is exogenous to the modified PBMCs. In other aspects, there is provided a plurality of modified PMBCs comprising an antigen, wherein the antigen is exogenous to the modified PBMCs, wherein the antigen is a cancer antigen, an infectious disease antigen or a viral-disease associated antigen. In some aspects, there is provided a conditioned plurality of modified PBMCs comprising an antigen, wherein the antigen is exogenous to the modified PBMCs. In some aspects, there is provided a conditioned plurality of modified PMBCs comprising an antigen, wherein the antigen is exogenous to the modified PBMCs, wherein the antigen is a cancer antigen, an infectious disease antigen or a viral-disease associated antigen. In certain aspects, there is a conditioned plurality of modified PBMCs comprising an antigen and an adjuvant, wherein the antigen is exogenous to the modified PBMCs. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs. In some embodiments, the plurality of PBMCs comprises a nucleic acid encoding an antigen. In some embodiments, the plurality of PBMCs comprises an mRNA encoding an antigen. In some embodiments, the one or more nucleic acids are carried in one or more vehicles, wherein the one or more vehicles are delivered to the input PBMCs. In some embodiments, the vehicle is a virus or a viral-associated particle. In some embodiments, the virus comprises one or more of: an adenovirus, an adeno-associated virus (AAV), a baculovirus, a herpes virus, or a retrovirus. In some embodiments, the virus comprises an AAV. In some embodiments, the vehicle is a lipid-based vehicle, e.g., a liposome. In some embodiments, the vehicle is a nanoparticle.

In some aspects, there is provided a plurality of modified PBMCs comprising an antigen comprising the amino acid sequence of any one of SEQ ID NOs: 18-25. In other aspects, there is provided a conditioned plurality of modified PBMCs comprising an antigen comprising the amino acid sequence of any one of SEQ ID NOs: 18-25.

In some aspects, there is provided a plurality of modified PBMCs comprising an antigen comprising the amino acid sequence of SEQ ID NO: 19. In other aspects, there is provided a conditioned plurality of modified PBMCs comprising an antigen comprising the amino acid sequence of SEQ ID NO: 19. In some aspects, there is provided a plurality of modified PBMCs comprising an antigen comprising the amino acid sequence of SEQ ID NO: 23. In other aspects, there is provided a conditioned plurality of modified PBMCs comprising an antigen comprising the amino acid sequence of SEQ ID NO: 23.

In some aspects, there is provided a conditioned plurality of PBMCs comprising an antigen, prepared by incubating the plurality of PBMCs comprising the antigen with an adjuvant for a sufficient time for the PBMCs to condition, thereby generating the conditioned plurality of PBMCs comprising the antigen. In other aspects, there is provided a conditioned plurality of PBMCs comprising an antigen, prepared by incubating the plurality of PBMCs with an adjuvant for a sufficient time for the PBMCs to condition prior to introducing the antigen to the PBMCs, thereby generating the conditioned plurality of PBMCs comprising the antigen.

In some aspects, there is provided a conditioned plurality of PBMCs comprising a nucleic acid (e.g., mRNA) encoding an antigen, prepared by incubating the plurality of PBMCs comprising the antigen with an adjuvant for a sufficient time for the PBMCs to condition, thereby generating the conditioned plurality of PBMCs comprising the antigen. In other aspects, there is provided a conditioned plurality of PBMCs comprising a nucleic acid (e.g., mRNA) encoding an antigen, prepared by incubating the plurality of PBMCs with an adjuvant for a sufficient time for the PBMCs to condition prior to introducing the antigen to the PBMCs, thereby generating the conditioned plurality of PBMCs comprising the antigen.

Antigens and/or adjuvants can be introduced into PBMCs using constriction-mediated delivery (SQZ). Therefore in some aspects, there is provided a plurality of modified PBMCs comprising an antigen, prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a conditioned plurality of modified PBMCs comprising an antigen, prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the process further comprises isolating the plurality of modified PBMCs comprising the antigen from the cell suspension before incubation with the adjuvant to condition the modified PBMCs. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs. In some embodiments, the one or more nucleic acids are carried in one or more vehicles, wherein the one or more vehicles are delivered to the input PBMCs. In some embodiments, the vehicle is a virus or a viral-associated particle. In some embodiments, the virus comprises one or more of: an adenovirus, an adeno-associated virus (AAV), a baculovirus, a herpes virus, or a retrovirus. In some embodiments, the virus comprises an AAV. In some embodiments, the vehicle is a lipid-based vehicle, e.g., a liposome. In some embodiments, the vehicle is a nanoparticle.

In some aspects, there is provided a plurality of modified PBMCs comprising an antigen and an adjuvant, prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen and the adjuvant to pass through to form a plurality of perturbed input PBMCs; and b) incubating the plurality of perturbed input PBMCs with the antigen and the adjuvant for a sufficient time to allow the antigen and the adjuvant to enter the perturbed input PBMCs; thereby generating the plurality of modified PBMCs comprising the antigen and adjuvant. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a conditioned plurality of modified PBMCs comprising an antigen, prepared by a process comprising the steps of: a) incubating a plurality of input PBMCs with an adjuvant for a sufficient time for the input PBMCs to condition, thereby generating a conditioned plurality of input PBMCs; b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and c) incubating the conditioned plurality of perturbed input PBMCs with the antigen for a sufficient time to allow the antigen to enter the perturbed input PBMCs, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In certain aspects, there is provided a plurality of modified PBMCs comprising an antigen and an adjuvant, prepared by a process comprising the steps of: a) passing a cell suspension comprising a plurality of input PBMCs comprising the adjuvant through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; and b) incubating the plurality of perturbed input PBMCs with the antigen for a sufficient time to allow the antigen to enter the perturbed input PBMCs, thereby generating the plurality of modified PBMCs comprising the antigen and the adjuvant. In other aspects, there is provided a plurality of modified PBMCs comprising an antigen and an adjuvant, prepared by a process comprising the steps of: a) passing a cell suspension comprising a plurality of input PBMCs comprising the antigen through a cell-deforming constriction, wherein a diameter of the constriction is a function of a diameter of the input PBMCs in the suspension, thereby causing perturbations of the input PBMCs large enough for the adjuvant to pass through to form a plurality of perturbed input PBMCs; and b) incubating the plurality of perturbed input PBMCs with the adjuvant for a sufficient time to allow the adjuvant to enter the perturbed input PBMCs, thereby generating the plurality of modified PBMCs comprising the antigen and the adjuvant.

In some aspects, there is provided a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a conditioned plurality of modified PBMCs comprising a human papillomavirus (HPV) antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; and c) incubating the plurality of modified PBMCs comprising the HPV antigen with a CpG ODN for a sufficient time for the modified PBMCs comprising the HPV antigen to condition, thereby generating the conditioned plurality of modified PBMCs comprising the HPV antigen. In some embodiments, the HPV antigen comprises one or more proteins. In some embodiments, the HPV antigen is encoded by one or more nucleic acids and enters the PBMC in the form of one or more nucleic acids, such as but not limited to DNAs, cDNAs, mRNAs, and plasmids. In some embodiments, the HPV antigen is encoded by one or more mRNAs and enters the PBMC in the form of one or more mRNAs.

In some aspects, there is provided a conditioned plurality of modified PBMCs comprising a HPV antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; and c) incubating the plurality of modified PBMCs comprising the HPV antigen with a CpG ODN for a sufficient time for the modified PBMCs comprising the HPV antigen to condition, wherein the CpG ODN is CpG 7909, thereby generating the conditioned plurality of modified PBMCs comprising the HPV antigen. In some embodiments, the HPV antigen comprises one or more proteins. In some embodiments, the HPV antigen is encoded by one or more nucleic acids and enters the PBMC in the form of one or more nucleic acids, such as but not limited to DNAs, cDNAs, mRNAs, and plasmids. In some embodiments, the HPV antigen is encoded by one or more mRNAs and enters the PBMC in the form of one or more mRNAs.

In some aspects, there is provided a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for about 1 hour to about 24 hours for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a conditioned plurality of modified PBMCs comprising a HPV antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; and c) incubating the plurality of modified PBMCs comprising the HPV antigen with a CpG ODN for about 1 hour to about 24 hours for the modified PBMCs comprising the HPV antigen to condition, thereby generating the conditioned plurality of modified PBMCs comprising the HPV antigen. In some embodiments, the HPV antigen comprises one or more proteins. In some embodiments, the HPV antigen is encoded by one or more nucleic acids and enters the PBMC in the form of one or more nucleic acids, such as but not limited to DNAs, cDNAs, mRNAs, and plasmids. In some embodiments, the HPV antigen is encoded by one or more mRNAs and enters the PBMC in the form of one or more mRNAs.

In some aspects, there is provided a conditioned plurality of modified PBMCs comprising a HPV antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; and c) incubating the plurality of modified PBMCs comprising the HPV antigen with a CpG ODN for about 1 hour to about 24 hours for the modified PBMCs comprising the HPV antigen to condition, wherein the CpG ODN is CpG 7909, thereby generating the conditioned plurality of modified PBMCs comprising the HPV antigen. In some embodiments, the HPV antigen comprises one or more proteins. In some embodiments, the HPV antigen is encoded by one or more nucleic acids and enters the PBMC in the form of one or more nucleic acids, such as but not limited to DNAs, cDNAs, mRNAs, and plasmids. In some embodiments, the HPV antigen is encoded by one or more mRNAs and enters the PBMC in the form of one or more mRNAs.

In some aspects, there is provided a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for about 1 hour to about 24 hours for the modified PBMCs comprising the antigen to condition, wherein the adjuvant is CpG 7909, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some embodiments according to any one of the pluralities of modified PBMCs described herein, the diameter of the constriction is (a) about 4.2 µm to about 6 µm; or (b) about 4.5 µm. In some embodiments, the HPV antigen is incubated with a CpG ODN for (a) about 2 hour to about 10 hours; (b) about 3 hours to about 6 hours; or (c) about 4 hours.

In some embodiments according to any one of the pluralities of modified PBMCs described herein, the diameter of the constriction is about 3 µm to about 6 µm. In some embodiments, the HPV antigen is incubated with a CpG ODN for (a) about 2 hour to about 10 hours; (b) about 3 hours to about 6 hours; or (c) about 4 hours.

In some embodiments according to any one of the pluralities of modified PBMCs described herein, the diameter of the constriction is (a) about 4.2 µm to about 6 µm; or (b) about 4.5 µm. In some embodiments, the modified PBMCs comprising the HPV antigen is incubated with a CpG ODN for (a) about 2 hour to about 10 hours; (b) about 3 hours to about 6 hours; or (c) about 4 hours.

In some embodiments according to any one of the pluralities of modified PBMCs described herein, the diameter of the constriction is about 3 µm to about 6 µm. In some embodiments, the modified PBMCs comprising the HPV antigen is incubated with a CpG ODN for (a) about 2 hour to about 10 hours; (b) about 3 hours to about 6 hours; or (c) about 4 hours.

In some aspects, there is provided a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for a sufficient time for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for a sufficient time for the modified PBMCs comprising the antigen to condition, wherein the CpG ODN is CpG 7909, thereby generating the conditioned plurality of modified PBMCs comprising the antigen.

In some aspects, there is provided a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for about 1 hour to about 24 hours for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a conditioned plurality of modified PBMCs comprising an antigen, prepared by a process comprising the steps of: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for about 1 hour to about 24 hours for the modified PBMCs comprising the antigen to condition, wherein the CpG ODN is CpG 7909, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some embodiments according to any one of the pluralities of modified PBMCs described herein, the diameter of the constriction is (a) about 4.2 µm to about 6 µm; or (b) about 4.5 µm. In some embodiments, the antigen is incubated with a CpG ODN for (a) about 2 hour to about 10 hours; (b) about 3 hours to about 6 hours; or (c) about 4 hours.

In some embodiments according to any one of the pluralities of modified PBMCs described herein, the diameter of the constriction is about 3 µm to about 6 µm. In some embodiments, the HPV antigen is incubated with a CpG ODN for (a) about 2 hour to about 10 hours; (b) about 3 hours to about 6 hours; or (c) about 4 hours.

In some embodiments according to any one of the pluralities of modified PBMCs described herein, the diameter of the constriction is (a) about 4.2 µm to about 6 µm; or (b) about 4.5 µm. In some embodiments, the modified PBMCs comprising the antigen is incubated with a CpG ODN for (a) about 2 hour to about 10 hours; (b) about 3 hours to about 6 hours; or (c) about 4 hours.

In some embodiments according to any one of the pluralities of modified PBMCs described herein, the diameter of the constriction is about 3 µm to about 6 µm. In some embodiments, the modified PBMCs comprising the HPV antigen is incubated with a CpG ODN for (a) about 2 hour to about 10 hours; (b) about 3 hours to about 6 hours; or (c) about 4 hours.

In some embodiments according to any one of the pluralities of modified PBMCs described herein, the concentration of the antigen incubated with the perturbed input PBMCs is between about 0.1 µM and about 1 mM and/or the concentration of the adjuvant incubated with the perturbed input PBMCs is between about 0.1 µM and about 1 mM. In some embodiments, the concentration of the antigen incubated with the perturbed input PBMCs is between about 0.1 µM and about 10 µM and/or the concentration of the adjuvant incubated with the perturbed input PBMCs is between about 0.1 µM and about 10 µM. In some embodiments, the concentration of the antigen incubated with the perturbed input PBMCs is about 1 µM and/or the concentration of the adjuvant incubated with the perturbed input PBMCs is about 1 µM. In some embodiments, the ratio of the antigen to the adjuvant incubated with the perturbed input PBMCs is between about 10000:1 to about 1:10000. In some embodiments, the ratio of the antigen to the adjuvant incubated with the perturbed input PBMCs is about 200:1. In some embodiments, the ratio of the antigen to the adjuvant incubated with the perturbed input PBMCs is about 20:1. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some embodiments according to any one of the pluralities of modified PBMCs described herein, the process further comprises: incubating the plurality of modified PBMCs comprising the antigen and/or adjuvant with a second adjuvant for a sufficient time for the modified PBMCs comprising the antigen to condition, thereby generating the conditioned plurality of modified PBMCs comprising the antigen and/or the adjuvant. In some embodiments, the process further comprises isolating the plurality of modified PBMCs comprising the antigen and/or the adjuvant from the cell suspension before incubation with the adjuvant to condition the modified PBMCs.

In some embodiments according to any one of the pluralities of modified PBMCs described herein, the antigen is present in the cytosol and the adjuvant is present in a vesicle of a cell in the plurality of modified PBMCs. In some embodiments, the vesicle is an endosome. In some embodiments, the antigen and/or the adjuvant are present in multiple compartments of a cell in the plurality of modified PBMCs. In further embodiments, the antigen and/or the adjuvant are present in at least about 70% of the cells in the plurality of PBMCs. In some embodiments, the antigen and/or the adjuvant are present in at least any one of about 70%, about 75%, about 80%, about 85%, about 95%, or about 99% of the cells in the plurality of PBMCs. In some embodiments, the antigen is bound to the surface of a cell in the plurality of modified PBMCs. In some embodiments, the antigen and/or the adjuvant are present in at least about 70% of cells of each of the T cells, B cells, NK cells, and monocytes in the plurality of PBMCs. In some embodiments, the antigen and/or the adjuvant are present in at least any one of about 70%, about 75%, about 80%, about 85%, about 95%, or about 99% of cells of each of the T cells, B cells, NK cells, and monocytes in the plurality of PBMCs. In some embodiments, the antigen and/or the adjuvant are present in at least about 70% of cells of one or more of the T cells, B cells, NK cells, or monocytes in the plurality of PBMCs. In some embodiments, the antigen and/or the adjuvant are present in at least any one of about 70%, about 75%, about 80%, about 85%, about 95%, or about 99% cells of one or more of the T cells, B cells, NK cells, or monocytes in the plurality of PBMCs.

In some embodiments, there is provided a composition comprising any one of the pluralities of modified PBMCs described herein. In some embodiments, there is provided a composition comprising any one of the pluralities of modified PBMCs described herein for use as a medicament. In some embodiments, there is provided a composition comprising the any one of the pluralities of modified PBMCs described herein for use in a method of treatment of the human or animal body by surgery, therapy or diagnosis. In some embodiments, there is provided a composition for use in treating a cancer or an infectious disease comprising any one of the pluralities of modified PBMCs described herein. In some embodiments, there is provided a composition comprising any one of the pluralities of modified PBMCs described herein for use in the treatment of a cancer, an infectious disease or a viral-associated disease. In some embodiments, the cancer is head and neck cancer, cervical cancer, vulvar cancer, vaginal cancer, penile cancer, anal cancer, perianal cancer, anogenital cancer, oral cancer or salivary cancer. In some embodiments, the infectious disease is associated with HIV, HPV, EBV, MCV, HBV or HCV. In some embodiments, there is a pharmaceutical composition comprising any one of the pluralities of modified PBMCs described herein, and a pharmaceutically acceptable carrier. In some embodiments, the composition is for treatment of cancers or infectious diseases.

In some embodiments according to any one of the methods, compositions or pluralities of modified PBMCs described herein, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs. In some embodiments, the plurality of PBMCs comprises a nucleic acid encoding an antigen. In some embodiments, the plurality of PBMCs comprises an mRNA encoding an antigen.

Compositions

In certain aspects, there is provided a composition comprising a conditioned plurality of modified PBMCs comprising an antigen for use as a medicament, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a composition comprising a conditioned plurality of modified PBMCs comprising an antigen for use in a method of treatment of the human or animal body by surgery, therapy or diagnosis, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a composition comprising a conditioned plurality of modified PBMCs comprising an antigen for use as a medicament, wherein the conditioned plurality of modified PBMCs is prepared by a process comprising the steps of: a) incubating a plurality of input PBMCs with an adjuvant for a sufficient time for the input PBMCs to condition, thereby generating a conditioned plurality of input PBMCs; b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and c) incubating the conditioned plurality of perturbed input PBMCs with the antigen for a sufficient time to allow the antigen to enter the perturbed input PBMCs, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a composition comprising a conditioned plurality of modified PBMCs comprising an antigen for use in a method of treatment of the human or animal body, wherein the conditioned plurality of modified PBMCs is prepared by a process comprising the steps of: a) incubating a plurality of input PBMCs with an adjuvant for a sufficient time for the input PBMCs to condition, thereby generating a conditioned plurality of input PBMCs; b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and c) incubating the conditioned plurality of perturbed input PBMCs with the antigen for a sufficient time to allow the antigen to enter the perturbed input PBMCs, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a composition comprising a conditioned plurality of modified PBMCs comprising an antigen for use in a method of treating cancer an infectious disease or a viral associated disease in an individual, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a composition comprising a conditioned plurality of modified PBMCs comprising an antigen for use in the treatment of cancer, an infectious disease or a viral associated disease in an individual, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a composition comprising a conditioned plurality of modified PBMCs comprising an antigen for use in a method of treating a HPV-associated disease in an individual, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a composition comprising a conditioned plurality of modified PBMCs comprising an antigen for use in the treatment of a HPV-associated disease in an individual, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a use of a composition comprising a conditioned plurality of modified PBMCs comprising an antigen in the manufacture of a medicament for treating cancer, an infectious disease or a viral-associated disease in an individual, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a use of a composition comprising a conditioned plurality of modified PBMCs comprising an antigen in the manufacture of a medicament for treating a HPV-associated disease, wherein the conditioned plurality of modified PBMCs is prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some embodiments according to any one of the compositions described herein, the concentration of the antigen incubated with the perturbed input PBMCs is between about 0.1 µM and about 1 mM and/or the concentration of the adjuvant incubated with the perturbed input PBMCs is between about 0.1 µM and about 1 mM. In some embodiments, the concentration of the antigen incubated with the perturbed input PBMCs is between about 0.1 µM and about 10 µM and/or the concentration of the adjuvant incubated with the perturbed input PBMCs is between about 0.1 µM and about 10 µM. In some embodiments, the concentration of the antigen incubated with the perturbed input PBMCs is about 1 µM and/or the concentration of the adjuvant incubated with the perturbed input PBMCs is about 1 µM. In some embodiments, the ratio of the antigen to the adjuvant incubated with the perturbed input PBMCs is between about 10000:1 to about 1:10000. In some embodiments, the ratio of the antigen to the adjuvant incubated with the perturbed input PBMCs is about 200:1. In some embodiments, the ratio of the antigen to the adjuvant incubated with the perturbed input PBMCs is about 20:1. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some embodiments according to any one of the compositions described herein, the process further comprises: incubating the plurality of modified PBMCs comprising the antigen and/or adjuvant with a second adjuvant for a sufficient time for the modified PBMCs comprising the antigen to condition, thereby generating the conditioned plurality of modified PBMCs comprising the antigen and/or the adjuvant. In some embodiments, the process further comprises isolating the plurality of modified PBMCs comprising the antigen and/or the adjuvant from the cell suspension before incubation with the adjuvant to condition the modified PBMCs.

In some embodiments according to any one of the compositions described herein, the antigen is present in the cytosol and the adjuvant is present in a vesicle of a cell in the plurality of modified PBMCs. In some embodiments, the vesicle is an endosome. In some embodiments, the antigen and/or the adjuvant are present in multiple compartments of a cell in the plurality of modified PBMCs. In further embodiments, the antigen and/or the adjuvant are present in at least about 70% of the cells in the plurality of PBMCs. In some embodiments, the antigen and/or the adjuvant are present in at least any one of about 70%, about 75%, about 80%, about 85%, about 95%, or about 99%, or 100% of the cells in the plurality of PBMCs. In some embodiments, the antigen is bound to the surface of a cell in the plurality of modified PBMCs.

In some embodiments according to any one of the methods, compositions or pluralities of modified PBMCs described herein, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs. In some embodiments, the plurality of PBMCs comprises a nucleic acid encoding an antigen. In some embodiments, the plurality of PBMCs comprises an mRNA encoding an antigen.

Methods of Generating a Plurality of Modified PBMCs

In some aspects, also provided is a method for generating a conditioned plurality of PBMCs comprising an antigen, comprising incubating a plurality of PBMCs comprising the antigen with an adjuvant for a sufficient time for the PBMCs to condition, thereby generating the conditioned plurality of PBMCs comprising the antigen.

In some aspects, there is a method for generating a conditioned plurality of modified PBMCs comprising an antigen, comprising: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for generating a plurality of modified PBMCs comprising an antigen, comprising: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; and b) incubating the plurality of perturbed input PBMCs with the antigen for a sufficient time to allow the antigen to enter the perturbed input PBMCs, thereby generating the plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for generating a plurality of modified PBMCs comprising an antigen and an adjuvant, comprising: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen and the adjuvant to pass through to form a plurality of perturbed input PBMCs; and b) incubating the plurality of perturbed input PBMCs with the antigen and the adjuvant for a sufficient time to allow the antigen and the adjuvant to enter the perturbed input PBMCs, thereby generating the plurality of modified PBMCs comprising the antigen and adjuvant. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method of generating a conditioned plurality of modified PBMCs comprising an antigen, comprising: a) incubating a plurality of input PBMCs with an adjuvant for a sufficient time for the input PBMCs to condition, thereby generating a conditioned plurality of input PBMCs; b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and c) incubating the conditioned plurality of perturbed input PBMCs with the antigen for a sufficient time to allow the antigen to enter the perturbed input PBMCs, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In certain aspects, there is provided a method for generating a plurality of modified PBMCs comprising an antigen and an adjuvant, comprising: a) passing a cell suspension comprising a plurality of input PBMCs comprising an adjuvant through a cell-deforming constriction, wherein a diameter of the constriction is a function of a diameter of the input PBMCs in the suspension, thereby causing perturbations of the input PBMCs large enough for an antigen to pass through to form a plurality of perturbed input PBMCs; and b) incubating the plurality of perturbed input PBMCs with the antigen for a sufficient time to allow the antigen to enter the perturbed input PBMCs, thereby generating the plurality of modified PBMCs comprising the antigen and the adjuvant. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for generating a plurality of modified PBMCs comprising an antigen and an adjuvant, comprising: a) passing a cell suspension comprising a plurality of input PBMCs comprising an antigen through a cell-deforming constriction, wherein a diameter of the constriction is a function of a diameter of the input PBMCs in the suspension, thereby causing perturbations of the input PBMCs large enough for an adjuvant to pass through to form a plurality of perturbed input PBMCs; and b) incubating the plurality of perturbed input PBMCs with the adjuvant for a sufficient time to allow the adjuvant to enter the perturbed input PBMCs, thereby generating the plurality of modified PBMCs comprising the antigen and the adjuvant.

In certain aspects, there is provided a method for generating a conditioned plurality of modified PBMCs comprising an antigen, comprising: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In certain aspects, there is provided a method for generating a conditioned plurality of modified PBMCs comprising a human papillomavirus (HPV) antigen, comprising: a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; and c) incubating the plurality of modified PBMCs comprising the HPV antigen with a CpG ODN for a sufficient time for the modified PBMCs comprising the HPV antigen to condition, thereby generating the conditioned plurality of modified PBMCs comprising the HPV antigen. In some embodiments, the HPV antigen comprises one or more proteins. In some embodiments, the HPV antigen is encoded by one or more nucleic acids and enters the PBMC in the form of one or more nucleic acids, such as but not limited to DNAs, cDNAs, mRNAs, and plasmids. In some embodiments, the HPV antigen is encoded by one or more mRNAs and enters the PBMC in the form of one or more mRNAs.

In some aspects, there is provided a method for generating a conditioned plurality of modified PBMCs comprising an HPV antigen, comprising: a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; and c) incubating the plurality of modified PBMCs comprising the HPV antigen with a CpG ODN for a sufficient time for the modified PBMCs comprising the HPV antigen to condition, wherein the CpG ODN is CpG 7909, thereby generating the conditioned plurality of modified PBMCs comprising the HPV antigen. In some embodiments, the HPV antigen comprises one or more proteins. In some embodiments, the HPV antigen is encoded by one or more nucleic acids and enters the PBMC in the form of one or more nucleic acids, such as but not limited to DNAs, cDNAs, mRNAs, and plasmids. In some embodiments, the HPV antigen is encoded by one or more mRNAs and enters the PBMC in the form of one or more mRNAs.

In some aspects, there is provided a method for generating a conditioned plurality of modified PBMCs comprising an HPV antigen, comprising: a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; and c) incubating the plurality of modified PBMCs comprising the HPV antigen with a CpG ODN for about 1 hour to about 24 hours for the modified PBMCs comprising the HPV antigen to condition, thereby generating the conditioned plurality of modified PBMCs comprising the HPV antigen. In some embodiments, the HPV antigen comprises one or more proteins. In some embodiments, the HPV antigen is encoded by one or more nucleic acids and enters the PBMC in the form of one or more nucleic acids, such as but not limited to DNAs, cDNAs, mRNAs, and plasmids. In some embodiments, the HPV antigen is encoded by one or more mRNAs and enters the PBMC in the form of one or more mRNAs.

In some aspects, there is provided a method for generating a conditioned plurality of modified PBMCs comprising an HPV antigen, comprising: a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; and c) incubating the plurality of modified PBMCs comprising the HPV antigen with a CpG ODN for about 1 hour to about 24 hours for the modified PBMCs comprising the HPV antigen to condition, wherein the CpG ODN is CpG 7909, thereby generating the conditioned plurality of modified PBMCs comprising the HPV antigen. In some embodiments, the HPV antigen comprises one or more proteins. In some embodiments, the HPV antigen is encoded by one or more nucleic acids and enters the PBMC in the form of one or more nucleic acids, such as but not limited to DNAs, cDNAs, mRNAs, and plasmids. In some embodiments, the HPV antigen is encoded by one or more mRNAs and enters the PBMC in the form of one or more mRNAs.

In some aspects, there is provided a method for generating a conditioned plurality of modified PBMCs comprising an antigen, comprising: a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for about 1 hour to about 24 hours for the modified PBMCs comprising the antigen to condition, wherein the adjuvant is CpG 7909, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some embodiments according to any one of the methods described herein, the diameter of the constriction is (a) about 4.2 μm to about 6 μm; or (b) about 4.5 μm. In some embodiments, the diameter of the constriction is about 3 μm to about 6 μm. In some embodiments, the plurality of modified PBMCs comprising the HPV antigen is incubated with a CpG ODN for (a) about 2 hour to about 10 hours; (b) about 3 hours to about 6 hours; or (c) about 4 hours.

In some embodiments according to any one of the methods described herein, the diameter of the constriction is (a) about 4.2 μm to about 6 μm; or (b) about 4.5 μm. In some embodiments, the diameter of the constriction is about 3 μm to about 6 μm. In some embodiments, the plurality of modified PBMCs comprising the antigen is incubated with an adjuvant for (a) about 2 hour to about 10 hours; (b) about 3 hours to about 6 hours; or (c) about 4 hours.

In some aspects, there is provided a method for generating a conditioned plurality of modified PBMCs comprising an antigen, comprising: a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for a sufficient time for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for generating a conditioned plurality of modified PBMCs comprising an antigen, comprising: a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for a sufficient time for the modified PBMCs comprising the antigen to condition, wherein the CpG ODN is CpG 7909, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for generating a conditioned plurality of modified PBMCs comprising an antigen, comprising: a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for about 1 hour to about 24 hours for the modified PBMCs comprising the antigen to condition, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for generating a conditioned plurality of modified PBMCs comprising an antigen, comprising: a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for about 1 hour to about 24 hours for the modified PBMCs comprising the antigen to condition, wherein the CpG ODN is CpG 7909, thereby generating the conditioned plurality of modified PBMCs comprising the antigen. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some embodiments according to any one of the methods described herein, the diameter of the constriction is (a) about 4.2 μm to about 6 μm; or (b) about 4.5 μm. In some embodiments, the diameter of the constriction is about 3 μm to about 6 μm. In some embodiments, the plurality of modified PBMCs comprising the antigen is incubated with a CpG ODN for (a) about 2 hour to about 10 hours; (b) about 3 hours to about 6 hours; or (c) about 4 hours.

In some embodiments according to any one of the methods described herein, the diameter of the constriction is (a) about 4.2 μm to about 6 μm; or (b) about 4.5 μm. In some embodiments, the diameter of the constriction is about 3 μm to about 6 μm. In some embodiments, the plurality of modified PBMCs comprising the antigen is incubated with an adjuvant for (a) about 2 hour to about 10 hours; (b) about 3 hours to about 6 hours; or (c) about 4 hours.

In some embodiments according to any one of the methods described herein, the concentration of the antigen incubated with the perturbed input PBMCs is between about 0.1 μM and about 1 mM and/or the concentration of the adjuvant incubated with the perturbed input PBMCs is between about 0.1 μM and about 1 mM. In some embodiments, the concentration of the antigen incubated with the perturbed input PBMCs is between about 0.1 μM and about 10 μM and/or the concentration of the adjuvant incubated with the perturbed input PBMCs is between about 0.1 μM and about 10 μM. In some embodiments, the concentration of the antigen incubated with the perturbed input PBMCs is about 1 μM and/or the concentration of the adjuvant incubated with the perturbed input PBMCs is about 1 μM. In some embodiments, the ratio of the antigen to the adjuvant incubated with the perturbed input PBMCs is between about 10000:1 to about 1:10000. In some embodiments, the ratio of the antigen to the adjuvant incubated with the perturbed input PBMCs is about 200:1. In some embodiments, the ratio of the antigen to the adjuvant incubated with the perturbed input PBMCs is about 20:1.

In some embodiments according to any one of the methods described herein, the process further comprises: incubating the plurality of modified PBMCs comprising the antigen and/or adjuvant with a second adjuvant for a sufficient time for the modified PBMCs comprising the antigen to condition, thereby generating the conditioned plurality of modified PBMCs comprising the antigen and/or the adjuvant. In some embodiments, the process further comprises isolating the plurality of modified PBMCs comprising the antigen and/or the adjuvant from the cell suspension before incubation with the adjuvant to condition the modified PBMCs.

In some embodiments according to any one of the methods described herein, the antigen is present in the cytosol and the adjuvant is present in a vesicle of a cell in the plurality of modified PBMCs. In some embodiments, the vesicle is an endosome. In some embodiments, the antigen and/or the adjuvant are present in multiple compartments of a cell in the plurality of modified PBMCs. In further embodiments, the antigen and/or the adjuvant are present in at least about 70% of the cells in the plurality of PBMCs. In some embodiments, the antigen and/or the adjuvant are present in at least any one of about 70%, about 75%, about 80%, about 85%, about 95%, or about 99%, or 100% of the cells in the plurality of PBMCs. In some embodiments, the antigen is bound to the surface of a cell in the plurality of modified PBMCs. In some embodiments, the antigen and/or the adjuvant are present in at least any one of about 70%, about 75%, about 80%, about 85%, about 95%, or about 99%, or 100% of cells of each of the T cells, B cells, NK cells, and monocytes within the plurality of modified PBMCs. In some embodiments, the antigen and/or the adjuvant are present in at least any one of about 70%, about 75%, about 80%, about 85%, about 95%, or about 99%, or 100% of cells of one or more of the T cells, B cells, NK cells, or monocytes within the plurality of modified PBMCs.

In some embodiments according to any one of the methods described herein, the process further comprises a step of incubating the input PBMCs and/or the modified PBMCs with an agent that enhances the viability and/or function of the modified PBMCs as compared to corresponding modified PBMCs prepared without the further incubation step.

Methods of Stimulating a Response in an Individual

In some aspects, the present invention provides methods for treating and preventing a cancer or an infectious disease, and/or modulating the immune response in an individual with a cancer or an infectious disease comprising administering to the individual a composition comprising a plurality of modified PBMCs, wherein the modified PBMCs comprise intracellularly an antigen associated with cancer or with an infectious disease.

In some embodiments, there is provided a method for stimulating an immune response in an individual, comprising administering to the individual any one of the pluralities of modified PBMCs, compositions, or pharmaceutical compositions described herein.

In certain aspects, there is provided a method for stimulating an immune response in an individual, comprising: a) administering a plurality of modified PBMCs comprising an antigen comprising the amino acid sequence of any one of SEQ ID NOs: 18-25 to the individual; and b) administering an adjuvant to the individual.

In certain aspects, there is provided a method for stimulating an immune response in an individual, comprising: a) incubating a plurality of PBMCs comprising an antigen with an adjuvant for a sufficient time for the PBMCs to condition, thereby generating a conditioned plurality of PBMCs comprising the antigen; b) administering the conditioned plurality of PBMCs comprising the antigen to the individual.

In some aspects, there is provided a method for stimulating an immune response in an individual, comprising: a) incubating a plurality of PBMCs with an adjuvant for a sufficient time for the PBMCs to condition, thereby generating a conditioned plurality of PBMCs comprising the antigen; b) introducing an antigen to the plurality of PBMCs; and c) administering the conditioned plurality of PBMCs comprising the antigen to the individual.

In some aspects, there is provided a method for stimulating an immune response in an individual, comprising: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for an antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; c) incubating the plurality of modified PBMCs comprising the antigen with an adjuvant for a sufficient time for the modified PBMCs comprising the antigen to condition, thereby generating a conditioned plurality of modified PBMCs comprising the antigen; and d) administering the conditioned plurality of modified PBMCs comprising the antigen to the individual. In some embodiments, the method further comprises isolating the plurality of modified PBMCs comprising the antigen from the cell suspension before incubation with the adjuvant. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for stimulating an immune response in an individual, comprising: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for an antigen and an adjuvant to pass through to form a plurality of perturbed input PBMCs; b) incubating the plurality of perturbed input PBMCs with the antigen and the adjuvant for a sufficient time to allow the antigen and the adjuvant to enter the perturbed input PBMCs, thereby generating a plurality of modified PBMCs comprising the antigen and adjuvant; and c) administering the plurality of modified PBMCs to the individual. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for stimulating an immune response in an individual, comprising: a) incubating a plurality of input PBMCs with an adjuvant for a sufficient time for the input PBMCs to condition, thereby generating a conditioned plurality of input PBMCs; b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for an antigen to pass through to form a conditioned plurality of perturbed input PBMCs; c) incubating the conditioned plurality of perturbed input PBMCs with the antigen for a sufficient time to allow the antigen to enter the perturbed input PBMCs, thereby generating the conditioned plurality of modified PBMCs comprising the antigen; and d) administering the conditioned plurality of modified PBMCs to the individual. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for stimulating an immune response in an individual, comprising: a) passing a cell suspension comprising a plurality of input PBMCs comprising an adjuvant through a cell-deforming constriction, wherein a diameter of the constriction is a function of a diameter of the input PBMCs in the suspension, thereby causing perturbations of the input PBMCs large enough for an antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen and the adjuvant; and c) administering the plurality of modified PBMCs to the individual. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In certain aspects, there is provided a method for stimulating an immune response in an individual, comprising: a) passing a cell suspension comprising an input PBMCs comprising an antigen through a cell-deforming constriction, wherein a diameter of the constriction is a function of a diameter of the input PBMCs in the suspension, thereby causing perturbations of the input PBMCs large enough for an adjuvant to pass through to form a plurality of perturbed input PBMCs; b) incubating the plurality of perturbed input PBMCs with the adjuvant for a sufficient time to allow the adjuvant to enter the perturbed input PBMCs, thereby generating a plurality of modified PBMCs comprising the antigen and the adjuvant; and c) administering the plurality of modified PBMCs to the individual. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for stimulating an immune response in an individual, comprising: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for an antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; c) administering the plurality of modified PBMCs to the individual; and d) administering an adjuvant to the individual. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for stimulating an immune response in an individual, comprising: a) passing a cell suspension comprising an input PBMCs comprising an antigen through a cell-deforming constriction, wherein a diameter of the constriction is a function of a diameter of the input PBMCs in the suspension, thereby causing perturbations of the input PBMCs large enough for an adjuvant to pass through to form a plurality of perturbed input PBMCs; b) incubating the plurality of perturbed input PBMCs with the adjuvant for a sufficient time to allow the adjuvant to enter the perturbed input PBMCs, thereby generating a plurality of modified PBMCs comprising the antigen and the adjuvant; and c) administering the plurality of modified PBMCs to the individual; and d) administering an adjuvant to the individual.

In some aspects, there is provided a method for stimulating an immune response against an HPV antigen in an individual, comprising: a) passing a cell suspension comprising a plurality of input PBMCs through a cell-deforming constriction, wherein a diameter of the constriction is about 3 μm to about 10 μm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; c) incubating the plurality of modified PBMCs comprising the HPV antigen with a CpG ODN for a sufficient time for the modified PBMCs comprising the HPV antigen to condition, thereby generating the conditioned plurality of modified PBMCs comprising the HPV antigen; and d) administering the conditioned plurality of modified PBMCs comprising the HPV antigen to the individual. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for stimulating an immune response against an HPV antigen in an individual, comprising: a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; c) incubating the plurality of modified PBMCs comprising the HPV antigen with a CpG ODN for a sufficient time for the modified PBMCs comprising the HPV antigen to condition, wherein the CpG ODN is CpG 7909, thereby generating the conditioned plurality of modified PBMCs comprising the HPV antigen; and d) administering the conditioned plurality of modified PBMCs comprising the HPV antigen to the individual. In some embodiments, the HPV antigen comprises one or more proteins. In some embodiments, the HPV antigen is encoded by one or more nucleic acids and enters the PBMC in the form of one or more nucleic acids, such as but not limited to DNAs, cDNAs, mRNAs, and plasmids. In some embodiments, the HPV antigen is encoded by one or more mRNAs and enters the PBMC in the form of one or more mRNAs In some aspects, there is provided a method for stimulating an immune response against an HPV antigen in an individual, comprising: a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; c) incubating the plurality of modified PBMCs comprising the HPV antigen with a CpG ODN for about 1 hour to about 24 hours for the modified PBMCs comprising the HPV antigen to condition, thereby generating the conditioned plurality of modified PBMCs comprising the HPV antigen; and d) administering the conditioned plurality of modified PBMCs comprising the HPV antigen to the individual. In some embodiments, the HPV antigen comprises one or more proteins. In some embodiments, the HPV antigen is encoded by one or more nucleic acids and enters the PBMC in the form of one or more nucleic acids, such as but not limited to DNAs, cDNAs, mRNAs, and plasmids. In some embodiments, the HPV antigen is encoded by one or more mRNAs and enters the PBMC in the form of one or more mRNAs In some aspects, there is provided a method for stimulating an immune response against an HPV antigen in an individual, comprising: a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs; b) incubating the plurality of perturbed input PBMCs with the HPV antigen for a sufficient time to allow the HPV antigen to enter the perturbed input PBMCs, thereby generating a plurality of modified PBMCs comprising the HPV antigen; c) incubating the plurality of modified PBMCs comprising the HPV antigen with a CpG ODN for about 1 hour to about 24 hours for the modified PBMCs comprising the HPV antigen to condition, wherein the CpG ODN is CpG 7909, thereby generating the conditioned plurality of modified PBMCs comprising the HPV antigen; and d) administering the conditioned plurality of modified PBMCs comprising the HPV antigen to the individual. In some embodiments, the HPV antigen comprises one or more proteins. In some embodiments, the HPV antigen is encoded by one or more nucleic acids and enters the PBMC in the form of one or more nucleic acids, such as but not limited to DNAs, cDNAs, mRNAs, and plasmids. In some embodiments, the HPV antigen is encoded by one or more mRNAs and enters the PBMC in the form of one or more mRNAs.

In some embodiments according to any one of the methods described herein, the diameter of the constriction is about 4 µm to about 10 µm. In some embodiments, the diameter of the constriction is about 3 µm to about 6 µm. In some embodiments, the diameter of the constriction is (a) about 4.2 µm to about 6 µm; or (b) about 4.5 µm. In some embodiments, the plurality of modified PBMCs comprising the HPV antigen is incubated with a CpG ODN for (a) about 2 hour to about 10 hours; (b) about 3 hours to about 6 hours; or (c) about 4 hours.

In some aspects, there is provided a method for stimulating an immune response in an individual, comprising: a) passing a cell suspension comprising a plurality of input PBMCs through a cell-deforming constriction, wherein a diameter of the constriction is about 3 µm to about 10 µm, thereby causing perturbations of the input PBMCs large enough for an antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; c) incubating the plurality of modified PBMCs comprising the antigen with a CpG ODN for a sufficient time for the modified PBMCs comprising the antigen to condition, thereby generating the conditioned plurality of modified PBMCs comprising the antigen; and d) administering the conditioned plurality of modified PBMCs comprising the antigen to the individual. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for stimulating an immune response in an individual, comprising: a) passing a cell suspension comprising a plurality of input PBMCs through a cell-deforming constriction, wherein a diameter of the constriction is about 3 µm to about 10 µm, thereby causing perturbations of the input PBMCs large enough for an antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; c) incubating the plurality of modified PBMCs comprising the antigen with a CpG ODN for a sufficient time for the modified PBMCs comprising the antigen to condition, wherein the CpG ODN is CpG 7909, thereby generating the conditioned plurality of modified PBMCs comprising the antigen; and d) administering the conditioned plurality of modified PBMCs comprising the antigen to the individual. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for stimulating an immune response in an individual, comprising: a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; c) incubating the plurality of modified PBMCs comprising the antigen with a CpG ODN for about 1 hour to about 24 hours for the modified PBMCs comprising the antigen to condition, thereby generating the conditioned plurality of modified PBMCs comprising the antigen; and d) administering the conditioned plurality of modified PBMCs comprising the antigen to the individual. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some aspects, there is provided a method for stimulating an immune response in an individual, comprising: a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs; b) incubating the plurality of perturbed input PBMCs with the antigen for a sufficient time to allow the antigen to enter the perturbed input PBMCs, thereby generating a plurality of modified PBMCs comprising the antigen; c) incubating the plurality of modified PBMCs comprising the antigen with a CpG ODN for about 1 hour to about 24 hours for the modified PBMCs comprising the antigen to condition, wherein the CpG ODN is CpG 7909, thereby generating the conditioned plurality of modified PBMCs comprising the antigen; and d) administering the conditioned plurality of modified PBMCs comprising the antigen to the individual. In some embodiments, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some embodiments according to any one of the methods described herein, the diameter of the constriction is about 4 μm to about 10 μm. In some embodiments, the diameter of the constriction is about 3 μm to about 6 μm. In some embodiments, the diameter of the constriction is (a) about 4.2 μm to about 6 μm; or (b) about 4.5 μm. In some embodiments, the plurality of modified PBMCs comprising the antigen is incubated with a CpG ODN for (a) about 2 hour to about 10 hours; (b) about 3 hours to about 6 hours; or (c) about 4 hours.

In some embodiments according to any one of the methods described herein, the concentration of the antigen incubated with the perturbed input PBMCs is between about 0.1 μM and about 1 mM and/or the concentration of the adjuvant incubated with the perturbed input PBMCs is between about 0.1 μM and about 1 mM. In some embodiments, the concentration of the antigen incubated with the perturbed input PBMCs is between about 0.1 μM and about 10 μM and/or the concentration of the adjuvant incubated with the perturbed input PBMCs is between about 0.1 μM and about 10 μM. In some embodiments, the concentration of the antigen incubated with the perturbed input PBMCs is about 1 μM and/or the concentration of the adjuvant incubated with the perturbed input PBMCs is about 1 μM. In some embodiments, the ratio of the antigen to the adjuvant incubated with the perturbed input PBMCs is between about 10000:1 to about 1:10000. In some embodiments, the ratio of the antigen to the adjuvant incubated with the perturbed input PBMCs is about 200:1. In some embodiments, the ratio of the antigen to the adjuvant incubated with the perturbed input PBMCs is about 20:1.

In some embodiments according to any one of the methods described herein, the process further comprises: incubating the plurality of modified PBMCs comprising the antigen and/or adjuvant with a second adjuvant for a sufficient time for the modified PBMCs comprising the antigen to condition, thereby generating the conditioned plurality of modified PBMCs comprising the antigen and/or the adjuvant. In some embodiments, the process further comprises isolating the plurality of modified PBMCs comprising the antigen and/or the adjuvant from the cell suspension before incubation with the adjuvant to condition the modified PBMCs.

In some embodiments according to any one of the methods described herein, the antigen is present in the cytosol and the adjuvant is present in a vesicle of a cell in the plurality of modified PBMCs. In some embodiments, the vesicle is an endosome. In some embodiments, the antigen and/or the adjuvant are present in multiple compartments of a cell in the plurality of modified PBMCs. In further embodiments, the antigen and/or the adjuvant are present in at least about 70% of the cells in the plurality of PBMCs. In some embodiments, the antigen and/or the adjuvant are present in at least any one of about 70%, about 75%, about 80%, about 85%, about 95%, or about 99%, or 100% of the cells in the plurality of PBMCs. In some embodiments, the antigen is bound to the surface of a cell in the plurality of modified PBMCs. In some embodiments, the antigen is presented in at least any one of about 50%, about 60%, about 70%, about 75%, about 80%, about 85%, about 95%, about 99%, or 100% of the cells in the plurality of modified PBMCs. In some embodiments, the antigen is presented in at least any one of about 50%, about 60%, about 70%, about 75%, about 80%, about 85%, about 95%, about 99%, or 100% of cells in one or more of the T cells, B cells, NK cells, or monocytes within the plurality of modified PBMCs. In some embodiments, the antigen is presented in at least any one of about 50%, about 60%, about 70%, about 75%, about 80%, about 85%, about 95%, about 99%, or 100% of cells of each of the T cells, B cells, NK cells, and monocytes within the plurality of modified PBMCs. In some embodiments, the antigen is presented in at least any one of about 50%, about 60%, about 70%, about 75%, about 80%, about 85%, about 95%, about 99%, or 100% of cells of one or more of the T cells, B cells, NK cells, and monocytes within the plurality of modified PBMCs.

In some embodiments according to any one of the methods described herein, the process further comprises a step of incubating the input PBMCs and/or the modified PBMCs with an agent that enhances the viability and/or function of the modified PBMCs as compared to corresponding modified PBMCs prepared without the further incubation step.

In some embodiments according to any one of the methods described herein, the method further comprises administering a third adjuvant to the individual. In some embodiments, the composition comprising the plurality of modified PBMCs and the third adjuvant are administered simultaneously. In some embodiments, the third adjuvant is administered before, concurrently with, or after administration of the plurality of modified PBMCs to the individual. In some embodiments, the composition comprising the plurality of modified PBMCs and the third adjuvant are administered sequentially. In some embodiments, the third adjuvant is the same as the constriction-delivered adjuvant. In some embodiments, the third adjuvant is the same as the conditioning adjuvant. In some embodiments, the third adjuvant is the different from the constriction-delivered adjuvant. In some embodiments, the third adjuvant is different from the conditioning adjuvant.

In some embodiments, the method comprises multiple administrations of the modified PBMCs. In some embodiments, the method comprises about 3 to about 9 administrations of the modified PBMCs. In some embodiments, the method comprises about any one of 1, 2, 3, 4, 5, 6, 7, 8, 9, 10, 11, 12, 13, 14 or 15 administrations of the modified PBMCs. In some embodiments, the method comprises continuous administrations of the modified PBMCs as needed. IN some embodiments, the time interval between two successive administrations of the plurality of modified PBMCs is between about 1 day and about 30 days. In some embodiments, the time interval between two successive administrations of the plurality of modified PBMCs is about 21 days. In some embodiments, the time the time interval between two successive administrations of the modified immune cells is about any one of 1, 2, 3, 4, 5, 6, 7, 8, 10, 12, 14, 16, 20, 25, 30, 35, 40, 45, 50, 55, 60, 65, 70, 75, 80, 85, 90, 95, 100, or 150 days. In some embodiments, the individual is positive for expression of HLA-A2. In some embodiments, at least one cell in the plurality of modified PBMCs is positive for expression of HLA-A2. In some embodiments, at least about any one of 10%, 20%, 30%, 40%, 50%, 60%, 70%, 80%, 90%, or 99% of the modified PBMCs is positive for expression of HLA-A2. In some embodiments, at least about any one of 10%, 20%, 30%, 40%, 50%, 60%, 70%, 80%, 90%, or 99% of T cells within the modified PBMCs are positive for expression of HLA-A2. In some embodiments, at least about any one of 10%, 20%, 30%, 40%, 50%, 60%, 70%, 80%, 90%, or 99% of B cells within the modified PBMCs are positive for expression of HLA-A2. In some embodiments, at least about any one of 10%, 20%, 30%, 40%, 50%, 60%, 70%, 80%, 90%, or 99% of NK cells within the modified PBMCs are positive for expression of HLA-A2. In some embodiments, at least about any one of 10%, 20%, 30%, 40%, 50%, 60%, 70%, 80%, 90%, or 99% of monocytes within the modified PBMCs are positive for expression of HLA-A2.

In some embodiments, the composition comprising the plurality of modified PBMCs is administered prior to administering the third adjuvant. For example, the composition comprising the plurality of modified PBMCs is administered from about 1 hour to about 1 week prior to administration of the third adjuvant. For example, in some embodiments, the composition comprising the plurality of modified PBMCs is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the third adjuvant. In some embodiments, the composition comprising the plurality of modified PBMCs is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the third adjuvant.

In some embodiments, the composition comprising the plurality of modified PBMCs is administered following administration of the third adjuvant. For example, the composition comprising the plurality of modified PBMCs is administered from about 1 hour to about 1 week following administration of the third adjuvant. For example, in some embodiments, the composition comprising the plurality of modified PBMCs is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the third adjuvant. In some embodiments, the composition comprising the plurality of modified PBMCs is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the third adjuvant.

In some embodiments, the third adjuvant is any one IFN-α or a CpG ODN. In some embodiments, the third adjuvant is CpG 7909.

In some embodiments according to any one of the methods described herein, the plurality of modified PBMCs is administered prior to, concurrently with, or following administration of a therapeutic agent. In some embodiments, the therapeutic agent comprises one or more of an immune checkpoint inhibitor, a chemotherapy, or a radiotherapy. In some embodiments, the therapeutic agent comprises one or more cytokines.

Immune checkpoints are regulators of the immune system and keep immune responses in check. Immune checkpoint inhibitors can be employed to facilitate the enhancement of immune response. In some embodiments, the composition comprising the plurality of modified PBMCs is administered in combination with administration of an immune checkpoint inhibitor. In some embodiments, the composition comprising the plurality of modified PBMCs and the immune checkpoint inhibitor are administered simultaneously. In some embodiments, the composition comprising the plurality of modified PBMCs and the immune checkpoint inhibitor are administered sequentially.

In some embodiments, the composition comprising the plurality of modified PBMCs is administered prior to administration of the immune checkpoint inhibitor. In some embodiments, the composition comprising the plurality of modified PBMCs is administered following administration of the immune checkpoint inhibitor. For example, the composition comprising the plurality of modified PBMCs is administered from about 1 hour to about 1 week prior to administration of the immune checkpoint inhibitor. For example, in some embodiments, the composition comprising the plurality of modified PBMCs is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the immune checkpoint inhibitor. In some embodiments, the composition comprising the plurality of modified PBMCs is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the immune checkpoint inhibitor.

In some embodiments, the composition comprising the plurality of modified PBMCs is administered about 7 days, about 10 days, about 14 days, about 18 days, about 21 days, about 24 days, about 28 days, about 30 days, about 35 days, about 40 days, about 45 days, or about 50 days prior to administration of the immune checkpoint inhibitor. In some embodiments, the composition comprising the plurality of modified PBMCs is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days prior to administration of the immune checkpoint inhibitor.

In some embodiments, the composition comprising the plurality of modified PBMCs is administered following administration of the immune checkpoint inhibitor. For example, the composition comprising the plurality of modified PBMCs is administered from about 1 hour to about 1 week following administration of the immune checkpoint inhibitor. For example, in some embodiments, the composition comprising the plurality of modified PBMCs is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the immune checkpoint inhibitor. In some embodiments, the composition comprising the plurality of modified PBMCs is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the immune checkpoint inhibitor.

In some embodiments, the composition comprising the plurality of modified PBMCs is administered about 7 days, about 10 days, about 14 days, about 18 days, about 21 days, about 24 days, about 28 days, about 30 days, about 35 days, about 40 days, about 45 days, or about 50 days following administration of the immune checkpoint inhibitor. In some embodiments, the composition comprising the plurality of modified PBMCs is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days following administration of the immune checkpoint inhibitor.

In some embodiments, the method comprises multiple administration of the composition comprising the plurality of modified PBMCs and/or multiple administration of the immune checkpoint inhibitor. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the plurality of modified PBMCs and/or the immune checkpoint inhibitor. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the plurality of modified PBMCs and/or the immune checkpoint inhibitor.

Exemplary immune checkpoint inhibitor is targeted to, without limitation, PD-1, PD-L1, CTLA-4, LAG3, TIM-3, TIGIT, VISTA, TIM1, B7-H4 (VTCN1) or BTLA. In some embodiments, the immune checkpoint inhibitor is targeted to one or more of PD-1, PD-L1, CTLA-4, LAG3, TIM-3, TIGIT, VISTA, TIM1, B7-H4 (VTCN1) or BTLA. In some embodiments, the immune checkpoint inhibitor is one or more of: an antibody that binds to PD-1, an antibody that binds PD-L1, an antibody that binds CTLA-4, an antibody that binds LAG3, or an antibody that binds TIM-3, an antibody that binds TIGIT, an antibody that binds VISTA, an antibody that binds TIM-1, an antibody that binds B7-H4, or an antibody that binds BTLA. In further embodiments, the antibody can be a full length antibody or any variants, for example but not limited to, an antibody fragment, a single chain variable fragment (ScFv), or a fragment antigen-binding (Fab). In further embodiments, the antibody can be bispecific, trispecific or multispecific. In some embodiments, the immune checkpoint inhibitor is one or more chemical compounds that binds to and/or inhibits one or more of PD-1, PD-L1, CTLA-4, LAG3, TIM-3, TIGIT, VISTA, TIM1, B7-H4 (VTCN1) or BTLA. In some embodiments, the immune checkpoint inhibitor is one or more peptides that binds to and/or inhibits one or more of PD-1, PD-L1, CTLA-4, LAG3, TIM-3, TIGIT, VISTA, TIM1, B7-H4 (VTCN1) or BTLA. In some embodiments, the immune checkpoint inhibitor is targeted to PD-1. In some embodiments, the immune checkpoint inhibitor is targeted to PD-L1.

Cytokines can be used in combination with any one of the pluralities of modified PBMCs described herein to achieve additive or synergistic effects against cancers, for example, HPV-associated cancers. In some embodiments, the composition comprising the plurality of modified PBMCs is administered in combination with administration of one or more cytokines. In some embodiments, the composition comprising the plurality of modified PBMCs and the cytokine are administered simultaneously. In some embodiments, the composition comprising the plurality of modified PBMCs and the cytokine are administered sequentially.

In some embodiments, the composition comprising the plurality of modified PBMCs is administered prior to administration of the cytokine. In some embodiments, the composition comprising the plurality of modified PBMCs is administered following administration of the cytokine. For example, the composition comprising the plurality of modified PBMCs is administered from about 1 hour to about 1 week prior to administration of the cytokine. For example, in some embodiments, the composition comprising the plurality of modified PBMCs is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the cytokine. In some embodiments, the composition comprising the plurality of modified PBMCs is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the cytokine.

In some embodiments, the composition comprising the plurality of modified PBMCs is administered about 7 days, about 10 days, about 14 days, about 18 days, about 21 days, about 24 days, about 28 days, about 30 days, about 35 days, about 40 days, about 45 days, or about 50 days prior to administration of the cytokine. In some embodiments, the composition comprising the plurality of modified PBMCs is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days prior to administration of the cytokine.

In some embodiments, the composition comprising the plurality of modified PBMCs is administered following administration of the cytokine. For example, the composition comprising the plurality of modified PBMCs is administered from about 1 hour to about 1 week following administration of the cytokine. For example, in some embodiments, the composition comprising the plurality of modified PBMCs is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the cytokine. In some embodiments, the composition comprising the plurality of modified PBMCs is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the cytokine.

Exemplary cytokines include but are not limited to chemokines, interferons, interleukins, lymphokines, and tumour necrosis factors. In some embodiments, the cytokine enhances cellular immune responses. In some embodiments, the cytokine enhances antibody responses. In some embodiments, the cytokine is a type I cytokine. In some embodiments, the cytokine is a type 2 cytokine. In some embodiments, the cytokine comprises one or more of: IL-2, IL-15, IL-10, IL-12, IFN-α, or IL-21. In some embodiments, the cytokine comprises IL-15.

Chemotherapy can be used in combination with any one of the pluralities of modified PBMCs described herein to achieve additive or synergistic effects against cancers, for example, HPV-associated cancers. In some embodiments, the composition comprising the plurality of modified PBMCs is administered in combination with administration of a chemotherapy. In some embodiments, the composition comprising the plurality of modified PBMCs and the chemotherapy are administered simultaneously. In some embodiments, the composition comprising the plurality of modified PBMCs and the chemotherapy are administered sequentially.

In some embodiments, the composition comprising the plurality of modified PBMCs is administered prior to administration of the chemotherapy. In some embodiments, the composition comprising the plurality of modified PBMCs is administered following administration of the chemotherapy. For example, the composition comprising the plurality of modified PBMCs is administered from about 1 hour to about 1 week prior to administration of the chemotherapy. For example, in some embodiments, the composition comprising the plurality of modified PBMCs is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the chemotherapy. In some embodiments, the composition comprising the plurality of modified PBMCs is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the chemotherapy.

In some embodiments, the composition comprising the plurality of modified PBMCs is administered following administration of the chemotherapy. For example, the composition comprising the plurality of modified PBMCs is administered from about 1 hour to about 1 week following administration of the chemotherapy. For example, in some embodiments, the composition comprising the plurality of modified PBMCs is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the chemotherapy. In some embodiments, the composition comprising the plurality of modified PBMCs is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the chemotherapy.

In some embodiments, the composition comprising the plurality of modified PBMCs is administered about 7 days, about 10 days, about 14 days, about 18 days, about 21 days, about 24 days, about 28 days, about 30 days, about 35 days, about 40 days, about 45 days, or about 50 days following administration of the chemotherapy. In some embodiments, the composition comprising the plurality of modified PBMCs is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days following administration of the chemotherapy.

In some embodiments, the method comprises multiple administration of the composition comprising the plurality of modified PBMCs and/or multiple administration of the chemotherapy. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the plurality of modified PBMCs and/or the chemotherapy. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the plurality of modified PBMCs and/or the chemotherapy.

Exemplary chemotherapy can be cell cycle dependent or cell cycle independent. In some embodiments, the chemotherapy comprises one or more chemotherapeutic agents. In some embodiments, a chemotherapeutic agent can target one or more of cell division, DNA, or metabolism in cancer. In some embodiments, the chemotherapeutic agent is a platinum-based agent, such as but not limited to cisplatin, oxaliplatin or carboplatin. In some embodiments, the chemotherapeutic agent is a taxane (such as docetaxel or paclitaxel). In some embodiments, the chemotherapeutic agent is 5-fluorouracil, doxorubicin, or irinotecan. In some embodiments, the chemotherapeutic agent is one or more of: an alkylating agent, an antimetabolite, an antitumor antibiotic, a topoisomerase inhibitor or a mitotic inhibitor. In some embodiments, the chemotherapy comprises cisplatin.

Radiotherapy can be used in combination with any one of the pluralities of modified PBMCs described herein to achieve additive or synergistic effects against cancers, for example, HPV-associated cancers. In some embodiments, the composition comprising the plurality of modified PBMCs is administered in combination with administration of a radiotherapy. In some embodiments, the composition comprising the plurality of modified PBMCs and the radiotherapy are administered simultaneously. In some embodiments, the composition comprising the plurality of modified PBMCs and the radiotherapy are administered sequentially. In some embodiments, the composition comprising the plurality of modified PBMCs is administered in combination with administration of a radiotherapy, in combination with a chemotherapy, and/or in combination with an immune checkpoint inhibitor.

In some embodiments, the composition comprising the plurality of modified PBMCs is administered prior to administration of the radiotherapy. In some embodiments, the composition comprising the plurality of modified PBMCs is administered following administration of the radiotherapy. For example, the composition comprising the plurality of modified PBMCs is administered from about 1 hour to about 1 week prior to administration of the radiotherapy. For example, in some embodiments, the composition comprising the plurality of modified PBMCs is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the radiotherapy. In some embodiments, the composition comprising the plurality of modified PBMCs is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the radiotherapy.

In some embodiments, the composition comprising the plurality of modified PBMCs is administered following administration of the radiotherapy. For example, the composition comprising the plurality of modified PBMCs is administered from about 1 hour to about 1 week following administration of the radiotherapy. For example, in some embodiments, the composition comprising the plurality of modified PBMCs is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the radiotherapy. In some embodiments, the composition comprising the plurality of modified PBMCs is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the radiotherapy.

In some embodiments, the composition comprising the plurality of modified PBMCs is administered about 7 days, about 10 days, about 14 days, about 18 days, about 21 days, about 24 days, about 28 days, about 30 days, about 35 days, about 40 days, about 45 days, or about 50 days following administration of the radiotherapy. In some embodiments, the composition comprising the plurality of modified PBMCs is administered from between about 7 days to about 10 days, from between about 10 days and about 14 days, from between about 14 days and about 18 days, from between about 18 days and about 21 days, from between about 21 days and about 24 days, from between about 24 days and about 28 days, from between about 28 days and about 30 days, from between about 30 days and about 35 days, from between about 35 days and about 40 days, from between about 40 days and about 45 days, or from between about 45 days and about 50 days following administration of the radiotherapy.

In some embodiments, the method comprises multiple administration of the composition comprising the plurality of modified PBMCs and/or multiple administration of the radiotherapy. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the plurality of modified PBMCs and/or the radiotherapy. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the plurality of modified PBMCs and/or the radiotherapy.

In some embodiments, there is provided a plurality of PBMCs comprising an antigen for use in a method of stimulating an immune response in an individual according to any one of the methods described herein.

In some methods according to any one of the methods described herein, the method stimulates an immune response against an HPV antigen in an individual. Papillomaviruses are small nonenveloped DNA viruses with a virion size of ~55 nm in diameter. More than 100 HPV genotypes are completely characterized, and a higher number is presumed to exist. HPV is a known cause of cervical cancers, as well as some vulvar, vaginal, penile, oropharyngeal, anal, and rectal cancers. Although most HPV infections are asymptomatic and clear spontaneously, persistent infections with one of the oncogenic HPV types can progress to precancer or cancer. Other HPV-associated diseases can include common warts, plantar warts, flat warts, anogenital warts, anal lesions, epidermodysplasia, focal epithelial hyperplasia, mouth papillomas, verrucous cysts, laryngeal papillomatosis, squamous intraepithelial lesions (SILs), cervical intraepithelial neoplasia (CIN), vulvar intraepithelial neoplasia (VIN) and vaginal intraepithelial neoplasia (VAIN). Many of the known human papillomavirus (HPV) types cause benign lesions with a subset being oncogenic. Based on epidemiologic and phylogenetic relationships, HPV types are classified into fifteen "high risk types" (HPV 16, 18, 31, 33, 35, 39, 45, 51, 52, 56, 58, 59, 68, 73, and 82) and three "probable high risk types" (HPV 26, 53, and 66), which together are known to manifest as low and high grade cervical changes and cancers, as well as other anogential cancers such as vulval, vaginal, penile, anal, and perianal cancer, as well as head and neck cancers. Recently, the association of high risk types HPV 16 and 18 with breast cancer was also described. Eleven HPV types classified as "low risk types" (HPV 6, 11, 40, 42, 43, 44, 54, 61, 70, 72, and 81) are known to manifest as benign low-grade cervical changes, genital warts and recurrent respiratory papillomatosis. Cutaneous HPV types 5, 8, and 92 are associated with skin cancer. In some HPV-associated cancers, the immune system is depressed and correspondingly, the antitumor response is significantly impaired. See Suresh and Burtness, *Am J Hematol Oncol* 13(6):20-27 (2017).

In some embodiments according to any one of the methods, compositions or pluralities of modified PBMCs described herein, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs. In some embodiments, the plurality of PBMCs comprises a nucleic acid encoding an antigen. In some embodiments, the plurality of PBMCs comprises an mRNA encoding an antigen.

PBMC Compositions

As used herein, PBMCs may be isolated by leukapheresis from whole blood obtained from an individual. Also provided are PBMC compositions are reconstituted by mixing different pools of PBMCs from the same individual or different individuals. In other examples, PBMCs may also be reconstituted by mixing different populations of cells into a mixed cell composition with a generated profile. In some embodiments, the populations of cells used for reconstituting PBMCs are mixed populations of cells (such as a mixture of one or more of T cells, B cells, NK cells or monocytes). In some embodiments, the populations of cells used for reconstituting PBMCs are purified populations of cells (such as purified T cells, B cells, NK cells or monocytes). In additional examples, the different populations of cells used in reconstituting a PBMC composition can be isolated from the same individual (e.g. autologous) or isolated from different individuals (e.g. allogenic and/or heterologous).

Therefore in some embodiments according to any one of the methods, compositions or pluralities of modified PBMCs described herein, the plurality of input PBMCs comprises one or more of T cells, B cells, NK cells, monocytes, dendritic cells or NK-T cells. In some embodiments, the plurality of input PBMCs comprises T cells, B cells, NK cells, monocytes, dendritic cells or NK-T cells. In some embodiments, the plurality of input PBMCs comprises one or more of CD3+ T cells, CD20+ B cells, CD14+ monocytes, CD56+NK cells. In some embodiments, the plurality of input PBMCs comprises T cells, B cells, NK cells and monocytes, and the ratio of T cells, B cells, NK cells and monocytes to the total number of PBMCs in the plurality of input PBMCs is essentially the same as the ratio of T cells, B cells, NK cells and monocytes to the total number of PBMCs in whole blood. In some embodiments, the plurality of input PBMCs comprises T cells, B cells, NK cells and monocytes, and the ratio of T cells, B cells, NK cells and monocytes to the total number of PBMCs in the plurality of input PBMCs is essentially the same as the ratio of T cells, B cells, NK cells and monocytes to the total number of PBMCs in a leukapheresis product from whole blood. In some embodiments, the plurality of input PBMCs comprises T cells, B cells, NK cells and monocytes, and the ratio of T cells, B cells, NK cells and monocytes to the total number of PBMCs in the plurality of input PBMCs differs by not more than any one of 1%, 2%, 5%, 10% 15%, 20%, 25%, 30%, 40%, or 50% from the ratio of T cells, B cells, NK cells and monocytes to the total number of PBMCs in whole blood. In some embodiments, the plurality of input PBMCs comprises T cells, B cells, NK cells and monocytes, and the ratio of T cells, B cells, NK cells and monocytes to the total number of PBMCs in the plurality of input PBMCs differs by not more than any one of 10% from the ratio of T cells, B cells, NK cells and monocytes to the total number of PBMCs in whole blood. In some embodiments, the plurality of input PBMCs comprises T cells, B cells, NK cells and monocytes, and the ratio of T cells, B cells, NK cells and monocytes to the total number of PBMCs in the plurality of input PBMCs differs by not more than any one of 1%, 2%, 5%, 10% 15%, 20%, 25%, 30%, 40%, or 50% from the ratio of T cells, B cells, NK cells and monocytes to the total number of PBMCs in a leukapheresis product from whole blood. In some embodiments, the plurality of input PBMCs comprises T cells, B cells, NK cells and monocytes, and the ratio of T cells, B cells, NK cells and monocytes to the total number of PBMCs in the plurality of input PBMCs differs by not more than any one of 10% from the ratio of T cells, B cells, NK cells and monocytes to the total number of PBMCs in a leukapheresis product from whole blood.

In some embodiments according to any one of the methods, compositions or pluralities of modified PBMCs described herein, about 25% to about 70% of the modified PBMCs are T cells. In some embodiments, about 2.5% to about 14% of the modified PBMCs are B cells. In some embodiments, about 3.5% to about 35% of the modified PBMCs are NK cells. In some embodiments, about 4% to about 25% of the modified PBMCs are NK cells.

In some embodiments according to any one of the methods, compositions or pluralities of modified PBMCs described herein, at least about 90% to about 99% of the input PBMCs consist of T cells, B cells, NK cells and monocytes. In some embodiments, at least any one of about 80% to about 85%, about 85% to about 90%, about 90% to about 95% or about 95% to about 99% of the input PBMCs consist of T cells, B cells, NK cells and monocytes. In some embodiments, at least about any one of 80%, 81%, 82%, 83%, 84%, 85%, 86%, 87%, 88%, 89%, 90%, 91%, 92%, 93%, 94%, 95%, 96%, 97%, 98%, or 99% of the input PBMCs consist of T cells, B cells, NK cells and monocytes. In some embodiments, at least about 90% of the input PBMCs consist of T cells, B cells, NK cells and monocytes. In some embodiments, the input PBMCs consist of T cells, B cells, NK cells and monocytes.

In some embodiments according to any one of the methods, compositions or pluralities of modified PBMCs described herein, at least about 90% to about 99% of the modified PBMCs consist of T cells, B cells, NK cells and monocytes. In some embodiments, at least any one of about 80% to about 85%, about 85% to about 90%, about 90% to about 95% or about 95% to about 99% of the modified PBMCs consist of T cells, B cells, NK cells and monocytes. In some embodiments, at least about any one of 80%, 81%, 82%, 83%, 84%, 85%, 86%, 87%, 88%, 89%, 90%, 91%, 92%, 93%, 94%, 95%, 96%, 97%, 98%, or 99% of the modified PBMCs consist of T cells, B cells, NK cells and monocytes. In some embodiments, at least about 90% of the modified PBMCs consist of T cells, B cells, NK cells and monocytes. In some embodiments, the modified PBMCs consist of T cells, B cells, NK cells and monocytes.

In some embodiments according to any one of the methods, compositions or pluralities of modified PBMCs described herein, at least about any one of 15%, 20%, 25%, 30%, 35%, 40%, 45%, 50%, 55%, 60%, 65%, 70%, or 75% of the input PBMCs are T cells. In some embodiments, at least about 25% of the input PBMCs are T cells. In some embodiments, at least about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 30% of the input PBMCs are B cells. In some embodiments, at least about 2.5% of the input PBMCs are B cells. In some embodiments, at least about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 30% of the input PBMCs are NK cells. In some embodiments, at least about 3.5% of the input PBMCs are NK cells. In some embodiments, at least about any one of 1%, 2%, 3%, 4%, 5%, 6%, 7%, 8%, 9%, 10%, 12%, 14%, 16%, 18%, 20%, 25%, 30%, 35% or 40% of the input PBMCs are monocytes. In some embodiments, at least about 4% of the input PBMCs are monocytes. In some embodiments, at least about 25% of the input PBMCs are T cells; at least about 2.5% of the input PBMCs are B cells; at least about 3.5% of the input PBMCs are NK cells; and at least about 4% of the input PBMCs are monocytes.

In some embodiments according to any one of the methods, compositions or pluralities of modified PBMCs described herein, at least about any one of 10%, 15%, 20%, 25%, 30%, 35%, 40%, 45%, 50%, 55%, 60%, 65%, or 70% of the modified PBMCs are T cells. In some embodiments, at least about 20% of the modified PBMCs are T cells. In some embodiments, at least about any one of 0.25%, 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25% or 30% of the modified PBMCs are B cells. In some embodiments, at least about 2% of the modified PBMCs are B cells. In some embodiments, at least about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 30% of the modified PBMCs are NK cells. In some embodiments, at least about 3% of the modified PBMCs are NK cells. In some embodiments, at least about any one of 1%, 2%, 3%, 4%, 5%, 6%, 7%, 8%, 9%, 10%, 12%, 14%, 16%, 18%, 20%, 25%, 30%, 35% or 40% of the modified PBMCs are monocytes. In some embodiments, at least about 3% of the modified PBMCs are monocytes. In some embodiments, at least about 20% of the modified PBMCs are T cells; at least about 2% of the modified PBMCs are B cells; at least about 3% of the modified PBMCs are NK cells; and at least about 3% of the modified PBMCs are monocytes.

In some embodiments according to any one of the methods, compositions or pluralities of modified PBMCs described herein, not more than about any one of 40%, 45%, 50%, 55%, 60%, 65%, 70%, 75%, 80%, 85%, or 90% of the input PBMCs are T cells. In some embodiments, not more than about 70% of the input PBMCs are T cells. In some embodiments, not more than about any one of 5%, 10%, 12%, 14%, 16%, 18%, 20%, 22%, 25%, 30%, 35%, 40%, or 50% of the input PBMCs are B cells. In some embodiments, not more than about 14% of the input PBMCs are B cells. In some embodiments, not more than about any one of 10%, 15%, 20%, 25%, 30%, 35%, 40%, 45%, 50% or 60% of the input PBMCs are NK cells. In some embodiments, not more than about 35% of the input PBMCs are NK cells. In some embodiments, not more than about any one of 5%, 10%, 12%, 14%, 16%, 18%, 20%, 22%, 25%, 30%, 35%, 40%, or 50% of the input PBMCs are monocytes. In some embodiments, not more than about 4% of the input PBMCs are monocytes. In some embodiments, not more than about 25% of the input PBMCs are T cells; not more than about 2.5% of the input PBMCs are B cells; not more than about 3.5% of the input PBMCs are NK cells; and not more than about 4% of the input PBMCs are monocytes.

In some embodiments according to any one of the methods, compositions or pluralities of modified PBMCs described herein, not more than about any one of 10%, 15%, 20%, 25%, 30%, 35%, 40%, 45%, 50%, 55%, 60%, 65%, or 70% of the modified PBMCs are T cells. In some embodiments, not more than about 20% of the modified PBMCs are T cells. In some embodiments, not more than about any one of 0.25%, 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25% or 30% of the modified PBMCs are B cells. In some embodiments, not more than about 2% of the modified PBMCs are B cells. In some embodiments, not more than about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 30% of the modified PBMCs are NK cells. In some embodiments, not more than about 3% of the modified PBMCs are NK cells. In some embodiments, not more than about any one of 1%, 2%, 3%, 4%, 5%, 6%, 7%, 8%, 9%, 10%, 12%, 14%, 16%, 18%, 20%, 25%, 30%, 35% or 40% of the modified PBMCs are monocytes. In some embodiments, not more than about 3% of the modified PBMCs are monocytes. In some embodiments, not more than about 20% of the modified PBMCs are T cells; not more than about 2% of the modified PBMCs are B cells; not more than about 3% of the modified PBMCs are NK cells; and not more than about 3% of the modified PBMCs are monocytes.

In some embodiments according to any one of the methods, compositions or pluralities of modified PBMCs described herein, about any one of 20% to 25%, 25% to 30%, 30% to 35%, 35% to 40%, 40% to 45%, 45% to 50%, 50% to 55%, 55% to 60%, 60% to 65%, 65% to 70%, or 70% to 75% of the modified PBMCs are T cells. In some embodiments, about 25% to about 70% of the modified PBMCs are T cells. In some embodiments, about any one of 1% to 2.5%, 2.5% to 4%, 4% to 6%, 6% to 8%, 8% to 10%, 10% to 12%, 12% to 14%, 14% to 16%, 16% to 20% or 20% to 25% of the modified PBMCs are B cells. In some embodiments, about 2.5% to about 14% of the modified PBMCs are B cells. In some embodiments, about any one of 1% to 2%, 2% to 3.5%, 3.5% to 5%, 5% to 8%, 8% to 10%, 10% to 12%, 12% to 14%, 14% to 16%, 16% to 20% or 20% to 25% of the modified PBMCs are B cells. In some embodiments, about 3.5% to about 35% of the modified PBMCs are NK cells. In some embodiments, about any one of 2% to 4%, 4% to 6%, 6% to 8%, 8% to 10%, 10% to 12%, 12% to 14%, 14% to 16%, 16% to 20%, 20% to 25%, 25% to 30%, 30% to 35%, or 35% to 40% of the modified PBMCs are monocytes. In some embodiments, about 4% to about 25% of the modified PBMCs are monocytes. In some embodiments, about 25% to about 70% of the modified PBMCs are T cells, about 2.5% to about 14% of the modified PBMCs are B cells, about 3.5% to about 35% of the modified PBMCs are NK cells, and about 4% to about 25% of the modified PBMCs are NK cells.

In some embodiments according to any one of the methods, compositions or pluralities of modified PBMCs described herein, about any one of 20% to 25%, 25% to 30%, 30% to 35%, 35% to 40%, 40% to 45%, 45% to 50%, 50% to 55%, 55% to 60%, 60% to 65%, 65% to 70%, or 70% to 75% of the modified PBMCs are T cells. In some embodiments, about 25% to about 70% of the modified PBMCs are T cells. In some embodiments, about any one of 1% to 2.5%, 2.5% to 4%, 4% to 6%, 6% to 8%, 8% to 10%, 10% to 12%, 12% to 14%, 14% to 16%, 16% to 20% or 20% to 25% of the modified PBMCs are B cells. In some embodiments, about 2.5% to about 14% of the modified PBMCs are B cells. In some embodiments, about any one of 1% to 2%, 2% to 3.5%, 3.5% to 5%, 5% to 8%, 8% to 10%, 10% to 12%, 12% to 14%, 14% to 16%, 16% to 20% or 20% to 25% of the modified PBMCs are NK cells. In some embodiments, about 3.5% to about 35% of the modified PBMCs are NK cells. In some embodiments, about any one of 2% to 4%, 4% to 6%, 6% to 8%, 8% to 10%, 10% to 12%, 12% to 14%, 14% to 16%, 16% to 20%, 20% to 25%, 25% to 30%, 30% to 35%, or 35% to 40% of the modified PBMCs are monocytes. In some embodiments, about 4% to about 25% of the modified PBMCs are monocytes. In some embodiments, about 25% to about 70% of the modified PBMCs are T cells, about 2.5% to about 14% of the modified PBMCs are B cells, about 3.5% to about 35% of the modified PBMCs are NK cells, and about 4% to about 25% of the modified PBMCs are NK cells.

As used herein, PBMCs can also be generated after manipulating the composition of a mixed cell population of mononuclear blood cells (such as lymphocytes and monocytes). In some instances, the input PBMCs are generated after reducing (such as depleting) certain subpopulations (such as B cells) within a mixed cell population of mononuclear blood cells. The composition in a mixed cell population of mononuclear blood cells in an individual can be manipulated to make the cell population more closely resemble a leukapheresis product from whole blood in the same individual. In other examples, the composition in a mixed cell population of mononuclear blood cells (for example, mouse splenocytes) can also be manipulated to make the cell population more closely resemble human PBMCs isolated from a leukapheresis product from human whole blood.

In some embodiments, the construction-mediated delivery does not differentially modulate the viability of different subpopulations (such as B cells, T cells, NK cells or monocytes) within PBMCs in a significant manner. In some embodiments, the conditioning process does not differentially modulate the viability of different subpopulations within PBMCs in a significant manner. In some embodiments, the further addition of agents (including but not limited to any one of: biopreservation agents or agents that enhance the function and/or viability of PBMCs) does not differentially modulate the viability of various subpopulations within PBMCs in a significant manner. Therefore in some embodiments according to any one of the methods, compositions or pluralities of modified PBMCs described herein, the percentage of T cells within the plurality of modified PBMCs and the percentage of T cells within the plurality of input PBMCs differ by no more than about 10% by number. In some embodiments, the percentage of T cells within the plurality of modified PBMCs and the percentage of T cells within the plurality of input PBMCs differ by no more than about any one of 5%, 8%, 10%, 12%, 14%, 16%, 18% or 20% by number. In some embodiments, the percentage of B cells within the plurality of modified PBMCs and the percentage of B cells within the plurality of input PBMCs differ by no more than about 10% by number. In some embodiments, the percentage of B cells within the plurality of modified PBMCs and the percentage of B cells within the plurality of input PBMCs differ by no more than about any one of 5%, 8%, 10%, 12%, 14%, 16%, 18% or 20% by number. In some embodiments, the percentage of NK cells within the plurality of modified PBMCs and the percentage of NK cells within the plurality of input PBMCs differ by no more than about 10% by number. In some embodiments, the percentage of NK cells within the plurality of modified PBMCs and the percentage of NK cells within the plurality of input PBMCs differ by no more than about any one of 5%, 8%, 10%, 12%, 14%, 16%, 18% or 20% by number. In some embodiments, the percentage of monocytes within the plurality of modified PBMCs and the percentage of monocytes within the plurality of input PBMCs differ by no more than about 10% by number. In some embodiments, the percentage of monocytes within the plurality of modified PBMCs and the percentage of monocytes within the plurality of input PBMCs differ by no more than about any one of 5%, 8%, 10%, 12%, 14%, 16%, 18% or 20% by number.

Antigens

In some embodiments according to any one of the methods, compositions or pluralities of modified PBMCs described herein, the antigen is a disease-associated antigen. In some embodiments, the antigen is derived from peptides or mRNA isolated from a diseased cell. In some embodiments, the antigen is a non-self antigen. In some embodiments, the antigen is a tumor antigen, viral antigen, bacterial antigen, or fungal antigen. In some embodiments, the antigen is derived from a lysate, such as a lysate of disease cells. In some embodiments, the antigen is derived from a tumor lysate. In some embodiments, the antigen is a tumor antigen or a tumor associated antigen. In some embodiments, the antigen is associated with a cancer. In some embodiments, the cancer is head and neck cancer, cervical cancer, vulvar cancer, vaginal cancer, penile cancer, anal cancer, perianal cancer, anogenital cancer, oral cancer or salivary cancer. In some embodiments, the antigen is a head and neck cancer antigen, a cervical cancer antigen, a vulvar cancer antigen, a vaginal cancer antigen, a penile cancer antigen, an anal cancer antigen, a perianal cancer antigen, an anogenital cancer antigen, an oral cancer antigen, a salivary cancer antigen, a breast cancer antigen, a skin cancer antigen, a bladder cancer antigen, a colon cancer, a rectal cancer antigen, an endometrial cancer antigen, a kidney cancer antigen, a leukemia antigen, a lung cancer antigen, a melanoma antigen, a non-Hodgkin lymphoma antigen, a pancreatic cancer antigen, a prostate cancer antigen, or a thyroid cancer antigen, In some embodiments, the cancer is a solid cancer. In some embodiments, the cancer is a hematologic cancer. In some embodiments, the cancer is a virus-associated cancer. In some embodiments, the cancer is a HPV-associated cancer. In some embodiments, the cancer is a localized cancer. In some embodiments, the cancer is a metastatic cancer. In some embodiments, the antigen is associated with an infectious disease. In some embodiments, the infectious disease is associated with HIV, HPV, EBV, MCV, HBV or HCV.

In some embodiments according to any one of the methods, compositions or pluralities of modified PBMCs described herein, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

In some embodiments according to any one of the methods, compositions or pluralities of modified PBMCs described herein, the antigen is a human papillomavirus (HPV) antigen. Papillomaviruses are small nonenveloped DNA viruses with a virion size of ~55 nm in diameter. More than 100 HPV genotypes are completely characterized, and a higher number is presumed to exist. HPV is a known cause of cervical cancers, as well as some vulvar, vaginal, penile, oropharyngeal, anal, and rectal cancers. Although most HPV infections are asymptomatic and clear spontaneously, persistent infections with one of the oncogenic HPV types can progress to precancer or cancer. Other HPV-associated diseases can include common warts, plantar warts, flat warts, anogenital warts, anal lesions, epidermodysplasia, focal epithelial hyperplasia, mouth papillomas, verrucous cysts, laryngeal papillomatosis, squamous intraepithelial lesions (SILs), cervical intraepithelial neoplasia (CIN), vulvar intraepithelial neoplasia (VIN) and vaginal intraepithelial neoplasia (VAIN). Many of the known human papillomavirus (HPV) types cause benign lesions with a subset being oncogenic. Based on epidemiologic and phylogenetic relationships, HPV types are classified into fifteen "high risk types" (HPV 16, 18, 31, 33, 35, 39, 45, 51, 52, 56, 58, 59, 68, 73, and 82) and three "probable high risk types" (HPV 26, 53, and 66), which together are known to manifest as low and high grade cervical changes and cancers, as well as other anogential cancers such as vulval, vaginal, penile, anal, and perianal cancer, as well as head and neck cancers. Recently, the association of high risk types HPV 16 and 18 with breast cancer was also described. Eleven HPV types classified as "low risk types" (HPV 6, 11, 40, 42, 43, 44, 54, 61, 70, 72, and 81) are known to manifest as benign low-grade cervical changes, genital warts and recurrent respiratory papillomatosis. Cutaneous HPV types 5, 8, and 92 are associated with skin cancer. In some HPV-associated cancers, the immune system is depressed and correspondingly, the antitumor response is significantly impaired. See Suresh and Burtness, *Am J Hematol Oncol* 13(6):20-27 (2017). In some embodiments, the antigen is a pool of multiple polypeptides that elicit a response against the same and or different antigens. In some embodiments, an antigen in the pool of multiple antigens does not decrease the immune response directed toward other antigens in the pool of multiple antigens. In some embodiments, the HPV antigen is a polypeptide comprising an antigenic HPV epitope and one or more heterologous peptide sequences. In some embodiments, the HPV antigen complexes with itself, with other antigens, or with the adjuvant. In some embodiments, the HPV is HPV-16 or HPV-18. In some embodiments, the HPV antigen is comprised of an HLA-A2-specific epitope. In some embodiments, the HPV antigen is an HPV E6 antigen or an HPV E7 antigen. In some embodiments, the antigen comprises a peptide derived from HPV E6 and/or E7. In some embodiments, the antigen comprises an HLA-A2-restricted peptide derived from HPV E6 and/or E7. In some embodiments, the HLA-A2-restricted peptide comprises the amino acid sequence of any one of SEQ ID NOs: 1-4. In some embodiments, the HPV antigen comprises an amino acid sequence with at least 90% similarity to any one of SEQ ID NOs: 18-25. In some embodiments, the HPV antigen comprises an amino acid sequence with at least 90% similarity to SEQ ID NO: 19. In some embodiments, the HPV antigen comprises an amino acid sequence with at least 90% similarity to SEQ ID NO: 23. In some embodiments, the HPV antigen comprises the amino acid sequence of SEQ ID NO: 19. In a preferred embodiment, the HPV antigen consists of the amino acid sequence of SEQ ID NO: 19. In some embodiments, the HPV antigen comprises the amino acid sequence of SEQ ID NO: 23. In a preferred embodiment, the HPV antigen consists of the amino acid sequence of SEQ ID NO: 23. In some embodiments, the antigen comprises the amino acid sequence of any one of SEQ ID NOs: 18-25. In some embodiments, the antigen is a plurality of antigens comprising at least one of the amino acid sequences of any one of SEQ ID NOs: 18-25. In some embodiments, the antigen is a plurality of antigens comprising 2, 3, 4, 5, 6, 7 or 8 of the amino acid sequences of any one of SEQ ID NOs 18-25. In some embodiments, the antigen is a plurality of antigens comprising an amino acid sequence with at least 90% similarity to SEQ ID NO: 19 and an amino acid sequence with at least 90% similarity to SEQ ID NO: 23. In a preferred embodiment, the antigen is a plurality of antigens comprising the amino acid sequence of SEQ ID NO: 19 and the amino acid sequence of SEQ ID NO: 23. In some embodiments, the plurality of antigens is contained within a pool of non-covalently linked peptides. In some embodiments, the plurality of antigens is contained within a pool of non-covalently linked peptides, wherein each peptide comprises no more than one antigen. In some embodiments, the plurality of antigens is contained within a pool of non-covalently linked peptides, wherein the amino acid sequence of SEQ ID NO: 19 and the amino acid sequence of SEQ ID NO: 23 are contained within separate peptides.

In some embodiments according to any one of the methods, compositions or pluralities of modified PBMCs described herein, the modified PBMCs comprise a plurality of antigens that comprise a plurality of immunogenic epitopes. In further embodiments, following administration to an individual of the modified PBMCs comprising the plurality of antigens that comprise the plurality of immunogenic epitopes, none of the plurality of immunogenic epitopes decreases an immune response in the individual to any of the other immunogenic epitopes. In some embodiments, the antigen is a polypeptide and the immunogenic epitope is an immunogenic peptide epitope. In some embodiments, the immunogenic peptide epitope is fused to an N-terminal flanking polypeptide and/or a C-terminal flanking polypeptide. In some embodiments, the antigen is a polypeptide comprising an immunogenic peptide epitope and one or more heterologous peptide sequences. In some embodiments, the antigen is a polypeptide comprising an immunogenic peptide epitope that is flanked on the N-terminus and/or the C-terminus by heterologous peptide sequences. In some embodiments, the flanking heterologous peptide sequences are derived from disease-associated immunogenic peptides. In some embodiments, the flanking heterologous peptide sequences are non-naturally occurring sequence. In some embodiments, the flanking heterologous peptide sequences are derived from an immunogenic synthetic long peptide (SLP). In some embodiments, the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17. In some embodiments, the antigen is capable of being processed into an MHC class I-restricted peptide and/or an MHC class II-restricted peptide.

Adjuvants

As used herein, the term "adjuvant" can refer to a substance which either directly or indirectly modulates and/or engenders an immune response. In some embodiments of the invention, an adjuvant is used to condition a population of PBMCs (i.e, the PBMCs are incubated with an adjuvant prior to administration to an individual). In some instances, the adjuvant is administered in conjunction with an antigen to effect enhancement of an immune response to the antigen as compared to antigen alone. Therefore, adjuvants can be used to boost elicitation of an immune cell response (e.g. T cell response) to an antigen. In some embodiments, the invention provides PBMCs modified to comprise intracellularly an antigen (such as an HPV antigen) and intracellularly an adjuvant. In some embodiments, the PBMCs perturbed as described herein are incubated with both the antigen and an adjuvant. Exemplary adjuvants include, without limitation, stimulator of interferon genes (STING) agonists, retinoic acid-inducible gene I (RIG-I) agonists, and agonists for TLR3, TLR4, TLR7, TLR8 and/or TLR9. Exemplary adjuvants include, without limitation, CpG ODN, interferon-α (IFN-α), polyinosinic:polycytidylic acid (polyI:C), imiquimod (R837), resiquimod (R848), or lipopolysaccharide (LPS). In some embodiments, the adjuvant is CpG ODN, LPS, IFN-α, STING agonists, RIG-I agonists, poly I:C, R837, R848, a TLR3 agonist, a TLR4 agonist or a TLR 9 agonist. In particular embodiments, the adjuvant is a CpG ODN. In some embodiments, the adjuvant is a CpG ODN. In some embodiments, the CpG ODN is a Class A CpG ODN, a Class B CpG ODN, or a Class C CpG ODN. In some embodiments, the CpG ODN adjuvant comprise of a selection from the group of CpG ODN 1018, CpG ODN 1585, CpG ODN 2216, CpG ODN 2336, CpG ODN 1668, CpG ODN 1826, CPG ODN 2006, CpG ODN 2007, CpG ODN BW006, CpG ODN D-SL01, CpG ODN 2395, CpG ODN M362, CpG ODN D-SL03. In some embodiments, the CpG ODN adjuvant is CpG ODN 1826 (TC-CATGACGTTCCTGACGTT (SEQ ID NO: 30)) or CpG ODN 2006 (also known as CpG 7909) (TCGTCGTTTTGTCGTTTTGTCGTT (SEQ ID NO: 31)) oligonucleotide. In some embodiments, the adjuvant is CpG 7909. In some embodiments, the RIG-I agonist comprises polyinosinic:polycytidylic acid (polyI:C). Multiple adjuvants can also be used in conjunction with antigens to enhance the elicitation of immune response. In some embodiments, the modified PBMCs comprise more than one adjuvant. Multiple adjuvants can also be used in conjunction with antigens to enhance the elicitation of immune response. In some embodiments, the modified PBMCs comprise more than one adjuvant. In some embodiments, the modified PBMCs comprise any combination of the adjuvants CpG ODN, LPS, IFN-α, STING agonists, RIG-I agonists, poly I:C, R837, R848, a TLR3 agonist, a TLR4 agonist or a TLR 9 agonist.

In any of the embodiments described herein, unless otherwise indicated, the adjuvant may refer to (a) an adjuvant that is incubated with and passes through a perturbed input PBMCs, (b) an adjuvant incubated with PBMCs for the PBMCs to condition, (c) an adjuvant co-administered with modified PBMCs to an individual.

In some embodiments, the concentration of adjuvant incubated with the perturbed input PBMCs is between about 0.01 µM and about 10 mM. For example, in some embodiments, the concentration of adjuvant incubated with the perturbed input PBMCs is any of less than about 0.01 µM, about 0.1 µM, about 1 µM, about 10 µM, about 100 µM, about 1 mM or about 10 mM. In some embodiments, the concentration of adjuvant incubated with the perturbed input PBMCs is greater than about 10 mM. In some embodiments, the concentration of adjuvant incubated with the perturbed input PBMCs is any of between about 0.01 µM and about 0.1 µM, between about 0.1 µM and about 1 µM, between about 1 µM and about 10 µM, between about 10 µM and about 100 µM, between about 100 µM and about 1 mM, or between 1 mM and about 10 mM. In some embodiments, the concentration of adjuvant incubated with the perturbed input PBMCs is between about 0.1 µM and about 1 mM. In some embodiments, the concentration of adjuvant incubated with the perturbed input PBMCs is between about 0.1 µM and about 10 µM. In some embodiments, the concentration of adjuvant incubated with the perturbed input PBMCs is 1 µM.

In some embodiments, the concentration of antigen incubated with the perturbed input PBMCs is between about 0.01 µM and about 10 mM. For example, in some embodiments, the concentration of antigen incubated with the perturbed input PBMCs is any of less than about 0.01 µM, about 0.1

μM, about 1 μM, about 10 μM, about 100 μM, about 1 mM or about 10 mM. In some embodiments, the concentration of antigen incubated with the perturbed input PBMCs is greater than about 10 mM. In some embodiments, the concentration of antigen incubated with the perturbed input PBMCs is any of between about 0.01 μM and about 0.1 μM, between about 0.1 μM and about 1 μM, between about 1 μM and about 10 μM, between about 10 μM and about 100 μM, between about 100 μM and about 1 mM, or between 1 mM and about 10 mM. In some embodiments, the concentration of antigen incubated with the perturbed input PBMCs is between about 0.1 μM and about 1 mM. In some embodiments, the concentration of antigen incubated with the perturbed input PBMCs is between about 0.1 μM and about 10 μM. In some embodiments, the concentration of antigen incubated with the perturbed input PBMCs is 1 μM.

In some embodiments, the molar ratio of antigen to adjuvant incubated with the perturbed input PBMCs is any of between about 10000:1 to about 1:10000. For example, in some embodiments, the molar ratio of antigen to adjuvant incubated with the perturbed input PBMCs is about any of 10000:1, about 1000:1, about 100:1, about 10:1, about 1:1, about 1:10, about 1:100, about 1:1000, or about 1:10000. In some embodiments, the molar ratio of antigen to adjuvant incubated with the perturbed input PBMCs is any of between about 10000:1 and about 1000:1, between about 1000:1 and about 100:1, between about 100:1 and about 10:1, between about 10:1 and about 1:1, between about 1:1 and about 1:10, between about 1:10 and about 1:100, between about 1:100 and about 1:1000, between about 1:1000 and about 1:10000. In some embodiments, the molar ratio of antigen to adjuvant incubated with the perturbed input PBMCs is about 200:1. In some embodiments, the molar ratio of antigen to adjuvant incubated with the perturbed input PBMCs is about 20:1.

In some embodiments, the modified PBMCs comprise the adjuvant at a concentration between about 1 nM and about 1 mM. For example, in some embodiments, the modified PBMCs comprise the adjuvant at a concentration of any of less than about 0.01 μM, about 0.1 μM, about 1 μM, about 10 μM, about 100 μM, about 1 mM or about 10 mM. In some embodiments, the modified PBMCs comprise the adjuvant at a concentration of greater than about any of 10 mM. in some embodiments, the modified PBMCs comprise the adjuvant at a concentration of any of between about 1 nM to about 10 nM, about 0.1 μM and about 1 μM, between about 1 μM and about 10 μM, between about 10 μM and about 100 μM, between about 100 μM and about 1 mM, or between 1 mM and about 10 mM. In some embodiments, the modified PBMCs comprise the adjuvant at a concentration between about 0.1 μM and about 1 mM. In some embodiments, the modified PBMCs comprise the adjuvant at a concentration of about 1 μM.

In some embodiments, the modified PBMCs comprise the antigen at a concentration between about 1 nM and about 1 mM. For example, in some embodiments, the modified PBMCs comprises the antigen at a concentration of any of less than about 0.01 μM, about 0.1 μM, about 1 μM, about 10 μM, about 100 μM, about 1 mM or about 10 mM. In some embodiments, the modified PBMCs comprise the antigen at a concentration of greater than about any of 10 mM. in some embodiments, the modified PBMCs comprise the antigen at a concentration of any of between about 1 nM to about 10 nM, about 0.1 μM and about 1 μM, between about 1 μM and about 10 μM, between about 10 μM and about 100 μM, between about 100 μM and about 1 mM, or between 1 mM and about 10 mM. In some embodiments, the modified PBMCs comprise the antigen at a concentration between about 0.1 μM and about 1 mM. In some embodiments, the modified PBMCs comprise the antigen at a concentration of about 1 μM.

In some embodiments, the modified PBMCs comprise the nucleic acid encoding the antigen at a concentration between about 1 nM and about 1 mM. In some embodiments, the modified PBMCs comprises the nucleic acid encoding the antigen at a concentration of any of less than about 0.1 nM, about 1 nM, about 0.01 μM, about 0.1 μM, about 1 μM, about 10 μM, about 100 μM, about 1 mM or about 10 mM. In some embodiments, the modified PBMCs comprise the nucleic acid encoding the antigen at a concentration of greater than about 10 mM. In some embodiments, the modified PBMCs comprise the nucleic acid encoding the antigen at a concentration of any of between about 0.1 nM to about 1 nM, about 1 nM to about 10 nM, about 10 nM to about 100 nM, about 0.1 μM and about 1 μM, between about 1 μM and about 10 μM, between about 10 μM and about 100 μM, between about 100 μM and about 1 mM, or between 1 mM and about 10 mM. In some embodiments, the modified PBMCs comprise the nucleic acid encoding the antigen at a concentration between about 10 nM and about 100 nM. In some embodiments, the modified PBMCs comprise the nucleic acid encoding the antigen at a concentration between about 1 nM and about 10 nM. In some embodiments, the modified PBMCs comprise the antigen at a concentration of about 50 nM. In some embodiments, the nucleic acid is an mRNA.

In some embodiments, the modified PBMCs comprise the nucleic acid encoding the antigen at a concentration between about 0.01 μg/mL to about 10 mg/mL. In some embodiments, the modified PBMCs comprises the nucleic acid encoding the antigen at a concentration of any of less than about 0.01 μg/mL, about 0.1 μg/mL, about 1 μg/mL, about 10 μg/mL, about 100 μg/mL, about 1 mg/mL or about 10 mg/mL. In some embodiments, the modified PBMCs comprise the nucleic acid encoding the antigen at a concentration of greater than about 10 μg/mL. in some embodiments, the modified PBMCs comprise the nucleic acid encoding the antigen at a concentration of any of between about 0.001 μg/mL to about 0.1 μg/mL, about 0.1 μg/mL and about 1 μg/mL, between about 1 μg/mL and about 10 μg/mL, between about 10 μg/mL and about 100 μg/mL, between about 100 μg/mL and about 1 mg/mL, or between 1 mg/mL and about 10 mg/mL. In some embodiments, the modified PBMCs comprise the nucleic acid encoding the antigen at a concentration between about 0.1 μg/mL and about 1 mg/mL. In some embodiments, the modified PBMCs comprise the antigen at a concentration of any one of about 1 μg/mL, about 2 μg/mL, about 5 μg/mL, about 10 μg/mL, about 20 μg/mL, about 25 mg/mL, about 40 μg/mL, about 50 μg/mL, about 70 μg/mL, about 100 μg/mL, about 200 μg/mL, or about 300 μg/mL, or about 500 μg/mL. In some embodiments, the nucleic acid is an mRNA.

In some embodiments, the molar ratio of antigen to adjuvant in the modified PBMCs is any of between about 10000:1 to about 1:10000. For example, in some embodiments, the molar ratio of antigen to adjuvant in the modified PBMCs is about any of 10000:1, about 1000:1, about 100:1, about 10:1, about 1:1, about 1:10, about 1:100, about 1:1000, or about 1:10000. In some embodiments, the molar ratio of antigen to adjuvant in the modified PBMCs is any of between about 10000:1 and about 1000:1, between about 1000:1 and about 100:1, between about 100:1 and about 10:1, between about 10:1 and about 1:1, between about 1:1 and about 1:10, between about 1:10 and about 1:100, between about 1:100 and about 1:1000, between about 1:1000 and about 1:10000. In some embodiments, the molar ratio of antigen to adjuvant in the modified PBMCs is about 200:1. In some embodiments, the molar ratio of antigen to adjuvant in the modified PBMCs is about 20:1.

In some embodiments, the antigen complexes with itself, with other antigens, or with the adjuvant. In some embodiments, the modified PBMCs comprise a complex comprising: a) the antigen, b) the antigen and at least one other antigen, and/or c) the antigen and the adjuvant.

Further Modifications of PBMC Characteristics

In some embodiments according to any one of the methods, compositions or pluralities of modified PBMCs described herein, the plurality of modified PBMCs further comprises an agent that enhances the viability and/or function of the modified PBMCs as compared to a corresponding plurality of modified PBMCs that does not comprise the agent. In some embodiments, the plurality of modified PBMCs further comprises an agent that enhances the viability and/or function of the modified PBMCs upon freeze-thaw cycle as compared to a corresponding plurality of modified PBMCs that does not comprise the agent. In some embodiments, the agent is a cyropreservation agent and/or a hypothermic preservation agent. In some embodiments, the cyropreservation agent nor the hypothermic preservation agent cause not more than 10% or 20% of cell death in a plurality of PBMCs comprising the agent compared to a corresponding plurality of PBMCs that does not comprise the agent before any freeze-thaw cycles. In some embodiments, at least about 70%, about 80%, or about 90% of the plurality of modified PBMCs are viable after up to 1, 2, 3, 4, 5 freeze-thaw cycles. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is human albumin. In some embodiments, the agent is one or more of: a divalent metal cation, glucose, ATP, potassium, glycerol, trehalose, D-sucrose, PEG1500, L-arginine, L-glutamine, or EDTA. In some embodiments, the divalent metal cation is one more of $Mg^{2+}$, $Zn^{2+}$ or $Ca^{2+}$. In some embodiments, the agent is one or more of: sodium pyruvate, adenine, trehalose, dextrose, mannose, sucrose, human serum albumin (HSA), DMSO, HEPES, glycerol, glutathione, inosine, dibasic sodium phosphate, monobasic sodium phosphate, sodium metal ions, potassium metal ions, magnesium metal ions, chloride, acetate, gluoconate, sucrose, potassium hydroxide, or sodium hydroxide. In some embodiments, the agent is one or more of: Sodium pyruvate, adenine, Rejuvesol®, trehalose, dextrose, mannose, sucrose, human serum albumin (HSA), PlasmaLyte®, DMSO, Cryostor® CS2, Cryostor® CS5, Cryostor® CS10, Cryostor® CS15, HEPES, glycerol, glutathione, HypoThermosol®.

In some embodiments according to any one of the methods, compositions or pluralities of modified PBMCs described herein, the modified PBMCs are further modified to increase expression of one or more of co-stimulatory molecules. In some embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the plurality of modified PBMCs comprises a nucleic acid that results in increased expression of the one or more co-stimulatory molecules. In some embodiments, the plurality of modified PBMCs comprises an mRNA that results in increased expression of the one or more co-stimulatory molecules. In some embodiments, the co-stimulatory molecule is a Signal 2 effector in stimulating T cell activation.

In some embodiments according to any one of the methods, compositions or pluralities of modified PBMCs described herein, the modified PBMCs are further modified to increase expression of one or more cytokines. In some embodiments, the cytokine is one or more of IL-2, IL-12, IL-21, or IFNα2. In some embodiments, the plurality of modified PBMCs comprises a nucleic acid that results in increased expression and/or secretion of the one or more cytokines. In some embodiments, the cytokine is a Signal 3 effector in stimulating T cell activation.

In some embodiments according to any one of the methods, compositions or pluralities of modified PBMCs described herein, at least one cell in the plurality of modified PBMCs is positive for expression of HLA-A2. In some embodiments, the modified PBMCs comprise a further modification to modulate MHC class I expression. In some embodiments, the modified PBMCs comprise a further modification to modulate expression of HLA-A02 MHC class I. In some embodiments, the modified PBMCs comprise a further modification to modulate MHC class II expression. In some embodiments, an innate immune response mounted in an individual in response to administration, in an allogeneic context, of the modified PBMCs is reduced compared to an innate immune response mounted in an individual in response to administration, in an allogeneic context, of corresponding modified PBMCs that do not comprise the further modification. In some embodiments, the circulating half-life of the modified PBMCs in an individual to which they were administered is increased compared to the circulating half-life of corresponding modified PBMCs that do not comprise the further modification in an individual to which they were administered. In some embodiments, the circulating half-life of the modified PBMCs in an individual to which they were administered is increased by about any one of 10%, 25%, 50%, 75%, 100%, 2-fold, 3-fold, 4-fold, 5-fold, 10-fold, 25-fold, 50-fold, 100-fold, 200-fold, or 500-fold or more compared to the circulating half-life of corresponding modified PBMCs that do not comprise the further modification in an individual to which they were administered. In some embodiments, the circulating half-life of the modified PBMCs in an individual to which they were administered is essentially the same as the circulating half-life of corresponding modified PBMCs that do not comprise the further modification in an individual to which they were administered.

In some embodiments according to any one of the methods, compositions or pluralities of modified PBMCs described herein, the process further comprises a step of incubating the input PBMCs and/or the modified PBMCs with an agent that enhances the viability and/or function of the modified PBMCs as compared to corresponding modified PBMCs prepared without the further incubation step.

Conditioning of PBMCs

In some embodiments according to any one of methods, compositions or pluralities of modified PBMCs described herein; the plurality of modified PBMCs is conditioned. In further embodiments, the plurality of modified PBMCs is matured. In some embodiments, the plurality of PBMCs is conditioned subsequent to constriction mediated delivery. In some embodiments, the plurality of modified PBMCs comprising the antigen and/or adjuvant is incubated with a second adjuvant for a sufficient time for the modified PBMCs comprising the constriction-delivered antigen and/or adjuvant to condition, thereby generating a conditioned plurality of modified PBMCs comprising the antigen and/or the adjuvant. In some embodiments, the plurality of modified PBMCs comprising the antigen and/or the adjuvant is isolated from the cell suspension before incubation with the second adjuvant to condition the modified PBMCs. In some embodiments, the plurality of PBMCs is conditioned subsequent to constriction mediated delivery. In some embodiments, the plurality of modified PBMCs comprising the constriction-delivered antigen and/or adjuvant is incubated with a second adjuvant for a sufficient time for the modified PBMCs comprising the constriction-delivered antigen and/or adjuvant to condition, thereby generating a conditioned plurality of modified PBMCs comprising the antigen and/or the adjuvant. In some aspects, there is provided a conditioned plurality of modified PBMCs comprising an antigen and/or an adjuvant, prepared by a process comprising the steps of: a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen and/or the adjuvant to pass through to form a plurality of perturbed input PBMCs; b) incubating the plurality of perturbed input PBMCs with the antigen and/or the adjuvant for a sufficient time to allow the antigen to enter the perturbed input PBMCs, thereby generating a plurality of modified PBMCs comprising the antigen and/or the adjuvant; and c) incubating the plurality of modified PBMCs comprising the constriction-delivered antigen and/or adjuvant with a second adjuvant for a sufficient time for the modified PBMCs comprising the constriction-delivered antigen and/or adjuvant to condition, thereby generating the conditioned plurality of modified PBMCs comprising the antigen and/or the adjuvant. In some embodiments, the process further comprises isolating the plurality of modified PBMCs comprising the antigen and/or the adjuvant from the cell suspension before incubation with the second adjuvant to condition the modified PBMCs. In some embodiments, the constriction-delivered adjuvant is the same as the conditioning adjuvant. In some embodiments, the constriction-delivered adjuvant is different from the conditioning adjuvant.

In some embodiments, the concentration of antigen incubated with the modified PBMCs is between about 0.01 µM and about 10 mM. For example, in some embodiments, the concentration of antigen incubated with the modified PBMCs is any of less than about 0.01 µM, about 0.1 µM, about 1 µM, about 10 µM, about 100 µM, about 1 mM or about 10 mM. In some embodiments, the concentration of antigen incubated with the modified PBMCs is greater than about 10 mM. In some embodiments, the concentration of antigen incubated with the modified PBMCs is any of between about 0.01 µM and about 0.1 µM, between about 0.1 µM and about 1 µM, between about 1 µM and about 10 µM, between about 10 µM and about 100 µM, between about 100 µM and about 1 mM, or between 1 mM and about 10 mM. In some embodiments, the concentration of antigen incubated with the modified PBMCs is between about 0.1 µM and about 1 mM. In some embodiments, the concentration of antigen incubated with the modified PBMCs is between about 0.1 µM and about 10 µM. In some embodiments, the concentration of antigen incubated with the modified PBMCs is 1 µM.

In some embodiments according to any one of methods, compositions or pluralities of modified PBMCs described herein, the plurality of modified PBMCs is incubated with the adjuvant for about 1 to about 24 hours for the modified PBMCs to condition. In some embodiments, the plurality of modified PBMCs is incubated with the adjuvant for about 2 to about 10 hours for the modified PBMCs to condition. In some embodiments, the plurality of modified PBMCs is incubated with the adjuvant for about 3 to about 6 hours for the modified PBMCs to condition. In some embodiments, the plurality of modified PBMCs is incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the modified PBMCs to condition. In some embodiments, the plurality of modified PBMCs is incubated with the adjuvant for about 4 hours for the modified PBMCs to condition.

In some embodiments, the plurality of PBMCs is conditioned prior to constriction mediated delivery. In some embodiments, the plurality of input PBMCs is incubated with an adjuvant for a sufficient time for the input PBMCs to condition, thereby generating a conditioned plurality of input PBMCs. In some embodiments, there is provided a conditioned plurality of modified PBMCs comprising an antigen, prepared by a process comprising the steps of: a) incubating a plurality of input PBMCs with an adjuvant for a sufficient time for the input PBMCs to condition, thereby generating a conditioned plurality of input PBMCs; b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and c) incubating the conditioned plurality of perturbed input PBMCs with the antigen for a sufficient time to allow the antigen to enter the perturbed input PBMCs, thereby generating the conditioned plurality of modified PBMCs comprising the antigen. In some embodiments, the process further comprises isolating the conditioned plurality of input PBMCs from the conditioning adjuvant before passing the conditioned plurality of input PBMCs through a cell-deforming constriction. In some embodiments, there is provided a conditioned plurality of modified PBMCs comprising an antigen and/or an adjuvant, prepared by a process comprising the steps of: a) incubating a plurality of input PBMCs with a conditioning adjuvant for a sufficient time for the input PBMCs to condition, thereby generating a conditioned plurality of input PBMCs; b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen and/or the adjuvant to pass through to form a conditioned plurality of perturbed input PBMCs; and c) incubating the conditioned plurality of perturbed input PBMCs with the antigen and/or the adjuvant for a sufficient time to allow the antigen and/or the adjuvant to enter the perturbed input PBMCs, thereby generating the conditioned plurality of modified PBMCs comprising the antigen and/or the adjuvant. In some embodiments, the process further comprises isolating the conditioned plurality of input PBMCs from the conditioning adjuvant before passing the conditioned plurality of input PBMCs through a cell-deforming constriction. In some embodiments, the constriction-delivered adjuvant is the same as the conditioning adjuvant. In some embodiments, the constriction-delivered adjuvant is different from the conditioning adjuvant.

In some embodiments, the concentration of antigen incubated with the input PBMCs is between about 0.01 µM and about 10 mM. For example, in some embodiments, the concentration of antigen incubated with the input PBMCs is any of less than about 0.01 µM, about 0.1 µM, about 1 µM, about 10 µM, about 100 µM, about 1 mM or about 10 mM. In some embodiments, the concentration of antigen incubated with the input PBMCs is greater than about 10 mM. In some embodiments, the concentration of antigen incubated with the input PBMCs is any of between about 0.01 µM and about 0.1 µM, between about 0.1 µM and about 1 µM, between about 1 µM and about 10 µM, between about 10 µM and about 100 µM, between about 100 µM and about 1 mM, or between 1 mM and about 10 mM. In some embodiments, the concentration of antigen incubated with the input PBMCs is between about 0.1 µM and about 1 mM. In some embodiments, the concentration of antigen incubated with the input PBMCs is between about 0.1 µM and about 10 µM. In some embodiments, the concentration of antigen incubated with the input PBMCs is 1 µM.

In some embodiments according to any one of methods, compositions or pluralities of modified PBMCs described herein, the plurality of input PBMCs is incubated with the adjuvant for about 1 to about 24 hours for the input PBMCs to condition. In some embodiments, the plurality of input PBMCs is incubated with the adjuvant for about 2 to about 10 hours for the input PBMCs to condition. In some embodiments, the plurality of input PBMCs is incubated with the adjuvant for about 3 to about 6 hours for the input PBMCs to condition. In some embodiments, the plurality of input PBMCs is incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the input PBMCs to condition. In some embodiments, the plurality of input PBMCs is incubated with the adjuvant for about 4 hours for the input PBMCs to condition.

In some embodiments, there is provided a conditioned plurality of PBMCs comprising an antigen, prepared by incubating the plurality of PBMCs comprising the antigen with an adjuvant for a sufficient time for the PBMCs to condition, thereby generating the conditioned plurality of PBMCs comprising the antigen. In some embodiments, there is provided a conditioned plurality of PBMCs comprising an antigen, prepared by incubating the plurality of PBMCs with an adjuvant for a sufficient time for the PBMCs to condition prior to introducing the antigen to the PBMCs, thereby generating the conditioned plurality of PBMCs comprising the antigen.

In some embodiments according to any one of the methods, compositions or pluralities of PBMCs described above, the concentration of antigen incubated with the PBMCs is between about 0.01 µM and about 10 mM. For example, in some embodiments, the concentration of antigen incubated with the PBMCs is any of less than about 0.01 µM, about 0.1 µM, about 1 µM, about 10 µM, about 100 µM, about 1 mM or about 10 mM. In some embodiments, the concentration of antigen incubated with the PBMCs is greater than about 10 mM. In some embodiments, the concentration of antigen incubated with the PBMCs is any of between about 0.01 µM and about 0.1 µM, between about 0.1 µM and about 1 µM, between about 1 µM and about 10 µM, between about 10 µM and about 100 µM, between about 100 µM and about 1 mM, or between 1 mM and about 10 mM. In some embodiments, the concentration of antigen incubated with the PBMCs is between about 0.1 µM and about 1 mM. In some embodiments, the concentration of antigen incubated with the PBMCs is between about 0.1 µM and about 10 µM. In some embodiments, the concentration of antigen incubated with the PBMCs is 1 µM.

In some embodiments according to any of the conditioned plurality of PBMCs described herein, the plurality of PBMCs is incubated with the adjuvant for about 1 to about 24 hours for the PBMCs to condition. In some embodiments, the plurality of PBMCs is incubated with the adjuvant for about 2 to about 10 hours for the PBMCs to condition. In some embodiments, the plurality of PBMCs is incubated with the adjuvant for about 3 to about 6 hours for the PBMCs to condition. In some embodiments, the plurality of PBMCs is incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the PBMCs to condition. In some embodiments, the plurality of PBMCs is incubated with the adjuvant for about 4 hours for the PBMCs to condition.

In some embodiments according to any one of the conditioned plurality of PBMCs described herein, one or more co-stimulatory molecules are upregulated in the conditioned plurality of modified PBMCs compared to an unconditioned plurality of modified PBMCs. In some embodiments, one or more co-stimulatory molecules are upregulated in a subpopulation of cells in the conditioned plurality of modified PBMCs compared to the subpopulation of cells in an unconditioned plurality of modified PBMCs. In some embodiments, one or more co-stimulatory molecules are upregulated in the B cells of the conditioned plurality of modified PBMCs compared to the B cells in an unconditioned plurality of modified PBMCs. In some embodiments, the co-stimulatory molecule is CD80 and/or CD86. In some embodiments, the co-stimulatory molecule is CD86. In some embodiments, the CD80 and/or CD86 is upregulated in the B cells of the conditioned plurality of modified PBMCs by more than about 1.2-fold, 1.5-fold, 1.8-fold, 2-fold, 3-fold, 4-fold, 5-fold, 8-fold, or more than 10-fold compared to the B cells in an unconditioned plurality of modified PBMCs. In some embodiments, the CD80 and/or CD86 is upregulated in the B cells of the conditioned plurality of modified PBMCs by any of about 1.2-fold to about 1.5-fold, about 1.5-fold to about 1.8-fold, about 1.8-fold to about 2-fold, about 2-fold to about 3-fold, about 3-fold to about 4-fold, about 4-fold to about 5-fold, about 5-fold to about 8-fold, about 8-fold to about 10-fold, about 10-fold to about 20-fold, about 20-fold to about 50-fold, about 50-fold to about 100-fold, about 100-fold to about 200-fold, about 200-fold to about 500-fold, or more than about 500-fold compared to the B cells in an unconditioned plurality of modified PBMCs. In some embodiments, the expression of one or more of IFN-γ, IL-6, MCP-1, MIP-1β, IP-10, or TNF-α is increased in the conditioned plurality of modified PBMCs compared to an unconditioned plurality of modified PBMCs. In some embodiments, the expression of one or more of IFN-γ, IL-6, MCP-1, MIP-1β, IP-10, or TNF-α is increased a subpopulation of cells in the conditioned plurality compared to the subpopulation of cells in an unconditioned plurality of modified PBMCs. In some embodiments, the expression of one or more of IFN-γ, IL-6, MCP-1, MIP-1β, IP-10, or TNF-α is increased by about 1.2-fold, 1.5-fold, 1.8-fold, 2-fold, 3-fold, 4-fold, 5-fold, 8-fold, or more than 10-fold in the conditioned plurality of modified PBMCs compared to an unconditioned plurality of modified PBMCs. In some embodiments, the expression of one or more of IFN-γ, IL-6, MCP-1, MIP-1β, IP-10, or TNF-α is increased by any of about 1.2-fold to about 1.5-fold, about 1.5-fold to about 1.8-fold, about 1.8-fold to about 2-fold, about 2-fold to about 3-fold, about 3-fold to about 4-fold, about 4-fold to about 5-fold, about 5-fold to about 8-fold, about 8-fold to about 10-fold, about 10-fold to about 20-fold, about 20-fold to about 50-fold, about 50-fold to about 100-fold, about 100-fold to about 200-fold, about 200-fold to about 500-fold, or more than about 500-fold in the conditioned plurality of modified PBMCs compared to an unconditioned plurality of modified PBMCs.

In some embodiments according to any one of the methods, compositions or pluralities of modified PBMCs described herein, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs. In some embodiments, the plurality of PBMCs comprises a nucleic acid encoding an antigen. In some embodiments, the plurality of PBMCs comprises an mRNA encoding an antigen.

Microfluidic Systems and Components Thereof
Microfluidic Channels to Provide Cell-Deforming Constrictions In some embodiments, the invention provides methods for modulating an immune response by passing a cell suspension comprising a PBMCs through a constriction, wherein the constriction deforms the PBMCs thereby causing a perturbation of the PBMCs such that an antigen and/or adjuvant enters the PBMCs, wherein the constriction is contained within a microfluidic channel. In some embodiments, multiple constrictions can be placed in parallel and/or in series within the microfluidic channel. Exemplary microfluidic channels containing cell-deforming constrictions for use in the methods disclosed herein are described in WO2013059343. Exemplary surfaces having pores for use in the methods disclosed herein are described in WO2017041050.

In some embodiments, the microfluidic channel includes a lumen and is configured such that PBMCs suspended in a buffer can pass through, wherein the microfluidic channel includes a constriction. The microfluidic channel can be made of any one of a number of materials, including silicon, metal (e.g., stainless steel), plastic (e.g., polystyrene), ceramics, glass, crystalline substrates, amorphous substrates, or polymers (e.g., Poly-methyl methacrylate (PMMA), PDMS, Cyclic Olefin Copolymer (COC), etc.). Fabrication of the microfluidic channel can be performed by any method known in the art, including dry etching, wet etching, photolithography, injection molding, laser ablation, or SU-8 masks.

In some embodiments, the constriction within the microfluidic channel includes an entrance portion, a centerpoint, and an exit portion. In some embodiments, the length, depth, and width of the constriction within the microfluidic channel can vary. In some embodiments, the diameter of the constriction within the microfluidic channel is a function of the diameter of the input PBMCs. Methods to determine the diameter of a PBMC are known in the art; for example, high-content imaging, cell counters or flow cytometry. In some embodiments, the diameter of the constriction within the microfluidic channel is about 20%, to about 99% of the mean diameter of the plurality of input PBMCs. In some embodiments, the constriction size is about 20%, about 30%, about 40%, about 50%, about 60%, about 70%, about 80%, about 90%, or about 99% of the mean diameter of PBMCs or mean diameter of a subpopulation of PBMCs. In some embodiments, the constriction size is about 20%, about 30%, about 40%, about 50%, about 60%, about 70%, about 80%, about 90%, or about 99% of the mean of minimum cross-sectional distance of the plurality of input PBMCs. In some embodiments, the channel comprises a constriction width of between about 2 μm and about 10 μm or any width or range of widths therebetween. In some embodiments, the channel comprises a constriction width of between about 3 μm and about 10 μm. In some embodiments, the channel comprises a constriction width of between about 3 μm and about 6 μm. In some embodiments, the channel comprises a constriction width of between about 4.2 μm and about 4.8 μm. For example, the constriction width can be any one of about 2 μm, about 2.5 μm, about 3 μm, about 3.5 μm, about 4 μm, about 4.5 μm, about 5 μm, about 5.5 μm, about 6 μm, about 6.5 μm, or about 7 μm. In some embodiments, the channel comprises a constriction length of about 10 μm and a constriction width of about 3.5 μm. In some embodiments, the channel comprises a constriction length of about 10 μm and a constriction width of about 4 μm. In some embodiments, the channel comprises a constriction length of about 10 μm and a constriction width of about 4.5 μm. The cross-section of the channel, the entrance portion, the centerpoint, and the exit portion can also vary. For example, the cross-sections can be circular, elliptical, an elongated slit, square, hexagonal, or triangular in shape. The entrance portion defines a constriction angle, wherein the constriction angle is optimized to reduce clogging of the channel and optimized for enhanced delivery of a compound into the PBMCs. The angle of the exit portion can vary as well. For example, the angle of the exit portion is configured to reduce the likelihood of turbulence that can result in non-laminar flow. In some embodiments, the walls of the entrance portion and/or the exit portion are linear. In other embodiments, the walls of the entrance portion and/or the exit portion are curved.

Surface having pores to provide cell-deforming constrictions

In some embodiments, the invention provides methods for modulating an immune response by passing a cell suspension comprising a plurality of PBMCs through a constriction, wherein the constriction deforms the PBMCs thereby causing a perturbation of the PBMCs such that an antigen and/or adjuvant enters the PBMCs, wherein the constriction is a pore or contained within a pore. In some embodiments, the pore is contained in a surface. Exemplary surfaces having pores for use in the methods disclosed herein are described in WO2017041050.

The surfaces as disclosed herein can be made of any one of a number of materials and take any one of a number of forms. In some embodiments, the surface is a filter. In some embodiments, the surface is a membrane. In some embodiments, the filter is a tangential flow filter. In some embodiments, the surface is a sponge or sponge-like matrix. In some embodiments, the surface is a matrix.

In some embodiments the surface is a tortuous path surface. In some embodiments, the tortuous path surface comprises cellulose acetate. In some embodiments, the surface comprises a material selected from, without limitation, synthetic or natural polymers, polycarbonate, silicon, glass, metal, alloy, cellulose nitrate, silver, cellulose acetate, nylon, polyester, polyethersulfone, polyacrylonitrile (PAN), polypropylene, PVDF, polytetrafluorethylene, mixed cellulose ester, porcelain, and ceramic.

The surface disclosed herein can have any shape known in the art; e.g. a 3-dimensional shape. The 2-dimensional shape of the surface can be, without limitation, circular, elliptical, round, square, star-shaped, triangular, polygonal, pentagonal, hexagonal, heptagonal, or octagonal. In some embodiments, the surface is round in shape. In some embodiments, the surface 3-dimensional shape is cylindrical, conical, or cuboidal.

The surface can have various cross-sectional widths and thicknesses. In some embodiments, the surface cross-sectional width is between about 1 mm and about 1 m or any cross-sectional width or range of cross-sectional widths therebetween. In some embodiments, the surface has a defined thickness. In some embodiments, the surface thickness is uniform. In some embodiments, the surface thickness is variable. For example, in some embodiments, portions of the surface are thicker or thinner than other portions of the surface. In some embodiments, the surface thickness varies by about 1% to about 90% or any percentage or range of percentages therebetween. In some embodiments, the surface is between about 0.01 µm to about 5 mm thick or any thickness or range of thicknesses therebetween.

The entrances and exits of the pore passage may have a variety of angles. The pore angle can be selected to minimize clogging of the pore while PBMCs are passing through. In some embodiments the flow rate through the surface is between about 0.001 mL/cm$^2$/sec to about 100 L/cm$^2$/sec or any rate or range of rates therebetween. For example, the angle of the entrance or exit portion can be between about 0 and about 90 degrees. In some embodiments, the entrance or exit portion can be greater than 90 degrees. In some embodiments, the pores have identical entrance and exit angles. In some embodiments, the pores have different entrance and exit angles. In some embodiments, the pore edge is smooth, e.g. rounded or curved. A smooth pore edge has a continuous, flat, and even surface without bumps, ridges, or uneven parts. In some embodiments, the pore edge is sharp. A sharp pore edge has a thin edge that is pointed or at an acute angle. In some embodiments, the pore passage is straight. A straight pore passage does not contain curves, bends, angles, or other irregularities. In some embodiments, the pore passage is curved. A curved pore passage is bent or deviates from a straight line. In some embodiments, the pore passage has multiple curves, e.g. about 2, 3, 4, 5, 6, 7, 8, 9, 10 or more curves.

The pores can have any shape known in the art, including a 2-dimensional or 3-dimensional shape. The pore shape (e.g., the cross-sectional shape) can be, without limitation, circular, elliptical, round, square, star-shaped, triangular, polygonal, pentagonal, hexagonal, heptagonal, and octagonal. In some embodiments, the cross-section of the pore is round in shape. In some embodiments, the 3-dimensional shape of the pore is cylindrical or conical. In some embodiments, the pore has a fluted entrance and exit shape. In some embodiments, the pore shape is homogenous (i.e. consistent or regular) among pores within a given surface. In some embodiments, the pore shape is heterogeneous (i.e. mixed or varied) among pores within a given surface.

The surfaces described herein can have a range of total pore numbers. In some embodiments, the pores encompass about 10% to about 80% of the total surface area. In some embodiments, the surface contains about $1.0 \times 10^5$ to about $1.0 \times 10^{30}$ total pores or any number or range of numbers therebetween. In some embodiments, the surface comprises between about 10 and about $1.0 \times 10^{15}$ pores/mm$^2$ surface area.

The pores can be distributed in numerous ways within a given surface. In some embodiments, the pores are distributed in parallel within a given surface. In one such example, the pores are distributed side-by-side in the same direction and are the same distance apart within a given surface. In some embodiments, the pore distribution is ordered or homogeneous. In one such example, the pores are distributed in a regular, systematic pattern or are the same distance apart within a given surface. In some embodiments, the pore distribution is random or heterogeneous. In one such example, the pores are distributed in an irregular, disordered pattern or are different distances apart within a given surface. In some embodiments, multiple surfaces are distributed in series. The multiple surfaces can be homogeneous or heterogeneous in surface size, shape, and/or roughness. The multiple surfaces can further contain pores with homogeneous or heterogeneous pore size, shape, and/or number, thereby enabling the simultaneous delivery of a range of compounds into different PBMC types.

In some embodiments, an individual pore has a uniform width dimension (i.e. constant width along the length of the pore passage). In some embodiments, an individual pore has a variable width (i.e. increasing or decreasing width along the length of the pore passage). In some embodiments, pores within a given surface have the same individual pore depths. In some embodiments, pores within a given surface have different individual pore depths. In some embodiments, the pores are immediately adjacent to each other. In some embodiments, the pores are separated from each other by a distance. In some embodiments, the pores are separated from each other by a distance of about 0.001 µm to about 30 mm or any distance or range of distances therebetween.

In some embodiments, the surface is coated with a material. The material can be selected from any material known in the art, including, without limitation, Teflon, an adhesive coating, surfactants, proteins, adhesion molecules, antibodies, anticoagulants, factors that modulate cellular function, nucleic acids, lipids, carbohydrates, or transmembrane proteins. In some embodiments, the surface is coated with polyvinylpyrrolidone (PVP). In some embodiments, the material is covalently attached to the surface. In some embodiments, the material is non-covalently attached or adsorbed to the surface. In some embodiments, the surface molecules are released as the PBMCs pass through the pores.

In some embodiments, the surface has modified chemical properties. In some embodiments, the surface is polar. In some embodiments, the surface is hydrophilic. In some embodiments, the surface is non-polar. In some embodiments, the surface is hydrophobic. In some embodiments, the surface is charged. In some embodiments, the surface is positively and/or negatively charged. In some embodiments, the surface can be positively charged in some regions and negatively charged in other regions. In some embodiments, the surface has an overall positive or overall negative charge. In some embodiments, the surface can be any one of smooth, electropolished, rough, or plasma treated. In some embodiments, the surface comprises a zwitterion or dipolar compound. In some embodiments, the surface is plasma treated.

In some embodiments, the surface is contained within a larger module. In some embodiments, the surface is contained within a syringe, such as a plastic or glass syringe. In some embodiments, the surface is contained within a plastic filter holder. In some embodiments, the surface is contained within a pipette tip.

In some embodiments according to any one of the methods, compositions or pluralities of modified PBMCs described herein, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs. In some embodiments, the one or more nucleic acids are carried in one or more vehicles, wherein the one or more vehicles are delivered to the input PBMCs. In some embodiments, the vehicle is a virus or a viral-associated particle. In some embodiments, the virus comprises one or more of: an adenovirus, an adeno-associated virus (AAV), a baculovirus, a herpes virus, or a retrovirus. In some embodiments, the virus comprises an AAV. In some embodiments, the vehicle is a lipid-based vehicle, e.g., a liposome. In some embodiments, the vehicle is a nanoparticle.

Cell Perturbations

In some embodiments, the invention provides methods for modulating an immune response by passing a cell suspension comprising PBMCs through a constriction, wherein the constriction deforms the PBMCs thereby causing a perturbation of the PBMCs such that an antigen and/or adjuvant enters the PBMCs, wherein the perturbation in the PBMCs is a breach in the PBMCs that allows material from outside the PBMCs to move into the PBMCs (e.g., a hole, tear, cavity, aperture, pore, break, gap, perforation). The deformation can be caused by, for example, mechanical strain or mechanical strain and shear forces. In some embodiments, the perturbation is a perturbation within the PBMCs cell membranes. In some embodiments, the perturbation is transient. In some embodiments, the PBMCs perturbation lasts from about $1.0 \times 10^{-9}$ seconds to about 2 hours, or any time or range of times therebetween. In some embodiments, the PBMCs perturbation lasts for about $1.0 \times 10^{-9}$ second to about 1 second, about 1 second to about 1 minute, or about 1 minute to about 1 hour. In some embodiments, the PBMCs perturbation lasts for between any one of about $1.0 \times 10^{-9}$ to about $1.0 \times 10^{-1}$, about $1.0 \times 10^{-9}$ to about $1.0 \times 10^{-2}$, about $1.0 \times 10^{-9}$ to about $1.0 \times 10^{-3}$, about $1.0 \times 10^{-9}$ to about $1.0 \times 10^{-4}$, about $1.0 \times 10^{-9}$ to about $1.0 \times 10^{-5}$, about $1.0 \times 10^{-9}$ to about $1.0 \times 10^{-6}$, about $1.0 \times 10^{-9}$ to about $1.0 \times 10^{-7}$, or about $1.0 \times 10^{-9}$ to about $1.0 \times 10^{-8}$ seconds. In some embodiment, the PBMCs perturbation lasts for any one of about $1.0 \times 10^{-8}$ to about $1.0 \times 10^{-1}$, about $1.0 \times 10^{-7}$ to about $1.0 \times 10^{-1}$, about $1.0 \times 10^{-6}$ to about $1.0 \times 10^{-1}$, about $1.0 \times 10^{-5}$ to about $1.0 \times 10^{-1}$, about $1.0 \times 10^{-4}$ to about $1.0 \times 10^{-1}$, about $1.0 \times 10^{-3}$ to about $1.0 \times 10^{-1}$, or about $1.0 \times 10^{-2}$ to about $1.0 \times 10^{-1}$ seconds. The PBMCs perturbations (e.g., pores or holes) created by the methods described herein are not formed as a result of assembly of protein subunits to form a multimeric pore structure such as that created by complement or bacterial hemolysins.

As the PBMCs passes through the constriction, the constriction temporarily imparts injury to the PBMCs membranes that allows for passive diffusion of material through the perturbation. In some embodiments, the PBMCs are only deformed for a brief period of time, on the order of 100 μs to minimize the chance of activating apoptotic pathways through cell signaling mechanisms, although other durations are possible (e.g., ranging from nanoseconds to hours). In some embodiments, the PBMCs are deformed for about $1.0 \times 10^{-9}$ seconds to about 2 hours, or any time or range of times therebetween. In some embodiments, the PBMCs are deformed for about $1.0 \times 10^{-9}$ second to about 1 second, about 1 second to about 1 minute, or about 1 minute to about 1 hour. In some embodiments, the PBMCs are deformed for between any one of about $1.0 \times 10^{-9}$ to about $1.0 \times 10^{-1}$, about $1.0 \times 10^{-9}$ to about $1.0 \times 10^{-2}$, about $1.0 \times 10^{-9}$ to about $1.0 \times 10^{-3}$, about $1.0 \times 10^{-9}$ to about $1.0 \times 10^{-4}$, about $1.0 \times 10^{-9}$ to about $1.0 \times 10^{-5}$, about $1.0 \times 10^{-9}$ to about $1.0 \times 10^{-6}$, about $1.0 \times 10^{-9}$ to about $1.0 \times 10^{-7}$, or about $1.0 \times 10^{-9}$ to about $1.0 \times 10^{-5}$ seconds. In some embodiment, the PBMCs are deformed for any one of about $1.0 \times 10^{-8}$ to about $1.0 \times 10^{-1}$, about $1.0 \times 10^{-7}$ to about $1.0 \times 10^{-1}$, about $1.0 \times 10^{-6}$ to about $1.0 \times 10^{-1}$, about $1.0 \times 10^{-5}$ to about $1.0 \times 10^{-1}$, about $1.0 \times 10^{-4}$ to about $1.0 \times 10^{-1}$, about $1.0 \times 10^{-3}$ to about $1.0 \times 10^{-1}$, or about $1.0 \times 10^{-2}$ to about $1.0 \times 10^{-1}$ seconds. In some embodiments, deforming the PBMCs includes deforming the PBMCs for a time ranging from, without limitation, about 1 μs to at least about 750 μs, e.g., at least about 1 μs, 10 μs, 50 μs, 100 μs, 500 μs, or 750 μs.

In some embodiments, the passage of the antigen and/or adjuvant into the PBMCs occurs simultaneously with the PBMCs passing through the constriction and/or the perturbation of the PBMCs. In some embodiments, passage of the compound into the PBMCs occurs after the PBMCs pass through the constriction. In some embodiments, passage of the compound into the PBMCs occurs on the order of minutes after the PBMCs pass through the constriction. In some embodiments, the passage of the compound into the PBMCs occurs from about $1.0 \times 10^{-2}$ seconds to at least about 30 minutes after the PBMCs pass through the constriction. For example, the passage of the compound into the PBMCs occurs from about $1.0 \times 10^{-2}$ seconds to about 1 second, about 1 second to about 1 minute, or about 1 minute to about 30 minutes after the PBMCs pass through the constriction. In some embodiments, the passage of the compound into the PBMCs occurs about $1.0 \times 10^{-2}$ seconds to about 10 minutes, about $1.0 \times 10^{-2}$ seconds to about 5 minutes, about $1.0 \times 10^{-2}$ seconds to about 1 minute, about $1.0 \times 10^{-2}$ seconds to about 30 seconds, about $1.0 \times 10^{-2}$ seconds to about 10 seconds, about $1.0 \times 10^{-2}$ seconds to about 1 second, or about $1.0 \times 10^{-2}$ seconds to about 0.1 second after the PBMCs passes through the constriction. In some embodiments, the passage of the compound into the PBMCs occurs about $1.0 \times 10^{-1}$ seconds to about 10 minutes, about 1 second to about 10 minutes, about 10 seconds to about 10 minutes, about 50 seconds to about 10 minutes, about 1 minute to about 10 minutes, or about 5 minutes to about 10 minutes after the PBMCs pass through the constriction. In some embodiments, a perturbation in the PBMCs after they pass through the constriction is corrected within the order of about five minutes after the PBMCs pass through the constriction.

In some embodiments, the cell viability after passing through a constriction is about 5% to about 100%. In some embodiments, the cell viability after passing through the constriction is at least about 5%, 10%, 20%, 30%, 40%, 50%, 60%, 70%, 75%, 80%, 85%, 90%, 95%, or 99%. In some embodiments, the cell viability is measured from about $1.0 \times 10^{-2}$ seconds to at least about 10 days after the PBMCs pass through the constriction. For example, the cell viability is measured from about $1.0 \times 10^{-2}$ seconds to about 1 second, about 1 second to about 1 minute, about 1 minute to about 30 minutes, or about 30 minutes to about 2 hours after the PBMCs pass through the constriction. In some embodiments, the cell viability is measured about $1.0 \times 10^{-2}$ seconds to about 2 hours, about $1.0 \times 10^{-2}$ seconds to about 1 hour, about $1.0 \times 10^{-2}$ seconds to about 30 minutes, about $1.0 \times 10^{-2}$ seconds to about 1 minute, about $1.0 \times 10^{-2}$ seconds to about 30 seconds, about $1.0 \times 10^{-2}$ seconds to about 1 second, or about $1.0 \times 10^{-2}$ seconds to about 0.1 second after the PBMCs pass through the constriction. In some embodiments, the cell viability is measured about 1.5 hours to about 2 hours, about 1 hour to about 2 hours, about 30 minutes to about 2 hours, about 15 minutes to about 2 hours, about 1 minute to about 2 hours, about 30 seconds to about 2 hours, or about 1 second to about 2 hours after the PBMCs pass through the constriction. In some embodiments, the cell viability is measured about 2 hours to about 5 hours, about 5 hours to about 12 hours, about 12 hours to about 24 hours, or about 24 hours to about 10 days after the PBMCs pass through the constriction.

Delivery Parameters

A number of parameters may influence the delivery of a compound to PBMCs for modulating an immune response by the methods described herein. In some embodiments, the cell suspension is contacted with the compound before, concurrently, or after passing through the constriction. The PBMCs may pass through the constriction suspended in a solution that includes the compound to deliver, although the compound can be added to the cell suspension after the PBMCs pass through the constriction. In some embodiments, the compound to be delivered is coated on the constriction.

Examples of parameters that may influence the delivery of the compound into the PBMCs include, but are not limited to, the dimensions of the constriction, the entrance angle of the constriction, the surface properties of the constrictions (e.g., roughness, chemical modification, hydrophilic, hydrophobic, etc.), the operating flow speeds (e.g., cell transit time through the constriction), the PBMC concentration, the concentration of the compound in the cell suspension, and the amount of time that the PBMCs recover or incubates after passing through the constrictions can affect the passage of the delivered compound into the PBMCs. Additional parameters influencing the delivery of the compound into the PBMCs can include the velocity of the PBMCs in the constriction, the shear rate in the constriction, the viscosity of the cell suspension, the velocity component that is perpendicular to flow velocity, and time in the constriction. In addition, multiple chips comprising channels in series and/or in parallel may impact delivery to PBMC. Multiple chips in parallel may be useful to enhance throughput. Such parameters can be designed to control delivery of the compound. In some embodiments, the PBMCs concentration ranges from about 10 to at least about $10^{12}$ cells/mL or any concentration or range of concentrations therebetween. In some embodiments, delivery compound concentrations can range from about 10 µg/mL to about 1 g/mL or any concentration or range of concentrations therebetween. In some embodiments, delivery compound concentrations can range from about 1 pM to at least about 2 M or any concentration or range of concentrations therebetween.

The temperature used in the methods of the present disclosure can be adjusted to affect compound delivery and cell viability. In some embodiments, the method is performed between about −5° C. and about 45° C. For example, the methods can be carried out at room temperature (e.g., about 20° C.), physiological temperature (e.g., about 37° C.), higher than physiological temperature (e.g., greater than about 37° C. to 45° C. or more), or reduced temperature (e.g., about −5° C. to about 4° C.), or temperatures between these exemplary temperatures.

Various methods can be utilized to drive the PBMCs through the constrictions. For example, pressure can be applied by a pump on the entrance side (e.g., compressor), a vacuum can be applied by a vacuum pump on the exit side, capillary action can be applied through a tube, and/or the system can be gravity fed. Displacement based flow systems can also be used (e.g., syringe pump, peristaltic pump, manual syringe or pipette, pistons, etc.). In some embodiments, the PBMCs are passed through the constrictions by positive pressure or negative pressure. In some embodiments, the PBMCs are passed through the constrictions by constant pressure or variable pressure. In some embodiments, pressure is applied using a syringe. In some embodiments, the pressure is positive pressure applied using a gas (e.g., from a gas cylinder). In some embodiments, pressure is applied using a pump. In some embodiments, the pump is a peristaltic pump or a diaphragm pump. In some embodiments, pressure is applied using a vacuum. In some embodiments, the PBMCs are passed through the constrictions by g-force. In some embodiments, the PBMCs are passed through the constrictions by centrifugal force. In some embodiments, the PBMCs are passed through the constrictions by capillary pressure.

In some embodiments, fluid flow directs the PBMCs through the constrictions. In some embodiments, the fluid flow is turbulent flow prior to the PBMCs passing through the constriction. Turbulent flow is a fluid flow in which the velocity at a given point varies erratically in magnitude and direction. In some embodiments, the fluid flow through the constriction is laminar flow. Laminar flow involves uninterrupted flow in a fluid near a solid boundary in which the direction of flow at every point remains constant. In some embodiments, the fluid flow is turbulent flow after the PBMCs pass through the constriction. The velocity at which the PBMCs pass through the constrictions can be varied. In some embodiments, the PBMCs pass through the constrictions at a uniform cell speed. In some embodiments, the PBMCs pass through the constrictions at a fluctuating cell speed.

In other embodiments, a combination treatment is used to modulate an immune response by passing a cell suspension comprising PBMCs through a constriction, wherein the constriction deforms the PBMCs thereby causing a perturbation of the PBMCs such that an antigen and/or adjuvant enters the PBMCs, e.g., the methods described herein, followed by exposure to an electric field downstream of the constriction. In some embodiments, the PBMCs are passed through an electric field generated by at least one electrode after passing through the constriction. In some embodiments, the electric field assists in delivery of compounds to a second location inside the PBMCs such as the PBMCs nuclei. For example, the combination of a cell-deforming constriction and an electric field delivers a plasmid encoding an antibody into the PBMCs (e.g., the cell nucleus), resulting in the de novo production of antibody. In some embodiments, one or more electrodes are in proximity to the cell-deforming constriction to generate an electric field. In some embodiments, the electric field is between about 0.1 kV/m to about 100 MV/m, or any number or range of numbers therebetween. In some embodiments, an integrated circuit is used to provide an electrical signal to drive the electrodes. In some embodiments, the PBMCs are exposed to the electric field for a pulse width of between about 1 ns to about 1 s and a period of between about 100 ns to about 10 s or any time or range of times therebetween.

Cell Suspensions for Delivery to PBMCs

The cell suspension may be a mixed or purified population or plurality of PBMCs. In some embodiments, the cell suspension is a mixed cell population, such as whole blood. In some embodiments, the cell suspension is a purified cell population, such as a purified population (e.g., plurality) of PBMCs. In other embodiments, the population (e.g., plurality) of PBMCs is depleted of one or more cells. In some embodiments, the population of PBMCs is depleted of one or more of T cells, B cells, NK cells, macrophages or dendritic cells.

The composition of the cell suspension (e.g., osmolarity, salt concentration, serum content, cell concentration, pH, etc.) can impact delivery of the compound for modulating an immune response. In some embodiments, the suspension comprises whole blood. Alternatively, the cell suspension is a mixture of cells in a physiological saline solution or physiological medium other than blood. In some embodiments, the cell suspension comprises an aqueous solution. In some embodiments, the aqueous solution comprises cell culture medium, phosphate buffered saline (PBS), salts, metal ions, sugars, growth factors, animal derived products, bulking materials, surfactants, lubricants, lipids, vitamins, amino acids, proteins, cell cycle inhibitors, and/or an agent that impacts actin polymerization. In some embodiments, the cell culture medium is DMEM, Opti-MEM®, IMDM, RPMI, X-Vivo 10™, and X-Vivo 15™. Additionally, solution buffer can include one or more lubricants (Pluronics® or other surfactants) that can be designed, for example, to reduce or eliminate clogging of the constriction or pore and improve cell viability. Exemplary surfactants include, without limitation, poloxamer, polysorbates, sugars or sugar alcohols such as mannitol, sorbitol, animal derived serum, and albumin protein.

In some configurations with certain types of PBMCs, the PBMCs can be incubated in one or more solutions that aid in the delivery of the compound to the interior of the PBMCs. In some embodiments, the aqueous solution comprises an agent that impacts actin polymerization. In some embodiments, the agent that impacts actin polymerization is Latrunculin A, Cytochalasin, and/or Colchicine. For example, the PBMCs can be incubated in a depolymerization solution such as Lantrunculin A (0.1 µg/mL) for 1 hour prior to delivery to depolymerize the actin cytoskeleton. As an additional example, the PBMCs can be incubated in 10 µM Colchicine (Sigma) for 2 hours prior to delivery to depolymerize the microtubule network.

The viscosity of the cell suspension can also impact the methods disclosed herein. In some embodiments, the viscosity of the cell suspension ranges from about $8.9 \times 10^{-4}$ Pa·s to about $4.0 \times 10^{-3}$ Pa·s or any value or range of values therebetween. In some embodiments, the viscosity ranges between any one of about $8.9 \times 10^{-4}$ Pa·s to about $4.0 \times 10^{-3}$ Pa·s, about $8.9 \times 10^{-4}$ Pa·s to about $3.0 \times 10^{-3}$ Pa·s, about $8.9 \times 10^{-4}$ Pa·s to about $2.0 \times 10^{-3}$ Pa·s, or about $8.9 \times 10^{-3}$ Pa·s to about $1.0 \times 10^{-3}$ Pa·s. In some embodiments, the viscosity ranges between any one of about 0.89 cP to about 4.0 cP, about 0.89 cP to about 3.0 cP, about 0.89 cP to about 2.0 cP, or about 0.89 cP to about 1.0 cP. In some embodiments, a shear thinning effect is observed, in which the viscosity of the cell suspension decreases under conditions of shear strain. Viscosity can be measured by any method known in the art, including without limitation, viscometers, such as a glass capillary viscometer, or rheometers. A viscometer measures viscosity under one flow condition, while a rheometer is used to measure viscosities which vary with flow conditions. In some embodiments, the viscosity is measured for a shear thinning solution such as blood. In some embodiments, the viscosity is measured between about −5° C. and about 45° C. For example, the viscosity is measured at room temperature (e.g., about 20° C.), physiological temperature (e.g., about 37° C.), higher than physiological temperature (e.g., greater than about 37° C. to 45° C. or more), reduced temperature (e.g., about −5° C. to about 4° C.), or temperatures between these exemplary temperatures.

Constriction Mediated Delivery

In some embodiments according to any one of the methods, compositions or pluralities of modified PBMCs described herein, the diameter of the constriction is a function of a diameter of the PBMCs, such as the mean diameter of a plurality of PBMCs, or a mean diameter of a subpopulation within plurality of the PBMCs. In some embodiments, the diameter of a cell is measured by the minimum cross-sectional distance of the cell (e.g. a cell within the plurality of PBMCs).

In some embodiments according to any one of the methods, compositions or pluralities of modified PBMCs described herein, the diameter of the constriction is about 10% to about 99% of the mean diameter of the plurality of input PBMCs. In some embodiments, the diameter of the constriction is any one of about 10% to about 90%, about 10% to about 80%, about 10% to about 70%, about 20% to about 60%, about 40% to about 60%, or about 30% to about 45% of the mean diameter of the plurality of input PBMCs. In some embodiments, the diameter of the constriction is any one of about 10% to about 20%, about 20% to about 30%, about 30% to about 40%, about 40% to about 50%, about 50% to about 60%, about 60% to about 70%, about 70% to about 80%, about 80% to about 90%, or about 90% to about 99% of the mean diameter of the plurality of input PBMCs. In some embodiments, the diameter of the constriction is any one of about 10%, 15%, 20%, 25%, 30%, 35%, 40%, 45%, 50%, 55%, 60%, 65%, 70%, 75%, 80%, 85%, 90%, 95%, or 99% of the mean diameter of the plurality of input PBMCs.

In some embodiments according to any one of the methods, compositions or pluralities of modified PBMCs described herein, the diameter of the constriction is about 10% to about 99% of the mean diameter of a subpopulation of cells having the smallest diameter within the plurality of input PBMCs. In some embodiments, the diameter of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of a subpopulation of cells having the smallest diameter within the plurality of input PBMCs. In some embodiments, the diameter of the constriction is any one of about 10% to about 20%, about 20% to about 30%, about 30% to about 40%, about 40% to about 50%, about 50% to about 60%, about 60% to about 70%, about 70% to about 80%, about 80% to about 90%, or about 90% to about 99% of the mean diameter of a subpopulation of cells having the smallest diameter within the plurality of input PBMCs. In some embodiments, the diameter of the constriction is any one of about 10%, 15%, 20%, 25%, 30%, 35%, 40%, 45%, 50%, 55%, 60%, 65%, 70%, 75%, 80%, 85%, 90%, 95%, or 99% of the mean diameter of a subpopulation of cells having the smallest diameter within the plurality of input PBMCs. In some embodiments, the subpopulation of cells having the smallest mean diameter within the plurality of input PBMCs is a population of lymphocytes, wherein the diameter of the population of lymphocytes is about 6 µm to about 10 µm. In some embodiments, the mean diameter of the population of lymphocytes is about 7 µm. In some embodiments, the population of lymphocytes is a population of T cells. In some embodiments, the lymphocytes are T cells. In some embodiments, the subpopulation of cells having the smallest mean diameter within the plurality of input PBMCs are T cells.

In some embodiments according to any one of the methods, compositions or pluralities of modified PBMCs described herein, the diameter of the constriction is about 10% to about 99% of the mean diameter of a subpopulation of cells having the largest diameter within the plurality of input PBMCs. In some embodiments, the diameter of the constriction is any one of about 10% to about 90%, about 10% to about 80%, about 10% to about 70%, about 20% to about 60%, about 40% to about 60%, about 30% to about 45%, about 15% to about 30%, about 15% to about 20%, about 20% to about 25%, about 25% to about 30%, about 20% to about 30%, about 30% to about 70%, or about 30% to about 60% of the mean diameter of a subpopulation of cells having the largest diameter within the plurality of input PBMCs. In some embodiments, the diameter of the constriction is any one of about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, or about 90% to about 99% of the mean diameter of a subpopulation of cells having the largest diameter within the plurality of input PBMCs. In some embodiments, the diameter of the constriction is any one of about 5%, 10%, 15%, 20%, 25%, 30%, 35%, 40%, 45%, 50%, 55%, 60%, 65%, 70%, 75%, 80%, 85%, 90%, 95%, or 99% of the mean diameter of a subpopulation of cells having the largest diameter within the plurality of input PBMCs. In some embodiments, the subpopulation of cells having the largest mean diameter within the plurality of input PBMCs is a population of monocytes, wherein the diameter of the population of monocytes is about 15 μm to about 25 μm. In some embodiments, the mean diameter of the population of monocytes is about 20 μm. In some embodiments, the subpopulation of cells having the largest mean diameter within the plurality of input PBMCs are monocytes.

In some embodiments according to any one of the methods, compositions or pluralities of modified PBMCs described herein, the diameter of the constriction is about 3 μm to about 15 μm. In some embodiments, the diameter of the constriction is about 3 μm to about 10 μm. In some embodiments, the diameter of the constriction is about 3 μm to about 6 μm. In some embodiments, the diameter of the constriction is about 4 μm to about 10 μm. In some embodiments, the diameter of the constriction is about 4.2 μm to about 6 μm. In some embodiments, the diameter of the constriction is about 4.2 μm to about 4.8 μm. In some embodiments, the diameter of the constriction is any one of about 2 μm to about 14 μm, about 4 μm to about 12 μm, about 6 μm to about 9 μm, about 4 μm to about 6 μm, about 4 μm to about 5 μm, about 3.5 μm to about 7 μm, about 3.5 μm to about 6.3 μm, about 3.5 μm to about 5.6 μm, about 3.5 μm to about 4.9 μm, about 4.2 μm to about 6.3 μm, about 4.2 μm to about 5.6 μm, or about 4.2 μm to about 4.9 μm. In some embodiments, the diameter of the constriction is any one of about 2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the diameter of the constriction is any one of about 4.0 μm, 4.1 μm, 4.2 μm, 4.3 μm, 4.4 μm, 4.5 μm, 4.6 μm, 4.7 μm, 4.8 μm, 4.9 μm, or 5.0 μm. In some embodiments, the diameter of the constriction is about 4.5 μm.

In some embodiments according to any one of the methods, compositions or pluralities of modified PBMCs described herein, the plurality of input PBMCs is passed through the constriction under a pressure ranging from about 20 psi to about 150 psi. In some embodiments, the plurality of input PBMCs is passed through the constriction under a pressure ranging from about 30 psi to about 120 psi. In some embodiments, the plurality of input PBMCs is passed through the constriction under a pressure ranging from about 60 psi to about 90 psi. In some embodiments, the plurality of input PBMCs is passed through the constriction under a pressure ranging from any one of about 30 psi to about 40 psi, about 40 psi to about 50 psi, about 50 psi to about 60 psi, about 60 psi to about 70 psi, about 70 psi to about 80 psi, about 80 psi to about 90 psi, about 90 psi to about 100 psi, about 100 psi to about 110 psi, or about 110 psi to about 120 psi. In some embodiments, the plurality of input PBMCs is passed through the constriction under a pressure of about any one of 20 psi, 25 psi, 30 psi, 35 psi, 40 psi, 45 psi, 50 psi, 55 psi, 60 psi, 65 psi, 70 psi, 75 psi, 80 psi, 85 psi, 90 psi, 95 psi, 100 psi, 105 psi, 110 psi, 115 psi, or 120 psi.

In some embodiments according to any one of the methods, compositions or pluralities of modified PBMCs described herein, the plurality of input PBMCs is passed through the constriction under a pressure ranging from about 150 kPa to about 1000 kPa. In some embodiments, the plurality of input PBMCs is passed through the constriction under a pressure ranging from about 207 kPa to about 830 kPa. In some embodiments, the plurality of input PBMCs is passed through the constriction under a pressure ranging from about 415 kPa to about 621 kPa. In some embodiments, the plurality of input PBMCs is passed through the constriction under a pressure ranging from any one of about 200 kPa to about 250 kPa, about 250 kPa to about 300 kPa, 300 kPa to about 350 kPa, about 350 kPa to about 400 kPa, 400 kPa to about 450 kPa, about 450 kPa to about 500 kPa, 500 kPa to about 550 kPa, about 550 kPa to about 600 kPa, 600 kPa to about 650 kPa, about 650 kPa to about 700 kPa, 700 kPa to about 750 kPa, about 750 kPa to about 800 kPa, 800 kPa to about 850 kPa, about 850 kPa to about 900 kPa, 900 kPa to about 950 kPa, about 950 kPa to about 1000 kPa. In some embodiments, the plurality of input PBMCs is passed through the constriction under a pressure of about any one of 200 kPa, 250 kPa, 300 kPa, 350 kPa, 400 kPa, 415 kPa, 450 kPa, 500 kPa, 550 kPa, 600 kPa, 612 kPa, 650 kPa, 700 kPa, 750 kPa, 800 kPa, or 850 kPa.

In some embodiments according to any one of the methods, compositions or pluralities of modified PBMCs described herein, the plurality of input PBMCs is passed through the constriction at a temperature ranging from about 0° C. to about 37° C. In some embodiments the plurality of input PBMCs is passed through the constriction at a temperature ranging from about 0° C. to about 10° C. In some embodiments, the plurality of input PBMCs is passed through the constriction at a temperature ranging from about 2° C. to about 8° C. In some embodiments, the plurality of input PBMCs is passed through the constriction at a temperature ranging from any one of about 2° C. to about 6° C., about 5° C. to about 10° C., about 10° C. to about 15° C., about 15° C. to about 20° C., about 20° C. to about 25° C., about 25° C. to about 30° C., about 30° C. to about 35° C., or about 35° C. to about 37° C. In some embodiments, the plurality of input PBMCs is passed through the constriction at a temperature of any one of about 0° C., 1° C., 2° C., 3° C., 4° C., 5° C., 6° C., 7° C., 8° C., 9° C., 10° C., 15° C., 20° C., 25° C., 30° C. or 37° C.

In some embodiments according to any one of the methods, compositions or pluralities of modified PBMCs described herein, subsequent to passing through the constriction the plurality of modified PBMCs is incubated at a temperature of 37° C. for a sufficient time to allow the modified PBMCs to normalize to 37° C. In some embodiments, subsequent to passing through the constriction the plurality of modified PBMCs is incubated at a temperature of 25° C. for a sufficient time to allow the modified PBMCs to normalize to 25° C.

In some embodiments according to any one of the methods, compositions or pluralities of modified PBMCs described herein, the input PBMCs is passed through the constriction at a flow rate between about 0.001 mL/min to about 200 mL/min or any rate or range of rates therebetween. In some embodiments, the flow rate is between about 0.001 mL/min to about 175 mL/min, about 0.001 mL/min to about 150 mL/min, about 0.001 mL/min to about 125 mL/min, about 0.001 mL/min to about 100 mL/min, about 0.001 mL/min to about 50 mL/min, about 0.001 mL/min to about 25 mL/min, about 0.001 mL/min to about 10 mL/min, about 0.001 mL/min to about 7.5 mL/min, about 0.001 mL/min to about 5.0 mL/min, about 0.001 mL/min to about 2.5 mL/min, about 0.001 mL/min to about 1 mL/min, about 0.001 mL/min to about 0.1 mL/min or about 0.001 mL/min to about 0.01 mL/min. In some embodiments, the flow rate is between about 0.001 mL/min to about 200 mL/min, about 0.01 mL/min to about 200 mL/min, about 0.1 mL/min to about 200 mL/min, about 1 mL/min to about 200 mL/min, about 10 mL/min to about 200 mL/min, about 50 mL/min to about 200 mL/min, about 75 mL/min to about 200 mL/min, about 100 mL/min to about 200 mL/min, about 150 mL/min to about 200 mL/min, about 0.5 mL/min to about 200 mL/min, about 1 mL/min to about 200 mL/min, about 2.5 mL/min to about 200 mL/min, about 5 mL/min to about 200 mL/min, about 7.5 mL/min to about 200 mL/min, about 10 mL/min to about 200 mL/min, about 25 mL/min to about 200 mL/min, or about 175 mL/min to about 200 mL/min. In some embodiments, the plurality of input PBMCs is passed through the constriction at a flow rate between about 10 mL/min to about 200 mL/min. In some embodiments, the plurality of input PBMCs is passed through the constriction at a flow rate of about 100 mL/min.

In some embodiments according to any one of the methods, compositions or pluralities of modified PBMCs described herein, the constriction can have any shape known in the art; e.g. a 3-dimensional shape or a 2-dimensional shape. The 2-dimensional shape, such as the cross-sectional shape, of the constriction can be, without limitation, circular, elliptical, round, square, star-shaped, triangular, polygonal, pentagonal, hexagonal, heptagonal, or octagonal. The 3-dimensional shape of the constriction can be, without limitation, cylindrical, conical, or cuboidal. In some embodiments, the cross-sectional shape of the constriction is a rectangle. In some embodiments, the cross-sectional shape of the constriction is a slit. In some embodiments, the cross-sectional shape of the constriction is a slit comprising a width of about 3 μm to about 10 μm and/or a depth of about 1 μm to about 200 μm. In some embodiments, the cross-sectional shape of the constriction is a slit comprising a width of about 3 μm to about 6 μm and/or a depth of about 20 μm to about 120 μm. In some embodiments, the cross-sectional shape of the constriction is a slit comprising a width of about 4.2 μm to about 6 μm and/or a depth of about 20 μm to about 120 μm. In some embodiments, the cross-sectional shape of the constriction is a slit comprising a width of about 4.2 μm to about 6 μm and/or a depth of about 40 μm to about 100 μm. In some embodiments, the cross-sectional shape of the constriction is a slit comprising a width of about 4.2 μm to about 6 μm and/or a depth of about 20 μm to about 80 μm. In some embodiments, the cross-sectional shape of the constriction is a slit comprising a width of about 4.5 μm and/or a depth of about 80 μm. In some embodiments, the slit comprises a length of about 10 μm to about 30 μm. In some embodiments, the slit comprises a length of about 2 μm to about 50 μm. In some embodiments, the slit comprises a length of any one of about 2 μm to about 5 μm, about 5 μm to about 10 μm, about 10 μm to about 15 μm, about 15 μm to about 20 μm, about 20 μm to about 25 μm, about 25 μm to about 30 μm, about 30 μm to about 35 μm, about 35 μm to about 40 μm, about 40 μm to about 45 μm, or about 45 μm to about 50 μm. In some embodiments, the slit comprises a length of about 10 μm.

In some embodiments, the constriction comprises an entrance portion and an exit portion. The entrances and exits of the constriction may have a variety of angles. In some embodiments, the constrictions have identical entrance and exit angles. In some embodiments, the constrictions have different entrance and exit angles. The constriction angle can be selected to minimize clogging of the constriction while PBMCs are passing through. In some embodiments the flow rate through the surface is between about 0.001 mL/min to about 100 mL/min or any rate or range of rates therebetween. In some examples, the angle of the entrance and/or exit portion can be between about 0 and about 90 degrees. In some embodiments, the entrance and/or exit portion can be greater than 90 degrees. In some embodiments, the entrance portion defines an entrance angle and the entrance angle is between about 0 degree to about 90 degrees. In some embodiments, the entrance angle is between any one of about 10 degrees to about 40 degrees, about 12 degrees to about 45 degrees, between about 15 degrees to about 30 degrees. In some embodiments, the entrance angle is between about 20 degrees to about 22 degrees. In some embodiments, the exit portion defines an exit angle and the exit angle is between about 0 degree to about 90 degrees. In some embodiments, the exit angle is between any one of about 10 degrees to about 40 degrees, about 12 degrees to about 45 degrees, between about 15 degrees to about 30 degrees. In some embodiments, the exit angle is between about 20 degrees to about 22 degrees. In some embodiments, the entrance portion defines an entrance angle and the entrance angle is between about 20 degrees to about 22 degrees, and the exit portion defines an exit angle and the exit angle is between about 20 degrees to about 22 degrees.

In some embodiments according to any one of the methods, compositions or pluralities of modified PBMCs described herein, the constriction edge is smooth, e.g. rounded or curved. A smooth constriction edge has a continuous, flat, and even surface without bumps, ridges, or uneven parts. In some embodiments, the constriction edge is sharp. A sharp constriction edge has a thin edge that is pointed or at an acute angle. In some embodiments, the constriction passage is straight. A straight constriction passage does not contain curves, bends, angles, or other irregularities. In some embodiments, the constriction passage is curved. A curved constriction passage is bent or deviates from a straight line. In some embodiments, the constriction passage has multiple curves, e.g. about 2, 3, 4, 5, 6, 7, 8, 9, 10 or more curves.

In some embodiments according to any one of the methods, compositions or pluralities of modified PBMCs described herein, the cell suspension comprising the plurality of input PBMCs is passed through multiple constrictions, wherein the multiple constrictions are arranged in series and/or in parallel. In some embodiments, the multiple constrictions are arranged in series. In some embodiments, the multiple constrictions are arranged in parallel. In some embodiments, the multiple constrictions are arranged in series and/or in parallel. In some embodiments, the multiple constrictions arranged in series comprise about any one of 2, 3, 4, 5, 6, 7, 8, 9, 10, 50, 75, 100, 500, 1,000 or more constrictions in series. In some embodiments, the multiple constrictions arranged in parallel may comprise about any one of 2, 5, 10, 50, 75, 100, 500, 1,000 or more constrictions in series.

Exemplary microfluidic channels containing cell-deforming constrictions for use in the methods disclosed herein are described in WO2013059343. Exemplary surfaces having pores for use in the methods disclosed herein are described in WO2017041050.

Systems and Kits

In some aspects, the invention provides a system comprising one or more of a constriction, a PBMC suspension, antigens or adjuvants according to any of the embodiments described herein, such as for use in any of the methods described herein. The system can include any embodiment described for the compositions of matter and methods disclosed herein, including those disclosed in the above section titled "Microfluidic systems and components thereof" In some embodiment, the cell-deforming constrictions are sized for delivery to PBMCs. In some embodiments, the delivery parameters, such as operating flow speeds, cell and compound concentration, temperature, velocity of the cell in the constriction, and the composition of the cell suspension (e.g., osmolarity, salt concentration, serum content, cell concentration, pH, etc.) are optimized for maximum response of a compound for modulating an immune response.

Also provided are kits or articles of manufacture for use in modulating an immune response in an individual. In some embodiments, the kit comprises modified PBMCs comprising an antigen and/or an adjuvant, including any of the modified PBMCs described herein. In some embodiments, the kit comprises one or more of a constriction, a PBMC suspension, antigens or adjuvants for use in generating modified PBMCs for use in modulating an immune response in an individual. In some embodiments, the kits comprise components described herein (e.g. a microfluidic channel or surface containing pores, cell suspensions, and/or compounds) in suitable packaging. Suitable packaging materials are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The invention also provides kits comprising components of the methods described herein and may further comprise instructions for performing said methods to modulate an immune response in an individual and/or instructions for introducing an antigen and/or an adjuvant into PBMCs. The kits described herein may further include other materials, including buffers, diluents, filters, needles, syringes, and package inserts with instructions for performing any of the methods described herein; e.g., instructions for modulating an immune response in an individual or instructions for modifying a PBMCs to contain an antigen and/or an adjuvant. HPV and HPV-associated diseases.

In some embodiments according to any one of systems and kits described herein, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs.

Other Embodiments

Other embodiments provide any of the embodiments described herein with one or more of the following provisos:
the antigen is not an HPV antigen
the antigen is not an HPV E6 antigen
the antigen is not an HPV E7 antigen
the antigen is not an HPV E6 antigen and not an HPV E7 antigen
an adjuvant is not introduced into the PBMCs together with the antigen
an adjuvant is not presented in the cytosol of the PBMC comprising the antigen
the adjuvant is not administered to the individual In some embodiments according to any one of the methods, compositions or pluralities of modified PBMCs described herein, the plurality of modified PBMCs does not express an HPV antigen. In some embodiments, the plurality of modified PBMCs does not comprise a nucleic acid encoding an HPV antigen. In some embodiments, the plurality of modified PBMCs does not comprise an HPV E6 antigen. In some embodiments, the plurality of modified PBMCs does not comprise a nucleic acid encoding an HPV E6 antigen. In some embodiments, the plurality of modified PBMCs does not comprise an HPV E7 antigen. In some embodiments, the plurality of modified PBMCs does not comprise a nucleic acid encoding an HPV E7 antigen.

In some embodiments, the plurality of modified PBMCs does not comprise an HPV E6 antigen and does not comprise an HPV E7 antigen. In some embodiments, the plurality of modified PBMCs does not comprise a nucleic acid encoding an HPV E6 antigen and does not comprise a nucleic acid encoding an HPV E7 antigen.

In some embodiments according to any one of the methods, compositions or pluralities of modified PBMCs described herein, the plurality of PBMCs does comprise nucleic acid encoding an antigen. In some embodiments according to any one of the methods, compositions or pluralities of modified PBMCs described herein, the plurality of PBMCs do not express an antigen.

In some embodiments according to any one of the methods, compositions or pluralities of modified PBMCs described herein, the antigen comprises one or more proteins. In some embodiments, the antigen is encoded by one or more nucleic acids and enters the PBMC in the form of one or more nucleic acids, such as but not limited to DNAs, cDNAs, mRNAs, and plasmids. In some embodiments, the antigen is encoded by one or more mRNAs and enters the PBMC in the form of one or more mRNAs. In some embodiments, the plurality of PBMCs comprises a nucleic acid encoding an antigen. In some embodiments, the plurality of PBMCs comprises an mRNA encoding an antigen.

In some embodiments according to any one of the methods, compositions or pluralities of modified PBMCs described herein, the plurality of PBMCs does not induce tolerance in an individual. In some embodiments, the plurality of PBMCs does not suppress an immune response in an individual. In some embodiments, the plurality of PBMCs does not comprise a tolerogenic factor. In some embodiments, the plurality of PBMCs is not administered in combination with a tolerogenic factor. In some embodiments, the plurality of PBMCs is not administered before, simultaneous with, or after administration of a tolerogenic factor.

In some embodiments of the application, the terms "conditioned" and "matured" may be used interchangeably.

Exemplary Embodiments

The invention provides the following enumerated embodiments.

1. A plurality of modified PBMCs comprising an antigen, wherein the antigen is exogenous to the modified PBMCs.

2. A plurality of modified PMBCs comprising an antigen, wherein the antigen is exogenous to the modified PBMCs, wherein the antigen is a cancer antigen, an infectious disease antigen or a viral-disease associated antigen.

3. A conditioned plurality of modified PBMCs comprising an antigen, wherein the antigen is exogenous to the modified PBMCs.

4. A conditioned plurality of modified PMBCs comprising an antigen, wherein the antigen is exogenous to the modified PBMCs, wherein the antigen is a cancer antigen, an infectious disease antigen or a viral-disease associated antigen.

5. A conditioned plurality of modified PBMCs comprising an antigen and an adjuvant, wherein the antigen is exogenous to the modified PBMCs.

6. A plurality of modified PBMCs comprising an antigen comprising the amino acid sequence of any one of SEQ ID NOs: 18-25.

7. A conditioned plurality of modified PBMCs comprising an antigen comprising the amino acid sequence of any one of SEQ ID NOs: 18-25.

8. A conditioned plurality of PBMCs comprising an antigen, prepared by incubating the plurality of PBMCs comprising the antigen with an adjuvant for a sufficient time for the PBMCs to condition, thereby generating the conditioned plurality of PBMCs comprising the antigen.

9. A conditioned plurality of PBMCs comprising an antigen, prepared by incubating the plurality of PBMCs with an adjuvant for a sufficient time for the PBMCs to condition prior to introducing the antigen to the PBMCs, thereby generating the conditioned plurality of PBMCs comprising the antigen.

10. A plurality of modified PBMCs comprising an antigen, prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen.

11. A plurality of modified PBMCs comprising an antigen, prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen to pass through to form a plurality of perturbed input PBMCs;
b) incubating the plurality of perturbed input PBMCs with the nucleic acid encoding the antigen for a sufficient time to allow the nucleic acid encoding the antigen to enter the perturbed input PBMCs,
wherein the nucleic acid is expressed in the PBMCs to produce the antigen, thereby generating a plurality of modified PBMCs comprising the antigen.

12. A conditioned plurality of modified PBMCs comprising an antigen, prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with an adjuvant for a sufficient time for the modified PBMCs comprising the antigen to condition, thereby generating the conditioned plurality of modified PBMCs comprising the antigen.

13. A conditioned plurality of modified PBMCs comprising an antigen, prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen to pass through to form a plurality of perturbed input PBMCs;
b) incubating the plurality of perturbed input PBMCs with the nucleic acid encoding the antigen for a sufficient time to allow the nucleic acid encoding the antigen to enter the perturbed input PBMCs, thereby generating a plurality of modified PBMCs comprising the nucleic acid encoding the antigen; and
c) incubating the plurality of modified PBMCs with the nucleic acid encoding the antigen with an adjuvant for a sufficient time for the modified PBMCs comprising the nucleic acid encoding the antigen to condition,
wherein the nucleic acid is expressed in the PBMCs to produce the antigen, thereby generating the conditioned plurality of modified PBMCs comprising the antigen.

14. The conditioned plurality of modified PBMCs comprising an antigen of embodiment 12 or 13, wherein the process further comprises: isolating the plurality of modified PBMCs comprising the antigen from the cell suspension before incubation with the adjuvant to condition the modified PBMCs.

15. A plurality of modified PBMCs comprising an antigen and an adjuvant, prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen and the adjuvant to pass through to form a plurality of perturbed input PBMCs; and
b) incubating the plurality of perturbed input PBMCs with the antigen and the adjuvant for a sufficient time to allow the antigen and the adjuvant to enter the perturbed input PBMCs; thereby generating the plurality of modified PBMCs comprising the antigen and adjuvant.

16. A plurality of modified PBMCs comprising an antigen and an adjuvant, prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen and the adjuvant to pass through to form a plurality of perturbed input PBMCs; and
b) incubating the plurality of perturbed input PBMCs with the nucleic acid encoding the antigen and with the adjuvant for a sufficient time to allow the nucleic acid encoding the antigen and the adjuvant to enter the perturbed input PBMCs;
wherein the nucleic acid is expressed in the PBMCs to produce the antigen, thereby generating the plurality of modified PBMCs comprising the antigen and adjuvant.

17 The plurality of modified PBMCs of embodiment 15 or 16, wherein the concentration of the antigen incubated with the perturbed input PBMCs is between about 0.1 µM and about 1 mM and/or the concentration of the adjuvant incubated with the perturbed input PBMCs is between about 0.1 µM and about 1 mM.

18. The plurality of modified PBMCs of any one of embodiments 15-17, wherein: (a) the concentration of the antigen incubated with the perturbed input PBMCs is between about 0.1 µM and about 10 µM and/or the concentration of the adjuvant incubated with the perturbed input PBMCs is between about 0.1 µM and about 10 µM.

19. The plurality of modified PBMCs of any one of embodiments 15-18, wherein the concentration of the antigen incubated with the perturbed input PBMCs is about 1 µM and/or the concentration of the adjuvant incubated with the perturbed input PBMCs is about 1 µM.

20. The plurality of modified PBMCs of any one of embodiments 15-19, wherein the ratio of the antigen to the adjuvant incubated with the perturbed input PBMCs is between about 10000:1 to about 1:10000.

21. The plurality of modified PBMCs of any one of embodiments 15-20, wherein the ratio of the antigen to the adjuvant incubated with the perturbed input PBMCs is about 200:1.

22. A conditioned plurality of modified PBMCs comprising an antigen, prepared by a process comprising the steps of:
a) incubating a plurality of input PBMCs with an adjuvant for a sufficient time for the input PBMCs to condition, thereby generating a conditioned plurality of input PBMCs;
b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and
c) incubating the conditioned plurality of perturbed input PBMCs with the antigen for a sufficient time to allow the antigen to enter the perturbed input PBMCs, thereby generating the conditioned plurality of modified PBMCs comprising the antigen.

23. The plurality of modified PBMCs of embodiment 22, wherein the concentration of the adjuvant incubated with the input PBMCs is between about 0.1 µM and about 1 mM.

24. The plurality of modified PBMCs of embodiment 22 or 23, wherein the concentration of the adjuvant incubated with the input PBMCs is between about 0.1 µM and about 10 µM.

25. The plurality of modified PBMCs of any one of embodiments 22-24, wherein the concentration of the adjuvant incubated with the input PBMCs is about 1 µM.

26. A plurality of modified PBMCs comprising an antigen and an adjuvant, prepared by a process comprising the steps of:
a) passing a cell suspension comprising a plurality of input PBMCs comprising the adjuvant through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; and
b) incubating the plurality of perturbed input PBMCs with the antigen for a sufficient time to allow the antigen to enter the perturbed input PBMCs, thereby generating the plurality of modified PBMCs comprising the antigen and the adjuvant.

27. A plurality of modified PBMCs comprising an antigen and an adjuvant, prepared by a process comprising the steps of:
a) passing a cell suspension comprising a plurality of input PBMCs comprising the antigen through a cell-deforming constriction, wherein a diameter of the constriction is a function of a diameter of the input PBMCs in the suspension, thereby causing perturbations of the input PBMCs large enough for the adjuvant to pass through to form a plurality of perturbed input PBMCs; and
b) incubating the plurality of perturbed input PBMCs with the adjuvant for a sufficient time to allow the adjuvant to enter the perturbed input PBMCs, thereby generating the plurality of modified PBMCs comprising the antigen and the adjuvant.

28. The plurality of modified PBMCs of any one of embodiments 10-14, and 22-27, wherein the concentration of the antigen incubated with the perturbed input PBMCs is between about 0.1 µM and about 1 mM.

29. The plurality of modified PBMCs of any one of embodiments 10-14, and 22-28, wherein the concentration of the antigen incubated with the perturbed input PBMCs is between about 0.1 µM and about 10 µM.

30. The plurality of modified PBMCs of any one of embodiments 10-14, and 22-29 wherein the concentration of the antigen incubated with the perturbed input PBMCs is about 1 µM.

31. The plurality of modified PBMCs comprising the antigen and/or the adjuvant according to any one of embodiments 15-21, and 26-30, wherein the process further comprises: incubating the plurality of modified PBMCs comprising the antigen and/or adjuvant with a second adjuvant for a sufficient time for the modified PBMCs comprising the antigen to condition, thereby generating the conditioned plurality of modified PBMCs comprising the antigen and/or the adjuvant.

32. The plurality of modified PBMCs comprising an antigen and/or the adjuvant of embodiment 31, wherein the process further comprises: isolating the plurality of modified PBMCs comprising the antigen and/or the adjuvant from the cell suspension before incubation with the adjuvant to condition the modified PBMCs.

33. The plurality of modified PBMCs of any one of embodiments 8-31, wherein the concentration of the adjuvant incubated with the modified PBMCs is between about 0.1 µM and about 1 mM.

34. The plurality of modified PBMCs of any one of embodiments 8-33, wherein the concentration of the adjuvant incubated with the modified PBMCs is between about 0.1 µM and about 10 µM.

35. The plurality of modified PBMCs of any one of embodiments 8-34, wherein the concentration of the adjuvant incubated with the modified PBMCs is about 1 µM.

36. The plurality of modified PBMCs of any one of embodiments 8-35, wherein the process further comprises a step of incubating the input PBMCs and/or the modified PBMCs with an agent that enhances the viability and/or function of the modified PBMCs as compared to corresponding modified PBMCs prepared without the further incubation step.

37. The plurality of modified PBMCs of any one of embodiments 10-36, wherein the diameter of the constriction is about 10% to about 99% of the mean diameter of the plurality of input PBMCs.

38. The plurality of modified PBMCs of any one of embodiments 10-37, wherein the diameter of the constriction is about 10% to about 70% of the mean diameter of the plurality of input PBMCs.

39. The plurality of modified PBMCs of any one of embodiments 10-38, wherein the diameter of the constriction is about 20% to about 60% of the mean diameter of the plurality of input PBMCs.

40. The plurality of modified PBMCs of any one of embodiments 10-39, wherein the diameter of the constriction is about 40% to about 60% of the mean diameter of the plurality of input PBMCs.

41. The plurality of modified PBMCs of any one of embodiments 10-40, wherein the diameter of the constriction is about 30% to about 45% of the mean diameter of the plurality of input PBMCs.

42. The plurality of modified PBMCs of any one of embodiments 10-36, wherein the diameter of the constriction is about 10% to about 99% of the mean diameter of a subpopulation of cells having the smallest diameter within the plurality of input PBMCs.

43. The plurality of modified PBMCs of any one of embodiments 10-36 and 42, wherein the diameter of the constriction is about 10% to about 70% of the mean diameter of a subpopulation of cells having the smallest diameter within the plurality of input PBMCs.

44. The plurality of modified PBMCs of any one of embodiments 10-36, 42 and 43 wherein the diameter of the constriction is about 20% to about 60% of the mean diameter of a subpopulation of cells having the smallest diameter within the plurality of input PBMCs.

45. The plurality of modified PBMCs of any one of embodiments 10-36 and 42-44 wherein the diameter of the constriction is about 30% to about 45% of the mean diameter of a subpopulation of cells having the smallest diameter within the plurality of input PBMCs.

46. The plurality of modified PBMCs of any one of embodiments 10-36, wherein the diameter of the constriction is about 50% to about 99% of the mean diameter of a subpopulation of cells having the smallest diameter within the plurality of input PBMCs.

47. The plurality of modified PBMCs of any one of embodiments 10-36 and 46, wherein the diameter of the constriction is about 50% to about 90% of the mean diameter of a subpopulation of cells having the smallest diameter within the plurality of input PBMCs.

48. The plurality of modified PBMCs of any one of embodiments 10-36, 46 and 47, wherein the diameter of the constriction is about 50% to about 80% of the mean diameter of a subpopulation of cells having the smallest diameter within the plurality of input PBMCs.

49. The plurality of modified PBMCs of any one of embodiments 10-36 and 46-48, wherein the diameter of the constriction is about 50% to about 70% of the mean diameter of a subpopulation of cells having the smallest diameter within the plurality of input PBMCs.

50. The plurality of modified PBMCs of any one of embodiments 10-36, wherein the diameter of the constriction is about 60% to about 90% of the mean diameter of a subpopulation of cells having the smallest diameter within the plurality of input PBMCs.

51. The plurality of modified PBMCs of any one of embodiments 10-36 and 50, wherein the diameter of the constriction is about 60% to about 80% of the mean diameter of a subpopulation of cells having the smallest diameter within the plurality of input PBMCs.

52. The plurality of modified PBMCs of any one of embodiments 10-36, 50 and 51, wherein the diameter of the constriction is about 60% to about 70% of the mean diameter of a subpopulation of cells having the smallest diameter within the plurality of input PBMCs.

53. The plurality of modified PBMCs of any one of embodiments 10-52, wherein the diameter of the constriction is about 10% to about 99% of the mean diameter of a subpopulation of cells having the largest diameter within the plurality of input PBMCs.

54. The plurality of modified PBMCs of any one of embodiments 10-53, wherein the diameter of the constriction is about 10% to about 70% of the mean diameter of a subpopulation of cells having the largest diameter within the plurality of input PBMCs.

55. The plurality of modified PBMCs of any one of embodiments 10-54 wherein the diameter of the constriction is about 20% to about 60% of the mean diameter of a subpopulation of cells having the largest diameter within the plurality of input PBMCs.

56. The plurality of modified PBMCs of any one of embodiments 10-55 wherein the diameter of the constriction is about 20% to about 30% of the mean diameter of a subpopulation of cells having the largest diameter within the plurality of input PBMCs.

57. The plurality of modified PBMCs of any one of embodiments 10-56 wherein the diameter of the constriction is about 20% to about 25% of the mean diameter of a subpopulation of cells having the largest diameter within the plurality of input PBMCs.

58. The plurality of modified PBMCs of any one of embodiments 10-55 wherein the diameter of the constriction is about 30% to about 70% of the mean diameter of a subpopulation of cells having the largest diameter within the plurality of input PBMCs.

59. The plurality of modified PBMCs of any one of embodiments 10-55 and 58 wherein the diameter of the constriction is about 30% to about 60% of the mean diameter of a subpopulation of cells having the largest diameter within the plurality of input PBMCs.

60. The plurality of modified PBMCs of any one of embodiments 10-55, 58 and 59 wherein the diameter of the constriction is about 30% to about 45% of the mean diameter of a subpopulation of cells having the largest diameter within the plurality of input PBMCs.

61. The plurality of modified PBMCs of any one of embodiments 42-60, wherein the subpopulation of cells having the smallest diameter within the plurality of input PBMCs are T cells.

62. The plurality of modified PBMCs of any one of embodiments 53-61, wherein the subpopulation of cells having the largest diameter within the plurality of input PBMCs are monocytes.

63. The plurality of modified PBMCs of any one of embodiments 10-62, wherein the diameter of the constriction is about 3 μm to about 10 μm.

64. The plurality of modified PBMCs of any one of embodiments 10-63, wherein the diameter of the constriction is about 4 μm to about 10 μm.

65. The plurality of modified PBMCs of any one of embodiments 10-63, wherein the diameter of the constriction is about 3 μm to about 6 μm.

66. The plurality of modified PBMCs of any one of embodiments 10-65, wherein the diameter of the constriction is about 4.2 μm to about 6 μm.

67. The plurality of modified PBMCs of any one of embodiments 10-66, wherein the diameter of the constriction is about 4.5 μm.

68. The plurality of modified PBMCs of any one of embodiments 10-67, wherein the plurality of input PBMCs is passed through the constriction under a pressure ranging from about 30 psi to about 120 psi or about 60 psi to about 90 psi.

69. The plurality of modified PBMCs of any one of embodiments 10-67, wherein the plurality of input PBMCs is passed through the constriction under a pressure ranging from about 207 kPa to about 830 kPa or about 415 kPa to about 621 kPa.

70. The plurality of modified PBMCs of any one of embodiments 10-67, wherein the plurality of input PBMCs is passed through the constriction at a flow rate between about 0.001 mL/cm$^2$/sec to about 200 L/cm$^2$/sec.

71. The plurality of modified PBMCs of any one of embodiments 10-67, wherein the plurality of input PBMCs is passed through the constriction at a flow rate between about 0.1 mL/cm$^2$/sec to about 150 L/cm$^2$/sec.

72. The plurality of modified PBMCs of any one of embodiments 10-67, wherein the plurality of input PBMCs is passed through the constriction at a flow rate of about 100 mL/cm$^2$/sec.

73. The plurality of modified PBMCs of any one of embodiments 10-72, wherein the plurality of input PBMCs is passed through the constriction at a temperature ranging from about 0° C. to about 37° C.

74. The plurality of modified PBMCs of any one of embodiments 10-73, wherein subsequent to passing through the constriction the plurality of modified PBMCs is incubated at a temperature of 37° C. for a sufficient time to allow the modified PBMCs to normalize to 37° C.

75. The plurality of modified PBMCs of any one of embodiments 10-74, wherein subsequent to passing through the constriction the plurality of modified PBMCs is incubated at a temperature of 25° C. for a sufficient time to allow the modified PBMCs to normalize to 25° C.

76. The plurality of modified PBMCs of any one of embodiments 10-75, wherein the cross-sectional shape of the constriction is selected from the group consisting of: circular, elliptical, round, square, rectangular, star-shaped, triangular, polygonal, pentagonal, hexagonal, heptagonal, and octagonal.

77. The plurality of modified PBMCs of any one of embodiments 10-76, wherein the cross-sectional shape of the constriction is a slit.

78. The plurality of modified PBMCs embodiment 77, wherein slit comprises a width of about 3 μm-6 μm and/or a depth of about 20 μm-120 μm.

79. The plurality of modified PBMCs embodiment 78, wherein the slit comprises a width of about 4.2 μm-6 μm and/or a depth of about 20 μm-120 μm.

80. The plurality of modified PBMCs of any one of embodiments 77-79, wherein the slit comprises a width of about 4.5 μm and/or a depth of about 80 μm.

81. The plurality of modified PBMCs of any one of embodiments 10-80, wherein the cell suspension comprising the plurality of input PBMCs are passed through multiple constrictions wherein the multiple constrictions are arranged in series and/or in parallel.

82. The plurality of modified PBMCs of any one of embodiments 10-80, wherein the constriction comprises an entrance portion and an exit portion, wherein:
(a) the entrance portion defines an entrance angle and the entrance angle is between about 0 degree to about 90 degrees or between about 20-22 degrees; and/or
(b) the exit portion defines an exit angle and the exit angle is between about 0 degree to about 90 degrees or between about 20-22 degrees;
preferably between about 20-22 degrees for (a) and (b).

83. The plurality of modified PBMCs of any one of embodiments 10-82, wherein the cell suspension comprising the plurality of input PBMCs are passed through multiple constrictions wherein the multiple constrictions are arranged in series and/or in parallel.

84. The conditioned plurality of modified PBMCs of any one of embodiments 12-14, 22-25, 31-83, wherein the plurality of modified PBMCs is incubated with the adjuvant for about 1 to about 24 hours for the modified PBMCs to condition.

85. The conditioned plurality of modified PBMCs of any one of embodiments 12-14, 22-25, 31-84, wherein the plurality of modified PBMCs is incubated with the adjuvant for about 2 to about 10 hours for the modified PBMCs to condition.

86. The conditioned plurality of modified PBMCs of any one of embodiments 12-14, 22-25, 31-85, wherein the plurality of modified PBMCs is incubated with the adjuvant for about 3 to about 6 hours for the modified PBMCs to condition.

87. The conditioned plurality of modified PBMCs of any one of embodiments 12-14, 22-25, 31-86, wherein the plurality of modified PBMCs is incubated with the adjuvant for about 4 hours for the modified PBMCs to condition.

88. The plurality of modified PBMCs of any one of embodiments 1-87, wherein the antigen, the nucleic acid encoding the antigen, and/or adjuvant are present in the cytosol and/or a vesicle of a cell in the plurality of modified PBMCs.

89. The plurality of modified PBMCs of any one of embodiments 1-88, wherein the antigen and/or the nucleic acid encoding the antigen is present in the cytosol and the adjuvant is present in a vesicle of a cell in the plurality of modified PBMCs.

90. The plurality of modified PBMCs of embodiment 88 or 89, wherein the vesicle is an endosome.

91. The plurality of modified PBMCs of any one of embodiments 1-90, wherein the antigen, the nucleic acid encoding the antigen, and/or the adjuvant are present in multiple compartments of a cell in the plurality of modified PBMCs.

92. The plurality of modified PBMCs of any one of embodiments 1-91, wherein the antigen, the nucleic acid encoding the antigen, and/or the adjuvant are present in at least about 70% of the cells in the plurality of PBMCs.

93. The plurality of modified PBMCs of any one of embodiments 1-92, wherein the antigen, the nucleic acid encoding the antigen, and/or the adjuvant are present in at least about 70% of each of the T cells, B cells, NK cells, and monocytes in the plurality of PBMCs.

94. The plurality of modified PBMCs of any one of embodiments 1-93, wherein the antigen is bound to the surface of a cell in the plurality of modified PBMCs.

95. The plurality of modified PBMCs of any one of embodiments 5-94, wherein the adjuvant is a CpG oligodeoxynucleotide (ODN), LPS, IFN-α, STING agonists, RIG-I agonists, poly I:C, R837, R848, a TLR3 agonist, a TLR4 agonist or a TLR 9 agonist.

96. The plurality of modified PBMCs of embodiment 95, wherein the adjuvant is a CpG ODN.

97. The plurality of modified PBMCs of embodiment 96, wherein the CpG ODN is a Class A CpG ODN, a Class B CpG ODN, or a Class C CpG ODN.

98. The plurality of modified PBMCs of any one of embodiments 1-97, wherein the antigen is a disease-associated antigen.

99. The plurality of modified PBMCs of embodiment 98, wherein the antigen is derived from peptides or mRNA isolated from a diseased cell.

100. The plurality of modified PBMCs of any one of embodiments 1-99, wherein the antigen is a non-self antigen.

101. The plurality of modified PBMCs of any one of embodiments 1-100, wherein the antigen is a tumor antigen, viral antigen, bacterial antigen, or fungal antigen.

102. The plurality of modified PBMCs of any one of embodiments 1-5 and 8-101, wherein the antigen is derived from a tumor lysate.

103. The plurality of modified PBMCs of any one of embodiments 1-101, wherein the antigen is a human papillomavirus (HPV) antigen.

104. The plurality of modified PBMCs of embodiment 103, wherein the HPV is HPV-16 or HPV-18.

105. The plurality of modified PBMCs of embodiment 103 or 104, wherein the antigen comprises a peptide derived from HPV E6 and/or E7.

106. The plurality of modified PBMCs of embodiment 103 or 104, wherein the antigen comprises an HLA-A2-restricted peptide derived from HPV E6 and/or E7.

107. The plurality of modified PBMCs of embodiment 106, wherein the HLA-A2-restricted peptide comprises the amino acid sequence of any one of SEQ ID NOs: 1-4.

108. The plurality of modified PBMCs of embodiment 107, wherein the antigen comprises the amino acid sequence of any one of SEQ ID NOs: 18-25.

109. The plurality of modified PBMCs of any one of embodiments 1-108, wherein the modified PBMCs comprises a plurality of antigens that comprise a plurality of immunogenic epitopes.

110. The plurality of modified PBMCs of embodiment 109, wherein following administration to an individual of the modified PBMCs comprising the plurality of antigens that comprise the plurality of immunogenic epitopes, none of the plurality of immunogenic epitopes decreases an immune response in the individual to any of the other immunogenic epitopes.

111. The plurality of modified PBMCs of embodiment 110, wherein the antigen is a polypeptide and the immunogenic epitope is an immunogenic peptide epitope.

112. The plurality of modified PBMCs of embodiment 111, wherein the immunogenic peptide epitope is fused to an N-terminal flanking polypeptide and/or a C-terminal flanking polypeptide.

113. The plurality of modified PBMCs of embodiment 111, wherein the antigen is a polypeptide comprising an immunogenic peptide epitope and one or more heterologous peptide sequences.

114. The plurality of modified PBMCs of embodiment 111, wherein the antigen is a polypeptide comprising an immunogenic peptide epitope that is flanked on the N-terminus and/or the C-terminus by heterologous peptide sequences 115. The plurality of modified PBMCs of embodiment 114, wherein the flanking heterologous peptide sequences are derived from a disease-associated immunogenic peptide.

116. The plurality of modified PBMCs of embodiment 112, wherein the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17.

117. The plurality of modified PBMCs of any one of embodiments 1-116, wherein the antigen is capable of being processed into an MHC class I-restricted peptide and/or an MHC class II-restricted peptide.

118. The plurality of modified PBMCs of any one of embodiments 5, 15-21 and 26-117, wherein the modified PBMCs comprise the adjuvant at a concentration between about 1 nM and about 1 mM.

119. The plurality of modified PBMCs of any one of embodiments 1-118, wherein the modified PBMCs comprise the antigen at a concentration between about 1 nM and about 1 mM.

120. The plurality of modified PBMCs of any one of embodiments 1-119, wherein the ratio of the antigen to the adjuvant is between about 10000:1 to about 1:10000.

121. The plurality of modified PBMCs of any one of embodiments 1-120, wherein the ratio of the antigen to the adjuvant is about 200:1.

122. The plurality of modified PBMCs of any one of embodiments 1-118, wherein the modified PBMCs comprise a complex comprising: a) the antigen, b) the antigen and at least one other antigen, c) the antigen and the adjuvant, d) the nucleic acid encoding the antigen, e) the nucleic acid encoding the antigen and at least one other nucleic acid encoding one other antigen, and/or f) the nucleic acid encoding the antigen and the adjuvant.

123. The plurality of modified PBMCs of any one of embodiments 3-5, 7-9, 12-14, 22-25 and 31-122, wherein the plurality of modified PBMCs further comprises an agent that enhances the viability and/or function of the plurality of modified PBMCs as compared to a corresponding plurality of modified PBMCs that does not comprise the agent.

124. The plurality of modified PBMCs of any one of embodiments 3-5, 7-9, 12-14, 22-25 and 31-123, wherein the plurality of modified PBMCs further comprises an agent that enhances the viability and/or function of the plurality of modified PBMCs upon freeze-thaw cycle as compared to a corresponding plurality of modified PBMCs that does not comprise the agent.

125. The plurality of modified PBMCs of any one of embodiments 3-5, 7-9, 12-14, 22-25 and 31-124, wherein at least about 70%, about 80%, or about 90% of the conditioned plurality of modified PBMCs are viable after up to 1, 2, 3, 4, 5 freeze-thaw cycles.

126. The plurality of modified PBMCs of any one of embodiments 123-125, wherein the agent is a compound that enhances endocytosis, a stabilizing agent or a co-factor.

127. The plurality of modified PBMCs of any one of embodiments 123-126, wherein the agent is albumin.

128. The plurality of modified PBMCs of embodiment 127, wherein the albumin is mouse, bovine, or human albumin.

129. The plurality of modified PBMCs of any one of embodiments 123-125, wherein the agent is one or more of: a divalent metal cation, glucose, ATP, potassium, glycerol, trehalose, D-sucrose, PEG1500, L-arginine, L-glutamine, or EDTA.

130. The plurality of modified PBMCs of any one of embodiments 123-125, wherein the agent is one or more of:

Sodium pyruvate, adenine, Rejuvesol®, trehalose, dextrose, mannose, sucrose, human serum albumin (HSA), Plasma-Lyte®, DMSO, Cryostor® CS2, Cryostor® CS5, Cryostor® CS10, Cryostor® CS15, HEPES, glycerol, glutathione, HypoThermosol®

131. The plurality of modified PBMCs of embodiment 128, wherein the agent comprises mouse serum albumin (MSA).

132. The plurality of modified PBMCs of embodiment 128, wherein the agent comprises human serum albumin (HSA)

133. The plurality of modified PBMCs of any one of embodiments 1-132 wherein the cells are further modified to increase expression of one or more of co-stimulatory molecules.

134. The plurality of modified PBMCs of embodiment 133, wherein the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112.

135. The plurality of modified PBMCs of embodiment 133, wherein the co-stimulatory molecule is a Signal 2 effector.

136. The plurality of modified PBMCs of any one of embodiments 133-135, wherein the cell comprises a nucleic acid (e.g., mRNA) that results in increased expression of the one or more co-stimulatory molecules.

137. The plurality of modified PBMCs of embodiment 136, wherein the nucleic acid encodes the costimulatory molecule.

138. The plurality of modified PBMCs of any one of embodiments 1-137 wherein the cells are further modified to increase expression of one or more cytokines.

139. The plurality of modified PBMCs of embodiment 138, wherein the cytokine is IL-12, IL-2, IFN-α, or IL-21.

140. The plurality of modified PBMCs of embodiment 133, wherein the co-stimulatory molecule is a Signal 3 effector.

141. The plurality of modified PBMCs of any one of embodiments 138-140, wherein the cell comprises a nucleic acid (e.g., mRNA) that results in increased expression of the one or more cytokines.

142. The plurality of modified PBMCs of embodiment 141, wherein the nucleic acid encodes the cytokine.

143. The plurality of modified PBMCs of any one of embodiments 1-142, wherein at least one cell in the plurality of modified PBMCs is positive for expression of HLA-A2.

144. The plurality of modified PBMCs of any one of embodiments 1-142, wherein the modified PBMCs comprise a further modification to modulate MHC class I expression.

145. The plurality of modified PBMCs of any one of embodiments 1-142, wherein the modified PBMCs comprise a further modification to modulate HLA-A02 MHC I.

146. The plurality of modified PBMCs of any one of embodiments 1-145, wherein the modified PBMCs comprise a further modification to modulate MHC class II expression.

147. The plurality of modified PBMCs of embodiment 145, wherein an innate immune response mounted in an individual in response to administration, in an allogeneic context, of the modified PBMCs is reduced compared to an innate immune response mounted in an individual in response to administration, in an allogeneic context, of corresponding modified PBMCs that do not comprise the further modification.

148. The plurality of modified PBMCs of any one of embodiments 1-147, wherein the circulating half-life of the modified PBMCs in an individual to which they were administered is increased compared to the circulating half-life of corresponding modified PBMCs that do not comprise the further modification in an individual to which they were administered.

149. The plurality of modified PBMCs of any one of embodiments 1-147, wherein the circulating half-life of the modified PBMCs in an individual to which they were administered is essentially the same as the circulating half-life of corresponding modified PBMCs that do not comprise the further modification in an individual to which they were administered.

150. The plurality of modified PBMCs of any one of embodiments 1-147, wherein the circulating half-life of the modified PBMCs in an individual to which they were administered is essentially the same as the circulating half-life of corresponding unmodified PBMCs.

151. The plurality of modified PBMCs of any one of embodiments 1-150, wherein the plurality of PBMCs comprises one or more of T cell, B cell, NK cell, monocytes, dendritic cells or NK-T cells.

152. The plurality of modified PBMCs of any one of embodiments 1-151, wherein the plurality of PBMCs comprises two or more of T cell, B cell, NK cell, monocytes, dendritic cells or NK-T cells.

153. The plurality of modified PBMCs of any one of embodiments 1-152, wherein the plurality of PBMCs comprises one or more of CD3+ T cells, CD20+ B cells, CD14+ monocytes, CD56+NK cells.

154. The plurality of modified PBMCs of any one of embodiments 10-153, wherein the plurality of input PBMCs comprises T cells, B cells, NK cells and monocytes, and wherein the ratio of T cells, B cells, NK cells and monocytes to the total number of PBMCs in the plurality of input PBMCs is essentially the same as the ratio of T cells, B cells, NK cells and monocytes to the total number of PBMCs in whole blood.

155. The plurality of modified PBMCs of any one of embodiments 10-153, wherein the plurality of input PBMCs comprises T cells, B cells, NK cells and monocytes, and wherein the ratio of T cells, B cells, NK cells and monocytes to the total number of PBMCs in the plurality of input PBMCs is essentially the same as the ratio of T cells, B cells, NK cells and monocytes to the total number of PBMCs in a leukapheresis product from whole blood.

156. The plurality of modified PBMCs of any one of embodiments 10-153, wherein the plurality of input PBMCs comprises T cells, B cells, NK cells and monocytes, and wherein the ratio of T cells, B cells, NK cells and monocytes to the total number of PBMCs in the plurality of input PBMCs differs by not more than 10% from the ratio of T cells, B cells, NK cells and monocytes to the total number of PBMCs in whole blood.

157. The plurality of modified PBMCs of any one of embodiments 10-153, wherein the plurality of input PBMCs comprises T cells, B cells, NK cells and monocytes, and wherein the ratio of T cells, B cells, NK cells and monocytes to the total number of PBMCs in the plurality of input PBMCs differs by not more than 10% from the ratio of T cells, B cells, NK cells and monocytes to the total number of PBMCs in a leukapheresis product from whole blood.

158. The plurality of modified PBMCs of any one of embodiments 10-157, wherein:
(a) at least about 25% of the input PBMCs are T cells;
(b) at least about 2.5% of the input PBMCs are B cells;
(c) at least about 3.5% of the input PBMCs are NK cells; or
(d) at least about 4% of the input PBMCs are monocytes.

159. The plurality of modified PBMCs of any one of embodiments 1-158, wherein:
(a) at least about 20% of the modified PBMCs are T cells;
(b) at least about 2% of the modified PBMCs are B cells;
(c) at least about 3% of the modified PBMCs are NK cells; or
(d) at least about 3% of the modified PBMCs are monocytes.

160. The plurality of modified PBMCs of any one of embodiments 1-159, wherein:
(a) not more than about 70% of the input PBMCs are T cells;
(b) not more than about 14% of the input PBMCs are B cells;
(c) not more than about 35% of the input PBMCs are NK cells; or
(d) not more than about 25% of the input PBMCs are monocytes.

161. The plurality of modified PBMCs of any one of embodiments 1-160, wherein:
(a) not more than about 80% of the modified PBMCs are T cells;
(b) not more than about 16% of the modified PBMCs are B cells;
(c) not more than about 40% of the modified PBMCs are NK cells; or
(d) not more than about 30% of the modified PBMCs are monocytes.

162. The plurality of modified PBMCs of any one of embodiments 1-161, wherein:
(a) about 25% to about 70% of the modified PBMCs are T cells;
(b) about 2.5% to about 14% of the modified PBMCs are B cells;
(c) about 3.5% to about 35% of the modified PBMCs are NK cells; or
(d) about 4% to about 25% of the modified PBMCs are monocytes.

163. The plurality of modified PBMCs of any one of embodiments 1-162, wherein:
(a) the percentage of T cells within the plurality of modified PBMCs and the percentage of T cells within the plurality of input PBMCs differ by no more than about 10% by number;
(b) the percentage of B cells within the plurality of modified PBMCs and the percentage of B cells within the plurality of input PBMCs differ by no more than about 10% by number;
(c) the percentage of NK cells within the plurality of modified PBMCs and the percentage of NK cells within the plurality of input PBMCs differ by no more than about 10% by number; and/or
(d) the percentage of monocytes within the plurality of modified PBMCs and the percentage of monocytes within the plurality of input PBMCs differ by no more than about 10% by number.

164. The plurality of modified PBMCs of any one of embodiments 3-9 and 12-163, wherein: one or more co-stimulatory molecules is upregulated in the B cells of the conditioned plurality of modified PBMCs compared to the B cells in the plurality of unmodified PBMCs, wherein the co-stimulatory molecule is CD80 and/or CD86.

165. The plurality of modified PBMCs of embodiment 164, wherein the CD80 and/or CD86 is upregulated in the B cells of the conditioned plurality of modified PBMCs by more than about 1.2-fold, 1.5-fold, 1.8-fold, 2-fold, 3-fold, 4-fold, 5-fold, 8-fold, or more than 10-fold compared to the B cells in a plurality of unconditioned PBMCs.

166. The plurality of modified PBMCs of embodiment 164 or 165, wherein the co-stimulatory molecule is CD86.

167. The conditioned plurality of modified PBMCs of any one of embodiments 3-9 and 12-166, wherein the modified PBMCs have increased expression of one or more of IFN-γ, IL-6, MCP-1, MIP-1β, IP-10, or TNF-α compared to a plurality of unconditioned PBMCs.

168. The conditioned plurality of modified PBMCs of embodiment 167, wherein the expression of one or more of IFN-γ, IL-6, MCP-1, MIP-1β, IP-10, or TNF-α is increased by more than about 1.2-fold, 1.5-fold, 1.8-fold, 2-fold, 3-fold, 4-fold, 5-fold, 8-fold, or more than 10-fold compared to the plurality of unconditioned PBMCs.

169. A composition comprising the plurality of modified PBMCs of any one of embodiments 1-168.

170. A composition comprising the plurality of modified PBMCs of any one of embodiments 1-169 for use as a medicament.

171. A composition comprising the plurality of modified PBMCs of any one of embodiments 1-169 for use in a method of treatment of the human or animal body by surgery, therapy or diagnosis.

172. A composition comprising the plurality of modified PBMCs of any one of embodiments 1-169 for use in the treatment of a cancer, an infectious disease or a viral-associated disease.

173. The composition of embodiment 172, wherein the cancer is head and neck cancer, cervical cancer, vulvar cancer, vaginal cancer, penile cancer, anal cancer, perianal cancer, anogenital cancer, oral cancer or salivary cancer.

174. The composition of any one of embodiments 171-173, wherein the modified PBMCs is administered prior to, concurrently with, or following administration of an immune checkpoint inhibitor.

175. The composition of embodiment 174, wherein the immune checkpoint inhibitor is targeted to any one of PD-1, PD-L1, CTLA-4, LAG3, TIM-3, TIGIT, VISTA, TIM1, B7-H4 (VTCN1) or BTLA.

176. The composition of embodiment 175, wherein the immune checkpoint inhibitor is targeted to PD-1.

177. The composition of embodiment 175, wherein the immune checkpoint inhibitor is targeted to PD-L1.

178. The composition of any one of embodiments 171-177, wherein the modified PBMCs is administered prior to, concurrently with, or following administration of a therapeutic agent.

179. The composition of embodiment 178, wherein the therapeutic agent is a chemotherapeutic agent.

180. The composition of embodiment 172, wherein the infectious disease is associated with HIV, HPV, EBV, MCV, HBV or HCV.

181. A pharmaceutical composition comprising the modified PBMCs of any one of embodiments 1-168 and a pharmaceutically acceptable carrier.

182. The composition of embodiment any one of embodiments 171-181, wherein the composition is for treatment of cancers or infectious diseases.

183. A composition comprising a conditioned plurality of modified PBMCs comprising an antigen for use as a medicament, wherein the conditioned plurality of modified PBMCs is prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen.

184. A composition comprising a conditioned plurality of modified PBMCs comprising an antigen for use as a medicament, wherein the conditioned plurality of modified PBMCs is prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen to pass through to form a plurality of perturbed input PBMCs;
b) incubating the plurality of perturbed input PBMCs with the nucleic acid encoding the antigen for a sufficient time to allow the nucleic acid encoding the antigen to enter the perturbed input PBMCs, thereby generating a plurality of modified PBMCs comprising the nucleic acid encoding the antigen; and
c) incubating the plurality of modified PBMCs comprising the nucleic acid encoding the antigen with an adjuvant for a sufficient time for the modified PBMCs comprising the nucleic acid encoding the antigen to condition, wherein the nucleic acid is expressed in the PBMCs to produce the antigen, thereby generating the conditioned plurality of modified PBMCs comprising the antigen.

185. A composition comprising a conditioned plurality of modified PBMCs comprising an antigen for use in a method of treatment of the human or animal body by surgery, therapy or diagnosis, wherein the conditioned plurality of modified PBMCs is prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with an adjuvant for a sufficient time for the modified PBMCs comprising the antigen to condition, thereby generating the conditioned plurality of modified PBMCs comprising the antigen.

186. A composition comprising a conditioned plurality of modified PBMCs comprising an antigen for use in a method of treatment of the human or animal body by surgery, therapy or diagnosis, wherein the conditioned plurality of modified PBMCs is prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen to pass through to form a plurality of perturbed input PBMCs;
b) incubating the plurality of perturbed input PBMCs with the nucleic acid encoding the antigen for a sufficient time to allow the nucleic acid encoding the antigen to enter the perturbed input PBMCs, thereby generating a plurality of modified PBMCs comprising the nucleic acid encoding antigen; and
c) incubating the plurality of modified PBMCs comprising the nucleic acid encoding the antigen with an adjuvant for a sufficient time for the modified PBMCs comprising the nucleic acid encoding the antigen to condition,
wherein the nucleic acid is expressed in the PBMCs to produce the antigen, thereby generating the conditioned plurality of modified PBMCs comprising the antigen.

187. A composition comprising a conditioned plurality of modified PBMCs comprising an antigen for use as a medicament, wherein the conditioned plurality of modified PBMCs is prepared by a process comprising the steps of:
a) incubating a plurality of input PBMCs with an adjuvant for a sufficient time for the input PBMCs to condition, thereby generating a conditioned plurality of input PBMCs;
b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and
c) incubating the conditioned plurality of perturbed input PBMCs with the antigen for a sufficient time to allow the antigen to enter the perturbed input PBMCs, thereby generating the conditioned plurality of modified PBMCs comprising the antigen.

188. A composition comprising a conditioned plurality of modified PBMCs comprising an antigen for use as a medicament, wherein the conditioned plurality of modified PBMCs is prepared by a process comprising the steps of:
a) incubating a plurality of input PBMCs with an adjuvant for a sufficient time for the input PBMCs to condition, thereby generating a conditioned plurality of input PBMCs;
b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen to pass through to form a conditioned plurality of perturbed input PBMCs; and
c) incubating the conditioned plurality of perturbed input PBMCs with the nucleic acid encoding the antigen for a sufficient time to allow the nucleic acid encoding the antigen to enter the perturbed input PBMCs,
wherein the nucleic acid is expressed in the PBMCs to produce the antigen, thereby generating the conditioned plurality of modified PBMCs comprising the antigen.

189. A composition comprising a conditioned plurality of modified PBMCs comprising an antigen for use in a method of treatment of the human or animal body, wherein the conditioned plurality of modified PBMCs is prepared by a process comprising the steps of:
a) incubating a plurality of input PBMCs with an adjuvant for a sufficient time for the input PBMCs to condition, thereby generating a conditioned plurality of input PBMCs;
b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and
c) incubating the conditioned plurality of perturbed input PBMCs with the antigen for a sufficient time to allow the antigen to enter the perturbed input PBMCs, thereby generating the conditioned plurality of modified PBMCs comprising the antigen.

190. A composition comprising a conditioned plurality of modified PBMCs comprising an antigen for use in a method of treatment of the human or animal body, wherein the conditioned plurality of modified PBMCs is prepared by a process comprising the steps of:
a) incubating a plurality of input PBMCs with an adjuvant for a sufficient time for the input PBMCs to condition, thereby generating a conditioned plurality of input PBMCs;
b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen to pass through to form a conditioned plurality of perturbed input PBMCs; and
c) incubating the conditioned plurality of perturbed input PBMCs with the nucleic acid encoding the antigen for a sufficient time to allow the nucleic acid encoding the antigen to enter the perturbed input PBMCs,
wherein the nucleic acid is expressed in the PBMCs to produce the antigen, thereby generating the conditioned plurality of modified PBMCs comprising the antigen.

191. A composition comprising a conditioned plurality of modified PBMCs comprising an antigen for use in a method of treating cancer an infectious disease or a viral associated disease in an individual, wherein the conditioned plurality of modified PBMCs is prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with an adjuvant for a sufficient time for the modified PBMCs comprising the antigen to condition, thereby generating the conditioned plurality of modified PBMCs comprising the antigen.

192. A composition comprising a conditioned plurality of modified PBMCs comprising an antigen for use in a method of treating cancer an infectious disease or a viral associated disease in an individual, wherein the conditioned plurality of modified PBMCs is prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen to pass through to form a plurality of perturbed input PBMCs;
b) incubating the plurality of perturbed input PBMCs with the nucleic acid encoding the antigen for a sufficient time to allow the nucleic acid encoding the antigen to enter the perturbed input PBMCs, thereby generating a plurality of modified PBMCs comprising the nucleic acid encoding the antigen; and
c) incubating the plurality of modified PBMCs comprising the nucleic acid encoding the antigen with an adjuvant for a sufficient time for the modified PBMCs comprising the nucleic acid encoding the antigen to condition,
wherein the nucleic acid is expressed in the PBMCs to produce the antigen, thereby generating the conditioned plurality of modified PBMCs comprising the antigen.

193. A composition comprising a conditioned plurality of modified PBMCs comprising an antigen for use in the treatment of cancer, an infectious disease or a viral associated disease in an individual, wherein the conditioned plurality of modified PBMCs is prepared by a process comprising the steps of:
a) passing a cell suspension comprising a plurality of input PBMCs through a cell deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with an adjuvant for a sufficient time for the modified PBMCs comprising the antigen to condition, thereby generating the conditioned plurality of modified PBMCs comprising the antigen.

194. A composition comprising a conditioned plurality of modified PBMCs comprising an antigen for use in the treatment of cancer, an infectious disease or a viral associated disease in an individual, wherein the conditioned plurality of modified PBMCs is prepared by a process comprising the steps of:
a) passing a cell suspension comprising a plurality of input PBMCs through a cell deforming constriction, wherein a diameter of the constriction is a function of a diameter of the input PBMCs in the suspension, thereby causing perturbations of the input PBMCs large enough for a nucleic acid encoding the antigen to pass through to form a plurality of perturbed input PBMCs;
b) incubating the plurality of perturbed input PBMCs with the nucleic acid encoding the antigen for a sufficient time to allow the nucleic acid encoding the antigen to enter the perturbed input PBMCs, thereby generating a plurality of modified PBMCs comprising the nucleic acid encoding the antigen; and
c) incubating the plurality of modified PBMCs comprising the nucleic acid encoding antigen with an adjuvant for a sufficient time for the modified PBMCs comprising the nucleic acid encoding the antigen to condition,
wherein the nucleic acid is expressed in the PBMCs to produce the antigen, thereby generating the conditioned plurality of modified PBMCs comprising the antigen.

195. A composition comprising a conditioned plurality of modified PBMCs comprising an antigen for use in a method of treating a HPV-associated disease in an individual, wherein the conditioned plurality of modified PBMCs is prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with an adjuvant for a sufficient time for the modified PBMCs comprising the antigen to condition, thereby generating the conditioned plurality of modified PBMCs comprising the antigen.

196. A composition comprising a conditioned plurality of modified PBMCs comprising an antigen for use in a method of treating a HPV-associated disease in an individual, wherein the conditioned plurality of modified PBMCs is prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen to pass through to form a plurality of perturbed input PBMCs;
b) incubating the plurality of perturbed input PBMCs with the nucleic acid encoding the antigen for a sufficient time to allow the nucleic acid encoding the antigen to enter the perturbed input PBMCs, thereby generating a plurality of modified PBMCs comprising the nucleic acid encoding the antigen; and
c) incubating the plurality of modified PBMCs comprising the nucleic acid encoding the antigen with an adjuvant for a sufficient time for the modified PBMCs comprising the nucleic acid encoding the antigen to condition, wherein the nucleic acid is expressed in the PBMCs to produce the antigen, thereby generating the conditioned plurality of modified PBMCs comprising the antigen.

197. A composition comprising a conditioned plurality of modified PBMCs comprising an antigen for use in the treatment of a HPV-associated disease in an individual, wherein the conditioned plurality of modified PBMCs is prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with an adjuvant for a sufficient time for the modified PBMCs comprising the antigen to condition, thereby generating the conditioned plurality of modified PBMCs comprising the antigen.

198. A composition comprising a conditioned plurality of modified PBMCs comprising an antigen for use in the treatment of a HPV-associated disease in an individual, wherein the conditioned plurality of modified PBMCs is prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen to pass through to form a plurality of perturbed input PBMCs;
b) incubating the plurality of perturbed input PBMCs with the nucleic acid encoding the antigen for a sufficient time to allow the nucleic acid encoding the antigen to enter the perturbed input PBMCs, thereby generating a plurality of modified PBMCs comprising the nucleic acid encoding the antigen; and
c) incubating the plurality of modified PBMCs comprising the antigen with an adjuvant for a sufficient time for the modified PBMCs comprising the nucleic acid encoding the antigen to condition, wherein the nucleic acid is expressed in the PBMCs to produce the antigen, thereby generating the conditioned plurality of modified PBMCs comprising the antigen.

199. Use of a composition comprising a conditioned plurality of modified PBMCs comprising an antigen in the manufacture of a medicament for treating cancer, an infectious disease or a viral-associated disease in an individual, wherein the conditioned plurality of modified PBMCs is prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with an adjuvant for a sufficient time for the modified PBMCs comprising the antigen to condition, thereby generating the conditioned plurality of modified PBMCs comprising the antigen.

200. Use of a composition comprising a conditioned plurality of modified PBMCs comprising an antigen in the manufacture of a medicament for treating a HPV-associated disease, wherein the conditioned plurality of modified PBMCs is prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with an adjuvant for a sufficient time for the modified PBMCs comprising the antigen to condition, thereby generating the conditioned plurality of modified PBMCs comprising the antigen.

201. A conditioned plurality of modified PBMCs comprising a human papillomavirus (HPV) antigen, prepared by a process comprising the steps of:
a) passing a cell suspension comprising a plurality of input PBMCs through a cell-deforming constriction, wherein a diameter of the constriction is about 4 μm to about 10 μm, thereby causing perturbations of the input PBMCs large enough for the HPV antigen to pass through to form a plurality of perturbed input PBMCs;
b) incubating the plurality of perturbed input PBMCs with the HPV antigen for a sufficient time to allow the HPV antigen to enter the perturbed input PBMCs, thereby generating a plurality of modified PBMCs comprising the HPV antigen; and
c) incubating the plurality of modified PBMCs comprising the HPV antigen with a CpG ODN for a sufficient time for the modified PBMCs comprising the HPV antigen to condition, thereby generating the conditioned plurality of modified PBMCs comprising the HPV antigen.

202. A conditioned plurality of modified PBMCs comprising a HPV antigen, prepared by a process comprising the steps of:
a) passing a cell suspension comprising a plurality of input PBMCs through a cell-deforming constriction, wherein a diameter of the constriction is about 4 µm to about 10 µm, thereby causing perturbations of the input PBMCs large enough for the HPV antigen to pass through to form a plurality of perturbed input PBMCs;
b) incubating the plurality of perturbed input PBMCs with the HPV antigen for a sufficient time to allow the HPV antigen to enter the perturbed input PBMCs, thereby generating a plurality of modified PBMCs comprising the HPV antigen; and
c) incubating the plurality of modified PBMCs comprising the HPV antigen with a CpG ODN for a sufficient time for the modified PBMCs comprising the HPV antigen to condition, wherein the CpG ODN is CpG 7909, thereby generating the conditioned plurality of modified PBMCs comprising the HPV antigen.

203. A conditioned plurality of modified PBMCs comprising a HPV antigen, prepared by a process comprising the steps of:
a) passing a cell suspension comprising a plurality of input PBMCs through a cell-deforming constriction, wherein a diameter of the constriction is about 4 µm to about 10 µm, thereby causing perturbations of the input PBMCs large enough for the HPV antigen to pass through to form a plurality of perturbed input PBMCs;
b) incubating the plurality of perturbed input PBMCs with the HPV antigen for a sufficient time to allow the HPV antigen to enter the perturbed input PBMCs, thereby generating a plurality of modified PBMCs comprising the HPV antigen; and
c) incubating the plurality of modified PBMCs comprising the HPV antigen with a CpG ODN for about 1 hour to about 24 hours for the modified PBMCs comprising the HPV antigen to condition, thereby generating the conditioned plurality of modified PBMCs comprising the HPV antigen.

204. A conditioned plurality of modified PBMCs comprising a HPV antigen, prepared by a process comprising the steps of:
a) passing a cell suspension comprising a plurality of input PBMCs through a cell-deforming constriction, wherein a diameter of the constriction is about 4 µm to about 10 µm, thereby causing perturbations of the input PBMCs large enough for the HPV antigen to pass through to form a plurality of perturbed input PBMCs;
b) incubating the plurality of perturbed input PBMCs with the HPV antigen for a sufficient time to allow the HPV antigen to enter the perturbed input PBMCs, thereby generating a plurality of modified PBMCs comprising the HPV antigen; and
c) incubating the plurality of modified PBMCs comprising the HPV antigen with a CpG ODN for about 1 hour to about 24 hours for the modified PBMCs comprising the HPV antigen to condition, wherein the CpG ODN is CpG 7909, thereby generating the conditioned plurality of modified PBMCs comprising the HPV antigen.

205. The conditioned plurality of the modified PBMCs of any one of embodiments 201-204, wherein the diameter of the constriction is (a) about 4.2 µm to about 6 µm; or (b) about 4.5 µm.

206. The conditioned plurality of the modified PBMCs of any one of embodiments 201-205, wherein the plurality of modified PBMCs comprising the HPV antigen is incubated with a CpG ODN for (a) about 2 hour to about 10 hours; (b) about 3 hours to about 6 hours; or (c) about 4 hours.

207. A conditioned plurality of modified PBMCs comprising an antigen, prepared by a process comprising the steps of:
a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with a CpG ODN for a sufficient time for the modified PBMCs comprising the antigen to condition, thereby generating the conditioned plurality of modified PBMCs comprising the antigen.

208. A conditioned plurality of modified PBMCs comprising an antigen, prepared by a process comprising the steps of:
a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with a CpG ODN for a sufficient time for the modified PBMCs comprising the antigen to condition, wherein the CpG ODN is CpG 7909, thereby generating the conditioned plurality of modified PBMCs comprising the antigen.

209. A conditioned plurality of modified PBMCs comprising an antigen, prepared by a process comprising the steps of:
a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with a CpG ODN for about 1 hour to about 24 hours for the modified PBMCs comprising the antigen to condition, thereby generating the conditioned plurality of modified PBMCs comprising the antigen.

210. A conditioned plurality of modified PBMCs comprising an antigen, prepared by a process comprising the steps of:
a) passing a cell suspension comprising a plurality of input PBMCs through a cell-deforming constriction, wherein a diameter of the constriction is about 3 µm to about 10 µm, thereby causing perturbations of the input PBMCs large enough for the antigen to pass through to form a plurality of perturbed input PBMCs;

b) incubating the plurality of perturbed input PBMCs with the antigen for a sufficient time to allow the antigen to enter the perturbed input PBMCs, thereby generating a plurality of modified PBMCs comprising the antigen; and c) incubating the plurality of modified PBMCs comprising the antigen with a CpG ODN for about 1 hour to about 24 hours for the modified PBMCs comprising the antigen to condition, wherein the CpG ODN is CpG 7909, thereby generating the conditioned plurality of modified PBMCs comprising the antigen.

211. The conditioned plurality of the modified PBMCs of any one of embodiments 207-210, wherein the diameter of the constriction is about 4 µm to about 10 µm.

212. The conditioned plurality of the modified PBMCs of any one of embodiments 207-211, the diameter of the constriction is about 3 µm to about 6 µm.

213. The conditioned plurality of the modified PBMCs of any one of embodiments 207-212, wherein the diameter of the constriction is (a) about 4.2 µm to about 6 µm; or (b) about 4.5 µm.

214. The conditioned plurality of the modified PBMCs of any one of embodiments 207-213, wherein the plurality of modified PBMCs comprising the antigen is incubated with a CpG ODN for (a) about 2 hour to about 10 hours; (b) about 3 hours to about 6 hours; or (c) about 4 hours.

215. A method for stimulating an immune response in an individual, comprising administering to the individual the plurality of modified PBMCs of any one of embodiments 1-168, the composition of embodiment 169-180, or the pharmaceutical composition of embodiment 181.

216. A method for stimulating an immune response in an individual, comprising:
a) administering a plurality of modified PBMCs comprising an antigen comprising the amino acid sequence of any one of SEQ ID NOs: 18-25 to the individual; and
b) administering an adjuvant to the individual.

217. A method for stimulating an immune response in an individual, comprising:
a) incubating a plurality of PBMCs comprising an antigen with an adjuvant for a sufficient time for the PBMCs to condition, thereby generating a conditioned plurality of PBMCs comprising the antigen;
b) administering the conditioned plurality of PBMCs comprising the antigen to the individual.

218. A method for stimulating an immune response in an individual, comprising:
a) incubating a plurality of PBMCs with an adjuvant for a sufficient time for the PBMCs to condition, thereby generating a conditioned plurality of PBMCs comprising the antigen;
b) introducing an antigen to the plurality of PBMCs; and
c) administering the conditioned plurality of PBMCs comprising the antigen to the individual.

219. A method for stimulating an immune response in an individual, comprising:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for an antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen;
c) incubating the plurality of modified PBMCs comprising the antigen with an adjuvant for a sufficient time for the modified PBMCs comprising the antigen to condition, thereby generating a conditioned plurality of modified PBMCs comprising the antigen; and
d) administering the conditioned plurality of modified PBMCs comprising the antigen to the individual.

220. A method for stimulating an immune response in an individual, comprising:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for a nucleic acid encoding an antigen to pass through to form a plurality of perturbed input PBMCs;
b) incubating the plurality of perturbed input PBMCs with the nucleic acid encoding the antigen for a sufficient time to allow the nucleic acid encoding the antigen to enter the perturbed input PBMCs, thereby generating a plurality of modified PBMCs comprising the nucleic acid encoding the antigen;
c) incubating the plurality of modified PBMCs comprising the nucleic acid encoding the antigen with an adjuvant for a sufficient time for the modified PBMCs comprising the nucleic acid encoding the antigen to condition, wherein the nucleic acid is expressed in the PBMCs to produce the antigen, thereby generating a conditioned plurality of modified PBMCs comprising the antigen; and
d) administering the conditioned plurality of modified PBMCs comprising the antigen to the individual.

221. The method of embodiment 220, further comprising isolating the plurality of modified PBMCs comprising the antigen from the cell suspension before incubation with the adjuvant.

222. A method for stimulating an immune response in an individual, comprising:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for an antigen and an adjuvant to pass through to form a plurality of perturbed input PBMCs;
b) incubating the plurality of perturbed input PBMCs with the antigen and the adjuvant for a sufficient time to allow the antigen and the adjuvant to enter the perturbed input PBMCs, thereby generating a plurality of modified PBMCs comprising the antigen and adjuvant; and
c) administering the plurality of modified PBMCs to the individual.

223. A method for stimulating an immune response in an individual, comprising:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for a nuclein acid encoding an antigen and for an adjuvant to pass through to form a plurality of perturbed input PBMCs;
b) incubating the plurality of perturbed input PBMCs with the nucleic acid encoding the antigen and with the adjuvant for a sufficient time to allow the nucleic acid encoding the antigen and the adjuvant to enter the perturbed input PBMCs, wherein the nucleic acid is expressed in the PBMCs to produce the antigen, thereby generating a plurality of modified PBMCs comprising the antigen and adjuvant; and
c) administering the plurality of modified PBMCs comprising the antigen and the adjuvant to the individual.

224. The method of embodiment 223, wherein the concentration of the antigen incubated with the perturbed input PBMCs is between about 0.1 µM and about 1 mM and/or the concentration of the adjuvant incubated with the perturbed input PBMCs is between about 0.1 µM and about 1 mM.

225. The method of any one of embodiments 222-224, wherein the concentration of the antigen incubated with the perturbed input PBMCs is between about 0.1 µM and about 10 µM and/or the concentration of the adjuvant incubated with the perturbed input PBMCs is between about 0.1 µM and about 10 µM.

226. The method of any one of embodiments 222-225, wherein the concentration of the antigen incubated with the perturbed input PBMCs is about 1 µM and/or the concentration of the adjuvant incubated with the perturbed input PBMCs is about 1 µM.

227. The method of any one of embodiments 222-226, wherein the ratio of the antigen to the adjuvant incubated with the perturbed input PBMCs is between about 10000:1 to about 1:10000.

228. The method of any one of embodiments 222-227, wherein the ratio of the antigen to the adjuvant incubated with the perturbed input PBMCs is about 200:1.

229. A method for stimulating an immune response in an individual, comprising:
a) incubating a plurality of input PBMCs with an adjuvant for a sufficient time for the input PBMCs to condition, thereby generating a conditioned plurality of input PBMCs;
b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for an antigen to pass through to form a conditioned plurality of perturbed input PBMCs;
c) incubating the conditioned plurality of perturbed input PBMCs with the antigen for a sufficient time to allow the antigen to enter the perturbed input PBMCs, thereby generating the conditioned plurality of modified PBMCs comprising the antigen; and
d) administering the conditioned plurality of modified PBMCs to the individual.

230. The method of embodiment 229, wherein the concentration of the adjuvant incubated with the input PBMCs is between about 0.1 µM and about 1 mM.

231. The method of embodiment 229 or 230, wherein the concentration of the adjuvant incubated with the input PBMCs is between about 0.1 µM and about 10 µM.

232. The method of any one of embodiments 229-231, wherein the concentration of the adjuvant incubated with the input PBMCs is about 1 µM.

233. A method for stimulating an immune response in an individual, comprising:
a) passing a cell suspension comprising a plurality of input PBMCs comprising an adjuvant through a cell-deforming constriction, wherein a diameter of the constriction is a function of a diameter of the input PBMCs in the suspension, thereby causing perturbations of the input PBMCs large enough for an antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen and the adjuvant; and
c) administering the plurality of modified PBMCs to the individual.

234. A method for stimulating an immune response in an individual, comprising:
a) passing a cell suspension comprising an input PBMCs comprising an antigen through a cell-deforming constriction, wherein a diameter of the constriction is a function of a diameter of the input PBMCs in the suspension, thereby causing perturbations of the input PBMCs large enough for an adjuvant to pass through to form a plurality of perturbed input PBMCs;
b) incubating the plurality of perturbed input PBMCs with the adjuvant for a sufficient time to allow the adjuvant to enter the perturbed input PBMCs, thereby generating a plurality of modified PBMCs comprising the antigen and the adjuvant; and
c) administering the plurality of modified PBMCs to the individual.

235. The method of embodiment 234, wherein the concentration of the adjuvant incubated with the perturbed input PBMCs is between about 0.1 µM and about 1 mM.

236. The method of embodiment 234 or 235, wherein the concentration of the adjuvant incubated with the perturbed input PBMCs is between about 0.1 µM and about 10 µM.

237. The method of any one of embodiments 234-236, wherein the concentration of the adjuvant incubated with the perturbed input PBMCs is about 1 µM.

238. A method for stimulating an immune response in an individual, comprising:
a) passing a cell suspension comprising a plurality of input PBMCs through a cell-deforming constriction, wherein a diameter of the constriction is a function of a diameter of the input PBMs in the suspension, thereby causing perturbations of the input PBMCs large enough for an antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen;
c) administering the plurality of modified PBMCs to the individual; and
d) administering an adjuvant to the individual.

239. A method for stimulating an immune response in an individual, comprising:
a) passing a cell suspension comprising an input PBMCs comprising an antigen through a cell-deforming constriction, wherein a diameter of the constriction is a function of a diameter of the input PBMCs in the suspension, thereby causing perturbations of the input PBMCs large enough for an adjuvant to pass through to form a plurality of perturbed input PBMCs;
b) incubating the plurality of perturbed input PBMCs with the adjuvant for a sufficient time to allow the adjuvant to enter the perturbed input PBMCs, thereby generating a plurality of modified PBMCs comprising the antigen and the adjuvant; and
c) administering the plurality of modified PBMCs to the individual; and
d) administering an adjuvant to the individual.

240. The method of any one of embodiments 219-233, 238 and 239, wherein the concentration of the antigen incubated with the perturbed input PBMCs is between about 0.1 µM and about 1 mM.

241. The method of any one of embodiments 219-233 and 238-240, wherein the concentration of the antigen incubated with the perturbed input PBMCs is between about 0.1 µM and about 10 µM.

242. The method of any one of embodiments 219-233 and 238-241, wherein the concentration of the antigen incubated with the perturbed input PBMCs is about 1 µM.

243. The method of any one of embodiments 222-228 and 233-242, wherein the process further comprises:
incubating the plurality of modified PBMCs comprising the antigen and/or adjuvant with a second adjuvant for a sufficient time for the modified PBMCs comprising the antigen to condition, thereby generating the conditioned plurality of modified PBMCs comprising the antigen and/or adjuvant.

244 The method of embodiment 243, wherein the concentration of the second adjuvant incubated with the modified PBMCs is between about 0.1 µM and about 1 mM.

245. The method of embodiment 243 or 244, wherein the concentration of the second adjuvant incubated with the modified PBMCs is between about 0.1 µM and about 10 µM.

246. The plurality of modified PBMCs of any one of embodiments 243-245, wherein the concentration of the second adjuvant incubated with the modified PBMCs is about 1 µM.

247. A method for stimulating an immune response in an individual, comprising:
administering to the individual a plurality of PBMCs associated with an antigen, wherein the plurality of modified PBMCs is prepared by a process comprising the steps of:
a) incubating a plurality of input PBMCs with an antigen for a sufficient time to allow the antigen to associate with the cell surface of the input PBMCs, thereby generating the plurality of PBMCs associated with the antigen; and
b) administering the plurality of modified PBMCs to the individual.

248. The method of any one of embodiments 215-247, further comprising administering an adjuvant to the individual.

249. The method of embodiment 248, wherein the adjuvant is administered before, concurrently with, or after administration of the plurality of modified PBMCs to the individual.

250. A plurality of PBMCs comprising an antigen for use in a method of stimulating an immune response in an individual according to any one of embodiments 215-245 and 247-249.

251. A method for generating a conditioned plurality of PBMCs comprising an antigen, comprising incubating a plurality of PBMCs comprising the antigen with an adjuvant for a sufficient time for the PBMCs to condition, thereby generating the conditioned plurality of PBMCs comprising the antigen.

252. A method for generating a conditioned plurality of modified PBMCs comprising an antigen, comprising:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with an adjuvant for a sufficient time for the modified PBMCs comprising the antigen to condition, thereby generating the conditioned plurality of modified PBMCs comprising the antigen.

253. A method for generating a conditioned plurality of modified PBMCs comprising an antigen, comprising:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen to pass through to form a plurality of perturbed input PBMCs;
b) incubating the plurality of perturbed input PBMCs with the nucleic acid encoding the antigen for a sufficient time to allow the nucleic acid encoding the antigen to enter the perturbed input PBMCs, thereby generating a plurality of modified PBMCs comprising the nucleic acid encoding the antigen; and
c) incubating the plurality of modified PBMCs comprising the nucleic acid encoding the antigen with an adjuvant for a sufficient time for the modified PBMCs comprising the nucleic acid encoding the antigen to condition,
wherein the nucleic acid is expressed in the PBMCs to produce the antigen, thereby generating the conditioned plurality of modified PBMCs comprising the antigen.

254. The method of embodiment 252, further comprising isolating the plurality of modified PBMCs comprising the antigen from the cell suspension before incubation with the adjuvant.

255. The method of embodiment 253, further comprising isolating the plurality of modified PBMCs comprising the nucleic acid encoding the antigen from the cell suspension before incubation with the adjuvant.

256. A method for generating a plurality of modified PBMCs comprising an antigen, comprising:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs; and
b) incubating the plurality of perturbed input PBMCs with the antigen for a sufficient time to allow the antigen to enter the perturbed input PBMCs, thereby generating the plurality of modified PBMCs comprising the antigen.

257. A method for generating a plurality of modified PBMCs comprising an antigen, comprising:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen to pass through to form a plurality of perturbed input PBMCs; and
b) incubating the plurality of perturbed input PBMCs with the nucleic acid encoding the antigen for a sufficient time to allow the nucleic acid encoding the antigen to enter the perturbed input PBMCs,
wherein the nucleic acid is expressed in the PBMCs to produce the antigen, thereby generating the plurality of modified PBMCs comprising the antigen.

258. A method for generating a plurality of modified PBMCs comprising an antigen and an adjuvant, comprising:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen and the adjuvant to pass through to form a plurality of perturbed input PBMCs; and b) incubating the plurality of perturbed input PBMCs with the antigen and the adjuvant for a sufficient time to allow the antigen and the adjuvant to enter the perturbed input PBMCs, thereby generating the plurality of modified PBMCs comprising the antigen and adjuvant.

259. A method for generating a plurality of modified PBMCs comprising an antigen and an adjuvant, comprising:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen and for the adjuvant to pass through to form a plurality of perturbed input PBMCs; and
b) incubating the plurality of perturbed input PBMCs with the nucleic acid encoding the antigen and with the adjuvant for a sufficient time to allow the nucleic acid encoding the antigen and the adjuvant to enter the perturbed input PBMCs, wherein the nucleic acid is expressed in the PBMCs to produce the antigen, thereby generating the plurality of modified PBMCs comprising the antigen and adjuvant.

260. A method of generating a conditioned plurality of modified PBMCs comprising an antigen, comprising:
a) incubating a plurality of input PBMCs with an adjuvant for a sufficient time for the input PBMCs to condition, thereby generating a conditioned plurality of input PBMCs;
b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for the antigen to pass through to form a conditioned plurality of perturbed input PBMCs; and
c) incubating the conditioned plurality of perturbed input PBMCs with the antigen for a sufficient time to allow the antigen to enter the perturbed input PBMCs, thereby generating the conditioned plurality of modified PBMCs comprising the antigen.

261. A method of generating a conditioned plurality of modified PBMCs comprising an antigen, comprising:
a) incubating a plurality of input PBMCs with an adjuvant for a sufficient time for the input PBMCs to condition, thereby generating a conditioned plurality of input PBMCs;
b) passing a cell suspension comprising the conditioned plurality of input PBMCs through a cell-deforming constriction, wherein a diameter of the constriction is a function of a diameter of the input PBMCs in the suspension, thereby causing perturbations of the input PBMCs large enough for a nucleic acid encoding the antigen to pass through to form a conditioned plurality of perturbed input PBMCs; and
c) incubating the conditioned plurality of perturbed input PBMCs with the nucleic acid encoding the antigen for a sufficient time to allow the nucleic acid encoding the antigen to enter the perturbed input PBMCs, wherein the nucleic acid is expressed in the PBMCs to produce the antigen, thereby generating the conditioned plurality of modified PBMCs comprising the antigen.

262. A method for generating a plurality of modified PBMCs comprising an antigen and an adjuvant, comprising:
a) passing a cell suspension comprising a plurality of input PBMCs comprising an adjuvant through a cell-deforming constriction, wherein a diameter of the constriction is a function of a diameter of the input PBMCs in the suspension, thereby causing perturbations of the input PBMCs large enough for an antigen to pass through to form a plurality of perturbed input PBMCs; and
b) incubating the plurality of perturbed input PBMCs with the antigen for a sufficient time to allow the antigen to enter the perturbed input PBMCs, thereby generating the plurality of modified PBMCs comprising the antigen and the adjuvant.

263. A method for generating a plurality of modified PBMCs comprising an antigen and an adjuvant, comprising:
a) passing a cell suspension comprising a plurality of input PBMCs comprising an adjuvant through a cell-deforming constriction, wherein a diameter of the constriction is a function of a diameter of the input PBMCs in the suspension, thereby causing perturbations of the input PBMCs large enough for a nucleic acid encoding an antigen to pass through to form a plurality of perturbed input PBMCs; and
b) incubating the plurality of perturbed input PBMCs with the nucleic acid encoding the antigen for a sufficient time to allow the nucleic acid encoding the antigen to enter the perturbed input PBMCs,
wherein the nucleic acid is expressed in the PBMCs to produce the antigen, thereby generating the plurality of modified PBMCs comprising the antigen and the adjuvant.

264. A method for generating a plurality of modified PBMCs comprising an antigen and an adjuvant, comprising:
a) passing a cell suspension comprising a plurality of input PBMCs comprising an antigen through a cell-deforming constriction, wherein a diameter of the constriction is a function of a diameter of the input PBMCs in the suspension, thereby causing perturbations of the input PBMCs large enough for an adjuvant to pass through to form a plurality of perturbed input PBMCs; and b) incubating the plurality of perturbed input PBMCs with the adjuvant for a sufficient time to allow the adjuvant to enter the perturbed input PBMCs, thereby generating the plurality of modified PBMCs comprising the antigen and the adjuvant.

265. The method of any one of embodiments 219-245, 247-248 and 251-264 wherein the process further comprises a step of incubating the input PBMCs and/or the modified PBMCs with an agent that enhances the viability and/or function of the modified PBMCs as compared to corresponding modified PBMCs prepared without the further incubation step.

266. The method of any one of embodiments 219-245, 247-249 and 251-265, wherein the diameter of the constriction is about 10% to about 99% of the mean diameter of the plurality of input PBMCs.

267. The method of any one of embodiments 219-245, 247-249 and 251-265, wherein the diameter of the constriction is about 10% to about 70% of the mean diameter of the plurality of input PBMCs.

268. The method of any one of embodiments 219-245, 247-249 and 251-267, wherein the diameter of the constriction is about 20% to about 60% of the mean diameter of the plurality of input PBMCs.

269. The method of any one of embodiments 219-245, 247-249 and 251-268, wherein the diameter of the constriction is about 30% to about 45% of the mean diameter of the plurality of input PBMCs.

270. The method of any one of embodiments 219-245, 247-249 and 251-269, wherein the diameter of the constriction is about 10% to about 99% of the mean diameter of the subpopulation of cells having the smallest diameter within the plurality of input PBMCs.

271. The method of any one of embodiments 219-245, 247-249 and 251-270, wherein the diameter of the constriction is about 10% to about 70% of the mean diameter of a subpopulation of cells having the smallest diameter within the plurality of input PBMCs.

272. The method of any one of embodiments 219-245, 247-249 and 251-271, wherein the diameter of the constriction is about 20% to about 60% of the mean diameter of the subpopulation of cells having the smallest diameter within the plurality of input PBMCs.

273. The method of any one of embodiments 219-245, 247-249 and 251-272, wherein the diameter of the constriction is about 30% to about 45% of the mean diameter of the subpopulation of cells having the smallest diameter within the plurality of input PBMCs.

274. The method of any one of embodiments 219-245, 247-249 and 251-270, wherein the diameter of the constriction is about 50% to about 99% of the mean diameter of a subpopulation of cells having the smallest diameter within the plurality of input PBMCs.

275. The method of any one of embodiments 219-245, 247-249, 251-270 and 274, wherein the diameter of the constriction is about 50% to about 90% of the mean diameter of a subpopulation of cells having the smallest diameter within the plurality of input PBMCs.

276. The method of any one of embodiments 219-245, 247-249, 251-270 and 274-275, wherein the diameter of the constriction is about 50% to about 80% of the mean diameter of a subpopulation of cells having the smallest diameter within the plurality of input PBMCs.

277. The method of any one of embodiments 219-245, 247-249, 251-270 and 274-276, wherein the diameter of the constriction is about 50% to about 70% of the mean diameter of a subpopulation of cells having the smallest diameter within the plurality of input PBMCs.

278. The method of any one of embodiments 219-245, 247-249, and 251-270, wherein the diameter of the constriction is about 60% to about 90% of the mean diameter of a subpopulation of cells having the smallest diameter within the plurality of input PBMCs. 1

279. The method of any one of embodiments 219-245, 247-249, 251-270 and 278, wherein the diameter of the constriction is about 60% to about 80% of the mean diameter of a subpopulation of cells having the smallest diameter within the plurality of input PBMCs.

280. The method of any one of embodiments 219-245, 247-249, 251-270 and 278-279, wherein the diameter of the constriction is about 60% to about 70% of the mean diameter of a subpopulation of cells having the smallest diameter within the plurality of input PBMCs.

281. The method of any one of embodiments 219-245, 247-249, and 251-280, wherein the diameter of the constriction is about 10% to about 99% of the mean diameter of the subpopulation of cells having the largest diameter within the plurality of input PBMCs.

282. The method of any one of embodiments 219-245, 247-249, and 251-281 wherein the diameter of the constriction is about 10% to about 70% of the mean diameter of a subpopulation of cells having the largest diameter within the plurality of input PBMCs.

283. The method of any one of embodiments 219-245, 247-249, and 251-282, wherein the diameter of the constriction is about 20% to about 60% of the mean diameter of the subpopulation of cells having the largest diameter within the plurality of input PBMCs.

284. The method of any one of embodiments 219-245, 247-249, and 251-283, wherein the diameter of the constriction is about 20% to about 30% of the mean diameter of a subpopulation of cells having the largest diameter within the plurality of input PBMCs.

285. The method of any one of embodiments 219-245, 247-249, and 251-284, wherein the diameter of the constriction is about 20% to about 25% of the mean diameter of a subpopulation of cells having the largest diameter within the plurality of input PBMCs.

286. The method of any one of embodiments 219-245, 247-249, and 251-283, wherein the diameter of the constriction is about 30% to about 45% of the mean diameter of the subpopulation of cells having the largest diameter within the plurality of input PBMCs.

287. The method of any one of embodiments 270-286, wherein the subpopulation of cells having the smallest diameter within the plurality of input PBMCs are T cells.

288. The method of any one of embodiments 281-286, wherein the subpopulation of cells having the largest diameter within the plurality of input PBMCs are monocytes.

289. The method of any one of embodiments 219-245, 247-249 and 251-275, wherein the diameter of the constriction is about 3 µm to about 10 µm.

290. The method of any one of embodiments 219-245, 247-249 and 251-289, wherein the diameter of the constriction is about 3 µm to about 6 µm.

291. The method of any one of embodiments 219-245, 247-249 and 251-289, wherein the diameter of the constriction is about 4 µm to about 10 µm.

292. The method of any one of embodiments 219-245, 247-249 and 251-291, wherein the diameter of the constriction is about 4.2 µm to about 6 µm.

293. The method of any one of embodiments 219-245, 247-249 and 251-292, wherein the diameter of the constriction is about 4.5 µm.

294. The method of any one of embodiments 219-245, 247-249 and 251-293, wherein the plurality of input PBMCs is passed through the constriction under a pressure ranging from about 30 psi to about 90 psi.

295. The method of any one of embodiments 219-245, 247-249 and 251-293, wherein the plurality of input PBMCs is passed through the constriction under a pressure ranging from about 207 kPa to about 830 kPa or about 415 kPa to about 621 kPa.

296. The method of any one of embodiments 219-245, 247-249 and 251-295, wherein the plurality of input PBMCs is passed through the constriction at a flow rate between about 0.001 mL/cm$^2$/sec to about 200 L/cm$^2$/sec.

297. The method of any one of embodiments 219-245, 247-249 and 251-295, wherein the plurality of input PBMCs is passed through the constriction at a flow rate between about 0.1 mL/cm$^2$/sec to about 150 L/cm$^2$/sec.

298. The method of any one of embodiments 219-245, 247-249 and 251-297, wherein the plurality of input PBMCs is passed through the constriction at a flow rate or about 100 L/cm$^2$/sec.

299. The method of any one of embodiments 219-245, 247-249 and 251-298, wherein the plurality of input PBMCs is passed through the constriction at a temperature ranging from about 0° C. to about 37° C.

300. The method of any one of embodiments 219-245, 247-249 and 251-299, wherein subsequent to passing through the constriction the plurality of modified PBMCs is incubated at a temperature of about 37° C. for a sufficient time to allow the modified PBMCs to normalize to about 37° C.

301. The method of any one of embodiments 219-245, 247-249 and 251-300, wherein subsequent to passing through the constriction the plurality of modified PBMCs is incubated at a temperature of about 25° C. for a sufficient time to allow the modified PBMCs to normalize to about 25° C.

302. The method of any one of embodiments 219-245, 247-249 and 251-301, wherein the cross-sectional shape of the constriction is selected from the group consisting of: circular, elliptical, round, square, rectangular, star-shaped, triangular, polygonal, pentagonal, hexagonal, heptagonal, and octagonal.

303. The method of any one of embodiments 219-245, 247-249 and 251-302, wherein the cross-sectional shape of the constriction is a slit.

304. The method of embodiment 303, wherein slit comprises a width of about 3 µm-6 µm and/or a depth of about 20 µm-120 µm.

305. The method of embodiment 303, wherein the slit comprises a width of about 4.2 µm-6 µm and/or a depth of about 20-120 µm.

306. The method of embodiment 303-305, wherein the slit comprises a width of 4.5 µm and/or a depth of 80 µm.

307. The method of any one of embodiments 219-245, 247-249 and 251-306, wherein the cell suspension comprising the plurality of input PBMCs is passed through multiple constrictions wherein the multiple constrictions are arranged in series and/or in parallel.

308. The method of any one of embodiments 219-245, 247-249 and 251-307, wherein the constriction comprises an entrance portion and an exit portion, wherein:
(a) the entrance portion defines an entrance angle and the entrance angle is between about 0 degree to about 90 degrees or about 20-22 degrees; and/or
(b) the exit portion defines an exit angle and the exit angle is between about 0 degree to about 90 degrees or about 20-22 degrees;
preferably about 20-22 degrees for (a) and (b).

309. The method of any one of embodiments 219-245, 247-249 and 251-308, wherein the cell suspension comprising the plurality of input PBMCs are passed through multiple constrictions, wherein the multiple constrictions are arranged in series and/or in parallel.

310. The method of any one of embodiments 219-221, 229-232, 243-245, 247-249, 251 and 265-309, wherein the plurality of modified PBMCs is incubated with the adjuvant for about 1 to about 24 hours for the modified PBMCs to condition.

311. The method of any one of embodiments 219-221, 229-232, 243-245, 251 and 265-310, wherein the plurality of modified PBMCs is incubated with the adjuvant for about 2 to about 10 hours for the modified PBMCs to condition.

312. The method of any one of embodiments 219-221, 229-232, 243-245, 251 and 265-311, wherein the plurality of modified PBMCs is incubated with the adjuvant for about 3 to about 6 hours for the modified PBMCs to condition.

313. The method of any one of embodiments 219-221, 229-232, 243-245, 251 and 265-312, wherein the plurality of modified PBMCs is incubated with the adjuvant for about 4 hours for the modified PBMCs to condition.

314. The method of any one of embodiments 215-245, 247-249 and 251-313, wherein the antigen and/or adjuvant are present in the cytosol and/or a vesicle of a cell in plurality of modified PBMCs.

315. The method of embodiment 314, wherein the vesicle is an endosome.

316. The method of any one of embodiments 215-245, 247-249 and 251-315, wherein the antigen and/or the adjuvant are present in multiple compartments of a cell in plurality of modified PBMCs.

317. The method of any one of embodiments 222-228, 233-237, 247-249, and 251-316, wherein the antigen is present in the cytosol and the adjuvant is present in a vesicle of a cell in the plurality of modified PBMCs.

318. The method of any one of embodiments 215-245, 247-249 and 251-317, wherein the antigen is bound to the surface of a cell in plurality of modified PBMCs.

319. The method of any one of embodiments 215-245, 247-249 and 251-318, wherein the adjuvant is a CpG oligodeoxynucleotide (ODN), LPS, IFN-α, STING agonists, RIG-I agonists, poly I:C, R837, R848, a TLR3 agonist, a TLR4 agonist or a TLR 9 agonist.

320. The method of embodiment 319, wherein the adjuvant is a CpG ODN.

321. The method of embodiment 320, wherein the CpG ODN is a Class A CpG ODN, a Class B CpG ODN, or a Class C CpG ODN.

322. The method of any one of embodiments 215-245, 247-249 and 251-315, wherein the antigen is a disease-associated antigen.

323. The method of embodiment 322, wherein the antigen is derived from peptides or mRNA isolated from a diseased cell.

324. The method of any one of embodiments 215-245, 247-249 and 251-323, wherein the antigen is a non-self antigen.

325. The method of any one of embodiments 215-245, 247-249 and 251-324, wherein the antigen is a tumor antigen, viral antigen, bacterial antigen, or fungal antigen.

326. The method of any one of embodiment 215-245, 247-249 and 251-325, wherein the antigen is derived from a tumor lysate.

327. The method of embodiment 325, wherein the antigen is a human papillomavirus (HPV) antigen.

328. The method of embodiment 327, wherein the HPV is HPV-16 or HPV-18.

329. The method of embodiment 327 or 328, wherein the antigen comprises an HLA-A2-restricted peptide derived from HPV E6 and/or E7.

330. The method of embodiment 329, wherein the HLA-A2-restricted peptide comprises the amino acid sequence of any one of SEQ ID NOs: 1-4.

331. The method of embodiment 330, wherein the antigen comprises the amino acid sequence of any one of SEQ ID NOs: 18-25.

332. The method of any one of embodiments 215-245, 247-249 and 251-315, wherein the modified PBMCs comprise a plurality of antigens that comprise a plurality of immunogenic epitopes.

333. The method of embodiment 332, wherein following administration to an individual of the modified PBMCs comprising the plurality of antigens that comprise the plurality of immunogenic epitopes, none of the plurality of immunogenic epitopes decreases an immune response in the individual to any of the other immunogenic epitopes.

334. The method of any one of embodiments 215-245, 247-249 and 251-333, wherein the antigen is a polypeptide comprising an immunogenic peptide epitope.

335. The method of embodiment 334, wherein the immunogenic peptide epitope is fused to an N-terminal flanking polypeptide and/or a C-terminal flanking polypeptide.

336. The method of embodiment 334 or 335, wherein the antigen is a polypeptide comprising an immunogenic peptide epitope and one or more heterologous peptide sequences.

337. The method of embodiment 334, wherein the antigen is a polypeptide comprising an immunogenic peptide epitope that is flanked on the N-terminus and/or the C-terminus by heterologous peptide sequences.

338. The method of any one of embodiments 334-337, wherein the flanking heterologous peptide sequences are derived from a disease-associated immunogenic peptides.

339. The method of any one of embodiments 334-337, wherein the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17.

340. The method of any one of embodiments 215-245, 247-249 and 251-323, wherein the antigen is capable of being processed into an MHC class I-restricted peptide and/or an MHC class II-restricted peptide.

341. The method of any one of embodiments 217, 222-227, 233, 237, 239-245, 247-249 and 251-340, wherein the modified PBMCs comprise the adjuvant at a concentration between about 0.1 µM and about 1 mM.

342. The method of any one of embodiments 215-245, 247-249 and 251-325, wherein the modified PBMCs comprise the antigen at a concentration between about 0.1 µM and about 1 mM.

343. The method of any one of embodiments 217, 222-227, 233, 237, 239-245, 247-249 and 251-342, wherein the ratio of the antigen to the adjuvant is between about 10000:1 to about 1:10000.

344. The method of embodiment 317, wherein the ratio of the antigen to the adjuvant is about 200:1.

345. The method of any one of embodiments 215-245, 247-249 and 251-344, wherein the modified PBMCs comprise a complex comprising: a) the antigen, b) the antigen and at least one other antigen, c) the antigen and the adjuvant, d) the nucleic acid encoding the antigen, e) the nucleic acid encoding the antigen and at least one other nucleic acid encoding one other antigen, and/or f) the nucleic acid encoding the antigen and the adjuvant.

346. The method of any one of embodiments 215-245, 247-249 and 251-345, wherein the conditioned plurality of modified PBMCs further comprises an agent that enhances the viability and/or function of the modified PBMCs as compared to a corresponding modified PBMCs that does not comprise the agent.

347. The method of any one of embodiments 215-245, 247-249 and 251-346, wherein the conditioned plurality of modified PBMCs further comprises an agent that enhances the viability and/or function of the modified PBMCs upon freeze-thaw cycle as compared to a corresponding modified PBMCs that does not comprise the agent.

348. The method of any one of embodiments 215-245, 247-249 and 251-347, wherein at least about 70%, about 80%, or about 90% of the conditioned plurality of modified PBMCs are viable after up to 1, 2, 3, 4, 5 freeze-thaw cycles.

349. The method of embodiment 348, wherein the agent is a compound that enhances endocytosis, a stabilizing agent or a co-factor.

350. The method of embodiment 349, wherein the agent is albumin.

351. The method of embodiment 350, wherein the albumin is mouse, bovine, or human albumin.

352. The method of 351, wherein the agent is one or more of: a divalent metal cation, glucose, ATP, potassium, glycerol, trehalose, D-sucrose, PEG1500, L-arginine, L-glutamine, or EDTA.

353. The method of embodiment 351 or 352, wherein the agent is one or more of: Sodium pyruvate, adenine, Rejuvesol®, trehalose, dextrose, mannose, sucrose, human serum albumin (HSA), PlasmaLyte®, DMSO, Cryostor® CS2, Cryostor® CS5, Cryostor® CS10, Cryostor® CS15, HEPES, glycerol, glutathione, HypoThermosol®.

354. The method of embodiment 353, wherein the agent comprises mouse serum albumin (MSA).

355. The method of embodiment 354, wherein the agent comprises human serum albumin (HSA).

356. The method of any one of embodiments 215-245, 247-249 and 251-355 wherein the cells are further modified to increase expression of one or more of co-stimulatory molecules.

357. The method of embodiment 356, wherein the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, CD112, or scFv anti-CD28.

358. The method of embodiment 356, wherein the co-stimulatory molecule is a Signal 2 effector.

359. The method of any one of embodiments 356-358, wherein the cell comprises a nucleic acid (e.g., mRNA) that results in increased expression of the one or more co-stimulatory molecules.

360. The method of embodiment 359, wherein the nucleic acid is an mRNA encoding the co-stimulatory molecule.

361. The method of any one of embodiments 215-245, 247-249 and 251-360 wherein the cells are further modified to increase expression a cytokine.

362. The method of embodiment 361, wherein the cytokine is IL-12, IL-2, IFN-α, or IL-21.

363. The method of embodiment 356, wherein the co-stimulatory molecule is a Signal 3 effector.

364. The method of any one of embodiments 361-363, wherein the cell comprises a nucleic acid (e.g., mRNA) that results in increased expression of the one or more cytokines.

365. The method of embodiment 364, wherein the nucleic acid is an mRNA encoding the cytokine.

366. The method of any one of embodiments 215-245, 247-249 and 251-365, wherein the modified PBMCs comprise a further modification to modulate MHC class I expression.

367. The method of any one of embodiments 215-245, 247-249 and 251-366, wherein the modified PBMCs comprise a further modification to modulate MHC class II expression.

368. The method of embodiment 366, wherein an innate immune response mounted in an individual in response to administration, in an allogeneic context, of the modified PBMCs is reduced compared to an innate immune response mounted in an individual in response to administration, in an allogeneic context, of corresponding modified PBMCs that do not comprise the further modification.

369. The method of embodiment 366 or 367, wherein the circulating half-life of the modified PBMCs in an individual to which they were administered is increased compared to the circulating half-life of corresponding modified PBMCs that do not comprise the further modification in an individual to which they were administered.

370. The method of any one of embodiments 215-245, 247-249 and 251-369, wherein the plurality of input PBMCs comprises one or more of T cell, B cell, NK cell, monocytes, dendritic cells or NK-T cells.

371. The method of any one of embodiments 215-245, 247-249 and 251-370, wherein the plurality of input PBMCs comprises one or more of CD3+ T cells, CD20+ B cells, CD14+ monocytes, or CD56+NK cells.

372. The method of any one of embodiments 215-245, 247-249 and 251-371, wherein the plurality of input PBMCs comprises T cells, B cells, NK cells and monocytes, and wherein the ratio of T cells, B cells, NK cells and monocytes to the total number of PBMCs in the plurality of input PBMCs is essentially the same as the ratio of T cells, B cells, NK cells and monocytes to the total number of PBMCs in whole blood.

373. The method of any one of embodiments 215-245, 247-249 and 251-371, wherein the plurality of input PBMCs comprises T cells, B cells, NK cells and monocytes, and wherein the ratio of T cells, B cells, NK cells and monocytes to the total number of PBMCs in the plurality of input PBMCs is essentially the same as the ratio of T cells, B cells, NK cells and monocytes to the total number of PBMCs in a leukapheresis product from whole blood.

374. The method of any one of embodiments 215-245, 247-249 and 251-373, wherein the plurality of input PBMCs comprises T cells, B cells, NK cells and monocytes, and wherein the ratio of T cells, B cells, NK cells and monocytes to the total number of PBMCs in the plurality of input PBMCs differs by not more than 10% from the ratio of T cells, B cells, NK cells and monocytes to the total number of PBMCs in whole blood.

375. The method of any one of embodiments 215-245, 247-249 and 251-374, wherein the plurality of input PBMCs comprises T cells, B cells, NK cells and monocytes, and wherein the ratio of T cells, B cells, NK cells and monocytes to the total number of PBMCs in the plurality of input PBMCs differs by not more than 10% from the ratio of T cells, B cells, NK cells and monocytes to the total number of PBMCs in whole blood.

376. The method of any one of embodiments 215-245, 247-249 and 251-375, wherein:
(a) at least about 25% of the input PBMCs are T cells;
(b) at least about 2.5% of the input PBMCs are B cells;
(c) at least about 3.5% of the input PBMCs are NK cells; or
(d) at least about 4% of the input PBMCs are monocytes.

377. The method of any one of embodiments 215-245, 247-249 and 251-376, wherein:
(a) at least about 20% of the modified PBMCs are T cells;
(b) at least about 2% of the modified PBMCs are B cells;
(c) at least about 3% of the modified PBMCs are NK cells; or
(d) at least about 3% of the modified PBMCs are monocytes.

378. The method of any one of embodiments 215-245, 247-249 and 251-377, wherein:
(a) not more than about 70% of the input PBMCs are T cells;
(b) not more than about 14% of the input PBMCs are B cells;
(c) not more than about 35% of the input PBMCs are NK cells; or
(d) not more than about 25% of the input PBMCs are monocytes.

379. The method of any one of embodiments 215-245, 247-249 and 251-378, wherein:
(a) not more than about 80% of the modified PBMCs are T cells;
(b) not more than about 16% of the modified PBMCs are B cells;
(c) not more than about 40% of the modified PBMCs are NK cells; or
(d) not more than about 30% of the modified PBMCs are monocytes.

380. The method of any one of embodiments 215-245, 247-249 and 251-379, wherein:
(a) about 25% to about 70% of the modified PBMCs are T cells;
(b) about 2.5% to about 14% of the modified PBMCs are B cells;
(c) about 3.5% to about 35% of the modified PBMCs are NK cells; or
(d) about 4% to about 25% of the modified PBMCs are monocytes.

381. The method of any one of embodiments 215-245, 247-249 and 251-380, wherein:
(a) the percentage of T cells within the plurality of modified PBMCs and the percentage of T cells within the plurality of input PBMCs differ by no more than 10% by number;
(b) the percentage of B cells within the plurality of modified PBMCs and the percentage of B cells within the plurality of input PBMCs differ by no more than 10% by number;
(c) the percentage of NK cells within the plurality of modified PBMCs and the percentage of NK cells within the plurality of input PBMCs differ by no more than 10% by number; and/or
(d) the percentage of monocytes within the plurality of modified PBMCs and the percentage of monocytes within the plurality of input PBMCs differ by no more than 10% by number.

382. The method of any one of embodiments 215-245, 247-249 and 251-378, wherein: one or more co-stimulatory molecules is upregulated in the B cells of the conditioned plurality of modified PBMCs compared to the B cells in the plurality of input PBMCs, wherein the co-stimulatory molecule is CD80 or CD86.

383. The method of embodiment 382, wherein the CD80 and/or CD86 is upregulated in the B cells of the conditioned plurality of modified PBMCs by more than about 1.2-fold, 1.5-fold, 1.8-fold, 2-fold, 3-fold, 4-fold, 5-fold, 8-fold, or more than 10-fold compared to the B cells in a plurality of nonconditioned PBMCs.

384. The method of embodiment 382 or 383, wherein the co-stimulatory molecule is CD86.

385. The method of any one of embodiments 382-384, wherein the conditioned modified PBMCs have increased expression of one or more of IFN-γ, IL-6, MCP-1, MIP-10, IP-10, or TNF-α compared to a plurality of unconditioned PBMCs.

386. The method of embodiment 385, wherein the expression of one or more of IFN-γ, IL-6, MCP-1, MIP-10, IP-10, or TNF-α is increased by about 1.2-fold, 1.5-fold, 1.8-fold, 2-fold, 3-fold, 4-fold, 5-fold, 8-fold, or more than 10-fold compared to the plurality of unconditioned PBMCs.

387. The method of any one of embodiments 215-245, 247-249 and 251-385, wherein the modified PBMCs are allogeneic to the individual.

388. The method of any one of embodiments 215-245, 247-249 and 251-385, wherein the modified PBMCs are autologous to the individual.

389. The method of any one of embodiments 215-245, 247-249 and 251-388, wherein the individual is pre-conditioned to modulate inflammation and/or an immune response.

390. The method of any one of embodiments 215-245, 247-249 and 251-389, further comprising administering to the individual a third adjuvant.

391. The method of embodiment 390, wherein the third adjuvant is IFN-α or a CpG ODN.

392. The method of embodiment 390, wherein the third adjuvant is CpG 7909.

393. The method of any one of embodiments 390-392, wherein the plurality of modified PBMCs and the third adjuvant are administered concurrently or simultaneously.

394. The method of any one of embodiment 390-392, wherein the plurality of modified PBMCs and the third adjuvant are administered sequentially.

395. The method of any one of embodiments 390-394, wherein the plurality of modified PBMCs is administered prior to administering the third adjuvant.

396. The method of any one of embodiments 390-395, wherein the plurality of modified PBMCs is administered following administration of the third adjuvant.

397. The method of embodiments 215-245, 247-249 and 251-396, wherein the modified PBMCs is administered prior to, concurrently with, or following administration of a cytokine.

398. The method of embodiment 397, wherein the cytokine is one or more of: IL-2, IL-7, IL-12a IL-12b, or IL-15.

399. The method of embodiments 215-245, 247-249 and 251-398, wherein the modified PBMCs is administered prior to, concurrently with, or following administration of an immune checkpoint inhibitor.

400. The method of embodiment 399, wherein the immune checkpoint inhibitor is targeted to any one of PD-1, PD-L1, CTLA-4, LAG3, VISTA, and TIM-3.

401. The method of embodiment 400, wherein the immune checkpoint inhibitor is targeted to PD-1.

402. The method of embodiment 400, wherein the immune checkpoint inhibitor is targeted to PD-L1.

403. The method of embodiments 215-245, 247-249 and 251-402, wherein the modified PBMCs is administered prior to, concurrently with, or following administration of a therapeutic agent.

404. The method of embodiment 403, wherein the therapeutic agent is a chemotherapeutic agent.

405. The method of any one of embodiments 215-245, 247-249 and 251-404, wherein administration of the modified PBMCs to the individual results in activation and/or expansion of cytotoxic T lymphocytes (CTLs) specific for the antigen.

406. The method of any one of embodiments 215-245, 247-249 and 251-405 wherein administration of the modified PBMCs to the individual results in activation and/or expansion of helper T (Th) cells specific for the antigen.

407. The method of any one of embodiments 215-245, 247-249 and 251-406, wherein the amount of the modified PBMCs administered to the individual is between about $1\times10^4$ and about $1\times10^{12}$ cells.

408. The method of embodiment 407, wherein the amount of the modified PBMCs administered to the individual is between about $1\times10^5$ and about $1\times10^{12}$ cells.

409. The method of embodiment 407 or 408, wherein the amount of the modified PBMCs administered to the individual is between about be $5\times10^5$ and about $2.5\times10^6$ cells/kg body weight.

410. The method of any one of embodiments 215-245, 247-249 and 251-409, wherein the method comprises multiple administrations of the modified PBMCs.

411. The method of embodiment 410, wherein the method comprises about 3 to about 9 administrations.

412. The method of embodiment 410 or 411, wherein the time interval between two successive administrations of the plurality of modified PBMCs is between about 1 day and about 30 days.

413. The method of any one of embodiments 410-412, wherein the time interval between two successive administrations of the plurality of modified PBMCs is about 21 days.

414. The method of any one of embodiments 215-245, 247-249 and 251-413, wherein the individual is positive for expression of HLA-A2.

415. The method of any one of embodiments 215-245, 247-249 and 251-414, wherein at least one cell in the plurality of modified PBMCs is positive for expression of HLA-A2.

416. A method for generating a conditioned plurality of modified PBMCs comprising a human papillomavirus (HPV) antigen, comprising:
a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs;
b) incubating the plurality of perturbed input PBMCs with the HPV antigen for a sufficient time to allow the HPV antigen to enter the perturbed input PBMCs, thereby generating a plurality of modified PBMCs comprising the HPV antigen; and
c) incubating the plurality of modified PBMCs comprising the HPV antigen with a CpG ODN for a sufficient time for the modified PBMCs comprising the HPV antigen to condition, thereby generating the conditioned plurality of modified PBMCs comprising the HPV antigen.

417. A method for generating a conditioned plurality of modified PBMCs comprising an HPV antigen, comprising:
a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs;
b) incubating the plurality of perturbed input PBMCs with the HPV antigen for a sufficient time to allow the HPV antigen to enter the perturbed input PBMCs, thereby generating a plurality of modified PBMCs comprising the HPV antigen; and
c) incubating the plurality of modified PBMCs comprising the HPV antigen with a CpG ODN for a sufficient time for the modified PBMCs comprising the HPV antigen to condition, wherein the CpG ODN is CpG 7909, thereby generating the conditioned plurality of modified PBMCs comprising the HPV antigen.

418. A method for generating a conditioned plurality of modified PBMCs comprising an HPV antigen, comprising:
a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs;
b) incubating the plurality of perturbed input PBMCs with the HPV antigen for a sufficient time to allow the HPV antigen to enter the perturbed input PBMCs, thereby generating a plurality of modified PBMCs comprising the HPV antigen; and
c) incubating the plurality of modified PBMCs comprising the HPV antigen with a CpG ODN for about 1 hour to about 24 hours for the modified PBMCs comprising the HPV antigen to condition, thereby generating the conditioned plurality of modified PBMCs comprising the HPV antigen.

419. A method for generating a conditioned plurality of modified PBMCs comprising an HPV antigen, comprising:
a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs;
b) incubating the plurality of perturbed input PBMCs with the HPV antigen for a sufficient time to allow the HPV antigen to enter the perturbed input PBMCs, thereby generating a plurality of modified PBMCs comprising the HPV antigen; and
c) incubating the plurality of modified PBMCs comprising the HPV antigen with a CpG ODN for about 1 hour to about 24 hours for the modified PBMCs comprising the HPV antigen to condition, wherein the CpG ODN is CpG 7909, thereby generating the conditioned plurality of modified PBMCs comprising the HPV antigen.

420. The method of any one of embodiments 416-419, wherein the diameter of the constriction is about 4 μm to about 10 μm.

421. The method of any one of embodiments 416-420, wherein the diameter of the constriction is about 3 μm to about 6 μm.

422. The method of any one of embodiments 416-421, wherein the diameter of the constriction is (a) about 4.2 μm to about 6 μm; or (b) about 4.5 μm.

423. The method of any one of embodiments 416-422, wherein the plurality of modified PBMCs comprising the HPV antigen is incubated with a CpG ODN for (a) about 2 hour to about 10 hours; (b) about 3 hours to about 6 hours; or (c) about 4 hours.

424. A method for generating a conditioned plurality of modified PBMCs comprising an antigen, comprising:
a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with a CpG ODN for a sufficient time for the modified PBMCs comprising the antigen to condition, thereby generating the conditioned plurality of modified PBMCs comprising the antigen.

425. A method for generating a conditioned plurality of modified PBMCs comprising an antigen, comprising:
a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with a CpG ODN for a sufficient time for the modified PBMCs comprising the antigen to condition, wherein the CpG ODN is CpG 7909,
thereby generating the conditioned plurality of modified PBMCs comprising the antigen.

426. A method for generating a conditioned plurality of modified PBMCs comprising an antigen, comprising:
a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with a CpG ODN for about 1 hour to about 24 hours for the modified PBMCs comprising the antigen to condition, thereby generating the conditioned plurality of modified PBMCs comprising the antigen.

427. A method for generating a conditioned plurality of modified PBMCs comprising an antigen, comprising:
a) passing a cell suspension comprising a plurality of input PBMCs through a cell-deforming constriction, wherein a diameter of the constriction is about 3 μm to about 10 μm, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with a CpG ODN for about 1 hour to about 24 hours for the modified PBMCs comprising the antigen to condition, wherein the CpG ODN is CpG 7909,
thereby generating the conditioned plurality of modified PBMCs comprising the antigen.

428. The method of any one of embodiments 424-427, wherein the diameter of the constriction is about 4 μm to about 10 μm.

429. The method of any one of embodiments 424-428, wherein the diameter of the constriction is about 3 μm to about 6 μm.

430. The method of any one of embodiments 424-429, wherein the diameter of the constriction is (a) about 4.2 μm to about 6 μm; or (b) about 4.5 μm.

431. The method of any one of embodiments 424-430, wherein the plurality of modified PBMCs comprising the HPV antigen is incubated with a CpG ODN for (a) about 2 hours to about 10 hours; (b) about 3 hours to about 6 hours; or (c) about 4 hours.

432. A method for stimulating an immune response against an HPV antigen in an individual, comprising:
a) passing a cell suspension comprising a plurality of input PBMCs through a cell-deforming constriction, wherein a diameter of the constriction is about 3 μm to about 10 μm, thereby causing perturbations of the input PBMCs large enough for the HPV antigen to pass through to form a plurality of perturbed input PBMCs;
b) incubating the plurality of perturbed input PBMCs with the HPV antigen for a sufficient time to allow the HPV antigen to enter the perturbed input PBMCs, thereby generating a plurality of modified PBMCs comprising the HPV antigen;
c) incubating the plurality of modified PBMCs comprising the HPV antigen with a CpG ODN for a sufficient time for the modified PBMCs comprising the HPV antigen to condition, thereby generating the conditioned plurality of modified PBMCs comprising the HPV antigen; and
d) administering the conditioned plurality of modified PBMCs comprising the HPV antigen to the individual.

433. A method for stimulating an immune response against an HPV antigen in an individual, comprising:

a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs;
b) incubating the plurality of perturbed input PBMCs with the HPV antigen for a sufficient time to allow the HPV antigen to enter the perturbed input PBMCs, thereby generating a plurality of modified PBMCs comprising the HPV antigen;
c) incubating the plurality of modified PBMCs comprising the HPV antigen with a CpG ODN for a sufficient time for the modified PBMCs comprising the HPV antigen to condition, wherein the CpG ODN is CpG 7909, thereby generating the conditioned plurality of modified PBMCs comprising the HPV antigen; and
d) administering the conditioned plurality of modified PBMCs comprising the HPV antigen to the individual.

434. A method for stimulating an immune response against an HPV antigen in an individual, comprising:
a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs;
b) incubating the plurality of perturbed input PBMCs with the HPV antigen for a sufficient time to allow the HPV antigen to enter the perturbed input PBMCs, thereby generating a plurality of modified PBMCs comprising the HPV antigen;
c) incubating the plurality of modified PBMCs comprising the HPV antigen with a CpG ODN for about 1 hour to about 24 hours for the modified PBMCs comprising the HPV antigen to condition, thereby generating the conditioned plurality of modified PBMCs comprising the HPV antigen; and
d) administering the conditioned plurality of modified PBMCs comprising the HPV antigen to the individual.

435. A method for stimulating an immune response against an HPV antigen in an individual, comprising:
a) passing a cell suspension comprising a plurality of input PBMCs through a cell-deforming constriction, wherein a diameter of the constriction is about 3 µm to about 10 µm, thereby causing perturbations of the input PBMCs large enough for the HPV antigen to pass through to form a plurality of perturbed input PBMCs;
b) incubating the plurality of perturbed input PBMCs with the HPV antigen for a sufficient time to allow the HPV antigen to enter the perturbed input PBMCs, thereby generating a plurality of modified PBMCs comprising the HPV antigen;
c) incubating the plurality of modified PBMCs comprising the HPV antigen with a CpG ODN for about 1 hour to about 24 hours for the modified PBMCs comprising the HPV antigen to condition, wherein the CpG ODN is CpG 7909, thereby generating the conditioned plurality of modified PBMCs comprising the HPV antigen; and
d) administering the conditioned plurality of modified PBMCs comprising the HPV antigen to the individual.

436. The method of any one of embodiments 432-435, wherein the diameter of the constriction is about 4 µm to about 10 µm.

437. The method of any one of embodiments 432-436, wherein the diameter of the constriction is about 3 µm to about 6 µm.

438. The method of any one of embodiments 432-437, wherein the diameter of the constriction is (a) about 4.2 µm to about 6 µm; or (b) about 4.5 µm.

439. The method of any one of embodiments 432-438, wherein the plurality of modified PBMCs comprising the HPV antigen is incubated with a CpG ODN for (a) about 2 hours to about 10 hours; (b) about 3 hours to about 6 hours; or (c) about 4 hours.

440. A method for stimulating an immune response in an individual, comprising:
a) passing a cell suspension comprising a plurality of input PBMCs through a cell-deforming constriction, wherein a diameter of the constriction is about 3 µm to about 10 µm, thereby causing perturbations of the input PBMCs large enough for an antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen;
c) incubating the plurality of modified PBMCs comprising the antigen with a CpG ODN for a sufficient time for the modified PBMCs comprising the antigen to condition, thereby generating the conditioned plurality of modified PBMCs comprising the antigen; and
d) administering the conditioned plurality of modified PBMCs comprising the antigen to the individual.

441. A method for stimulating an immune response in an individual, comprising:
a) passing a cell suspension comprising a plurality of input PBMCs through a cell-deforming constriction, wherein a diameter of the constriction is about 3 µm to about 10 µm, thereby causing perturbations of the input PBMCs large enough for an antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen;
c) incubating the plurality of modified PBMCs comprising the antigen with a CpG ODN for a sufficient time for the modified PBMCs comprising the antigen to condition, wherein the CpG ODN is CpG 7909, thereby generating the conditioned plurality of modified PBMCs comprising the antigen; and
d) administering the conditioned plurality of modified PBMCs comprising the antigen to the individual.

442. A method for stimulating an immune response in an individual, comprising:
a) passing a cell suspension comprising a plurality of input PBMCs through a cell-deforming constriction, wherein a diameter of the constriction is about 3 µm to about 10 µm, thereby causing perturbations of the input PBMCs large enough for an antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen;
c) incubating the plurality of modified PBMCs comprising the antigen with a CpG ODN for about 1 hour to about 24 hours for the modified PBMCs comprising the antigen to condition, thereby generating the conditioned plurality of modified PBMCs comprising the antigen; and d) administering the conditioned plurality of modified PBMCs comprising the antigen to the individual.

443. A method for stimulating an immune response in an individual, comprising:
a) passing a cell suspension comprising a plurality of input PBMCs through a cell-deforming constriction, wherein a diameter of the constriction is about 3 µm to about 10 µm, thereby causing perturbations of the input PBMCs large enough for an antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen;
c) incubating the plurality of modified PBMCs comprising the antigen with a CpG ODN for about 1 hour to about 24 hours for the modified PBMCs comprising the antigen to condition, wherein the CpG ODN is CpG 7909, thereby generating the conditioned plurality of modified PBMCs comprising the antigen; and
d) administering the conditioned plurality of modified PBMCs comprising the antigen to the individual.

444. The method of any one of embodiments 440-443, wherein the diameter of the constriction is about 4 µm to about 10 µm.

445. The method of any one of embodiments 440-444, wherein the diameter of the constriction is about 3 µm to about 6 µm.

446. The method of any one of embodiments 440-445, wherein the diameter of the constriction is (a) about 4.2 µm to about 6 µm; or (b) about 4.5 µm.

447. The method of any one of embodiments 440-446, wherein the plurality of modified PBMCs comprising the HPV antigen is incubated with a CpG ODN for (a) about 2 hours to about 10 hours; (b) about 3 hours to about 6 hours; or (c) about 4 hours.

448. The method of any one of embodiments 432-447, further comprising administering to the individual a second adjuvant.

449. The method of embodiment 448, wherein the second adjuvant is IFN-α or a CpG ODN.

450. The method of embodiment 449, wherein the second adjuvant is CpG 7909.

451. The method of any one of embodiments 432-450, wherein the conditioned plurality of modified PBMCs further comprises an agent that enhances the viability and/or function of the modified PBMCs, optionally wherein the agent is one or more of: Sodium pyruvate, adenine, Rejuvesol®, trehalose, dextrose, mannose, sucrose, human serum albumin (HSA), PlasmaLyte®, DMSO, Cryostor® CS2, Cryostor® CS5, Cryostor® CS10, Cryostor® CS15, HEPES, glycerol, glutathione, HypoThermosol®.

452. The method of embodiments 432-451, wherein the modified PBMCs is administered prior to, concurrently with, or following administration of an immune checkpoint inhibitor.

453. The method of embodiment 452, wherein the immune checkpoint inhibitor is targeted to any one of PD-1, PD-L1, CTLA-4, LAG3, VISTA, and TIM-3.

454. The method of embodiment 453, wherein the immune checkpoint inhibitor is targeted to PD-1.

455. The method of embodiment 453, wherein the immune checkpoint inhibitor is targeted to PD-L1.

456. The method of embodiments 440-455, wherein the modified PBMCs is administered prior to, concurrently with, or following administration of a therapeutic agent.

457. The method of embodiment 456, wherein the therapeutic agent is a chemotherapeutic agent.

Additional Embodiments

1. A plurality of modified peripheral blood mononuclear cells (PMBCs) comprising an antigen, wherein the antigen is exogenous to the modified PBMCs and wherein the plurality of modified PBMCs comprises two or more of T cells, B cells, NK cells or monocytes, in particular wherein the antigen is a cancer antigen, an infectious disease antigen or a viral-disease associated antigen.

2. The plurality of modified PBMCs of embodiment 1, wherein the antigen is present in at least about 70% of the cells in the plurality of PBMCs.

3. The plurality of modified PBMCs according to embodiments 1 or 2, which is a conditioned plurality of modified PBMCs, in particular wherein the modified PBMCs comprise an adjuvant.

4. The plurality of modified PBMCs of embodiment 3, wherein the antigen is present in the cytosol and the adjuvant is present in a vesicle of a cell in the plurality of the modified PBMCs.

5. The plurality of modified PBMCs of any one of embodiments 3 or 4, wherein CD80 and/or CD86 is unregulated in the B cells of the plurality of conditioned PBMCs by more than about 1.2-fold, 1.5-fold, 1.8-fold, 2-fold, 3-fold, 4-fold, 5-fold, 8-fold, or more than 10-fold compared to the B cells in a plurality of unconditioned PBMCs.

6. The plurality of modified PBMCs of any one of embodiments 3-5, wherein the expression of one or more of IFN-γ, IL-6, MCP-1, MIP-1β, IP-10, or TNF-α is increased in the PBMCs of the plurality of conditioned PBMCs by more than about 1.2-fold, 1.5-fold, 1.8-fold, 2-fold, 3-fold, 4-fold, 5-fold, 8-fold, or more than 10-fold compared to the plurality of unconditioned PBMCs.

7. The plurality of modified PMBCs according to any one of embodiments 1-6, prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen.

8. The conditioned plurality of modified PBMCs according to any one of embodiments 3-7, prepared by a process comprising the steps of:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and
c) incubating the plurality of modified PBMCs comprising the antigen with the adjuvant for a sufficient time for the modified PBMCs comprising the antigen to condition, thereby generating the conditioned plurality of modified PBMCs comprising the antigen.

9. The plurality of modified PBMCs of any one of embodiments 1-8, wherein:
(a) the percentage of T cells within the plurality of modified PBMCs and the percentage of T cells within the plurality of input PBMCs differ by no more than about 10%;
(b) the percentage of B cells within the plurality of modified PBMCs and the percentage of B cells within the plurality of input PBMCs differ by no more than about 10%;
(c) the percentage of NK cells within the plurality of modified PBMCs and the percentage of NK cells within the plurality of input PBMCs differ by no more than about 10%; and/or (d) the percentage of monocytes within the plurality of modified PBMCs and the percentage of monocytes within the plurality of input PBMCs differ by no more than about 10%.

10. A method for generating a plurality of modified PBMCs comprising an antigen, comprising:
a) passing a cell suspension comprising a plurality of input PBMCs through a cell-deforming constriction, wherein a diameter of the constriction is a function of a diameter of the input PBMCs in the suspension, thereby causing perturbations of the input PBMCs large enough for the antigen to pass through to form a plurality of perturbed input PBMCs;
b) incubating the plurality of perturbed input PBMCs with the antigen for a sufficient time to allow the antigen to enter the perturbed input PBMCs, thereby generating a plurality of modified PBMCs comprising the antigen; and optionally
c) incubating the plurality of modified PBMCs comprising the antigen with an adjuvant for a sufficient time for the modified PBMCs comprising the antigen to condition, thereby generating a conditioned plurality of modified PBMCs comprising the antigen.

11. The plurality of modified or conditioned PBMCs of any one of embodiments 7-9 or the method of embodiment 10, wherein the diameter of the constriction is about 60% to about 90% of the mean diameter of a subpopulation of cells having the smallest diameter within the plurality of input PBMCs, and/or wherein the diameter of the constriction is about 20% to about 30% of the mean diameter of a subpopulation of cells having the largest diameter within the plurality of input PBMCs.

12. The plurality of modified or conditioned PBMCs of any one of embodiments 7-9 or 11, or the method of embodiment 10 or 11, wherein the diameter of the constriction is about 3 µm to about 10 µm, in particular about 3 µm to about 6 µm.

13. The conditioned plurality of modified PBMCs of any one of embodiments 8-9 or 11-12, or the method of any one of embodiments 10-12, wherein the plurality of modified PBMCs is incubated with the adjuvant for about 1 to about 24 hours for the modified PBMCs to condition, in particular for about 2 to about 10 hours.

14. The conditioned plurality of modified or conditioned PBMCs of any one of embodiments 3-9 or 11-13, or the method of any one of embodiments 10-13, wherein the adjuvant is a CpG oligodeoxynucleotide (ODN), LPS, IFN-α, STING agonists, RIG-I agonists, poly I:C, R837, R848, a TLR3 agonist, a TLR4 agonist or a TLR 9 agonist.

15. The plurality of modified or conditioned PBMCs of any one of embodiments 1-9 or 11-14, or the method of any one of embodiments 10-14, wherein the antigen is a human papillomavirus (HPV) antigen.

EXAMPLES

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Example 1

To investigate the efficacy of a conditioned plurality of PBMCs comprising an antigen in stimulating an immune response in an individual, a conditioned plurality of PBMCs comprising an HPV-derived antigen is generated and administered to individuals. The efficacy of conditioned PBMCs comprising a disease antigen for use as a therapeutic vaccine is studied, as a monotherapy or when combined with an additional therapeutic agent, such as a PD-L1 inhibitor and/or a chemotherapeutic agent.

PBMC-HPV drug substance consists of autologous PBMCs presenting HLA-A02 restricted E6 and E7 epitopes of HPV16 on MHC-I. The majority of PBMCs (>90%) consist of T cells, monocytes, NK cells, and B cells. An illustration of the structure of PBMC-HPV is presented in FIG. 1A, with the indicated lines representing full-length E6 and E7 synthetic long peptides (SLPs) that contain immunogenic epitopes of HPV16. The minimal epitope marked in red and green, respectively. Once delivered, SLPs are processed to generate the minimal epitopes, which are subsequently presented on the MHC-I.

Figure 1A:
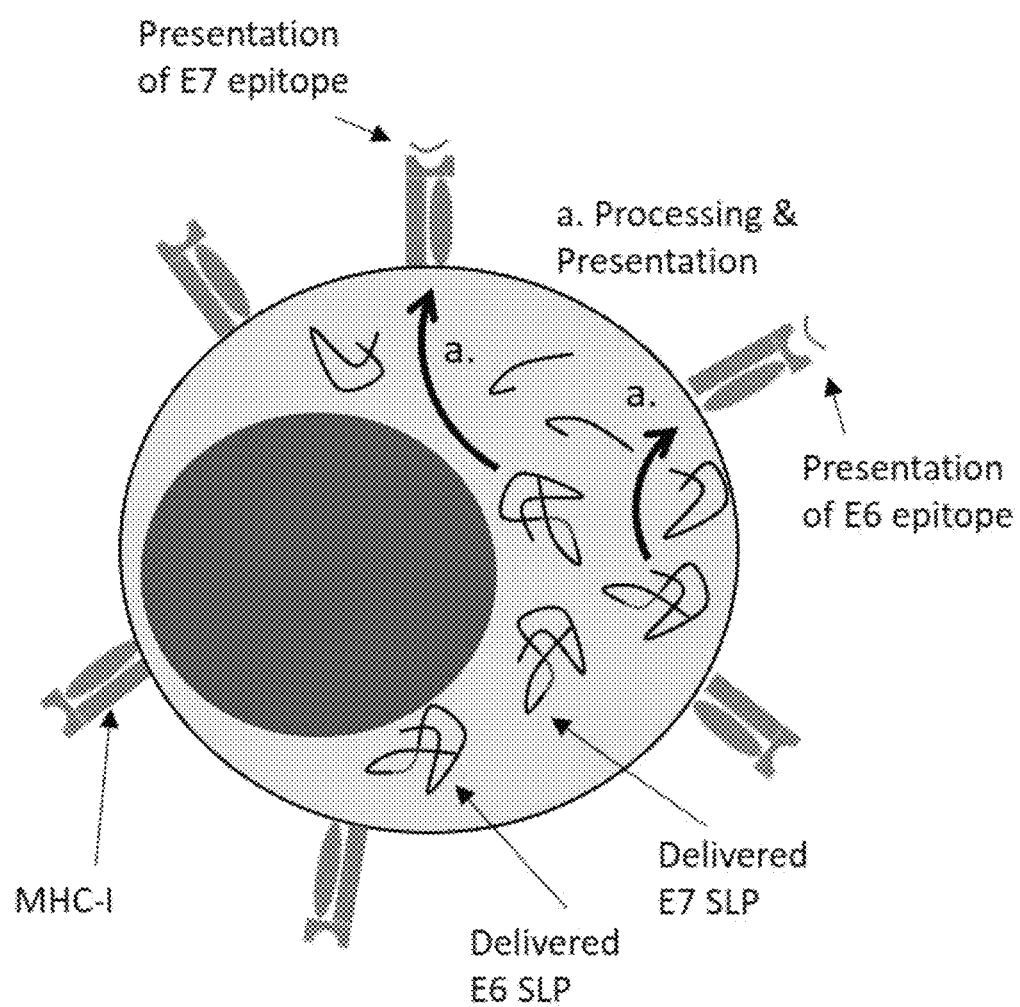
FIG. 1A is a schematic diagram of a representative cell within a plurality of PBMCs, displaying the SQZ-mediated delivery of E6 and/or E7 SLP; and the subsequent processing and presentation of E6 and E7 epitopes, respectively, on MHC-I. The representative cell can be any one of the PBMC cell types (such as T cells, monocytes, NK cells, and B cells).

The cell in the FIG. 1A represents any of the PBMC-HPV cell types (T cells, monocytes, NK cells, and B cells).

E6 SLP and E7 SLP used as starting materials in the production of the PBMC-HPV drug substance are shown below. These peptides contain antigenic epitopes for HPV16 (shown in bold letters).

E6 SLP:
(SEQ ID NO: 19)
QLCTELQTTIHDIILECVYCKQQLL

E7 SLP:
(SEQ ID NO: 23)
QLCTELQTYMLDLQPETTYCKQQLL

After being delivered into the cell cytosol during the manufacturing process, these peptides are processed by the cells and the resultant segments containing antigenic epitopes are presented on the MHC-I of the various PBMC cells. The E6 SLP is a 25 amino acid peptide from the native E6 protein that was chosen because it contains the HLA-A2 antigenic peptide TIHDIILECV (SEQ ID NO: 1), which has been cited as a HLA-A2 restricted immunodominant epitope in the E6 protein. The E7 SLP contains the HLA-A2 restricted immunodominant epitope YMLDLQPETT (SEQ ID NO: 3) within flanking amino acids from the E6 protein. This E7 epitope has been widely cited as an antigenic E7 peptide. The E7 epitope in this flanking sequence, which is not identical to the native E7 protein, was found to be more efficiently processed and presented in vitro by human antigen presenting cells than an SLP containing the native E7 flanking sequence.

As part of the PBMC-HPV drug substance manufacturing process, the PBMC-HPV cells are conditioned with CpG 7909, a CpG oligodeoxyribonucleotide (ODN) that stimulates toll-like receptor (TLR9) signaling. This maturation results in production of inflammatory cytokines (e.g. IL-6) by PBMC-HPV cells and upregulation of costimulatory molecules (e.g. CD86) and MHC-I on B cells. After the maturation period, the PBMC-HPV drug substance is washed to remove CpG 7909 and accumulated cytokines, and subsequently formulated into a composition comprising a conditioned plurality of PBMCs comprising an HPV antigen, called the SQZ-PBMC-HPV drug product.

The PBMC-HPV drug substance consists of the cells with E6 and E7 SLPs delivered to the cytosol and after CpG 7909 matures the cells, but immediately prior to washing away the CpG 7909, and the formulation and filling required to generate the SQZ-PBMC-HPV drug product.

To manufacture the drug product, the PBMC-HPV drug substance is washed twice and subsequently formulated in a solution. For example, the solution can contain containing 50% (v/v) of a cryogenic preservation media (such as CryoStor® CS10), 30% (v/v) of a hypothermic preservation media (such as HypoThermosol® FRS), and 20% (v/v) of albumin (such as Albuked™ 25 (25% Human Serum Albumin); NDC #76125-0792-10)

Approximately 6-8 days after leukapheresis, patients receive the SQZ-PBMC-HPV drug product intravenously (IV). The dose of the SQZ PBMC-HPV drug product varies according to the patient's dose cohort and is dosed on live cells/kg basis.

The first-in-human (FIH) study consists of an Escalation Phase and an Expansion Phase for SQZ-PBMC-HPV and SQZ-PBMC-HPV+atezolizumab The SQZ-PBMC-HPV Escalation Phase comprises the following cohorts:
(1) a low cell dose cohort with an initial administration followed by two boosters of SQZ-PBMC-HPV, one 3 weeks and one 6 weeks after the initial dose,
(2) a low cell dose initial administration followed by 5 boosters of SQZ-PBMC-HPV, administered in 3-week intervals,
(3) a high cell dose cohort with an initial administration followed by two boosters of SQZ-PBMC-HPV, one 3 weeks and one 6 weeks after the initial dose of 3 equal aliquots,
(4) a high cell dose cohort with an initial administration followed by two boosters of SQZ-PBMC-HPV, one 3 weeks and one 6 weeks after the initial dose. In this cohort, CpG 7909 will be co-administered each time following SQZ-PBMC-HPV.

While the main focus of the FIH study is be the evaluation of the administration of SQZ-PBMC-HPV, the study includes the evaluation of the co-administration of SQZ-PBMC-HPV and CpG 7909 in one cohort (Cohort 4). Cohort 4 provides information whether or not CpG7909 is co-administered for subsequent cohorts and the Expansion Phase. SQZ-PBMC-HPV is administered by IV first, followed by IV administration of CpG 7909 in Cohort 4.

Following the analysis of at least 4 patients in each cohort regarding safety, tolerability and the impact of co-administration of CpG 7909, a decision is made together with the study investigators whether the drug product SQZ-PBMC-HPV is co-administered with CpG 7909 or not in the Escalation Phase for SQZ-PBMC-HPV+atezolizumab. The following cohorts are tested:
(5) a low cell dose cohort+atezolizumab with an initial administration followed by two boosters of SQZ-PBMC-HPV+atezolizumab, one 3 weeks and one 6 weeks after the initial dose,
(6) a low cell dose cohort+atezolizumab with initial administration followed by at least 5 boosters (max. 9 dependent on number of harvested cells) of SQZ-PBMC-HPV+atezolizumab, administered in 3-week intervals,
(7) a high cell dose cohort+atezolizumab with an initial administration followed by two boosters of SQZ-PBMC-HPV+atezolizumab, one 3 weeks and one 6 weeks after the initial dose.

Figure 1B:
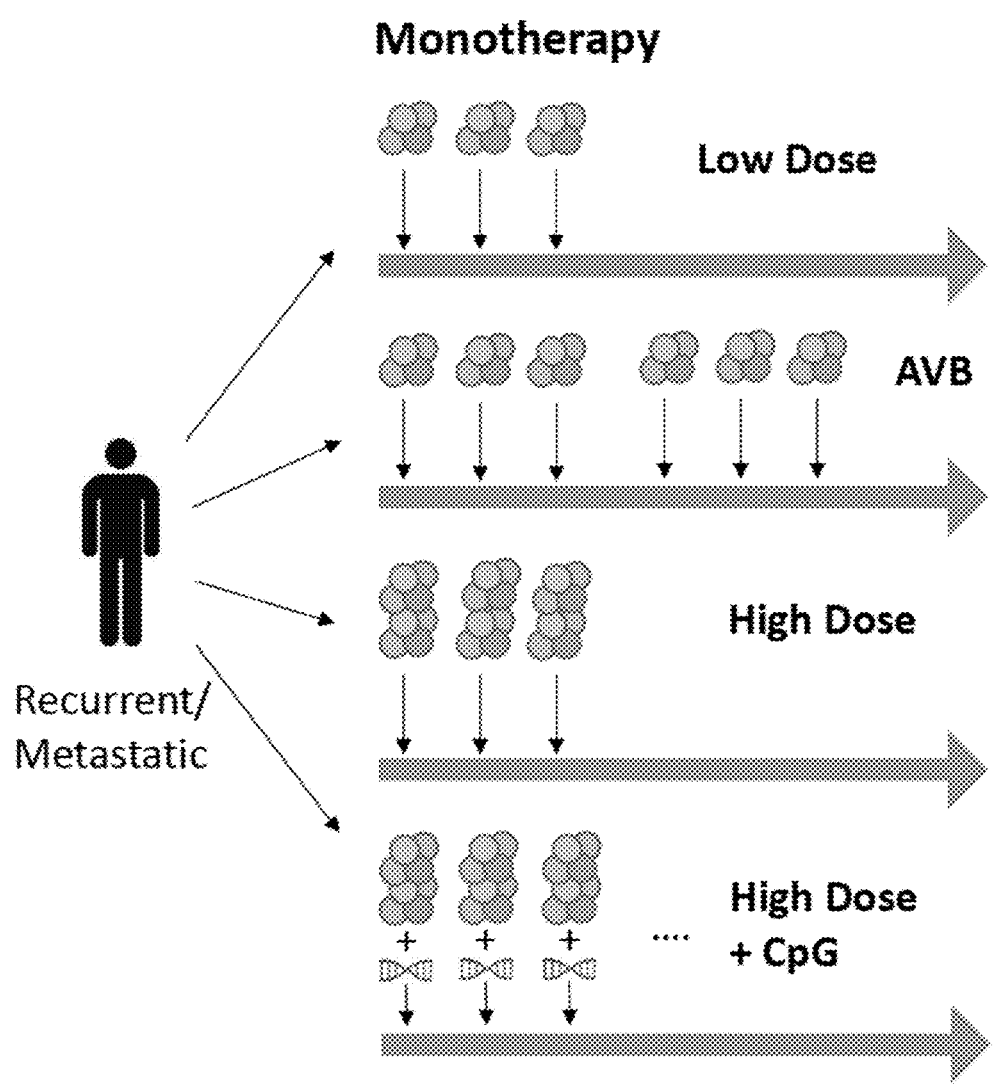
FIG. 1B is a schematic representative of cohorts in the escalation phase in the monotherapy administration of PBMCs comprising an HPV antigen to an individual, with or without co-administration of a CpG adjuvant. The amount of circles depicts relative doses of modified PBMCs, arrows depict administrations, double helix represents CpG adjuvant, and "AVB" indicates additional vaccine boosts.
Figure 1C:
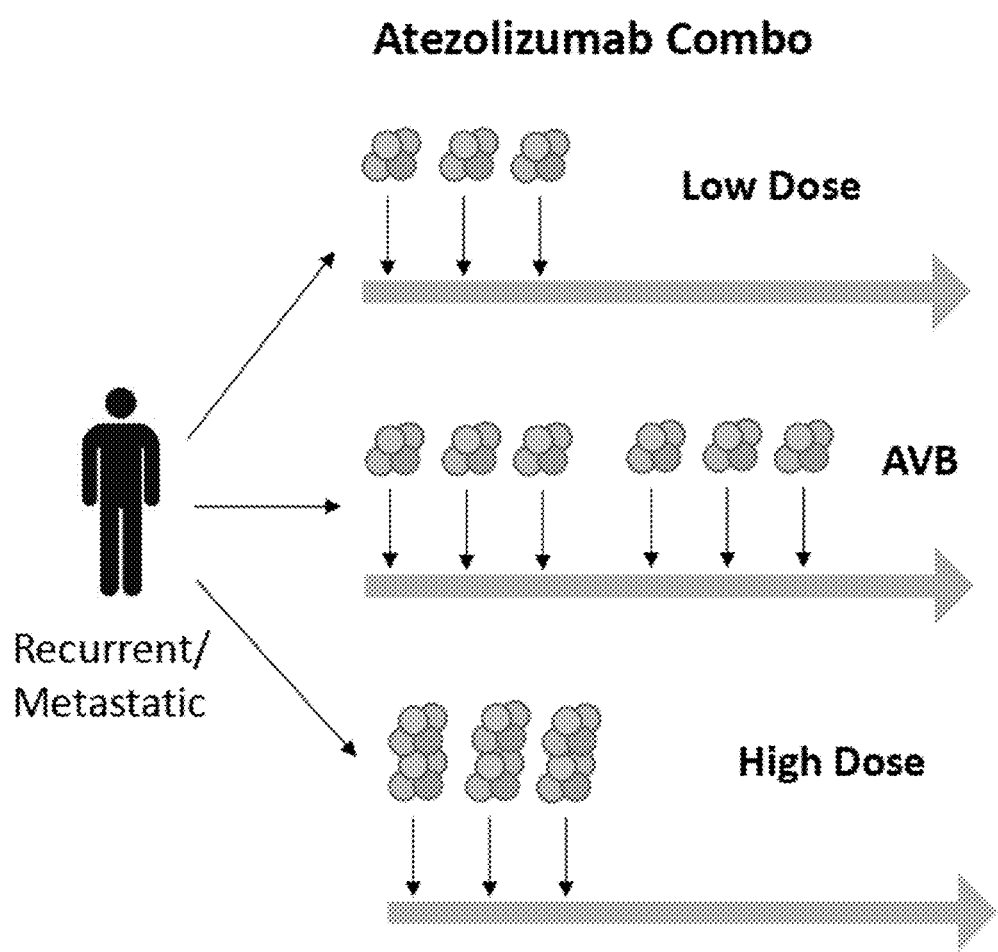
FIG. 1C is a schematic representative of cohorts in the escalation phase in the combination administration of PBMCs comprising an HPV antigen and atezolizumab to an individual. The amount of circles depicts relative doses of modified PBMCs, arrows depict administrations, and "AVB" indicates additional vaccine boosts.

FIG. 1B and FIG. 1C show representative schematics of cohort treatments for the SQZ-PBMC-HPV monotherapy and SQZ-PBMC-HPV+atezolizumab combination therapy, respectively For an Expansion Phase study, up to 3 baskets for dosing SQZ-PMBC-HPV as a monotherapy are:
(1) HPV16-positive Head & Neck Squamous Cell Cancer at the selected Recommended Phase 2 Dose (RP2D) Regimen,
(2) HPV16-positive Cervical Cancer at the selected Recommended Phase 2 Dose (RP2D) Regimen,
(3) Other HPV16-positive cancer at the selected Recommended Phase 2 Dose (RP2D) Regimen, Up to 3 baskets for SQZ-PBMC-HPV+atezolizumab are:
HPV16-positive Head and Neck Squamous Cell Cancer at the selected Recommended Phase 2 Dose (RP2D) regimen for SQZ-PBMC-HPV,
HPV16-positive Cervical Cancer at the selected Recommended Phase 2 Dose (RP2D) regimen for SQZ-PBMC-HPV,
Other HPV16-positive cancer at the selected Recommended Phase 2 Dose (RP2D) regimen for SQZ-PBMC-HPV Example 2

In order to quantify SQZ-mediated delivery to individual immune cell subsets, mouse splenocytes were loaded with a fluorescent tracer molecule and assessed for viability and delivery.

Method

Splenocytes were isolated from C57BL/6J female mice (20 M/mL) and loaded using SQZ (30, 60 and 90 psi; 4 μm constriction) with 100 μg/mL of fluorescently-labeled dextran (3 kDa) in RPMI and the viability and percent delivery of dextran to individual immune cell subsets within the mixed splenocyte population by flow cytometry.

Results

Figure 2A:
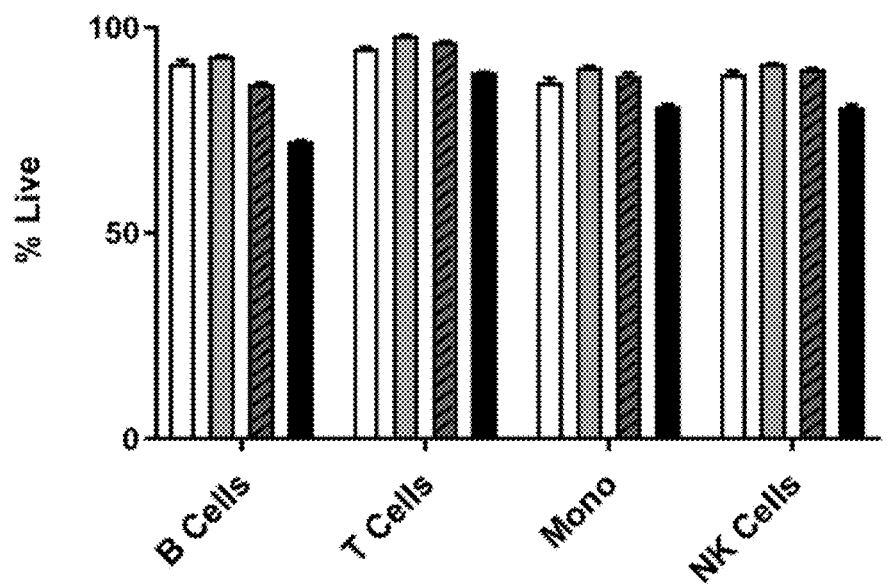
FIG. 2A shows the viability of subpopulations in splenocytes after incubation of dextran (endocytosis) and SQZ-mediated delivery of dextran under a driving pressure of 30, 60, and 90 psi.
Figure 2B:
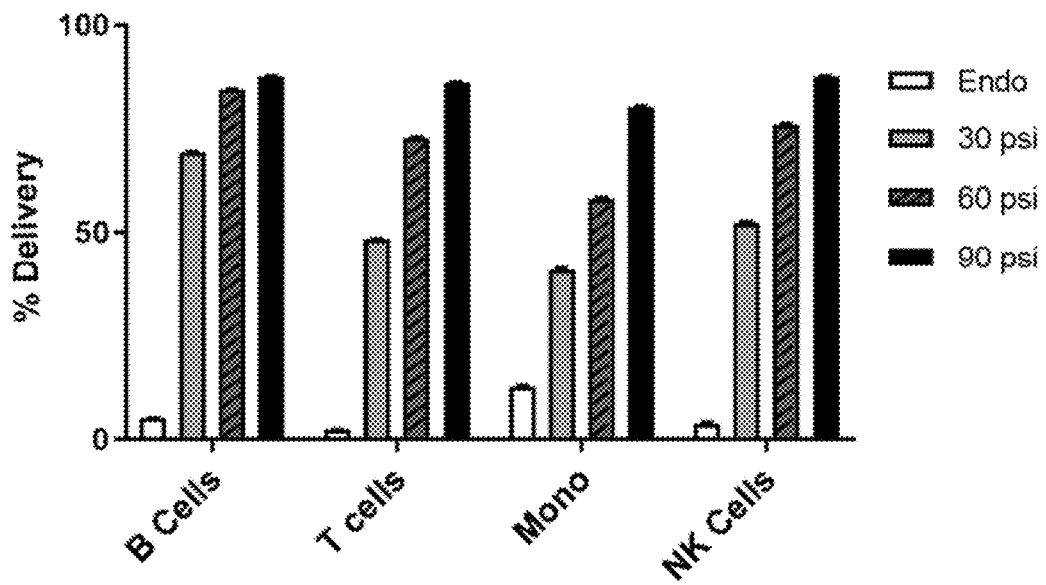
FIG. 2B shows the percentage of cells with dextran delivered by endocytosis or SQZ-mediated delivery under a driving pressure of 30, 60, and 90 psi.

As shown in FIG. 2, the percent delivery of dextran to splenocytes increased significantly ($P<0.001$; each condition relative to Endo) with increasing pressure, with only a slight decrease in viability with the 30 and 60 psi conditions, and a larger decrease in viability with the 90 psi condition. B and NK cells had the highest levels of delivery amongst the other cell populations, although there was still appreciable amount of delivery in T cells and monocytes. At the condition that gave the highest delivery with only minimal impact on viability (60 psi), all cell subsets had a percent delivery within ~15% (60-75% delivery across all cell types). These data show that SQZ can efficiently deliver molecules to each immune cell subset in a mixed population of murine splenocytes simultaneously, with little impact on viability.

Example 3

In order to evaluate the impact of different adjuvant strategies, mixed splenocytes and isolated B cells were loaded with a model antigen and conditioned and/or co-injected with adjuvant and the relative percentage of inflammatory cytokine IFN-γ+CD8+ T cells was measured by flow cytometry.

Method

At Day 0, splenocytes were obtained from spleens of female C57BL/6J donor mice, along with B cells isolated from the splenocytes for one group via immunomagnetic separation, loaded with Ova protein (400 μg/mL) by SQZ (60 psi; 4 μm constriction) and incubated in either media (R10) alone or media with CpG 1826 (1 μM) for 16 h. Female C57BL/6J recipient mice (5/group) were injected retro-orbitally on Day 1 with 100 μL of either vehicle (PBS), B cells (5×10$^6$ cells/mL), splenocytes (5×10$^6$ cells/mL) or splenocytes co-injected with 25 μg CpG1826. On Day 8, spleens were harvested, restimulated with SIINFEKL (SEQ ID NO: 54) (1 μg/mL) and the percentage of IFN-γ+CD8+ T cells was determined by intracellular cytokine staining (ICS).

Results

Figure 3:
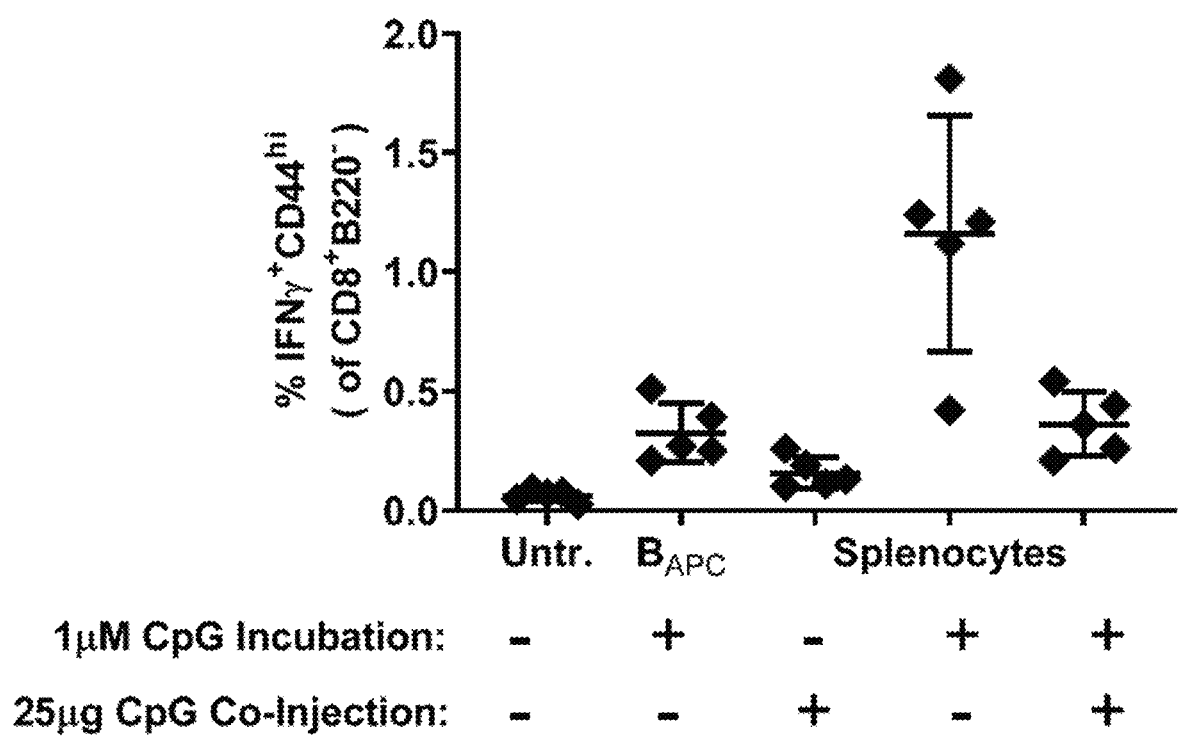
FIG. 3 shows the effects of cell conditioning and of co-administration of CpG on the antigen-specific immune response elicited by B cells or splenocytes SQZ-loaded with OVA.

As shown in FIG. 3, the percentage of IFN-γ+CD8+ T cells for mice treated with Ova-loaded splenocytes was significantly higher when splenocytes were conditioned with CpG for 16 h (P<0.005 relative to all other conditions; Data represents 3 independent experiments); however, there was no significant increase in % IFN-γ+CD8+ T cells when mice were co-injected with CpG or treated with CpG-matured B cells ($B_{APC}$). These data show that treatment with CpG-matured, Ova-loaded splenocytes lead to a significant increase in inflammatory cytokine production in antigen-specific CD8+ T cells, while Ova-loaded B cells, or splenocytes co-injected with CpG, did not induce an appreciable response.

Example 4

In order to determine if antigen-loaded splenocytes co-injected with lower doses of CpG can elicit an antigen-specific response, splenocytes were loaded with a model antigen and either matured with CpG, co-injected with CpG or matured and co-injected with increasing doses of CpG and the relative percentage of inflammatory cytokine IFN-γ+CD8+ T cells was measured by flow cytometry.

Methods

At Day 0, splenocytes were obtained from spleens of female C57BL/6J donor mice, and combined with splenocytes that have had their B cells depleted by negative immunomagnetic separation, leading to a splenocyte composition more representative of human PBMCs. These mixed splenocytes were then loaded with Ova protein (400 μg/mL) by SQZ (60 psi; 4 μm constriction) and incubated in either media (R10) alone or media with CpG 1826 (1 μM) for 16 h. Female C57BL/6J recipient mice (5/group) were injected retro-orbitally on Day 1 with 100 μL of either vehicle (PBS), splenocytes (1×10$^6$ cells/mouse) matured with CpG, splenocytes co-injected with 25 μg CpG1826 or splenocytes matured with CpG that are co-injected with different doses of CpG (0.1-10 μg). On Day 8, spleens were harvested, restimulated with SIINFEKL (SEQ ID NO: 54) (1 μg/mL) and the percentage of IFN-γ+CD8+ T cells was determined by intracellular cytokine staining (ICS).

Results

Figure 4:
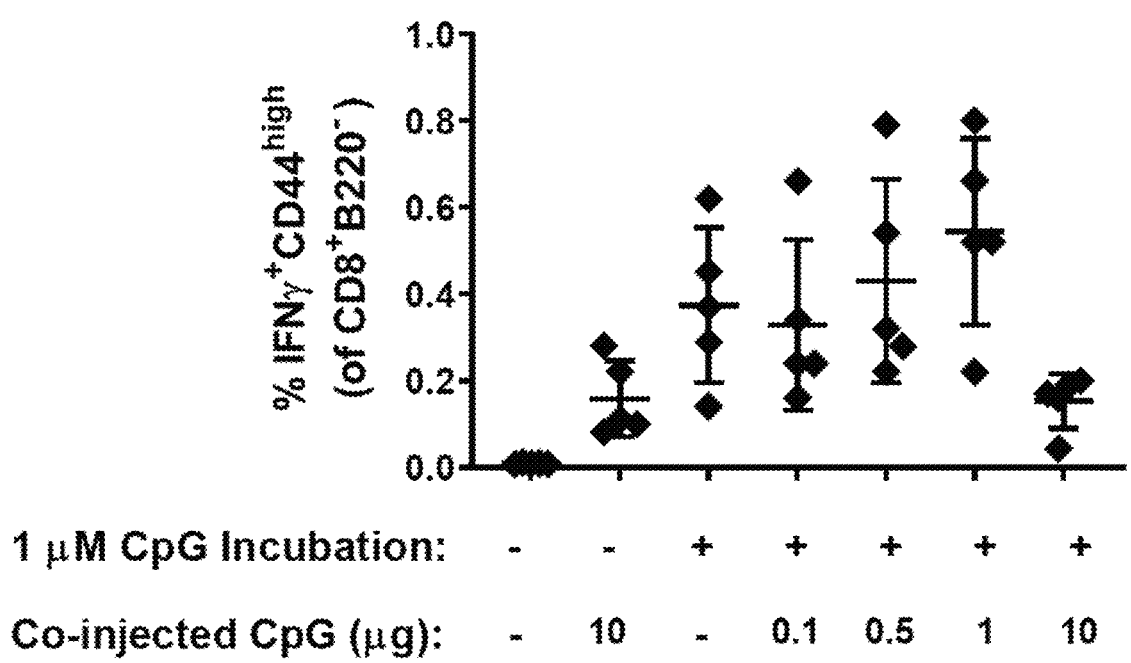
FIG. 4 shows the effects of splenocyte conditioning and of co-administration of CpG at various concentrations on the antigen-specific immune response elicited by crafted splenocytes SQZ-loaded with OVA.

As shown in FIG. 4, The percentage of IFN-γ+CD8+ T cells for mice treated with Ova-loaded splenocytes was significantly higher when splenocytes were matured with CpG for 16 h (P<0.05 relative to untreated); however, there was no significant increase in % IFN-γ+CD8+ T cells when mice were co-injected with CpG relative to control. Additionally, there was no statistically significant increase in the percentage of % IFN-γ+CD8+ T cells when splenocytes were matured with CpG compared to matured and co-injected with any dose of CpG, with an apparent slight decrease with the 5 μg CpG co-injection. These data show that co-injection of CpG combined with CpG-matured, Ova-loaded splenocytes does not lead to a significant increase in inflammatory cytokine production in antigen-specific CD8+ T cells.

Example 5

In order to determine if antigen-loaded splenocytes co-injected with different adjuvants can elicit an antigen-specific response, splenocytes were loaded with a model antigen and either matured with CpG, co-injected with CpG or matured with CpG and co-injected with either CpG or IFN-α and the relative percentage of inflammatory cytokine IFN-γ+CD8+ T cells was measured by flow cytometry.

Methods

At Day 0, splenocytes were obtained from spleens of female C57BL/6J donor mice, and combined with splenocytes that have had their B cells depleted by negative immunomagnetic separation, leading to a splenocyte composition more representative of human PBMCs. These mixed splenocytes were then loaded with Ova protein (400 μg/mL) by SQZ (60 psi; 4 μm constriction) and incubated in either media (R10) alone or media with CpG 1826 (1 μM) for 16 h. Female C57BL/6J recipient mice (5/group) were injected retro-orbitally on Day 1 with 100 μL of either vehicle (PBS), splenocytes (1×10$^6$ cells/mouse) matured with CpG, splenocytes co-injected with 1 μg CpG1826 or splenocytes matured with CpG that are co-injected with either CpG or 10000 U IFN-α. On Day 8, spleens were harvested, restimulated with SIINFEKL (SEQ ID NO: 54) (1 μg/mL) and the percentage of IFN-γ+CD8+ T cells was determined by intracellular cytokine staining (ICS).

Results

Figure 5:
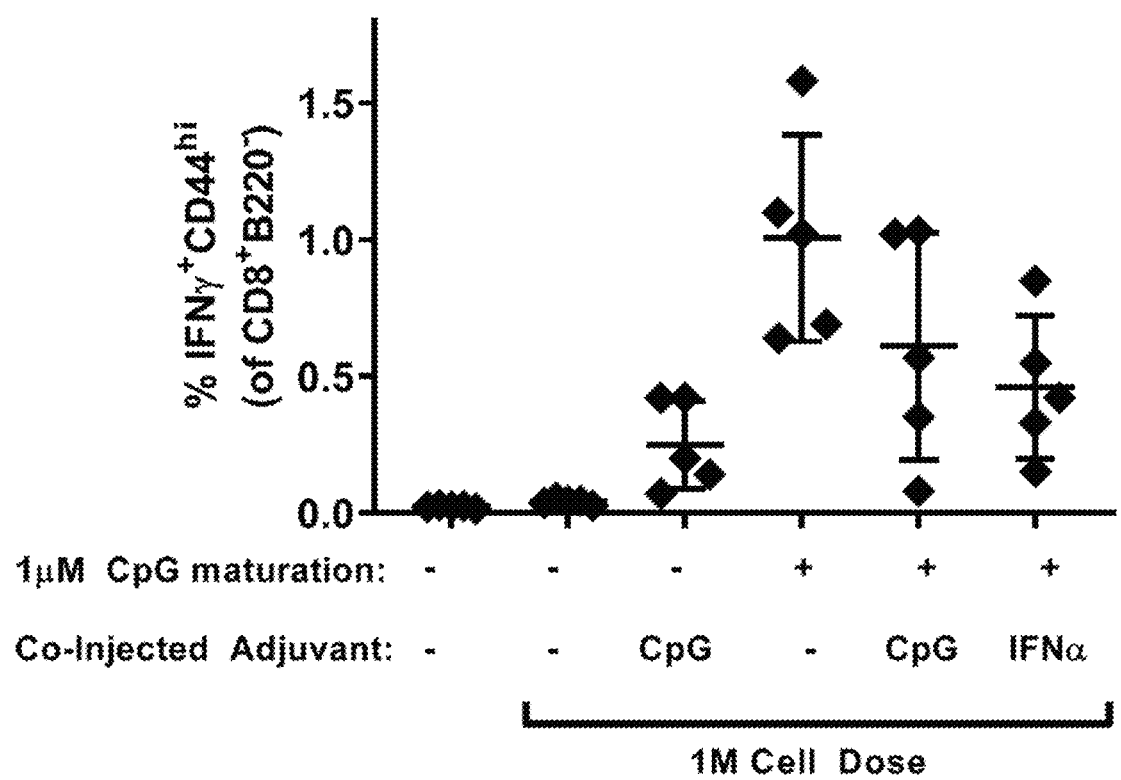
FIG. 5 shows the effects of splenocyte conditioning and of co-administration of CpG or IFNα on the antigen-specific immune response elicited by crafted splenocytes SQZ-loaded with OVA.

As shown in FIG. 5, the percentage of IFN-γ+CD8+ T cells for mice treated with Ova-loaded splenocytes was highest when splenocytes were matured with CpG for 16 h, with a significant increase when compared to untreated (P<0.0001) as well as co-injected CpG (P<0.005). There was no significant benefit to maturing splenocytes with CpG and co-injecting them with either adjuvant, with a trend towards the co-injected adjuvant blunting the effect. These data show that co-injection of CpG or IFN-α combined with CpG-matured, Ova-loaded splenocytes does not lead to a significant increase in inflammatory cytokine production in antigen-specific CD8+ T cells.

Example 6

In order to determine if boosting an antigen-specific splenocyte vaccine can elicit a greater antigen-specific response, splenocytes were loaded with a model antigen, matured with CpG, and injected into recipient mice once (Prime) or twice (Prime-Boost), with the relative percentage of inflammatory cytokine IFN-γ+CD8+ T cells measured by flow cytometry.

Methods

At Day −7, splenocytes were obtained from spleens of female C57BL/6J donor mice, and combined with splenocytes that have had their B cells depleted by negative immunomagnetic separation, leading to a splenocyte composition more representative of human PBMCs. These mixed splenocytes were then loaded with Ova protein (400 μg/mL) by SQZ (60 psi; 4 μm constriction) and with CpG 1826 (1 μM in R10) for 4 h. Female C57BL/6J recipient mice (5/group) were injected retro-orbitally on Day −7 and/or Day 0 with 100 µL of splenocytes ($1 \times 10^{5-6}$ cells/mouse). On Day 7, spleens were harvested, restimulated with SIINFEKL (SEQ ID NO: 54) (1 µg/mL) and the percentage of IFN-γ+CD8+ T cells was determined by intracellular cytokine staining (ICS).

Results

Figure 6:
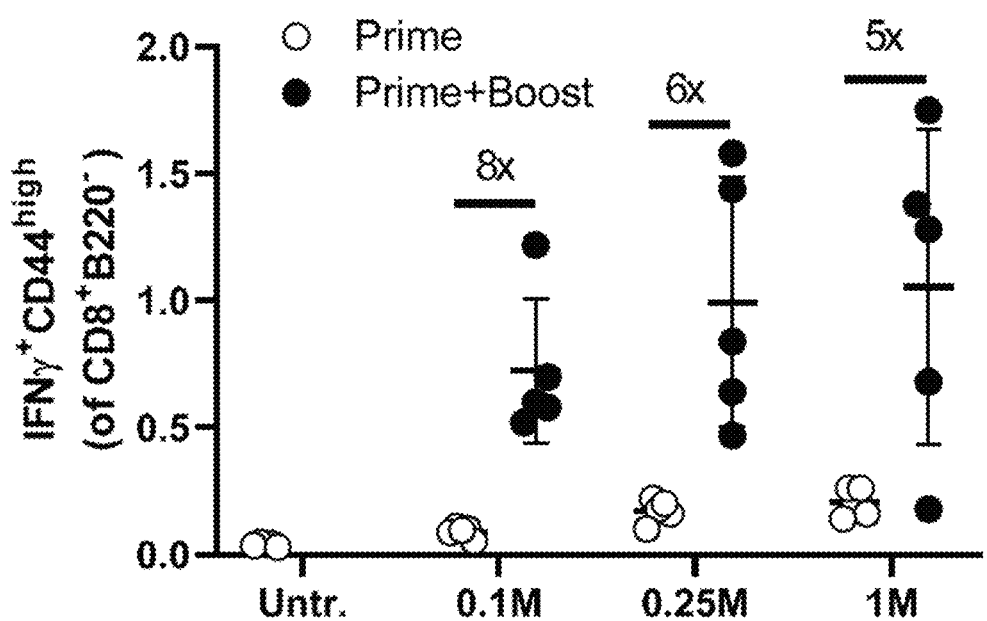
FIG. 6 shows the antigen-specific immune response elicited by conditioned crafted splenocytes SQZ-loaded with OVA when administered at different cell doses, with one administration (Prime) or two administrations (Prime-boost).

As shown in FIG. 6, while increasing splenocyte dose did lead to a modest increase in the percentage of IFN-γ+CD8+ T cells, the addition of a boost after 7 days led to a significant ($P<0.05$) increase in IFN-γ+ cells for all of the splenocyte doses tested. Interestingly, the boost enhancement was most pronounced with lower cell doses, with the 0.1M dose exhibiting an 8-fold increase in antigen-specific response. These data show that, for all doses tested, the use of a boost 7 days after priming leads to a significant enhancement in the antigen-specific CD8+ T cell response.

Example 7

In order to evaluate the importance of cell dose and relative efficacy of a B cell versus a mixed splenocyte vaccine, cells were loaded with a model antigen and matured with adjuvant and the relative percentage of inflammatory cytokine IFN-γ+CD8+ T cells was measured by flow cytometry.

Methods

At Day 0, splenocytes were obtained from spleens of female C57BL/6J donor mice, and combined with splenocytes that have had their B cells depleted by negative immunomagnetic separation, leading to a splenocyte composition more representative of human PBMCs. Additionally, isolated B cells were obtained from spleens of female donor mice via positive immunomagnetic separation. These different cell compositions were loaded with Ova protein (400 µg/mL) by SQZ (60 psi; 4 µm constriction) and incubated in either media (R10) alone or media with CpG 1826 (1 µM) for 16 h. Female C57BL/6J recipient mice (5/group) were injected retro-orbitally on Day 1 with 100 µL of either vehicle (PBS), B cells or splenocytes ($0.25-4 \times 10^6$ cells/mL). On Day 8, spleens were harvested, restimulated with SIINFEKL (SEQ ID NO: 54) (1 µg/mL) and the percentage of IFN-γ+CD8+ T cells was determined by intracellular cytokine staining (ICS).

Results

Figure 7:
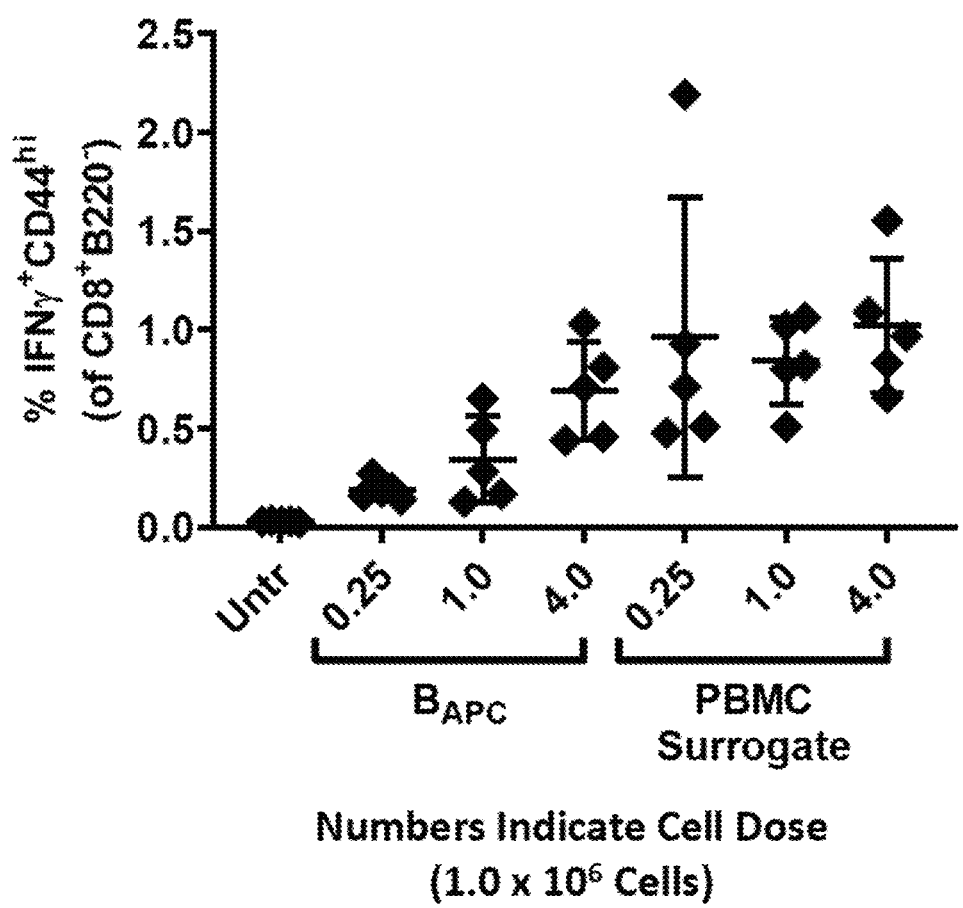
FIG. 7 shows the antigen-specific immune response elicited by (a) conditioned B cells SQZ-loaded with OVA or (b) conditioned crafted splenocytes SQZ-loaded with OVA when administered at different doses, with one administration (Prime) or two administrations (Prime-boost).

As shown in FIG. 7, The percentage of IFN-γ+CD8+ T cells for mice treated with Ova-loaded B cells or splenocytes exhibited a positive dose-response, with the 4M cell dose leading to the highest response for both cell types tested. Generally, all doses of splenocytes led to higher average responses then their BAPC counterparts, trending towards significance. This data show that higher cell numbers trend with increased responses and that splenocytes may induce a higher antigen-specific response.

Example 8

In order to evaluate the impact of CpG maturation time on the relative efficacy of mixed splenocytes to induce an antigen-specific response, splenocytes were loaded with a model antigen and matured with CpG for varying times and the relative percentage of inflammatory cytokine IFN-γ+CD8+ T cells was measured by flow cytometry.

Methods

At Day 0, splenocytes were obtained from spleens of female C57BL/6J donor mice, and combined with splenocytes that have had their B cells depleted by negative immunomagnetic separation, leading to a splenocyte composition more representative of human PBMCs. Splenocyte were loaded with Ova protein (400 µg/mL) by SQZ (60 psi; 4 µm constriction) and incubated in either media (R10) alone or media with CpG 1826 (1 µM) for varying times. Female C57BL/6J recipient mice (5/group) were injected retro-orbitally on Day 1 with 100 µL of either vehicle (PBS) or splenocytes ($1 \times 10^6$ cells/mL). On Day 8, spleens were harvested, restimulated with SIINFEKL (SEQ ID NO: 54) (1 µg/mL) and the percentage of IFN-γ+CD8+ T cells was determined by intracellular cytokine staining (ICS).

Results

Figure 8:
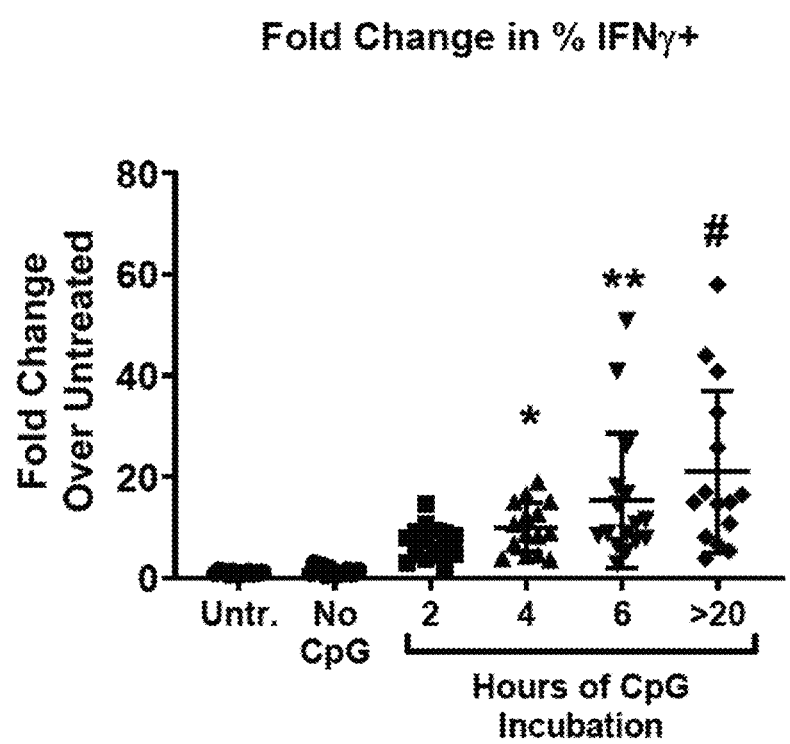
FIG. 8 shows the effect of duration of conditioning (CpG incubation) on antigen-specific immune response elicited by matured splenocytes SQZ-loaded with OVA.

As shown in FIG. 8, The percentage of IFN-γ+CD8+ T cells for mice treated with Ova-loaded splenocytes increased with longer CpG maturation times (*$P<0.05$, **$P<0.01$, #$P<0.005$, all comparisons made to No CpG). There was a significant increase in the response observed with all maturation times of at least 4 hours. These data show that at least 4 hours CpG maturation time post-SQZ is necessary to induce a significant antigen-specific response.

Example 9

In order to determine the minimum effective cell dose of splenocytes needed to lead to tumor growth inhibition in a therapeutic setting, four different doses of splenocytes were tested in the HPV E7-expressing TC1 tumor model, with the area of the tumors plotted against time.

Methods

At Day 0, C57BL/6J female mice were injected in the right rear flank with TC1 tumor cells (50 k cells/mouse) at Day 0. On Day 7 (prime), splenocytes were obtained from spleens of female C57BL/6J donor mice, and combined with splenocytes that have had their B cells depleted by negative immunomagnetic separation, leading to a splenocyte composition more representative of human PBMCs. Splenocyte were loaded with pre-complexed 20 µM E7 SLP (GQAEPDRAHYNIVTFSSKSDSTLRLSVQSTHVDIR (SEQ ID NO: 25))+20 µM mouse serum albumin (MSA) via SQZ (60 psi; 4 µm constriction) and incubated with CpG 1826 (1 µM in R10) for 4 hours. Female C57BL/6J recipient mice (10/group) were injected retro-orbitally on Day 7 with 100 µL of either vehicle (PBS) or splenocytes (0.05-1M cells/mouse). TC-1 tumor growth was measured beginning 1 week post-tumor implantation two times per week and compared to tumor growth in untreated mice for 30 days.

Results

Figure 9:
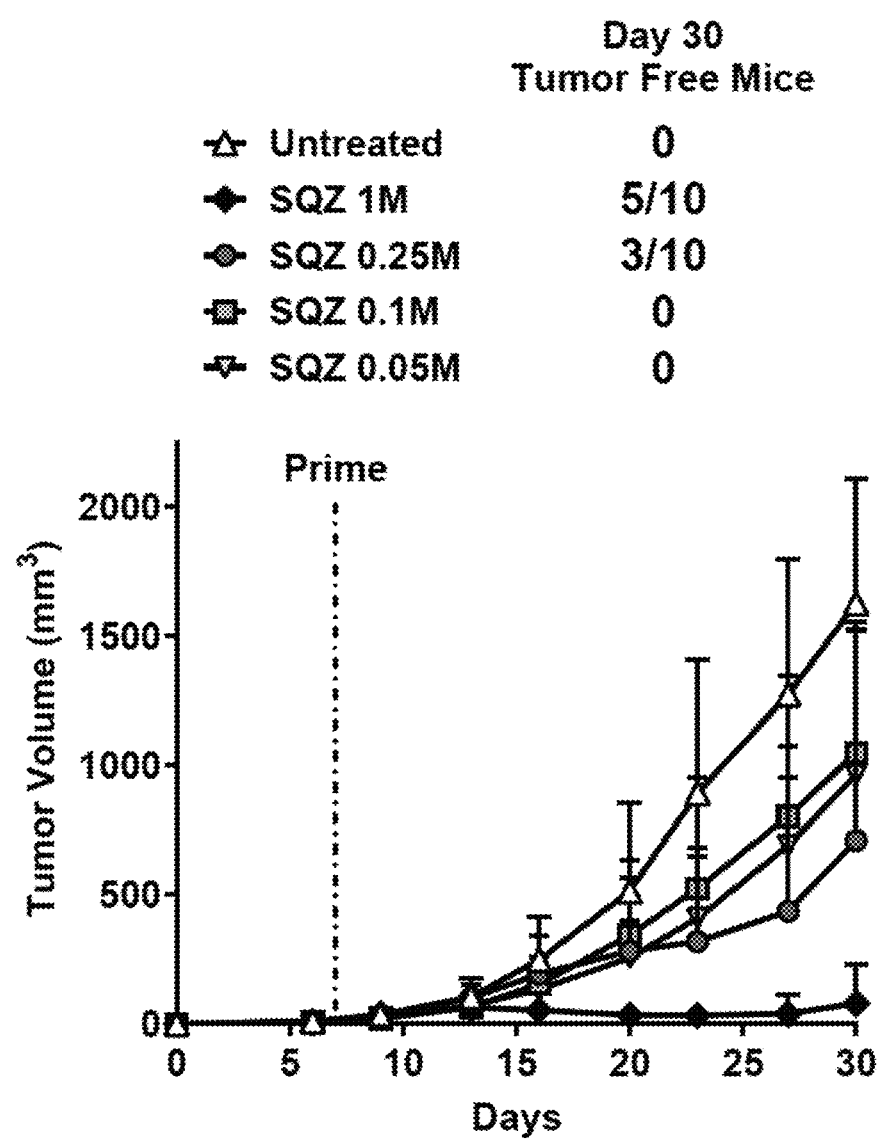
FIG. 9 shows the dose-dependent effect of matured splenocytes SQZ-loaded with E7 HPV antigen in inhibiting E7-expressing TC1 tumors.

As shown in FIG. 9, Tumor growth, as measured by the formula ((length×width2)/2), was compared between mice from the untreated group (no splenocytes) and groups treated with increasing numbers of HPV E7-loaded splenocytes. It was found that the greater the splenocyte dose, the better the tumor growth inhibition, with the 1M dose leading to complete tumor regression on average. After 30 days, there were 5 remaining mice that were tumor-free in the 1M treatment group, while the 0.25M group had 3 mice without tumors. These data show that splenocytes loaded by SQZ can induce tumor regression in a therapeutic model of HPV-associated cancer.

Example 10

In order to determine the effect of CpG maturation on B cells within a mixed population, human PBMCs and murine splenocytes were matured for various times with CpG, with the relative amount of activation marker CD86 was measured in the B cell population by flow cytometry and the levels of cytokines and chemokines were quantified by a multiplex assay.

Methods

Murine splenocytes were obtained from spleens of female C57BL/6J donor mice, and combined with splenocytes that have had their B cells depleted by negative immunomagnetic separation, leading to a splenocyte composition more representative of human PBMCs. Human PBMCs and splenocytes were incubated in R10 with CpG (2006 for human, 1826 for murine) for varying times (2-24 h) and concentrations (1-10 μM). After the CpG incubation, the cells were washed with R10 and assessed for levels of CD86 by flow cytometry, while supernatants were collected and the levels of cytokines were analyzed using a multiplex (29-plex) human cytokine/chemokine assay.

Results

Figure 10A:
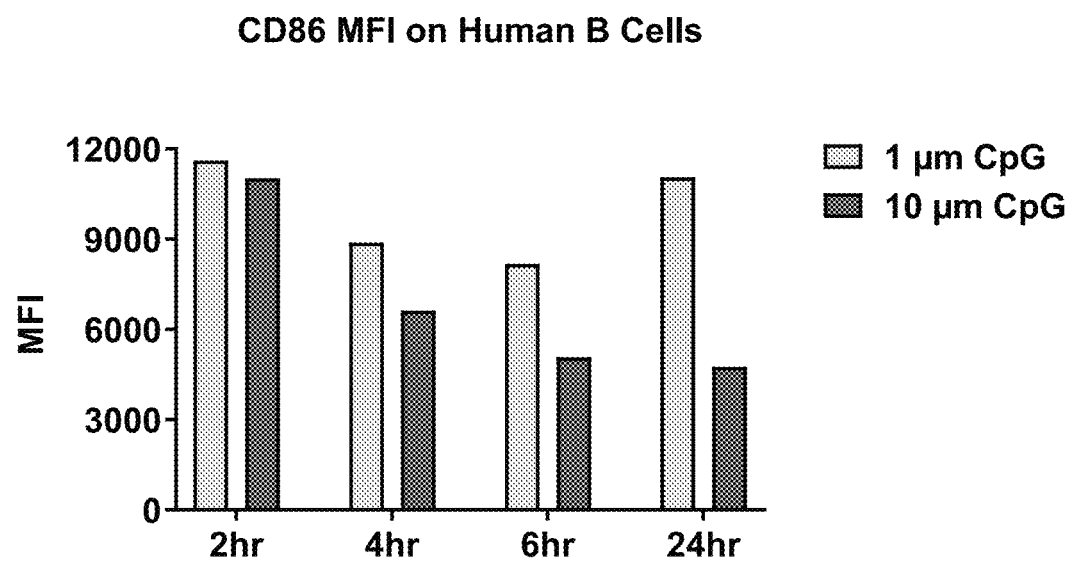
FIG. 10A shows the effect of CpG incubation on activation markers in B cell subpopulation within human PBMCs (top) and murine splenocytes (bottom).
Figure 10A:
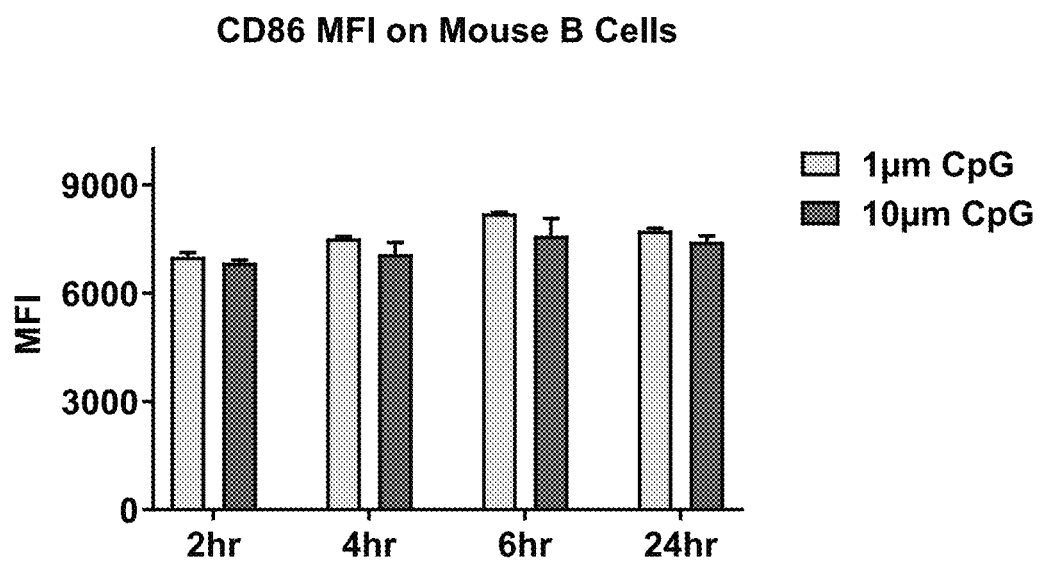

FIG. 10A shows the following results: Human (Top)—The higher 10 μM dose of CpG showed that the levels of CD86 in the B cell population of human PBMCs decreased over time after 2 hours. The lower 1 μM dose led to higher levels of CD86 than 10 μM for all time points, and it also exhibited a bimodal time course, with levels decreasing after 2 h and beginning to return after 24 h. These data show that lower levels of CpG can lead to higher B cell activation with all doses peaking at the earliest observed time point.

Murine (Bottom)—For murine B cells, there was no appreciable change in CD86 levels over time and at both concentrations. These data show that murine B cells do not upregulate CD86 in response to CpG maturation.

Figure 10B:
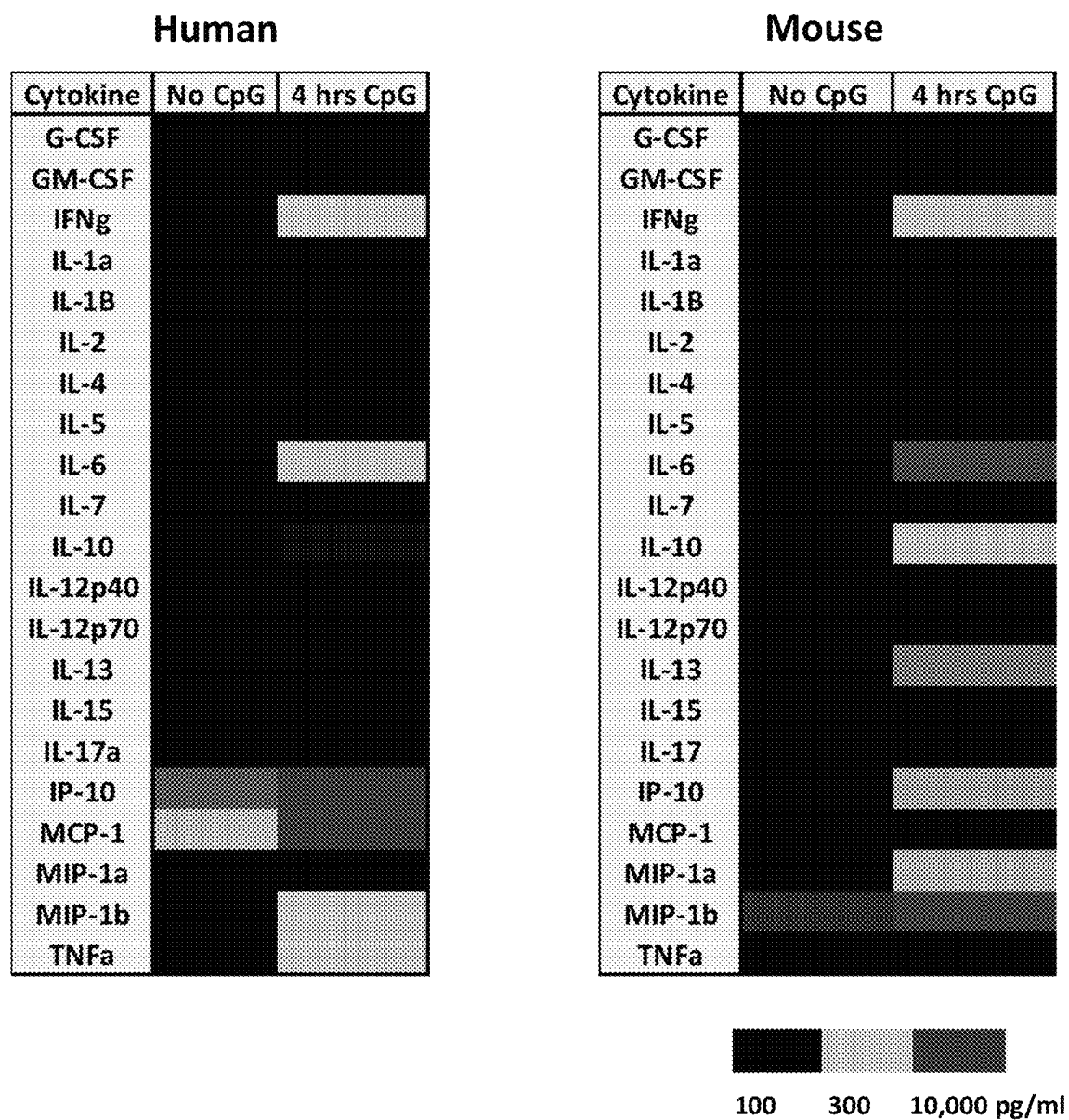
FIG. 10B shows the changes in cytokine/chemokine profiles when human PBMCs or murine splenocytes were subjected to incubation with CpG.

As shown in FIG. 10B, Cytokine/chemokine (FIG. 10B)—Results from both human and mouse chemokine/cytokine profiles exhibit similar trends, with many of the same proteins increasing in response to CpG treatment (IFN-γ, IL-6, MIP-1B), although IL-10 and IL-13 were increased only in murine splenocytes. These results indicate that human PBMCs and murine splenocytes have similar chemokine/cytokine responses to CpG, with IL-10 and IL-13 as notable exceptions.

Example 11

In order to determine the impact of SQZing on cell composition and MHC-I levels, human PBMCs are subjected to cell squeezing and the relative percentage of immune cells, as well as surface expression of MHC-I, was assessed by flow cytometry.

Methods

Human PBMCs from HLA-A2+ donors were incubated with (Endo) or loaded with fluorescently-labeled 3 kDa dextran (100 μg/mL) by SQZ (60 psi; 3.5-4 μm width) at room temperature. The loaded PBMCs were then analyzed for the relative composition of B cells, T cells, NK cells and monocytes, as well as HLA-A2 MHC-I surface expression via flow cytometry.

Results

Figure 11:
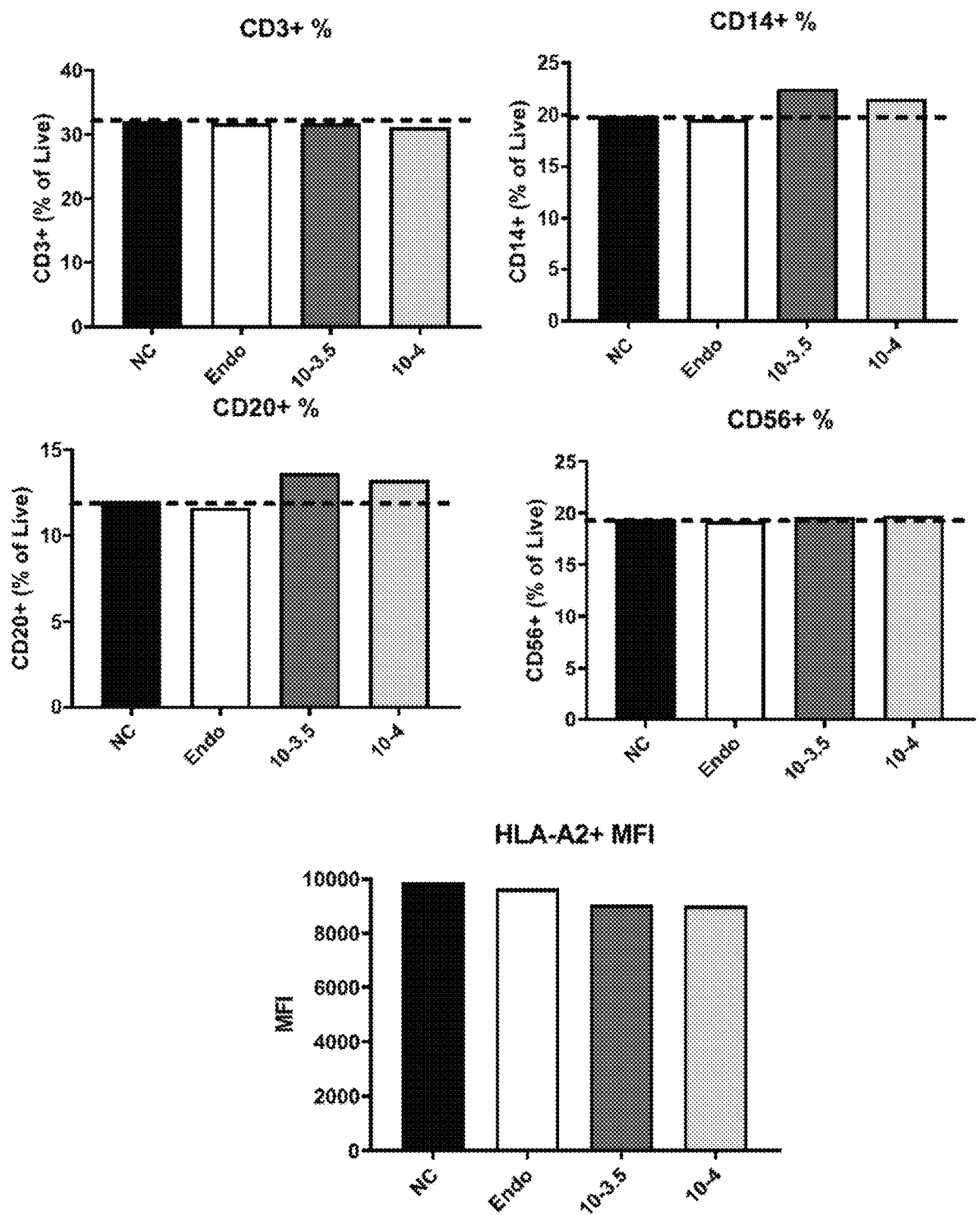
FIG. 11 shows the changes in cell composition and MHC-I levels when human PBMCs were subjected to SQZ-mediated delivery at a driving pressure of 60 psi and a constriction width of 3.5 μm or 4 μm.

As shown in FIG. 11, Loading human PBMCs using SQZ led to changes less than 5% for B cells (CD20), T cells (CD3), NK cells (CD56) and monocytes (CD14) [Top], coincident with a slight (12%) decrease in MHC-I levels after SQZ. For both cell composition and MHC-I levels, the 3.5 μm constriction width led to marginally higher alterations. Taken together, these data support that loading PBMCs with SQZ does not appreciably alter the relative abundance of the immune cell subsets and their MHC-I surface expression.

Example 12

In order to determine the delivery and impact of SQZing on individual cell subsets, human PBMCs are subjected to cell squeezing and the viability and delivery of a fluorescent compound to the different immune cell populations was assessed by flow cytometry.

Methods

Human PBMCs were incubated with (Endo) or loaded with fluorescently-labeled 3 kDa dextran (100 μg/mL) by SQZ (60 psi; 3.5-4 μm width) at room temperature. The loaded PBMCs were then analyzed for viability and delivery by flow cytometry.

Results

Figure 12A:
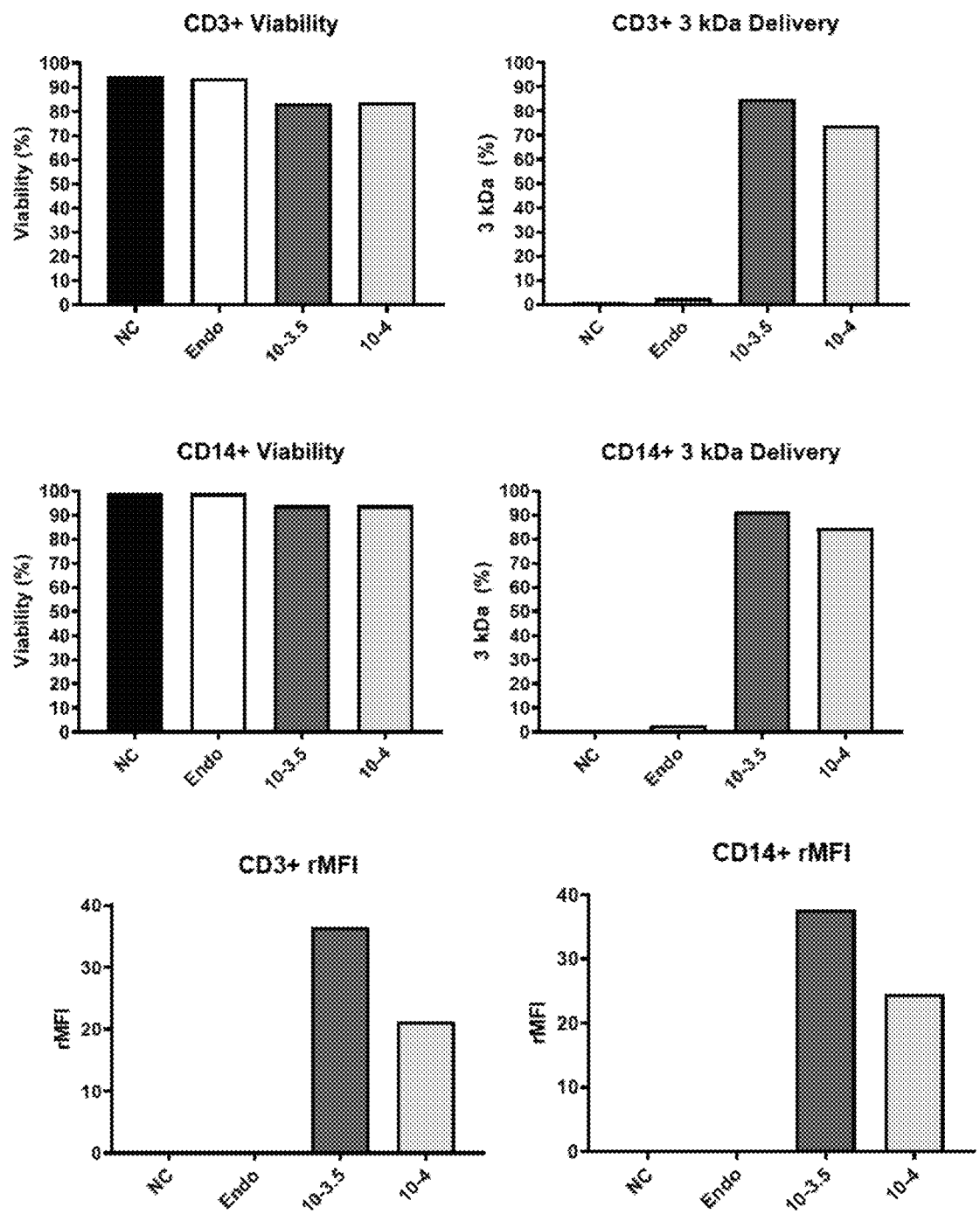
FIG. 12A shows the viability and payload delivery to $CD3^+$ T cells or $CD14^+$ monocytes within human PBMCs that were subjected to SQZ-mediated delivery at a driving pressure of 60 psi and with a constriction width of 3.5 μm or 4 μm.
Figure 12B:
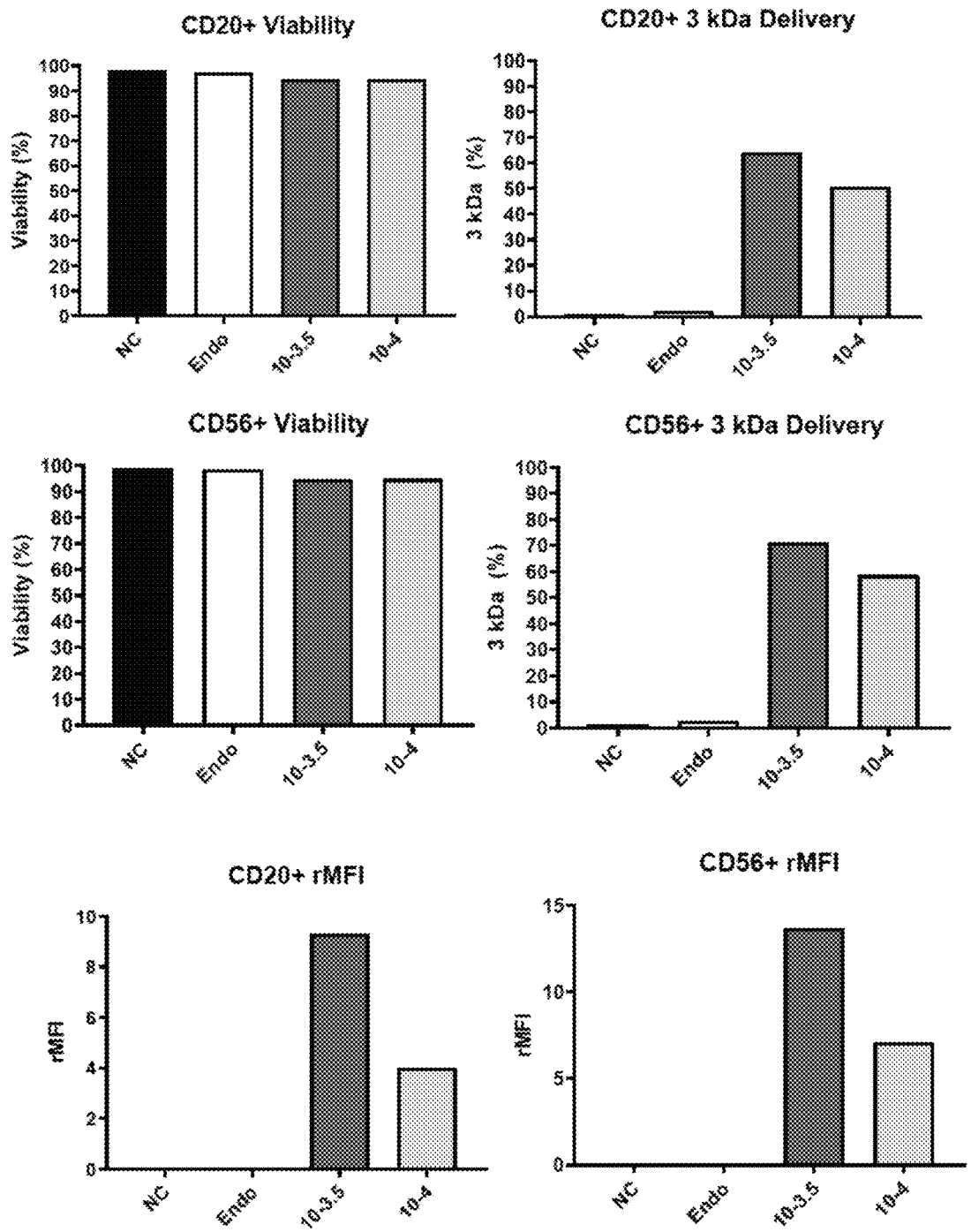
FIG. 12B shows the viability and payload delivery to $CD20^+$ B cells or $CD56^+$ NK cells within human PBMCs that were subjected to SQZ-mediated delivery at a driving pressure of 60 psi and with a constriction width of 3.5 μm or 4 μm.

As shown in FIGS. 12A and B, Loading human PBMCs using SQZ led to changes less than 10% for B cells (CD20), T cells (CD3), NK cells (CD56) and monocytes (CD14) in viability [left]. The percentage of cells delivered with dextran ranged between 60% (B cells) to 90% (monocytes) for the 3.5 μm width constriction, with the 4 μm width constriction led to ~10-20% less cells delivered across all cell types. There was up to a 35-fold increase in the amount of dextran loaded per cell for T cells and monocytes and ~5-10-fold for B cells and NK cells for the 3.5 μm width. The 4 μm width constriction generally decreased the amount of delivery by ~2-fold from the 3.5 μm width.

Example 13

In order to determine the effect of delivery to individual cell subsets on the overall functional response from a mixed population, human PBMCs were loaded with a disease-relevant antigen and a tagged dextran by SQZ and the ability to stimulate antigen-specific responder cells will be measured and compared to delivery of the tagged compound.

Methods

Human PBMCs from HLA-A02+ donors (10M cells/mL) were loaded in the presence of 50 μM E7 SLP (QLCTELQTYMLDLQPETTYCKQQLL (SEQ ID NO: 23)) and fluorescently-labeled 3 kDa dextran (100 μg/mL) by SQZ (60 psi, room temperature) and the level of delivery to the cell subsets between the differing constriction widths (3.5 and 4 μm) were quantified by flow cytometry. PBMCs were then co-cultured with E711-20-specific CD8+ responder cells in a ratio of 2:1 stimulator:responder cells and cultured in the presence of IL-2 (10 U/mL) and compared to untreated control or 2:1 stimulator:responder cells incubated with the minimal epitope (PP—0.1 μM—YMLDLQPETT (SEQ ID NO: 3)) overnight. After 24 h, supernatant is harvested from each condition and the level of IFN-γ production was assessed by IFN-γ ELISA.

Results

Figure 13:
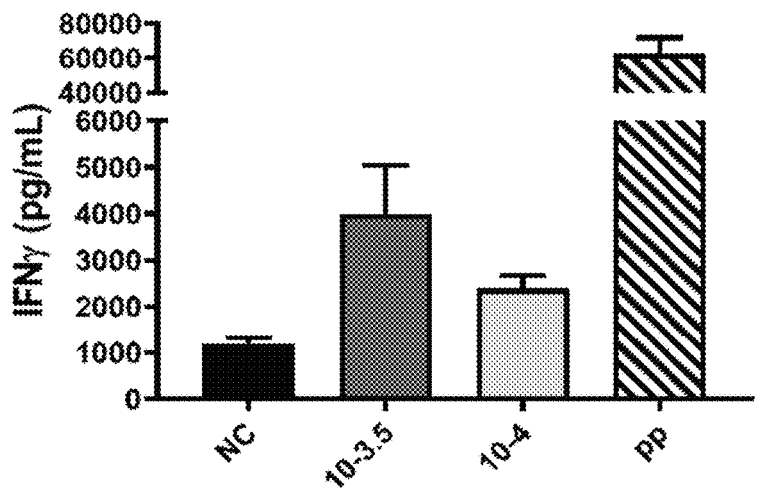
FIG. 13 shows the correlation of delivery in subsets with PBMC population (bottom) with the stimulation of E7-specific responder cells (top) when co-cultured with matured human PBMCs loaded with an E7 HPV antigen via a SQZ-mediated process using a 3.5 μm or 4 μm constriction width.
Figure 13:
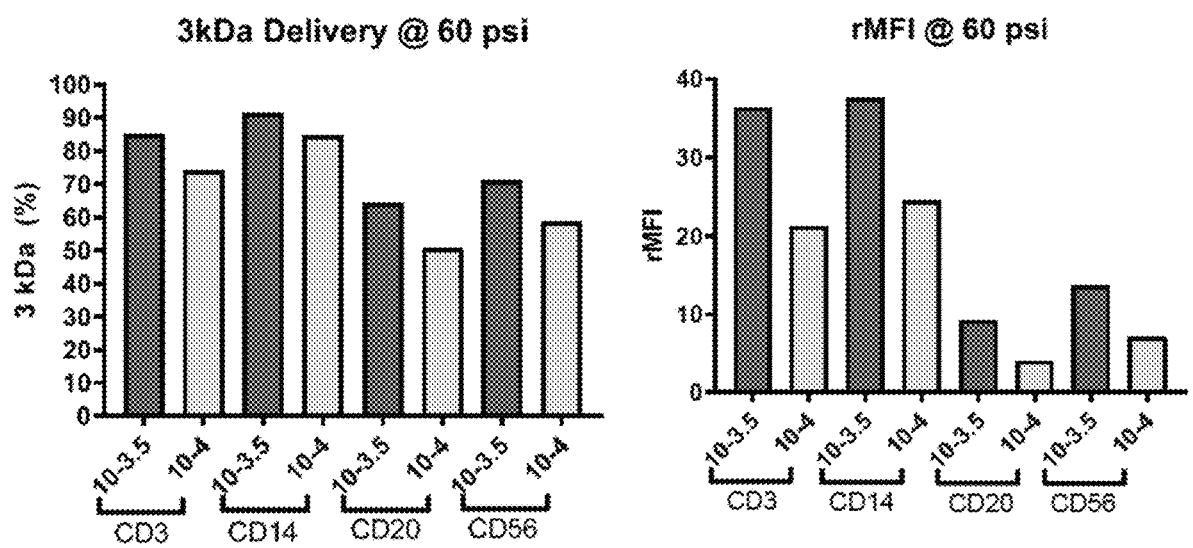

As shown in FIG. 13, loading human PBMCs using SQZ led to up to a ~4-fold increase (3.5 μm) in the level of IFN-γ production assessed by ELISA (top). Delivery via the 4 μm constriction exhibited approximately half the level of antigen-specific response to E7-specific responder T cells (middle and right—re-analysis of FIG. 11 data from same samples). This functional effect correlated with the higher delivery of E7 SLP by the 3.5 μm condition. These findings show that enhanced delivery can lead to increases in the cell antigen-presentation functionality of human PBMCs.

Example 14

Figure 14:
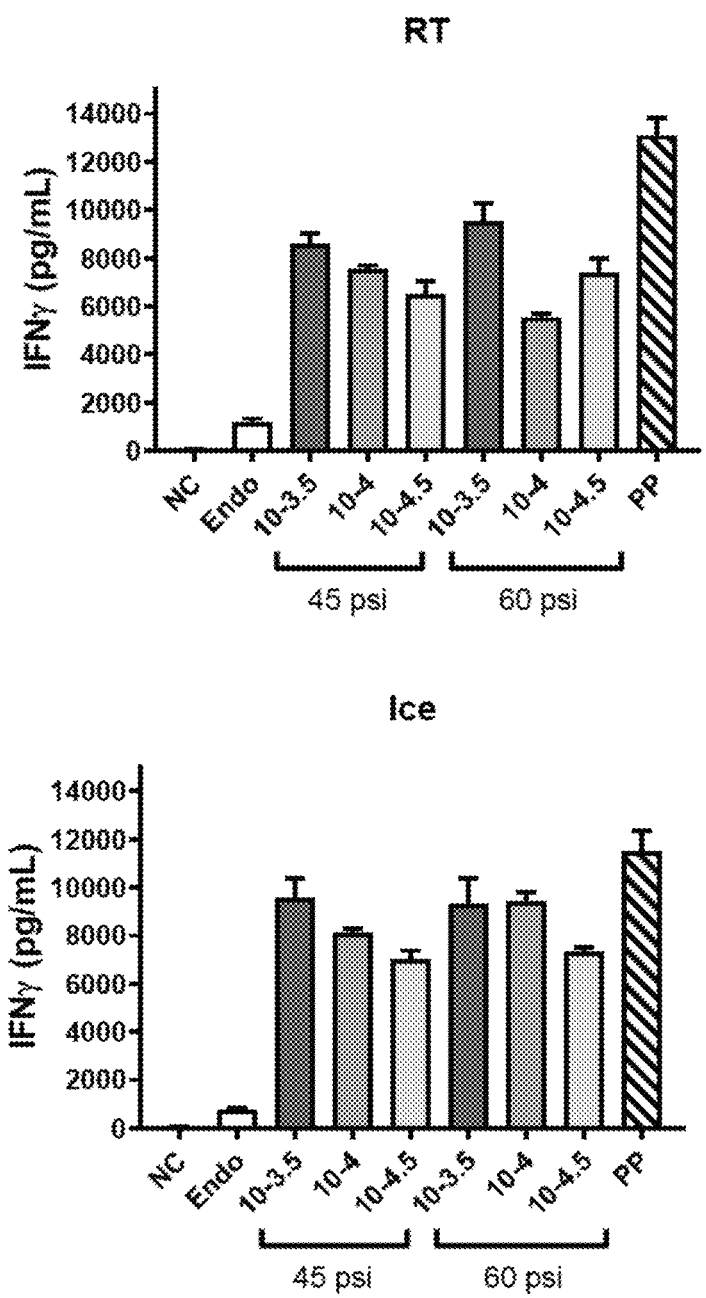
FIG. 14 shows the stimulation of E7-specific responder cells when co-cultured with matured human PBMCs loaded with an E7 HPV antigen via a SQZ-mediated process with a driving pressure of 45 psi or 60 psi, with constriction widths of 3.5 μm, 4 μm or 4.5 μm, and with the process carried out at RT (top) or on ice (bottom).

In order to determine the impact of various delivery parameters on the ability of immune cells to activate an antigen-specific response, human PBMCs were loaded with a disease-relevant antigen by SQZ and the ability to stimulate antigen-specific responder cells will be measured and compared across different SQZ conditions.
Methods Human PBMCs from HLA-A02+ donors (10M cells/mL) were loaded in the presence of 50 µM pp65 SLP (PPWQAGILARNLVPMVATVQGQNLKYQEF-FWDAND (SEQ ID NO: 51)) by SQZ and the pressure (45, 60 psi), temperature (room temperature ice) and constriction widths (3.5-4.5 µm) were altered. PBMCs were then co-cultured with pp65-specific CD8+ responder cells in a ratio of 2:1 stimulator:responder cells, cultured in the presence of IL-2 (10 U/mL) and compared to untreated control or 2:1 stimulator:responder cells incubated with the minimal epitope (PP—0.1 µM—NLVPMVATV (SEQ ID NO: 55)) overnight. After 24 h, supernatant is harvested from each condition and the level of IFN-γ production was assessed by IFN-γ ELISA.
Results As shown in FIG. 14, loading human PBMCs with pp65 SLP using SQZ led to a ~6-9-fold increase in the level of IFN-γ production assessed by ELISA. The narrower the constriction width (3.5 µm) and higher the pressure (60 psi) led to the higher responses, with progressively wider chips leading to loss of functionality, and this phenomenon is conserved between the room temperature (top) and ice (bottom) conditions. Taken together, there may be a slight benefit to ice during SQZ but all conditions led to a significant increase in IFN-γ production.

Example 15

Figure 15:
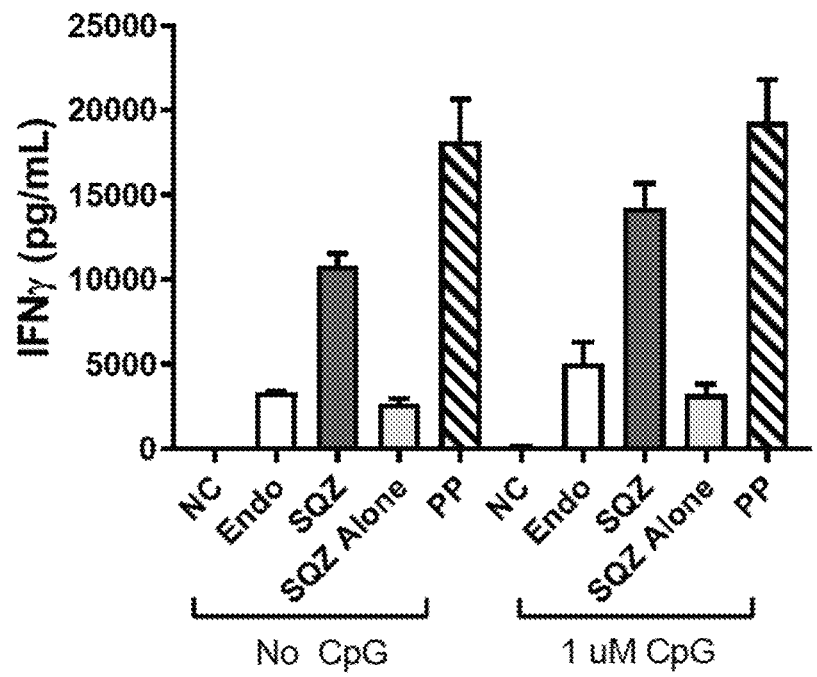
FIG. 15 top panel shows the stimulation of pp65-specific responder cells, when co-cultured (in the presence or absence of 1 μM CpG) with human PBMCs SQZ-loaded with pp65 or human PBMCs SQZ-loaded with pp65 and matured with adjuvant.
Figure 15:
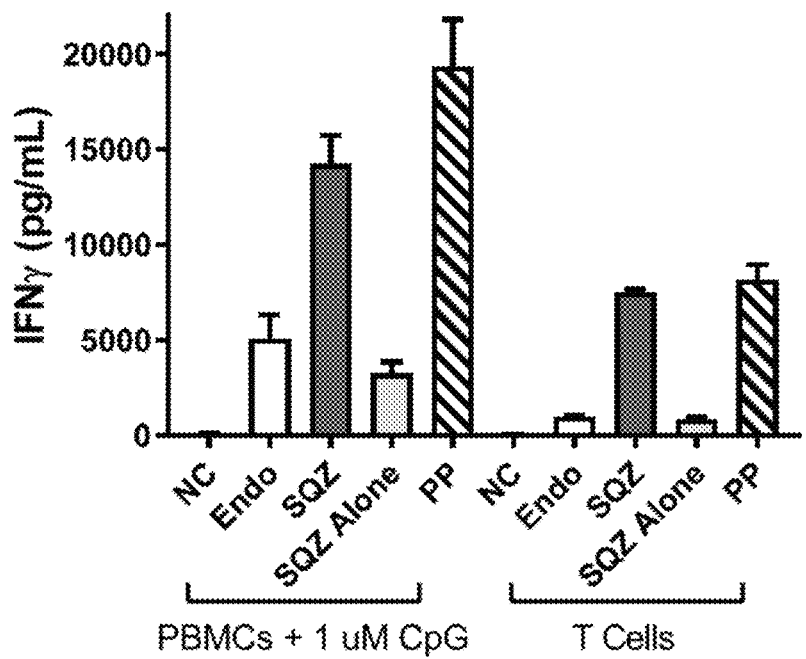

In order to determine the impact of CpG maturation on the ability of human immune cells to activate an antigen-specific response and to compare this response to loaded T cell APCs, human PBMCs or isolated T cells were loaded with a disease-relevant antigen by SQZ and the ability to stimulate antigen-specific responder cells was measured and compared to no CpG maturation.
Methods Human HLA-A02+ PBMCs or T cells isolated from PBMCs of HLA-A02+ donors (10M cells/mL) were loaded in the presence of 50 µM pp65 SLP (PPWQAGILARNLVPMVATVQGQNLKYQEFFWDAND (SEQ ID NO: 51)) by SQZ (45 psi; 3 µm constriction for PBMCs, 4.5 µm used for T cells). PBMCs were then co-cultured with pp65-specific CD8+ responder cells in a ratio of 2:1 stimulator:responder, cultured in the presence of IL-2 (10 U/mL)+/−CpG 2006 (1 µM) and compared to untreated control or 2:1 stimulator:responder cells incubated with the minimal epitope (PP—0.1 µM—NLVPMVATV (SEQ ID NO: 55)) overnight. After 24 h, supernatant is harvested from each condition and the level of IFN-γ production was assessed by IFN-γ ELISA.
Results As shown in FIG. 15, loading human PBMCs with pp65 SLP using SQZ led to greater IFN-γ production than cells that were incubated with the SLP (Endo) both with and without CpG. Additionally, there was a 30% increase in the response between SQZ loaded conditions co-cultured with CpG relative to without (P<0.05; top). T cells do not respond to CpG maturation, so the T cell condition was compared directly to the PBMC co-cultured with CpG conditions, and it was found that there was nearly double the response in the PBMC condition (P<0.001; bottom). Taken together, these data show that CpG co-culture enhances the antigen-specific response of human PBMCs and that PBMCs with CpG are nearly twice as potent at eliciting this response when compared with loaded T cells.

Example 16

Figure 16:
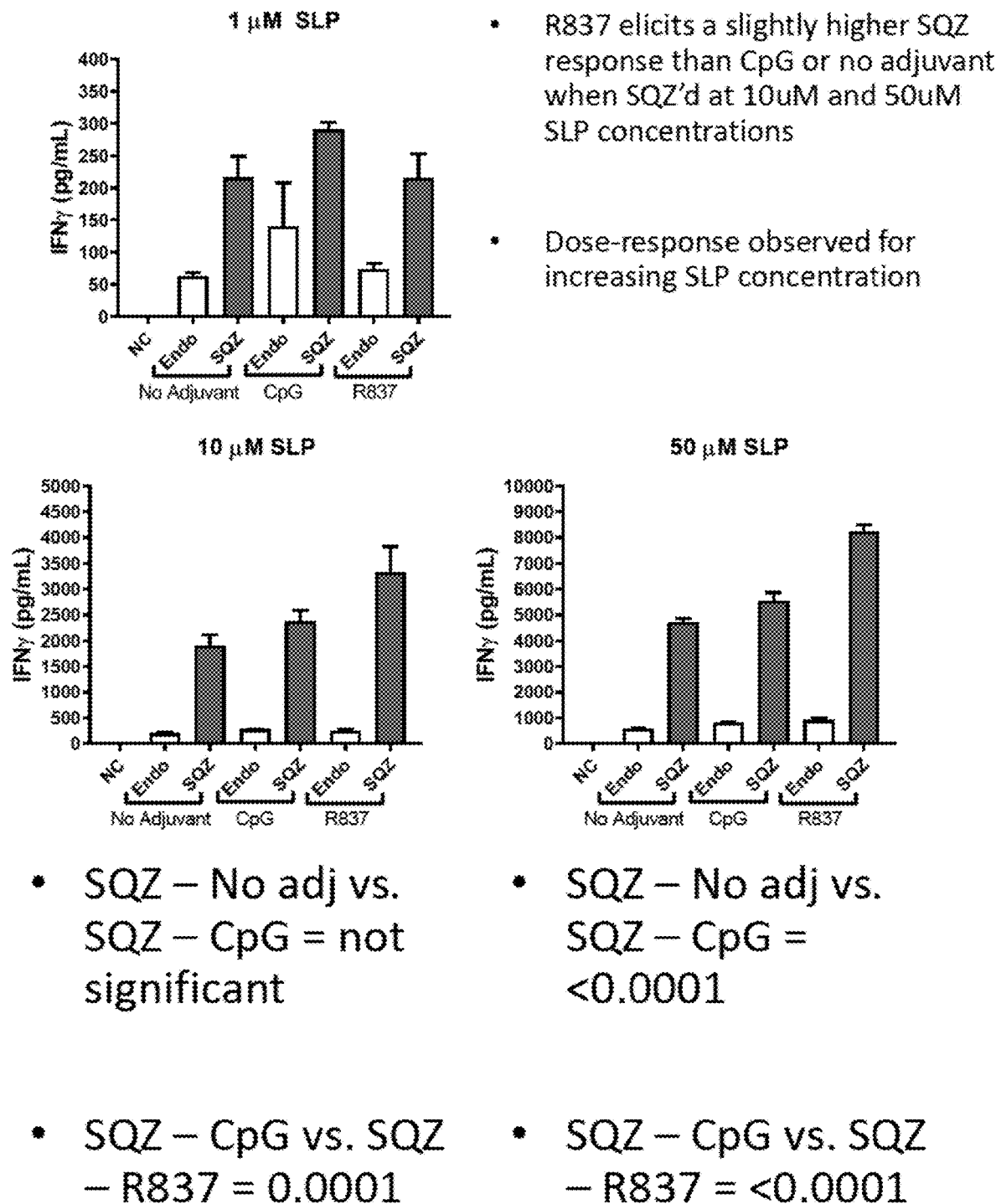
FIG. 16 shows the effects of (a) PBMC maturation by various adjuvants and (b) pp65 antigen concentration used in SQZ loading on the stimulation of pp65-specific responder cells, when responders were co-cultured with matured human PBMCs SQZ-loaded with pp65 CMV antigen.

In order to examine the effect of adjuvant and antigen concentration on the activation of an antigen-specific response in the human context, human PBMCs were loaded with different concentrations of a disease-relevant antigen by SQZ and the ability to stimulate antigen-specific responder cells was measured and compared among different adjuvants.
Methods Human PBMCs from HLA-A02+ donors (10M cells/mL) were loaded in the presence of different concentrations of pp65 SLP (PPWQAGILARNLVPMVATVQGQNLKYQ-EFFWDAND (SEQ ID NO: 51); 1, 10 and 50 µM) by SQZ (60 psi; 3.5 µm constriction). PBMCs were then co-cultured with pp65-specific CD8+ responder cells in a ratio of 2:1 stimulator:responder, cultured in the presence of IL-2 (10 U/mL)+/−CpG 2006 (1 µM) or R837 (1 µg/mL; imiquimod) and compared to untreated control or 2:1 stimulator:responder cells incubated with the minimal epitope (PP—0.1 µM—NLVPMVATV (SEQ ID NO: 55)) overnight. After 24 h, supernatant is harvested from each condition and the level of IFN-γ production was assessed by IFN-γ ELISA.
Results As shown in FIG. 16, while there were no significant differences between the function response of human PBMCs loaded with 1 µM pp65 SLP by SQZ with and without adjuvants, higher concentrations did show a significant benefit to co-culture with adjuvant. The 10 µM pp65 SLP condition showed a slight but not significant increase in the response of PBMCs co-cultured with CpG relative to without, but there was a significant increase (P<0.0001) when PBMCs co-cultured with R837 compared to no adjuvant. This effect was even more pronounced when using 50 µM of SLP, where CpG and R837 led to significant enhancement of the antigen-specific response (P<0.0001). In all cases, there was increasing benefit to co-culturing with either adjuvant, although R837 consistently led to the highest response, and this effect was potentiated by higher concentrations of pp65 SLP. Taken together, these data show that the use of an adjuvant during co-culture enhances the antigen-specific response of human PBMCs and that this effect is dependent on the concentration of antigen used.

Example 17

In order to examine the effect of adjuvant composition and maturation duration on the activation of an antigen-specific response in the human context, human PBMCs were loaded with a disease-relevant antigen by SQZ, matured with different adjuvants for different incubation times and the ability to stimulate antigen-specific responder cells was measured and compared among different adjuvants.
Methods Human PBMCs from HLA-A02+ donors (10M cells/mL) were loaded in the presence of 50 µM pp65 SLP (PPWQAGILARNLVPMVATVQGQNLKYQEF-FWDAND (SEQ ID NO: 51)) by SQZ (60 psi; 3.5 µm constriction). PBMCs were then matured with CpG 2006 (1 µM), R837 (1 µg/mL; imiquimod) or R848 (1 µg/mL; resiquimod) for either 3 or 24 h, followed by being co-cultured with pp65-specific CD8+ responder cells in a ratio of 2:1 stimulator:responder, in the presence of IL-2 (10

Figure 17:
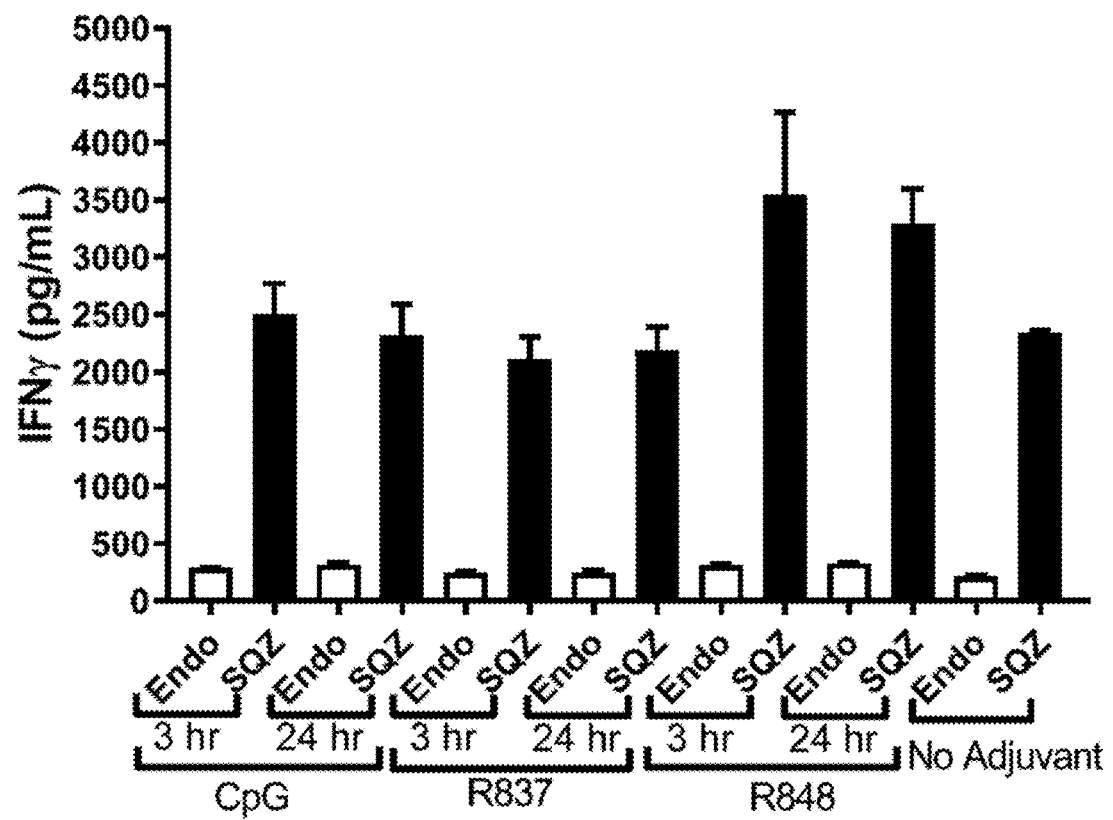
FIG. 17 shows the effects of PBMC maturation by different adjuvants CpG, R837, and R848 with incubation times of 3 or 24 hours, on the stimulation of pp65-specific responder cells when co-cultured with matured human PBMCs SQZ-loaded with pp65 CMV antigen.

U/mL) and compared to untreated control or 2:1 stimulator: responder cells incubated with the minimal epitope (PP—0.1 μM—NLVPMVATV (SEQ ID NO: 55)) overnight. After 24 h, supernatant is harvested from each condition and the level of IFN-γ production was assessed by IFN-γ ELISA.
Results
As shown in FIG. 17, There were no significant differences between the function response of human PBMCs loaded with pp65 SLP by SQZ with and without adjuvants, although the groups treated with R848 for either 3 or 24 h did afford the highest overall response. These data show that the use of an adjuvant to mature PBMCs post-SQZ may enhance the antigen-specific response but this effect was not found to lead to a significant increase in responses for all adjuvants and time points tested.

Example 18

Figure 18:
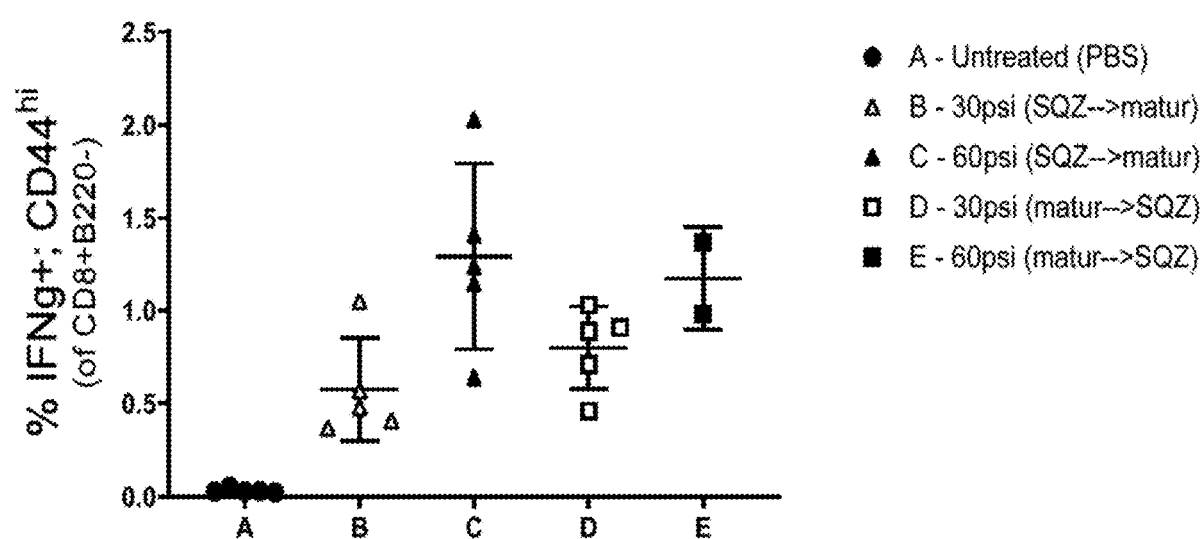
FIG. 18 shows the effect of conditioning of splenocytes, before versus after SQZ-mediated loading, on the antigen-specific response elicited by conditioned murine splenocytes SQZ-loaded with pp65 CMV antigen.

In order to quantify the impact of pre-SQZ or post-SQZ maturation on antigen-specific response, murine splenocytes were loaded with a model antigen, matured with CpG, and injected into recipient mice once (Prime) or twice (Prime-Boost), with the relative percentage of inflammatory cytokine IFN-γ+CD8+ T cells measured by flow cytometry.
Methods
On Day −1 (matur→SQZ) or Day 0 (SQZ→mater), splenocytes were obtained from spleens of female C57BL/6J donor mice, and either matured with CpG 1826 (1 μM in R10) for 4 h on Day −1 (matur→SQZ), then loaded with Ova protein (400 μg/mL) by SQZ (30, 60, 90 psi; 4 μm constriction) on Day 0 (SQZ→mater), or loaded with Ova by SQZ on Day 0 followed by 4 h incubation with CpG 1826. Female C57BL/6J recipient mice (5/group) were injected retro-orbitally on Day 0 with 100 μL of splenocytes ($1 \times 10^6$ cells/mouse). On Day 7, spleens were harvested, restimulated with SIINFEKL (SEQ ID NO: 54) (1 μg/mL) and the percentage of IFN-γ+CD8+ T cells was determined by intracellular cytokine staining (ICS).
Results
As shown in FIG. 18, While increasing pressure used to load Ova into the splenocytes led to a significant increase in the percentage of IFN-γ+CD8+ T cells ($P<0.05$), there was no significant change between splenocytes that were matured, then SQZ loaded or were SQZ loaded and then matured. These data show that there is no significant difference in the order of loading/maturing splenocytes on the ability to elicit an antigen-specific response in vivo.

Example 19

Figure 19:
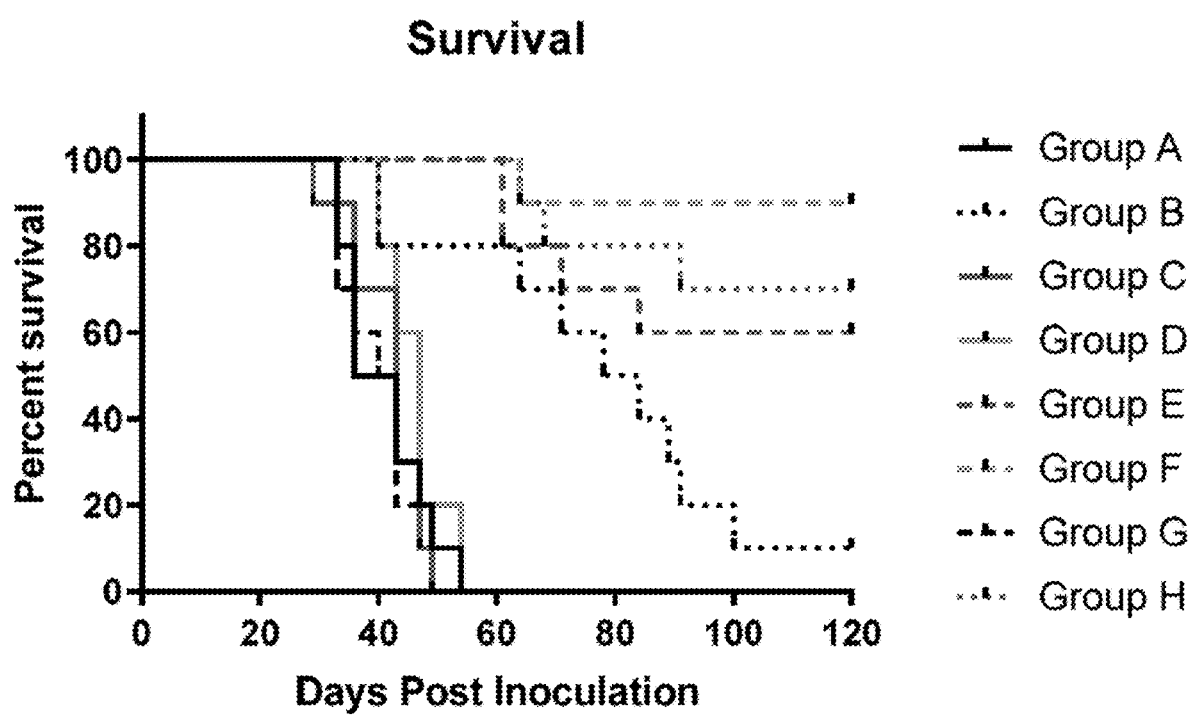
FIG. 19 shows the effect on tumor inhibition when mice carrying E7-expressing tumor was administered with pp65-loaded splenocytes alone (group B); chemotherapy (cisplatin) alone (groups C, D, G); or pp65-loaded splenocytes in combination with chemotherapy (groups E, F, H).

In order to determine if there is a benefit to co-treating animals with antigen-loaded splenocytes in combination with platinum-based chemotherapy, tumor growth inhibition of antigen-associated tumor cells was measured in an in vivo therapeutic model, with multiple splenocyte+/−chemotherapy treatment regimes compared, with the survival of mice in each group plotted against time.
Methods
At Day 0, C57BL/6J female mice were injected in the right rear flank with TC1 tumor cells (50 k cells/mouse; 10 mice/group) at Day 0. On Days 5 and 7, mice were either injected with vehicle or cisplatin (5 mg/kg) according to the groups. On Day 9, some animals also received a prime of splenocytes obtained from spleens of female C57BL/6J donor mice that were loaded with pre-complexed 20 μM E7 SLP (GQAEPDRAHYNIVTFSSKSD-STLRLSVQSTHVDIR (SEQ ID NO: 25))+20 μM mouse serum albumin (MSA) via SQZ (60 psi; 4 μm constriction) and incubated with CpG 1826 (1 μM in R10) for ~16 h. On Days 27 and 29, untreated mice or mice treated with splenocytes only on Day 9 were given 1-2 doses of cisplatin according to the groups outlined. The survival of each group of TC1 tumor-bearing mice was assessed and plotted over 120 days.
Results
As shown in FIG. 19, tumor growth, as measured by the formula ((length×width2)/2), was compared between mice that were untreated, treated with E7-loaded splenocytes alone, 1-2 doses of cisplatin alone or various combinations and the Kaplan-Meier survival curves were plotted. The four treatment groups that included splenocytes exhibited a large survival advantage over not just untreated animals, but those receiving cisplatin alone, with a median survival time beyond 50 days (and in the case of splenocyte+cisplatin treatment, the median survival time had still not been reached after 120 days). Of particular note, the splenocyte alone treated mice had a ~40 days survival advantage over the untreated and cisplatin alone groups, but the splenocyte+cisplatin groups had a larger survival advantage even over the splenocyte alone group. These data show that splenocytes loaded by SQZ can induce a survival advantage in a therapeutic model of HPV-associated cancer, and that the addition of cisplatin chemotherapy further potentiated the survival advantage of the splenocyte vaccine.

Example 20

Figure 20A:
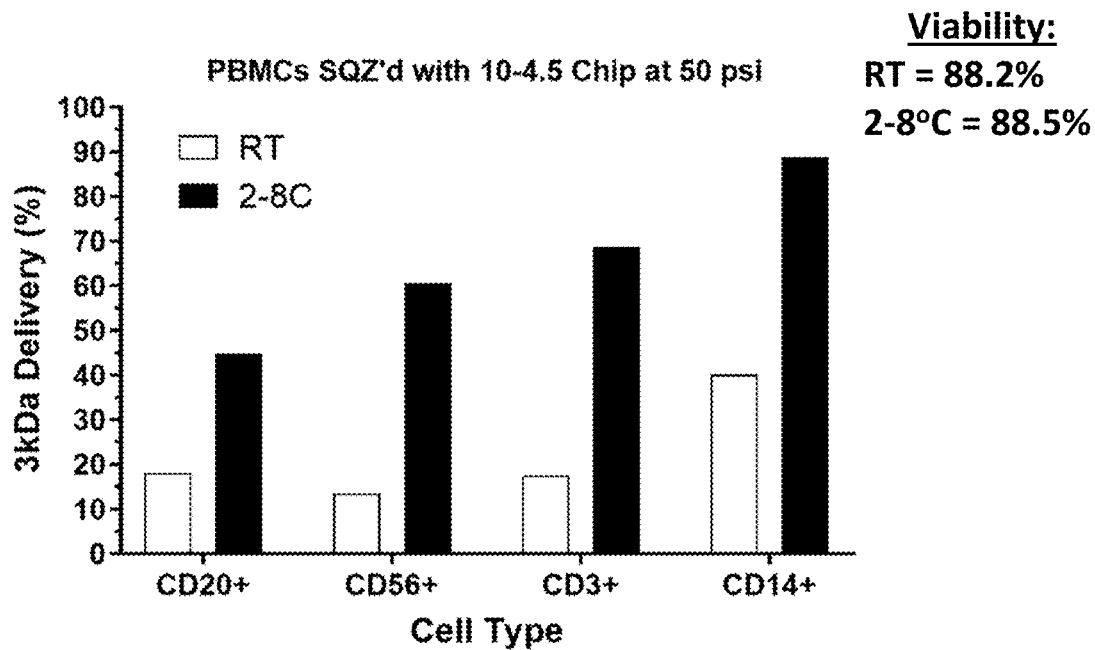
FIG. 20A shows the efficiency of SQZ-mediated delivery of 3 kDa dextran to subpopulations of human PBMCs at room temperature or on ice.
Figure 20B:
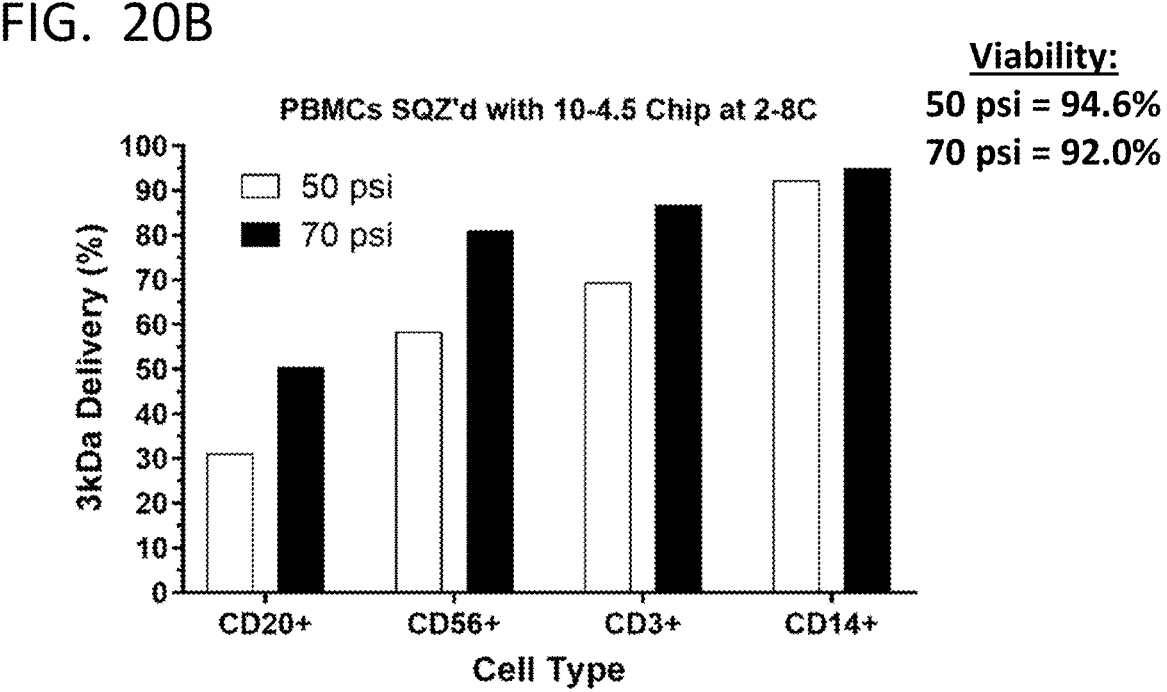
FIG. 20B shows the efficiency of SQZ-mediated delivery of 3 kDa dextran to subpopulations of human PBMCs at a driving pressure of 50 psi or 70 psi.

In order to determine the delivery and impact of different SQZing parameters on individual cell subsets using on a clinical-scale, human PBMCs are subjected to cell squeezing at different temperatures and pressures and the viability and delivery of a fluorescent compound to the different immune cell populations was assessed by flow cytometry.
Methods
Human PBMCs were loaded with fluorescently-labeled 3 kDa dextran (100 μg/mL) by SQZ (50-70 psi; 4.5 μm width) at room temperature and on ice. The loaded PBMCs were then analyzed for viability and delivery by flow cytometry.
Results
As shown in FIGS. 20A and B, loading human PBMCs using SQZ on a clinical scale still allowed for successful delivery of up to 80% of cells (monocytes on ice—FIG. 20A), with cells SQZ'd on ice leading to higher percentages (30-50% increase) of delivered cells across all cell subsets. The higher pressure (70 psi) afforded the highest percentage of delivered cells relative to 50 psi, but in all cases tested the viability was above 88% for the bulk PBMC population. Taken together, these data show that SQZ can be used to deliver to multiple cell types in a mixed population, and that SQZing on ice at slightly higher pressures led to the best overall delivery.

Example 21

In order to determine the impact the maturation+/−co-injection of adjuvant on the ability of antigen-loaded splenocytes to lead to tumor growth inhibition in a therapeutic setting, splenocytes were either matured with, co-injected with or matured and co-injected with adjuvant and tested in the HPV E7-expressing TC1 tumor model, with the area of the tumors and survival plotted against time.
Methods
At Day 0, C57BL/6J female mice were injected in the right rear flank with TC1 tumor cells (50 k cells/mouse). On Day 10 (prime), splenocytes were obtained from spleens of female C57BL/6J donor mice, and combined with splenocytes that have had their B cells depleted by negative immunomagnetic separation to better mimic human PBMCs, leading to a splenocyte composition more representative of human PBMCs (i.e., crafted splenocytes). Splenocyte were loaded with pre-complexed 20 µM E7 SLP (GQAEPDRAHYNIVTFSSKSDSTLRLSVQSTHVDIR (SEQ ID NO: 25))+20 µM mouse serum albumin (MSA) via SQZ (60 psi; 4 µm constriction, room temperature) and incubated with CpG 1826 (1 µM in R10) for 4 hours. Female C57BL/6J recipient mice (10/group) were injected retro-orbitally on Day 10 with 100 µL of either vehicle (PBS), splenocytes (1M cells/mouse) or splenocytes+CpG (1 µg/mouse). TC-1 tumor growth was measured beginning 1 week post-tumor implantation two times per week and compared to tumor growth in untreated mice for 32 days.

Results

Figure 21A:
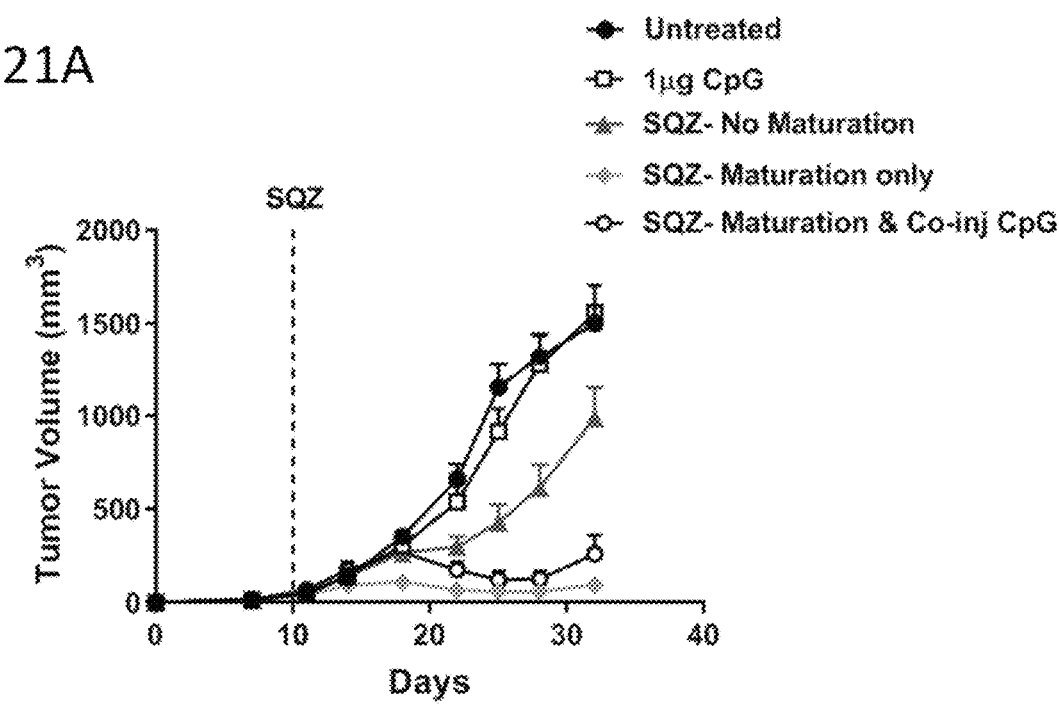
FIGS. 21A and 21B shows the effect of splenocyte conditioning or CpG co-administration on tumor inhibition (FIG. 21A) and survival improvement (FIG. 21B) when mice carrying an E7-expressing tumor was administered with crafted murine splenocytes SQZ-loaded with E7 HPV antigen.
Figure 21B:
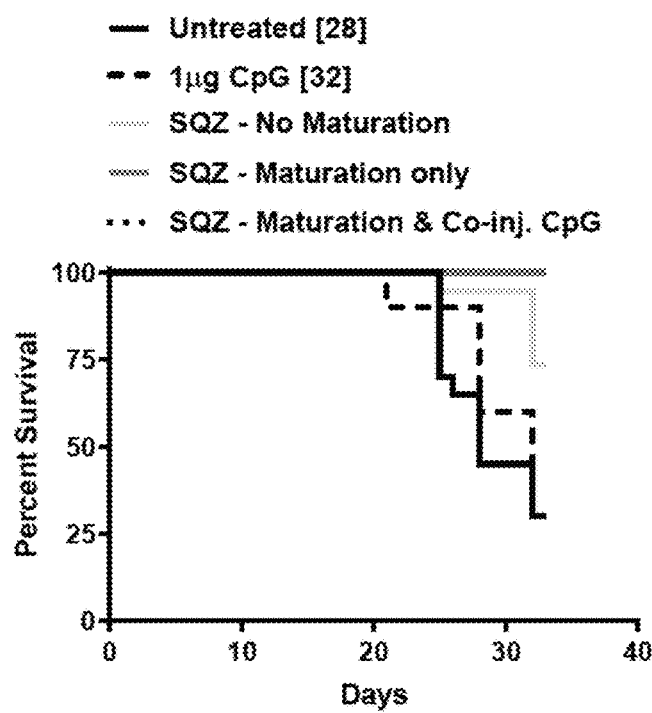

Tumor growth, as measured by the formula ((length×width$^2$)/2), was compared between mice from the untreated group (no splenocytes) and groups treated with adjuvant alone (CpG), splenocytes or splenocytes+co-injected adjuvant. As shown in FIGS. 21A and B, while there was no observable difference between the tumor growth of untreated animals and those treated with CpG alone (median survival of 28 and 32 days, respectively), there was a slight inhibition in the rate of tumor growth for un-matured splenocytes loaded with E7. However, the groups that received either matured, loaded splenocytes+/−co-injection of CpG led to tumor regression, with tumors not reaching their initial maximum over the course of the study. Additionally, none of the splenocyte-treated groups reached the median survival point by day 32. These data show that splenocytes loaded by SQZ and matured with adjuvant (with or without adjuvant co-injection) can induce tumor regression in a therapeutic model of HPV-associated cancer.

Example 22

In order to determine if antigen-loaded splenocytes co-injected with different adjuvants can elicit an antigen-specific response, splenocytes were loaded with a model antigen and either matured with CpG, co-injected with CpG or matured with CpG and co-injected with either CpG or IFN-α, with mice receiving prime and boost, and the relative percentage of inflammatory cytokine IFN-γ+CD8+ T cells was measured by flow cytometry.

Methods

At Day 0, splenocytes were obtained from spleens of female C57BL/6J donor mice, and combined with splenocytes that have had their B cells depleted by negative immunomagnetic separation, leading to a splenocyte composition more representative of human PBMCs. These mixed splenocytes were then loaded with Ova protein (400 µg/mL) by SQZ (60 psi; 4 µm constriction) and incubated in either media (R10) alone or media with CpG 1826 (1 µM) for 4 h. Female C57BL/6J recipient mice (5/group) were injected retro-orbitally on Day 1 with 100 µL of either vehicle (PBS), splenocytes (1×10$^6$ cells/mouse) matured with CpG, splenocytes co-injected with 1 µg CpG1826 or splenocytes matured with CpG that are co-injected with either CpG or 10000 U IFN-α. On Day 7, recipient mice were boosted in an identical fashion to the prime on Day 0. On Day 14, spleens were harvested, restimulated with SIINFEKL (SEQ ID NO: 54) (1 µg/mL) and the percentage of IFN-γ+CD8+ T cells was determined by intracellular cytokine staining (ICS).

Results

Figure 22:
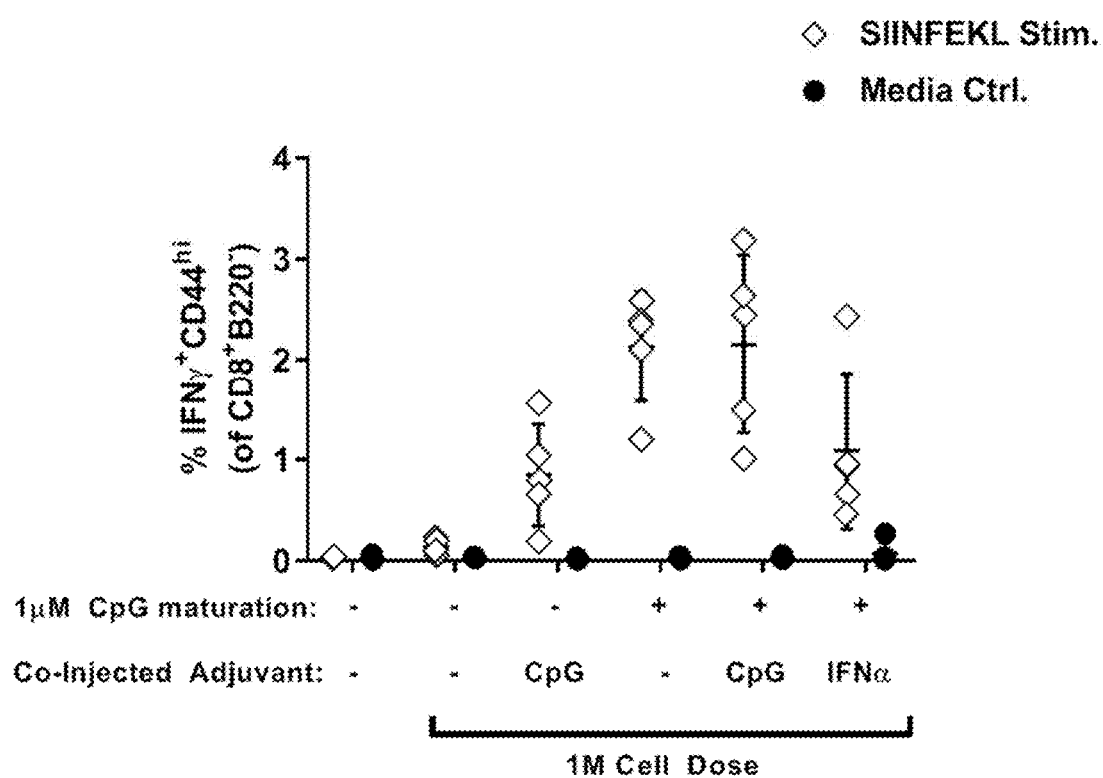
FIG. 22 shows the effect of splenocyte conditioning, with or without co-administration with CpG or IFNα, on the antigen-specific response elicited by crafted murine splenocytes SQZ-loaded with OVA antigen.
Figure 23A:
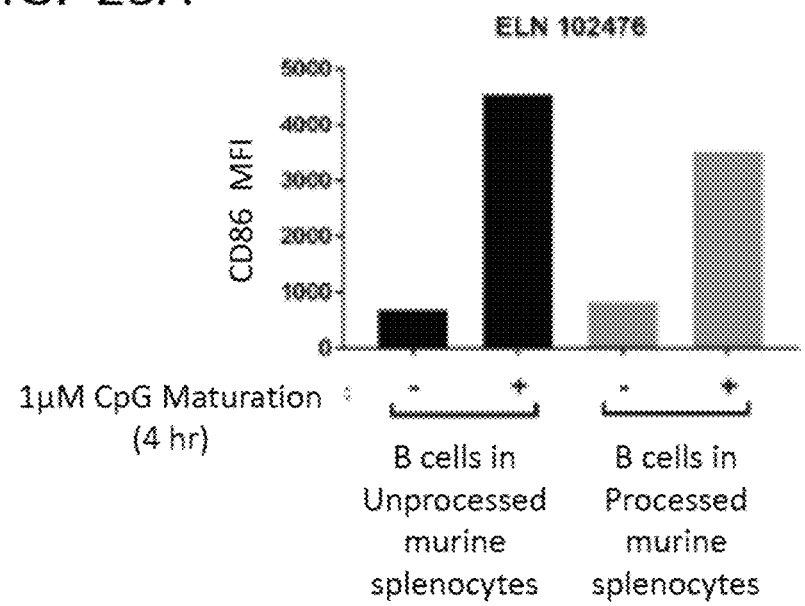
FIGS. 23A-23H show the effect of splenocyte conditioning, with or without incubation with CpG 1826, on the expression of B cell markers CD86 (FIGS. 23A-D) and H-2Kb (FIGS. 23E-H) within crafted murine splenocytes that were either subjected to SQZ-processing or unprocessed.
Figure 23B:
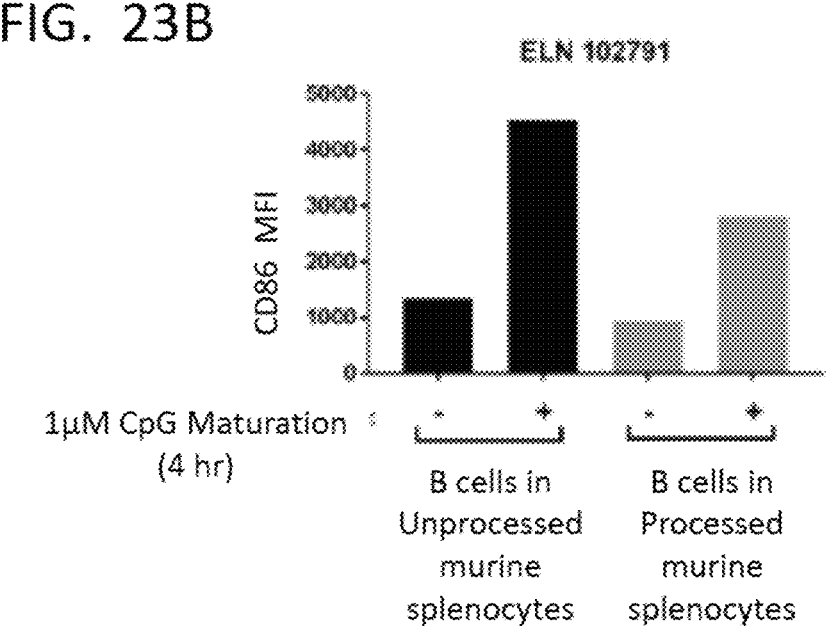
Figure 23C:
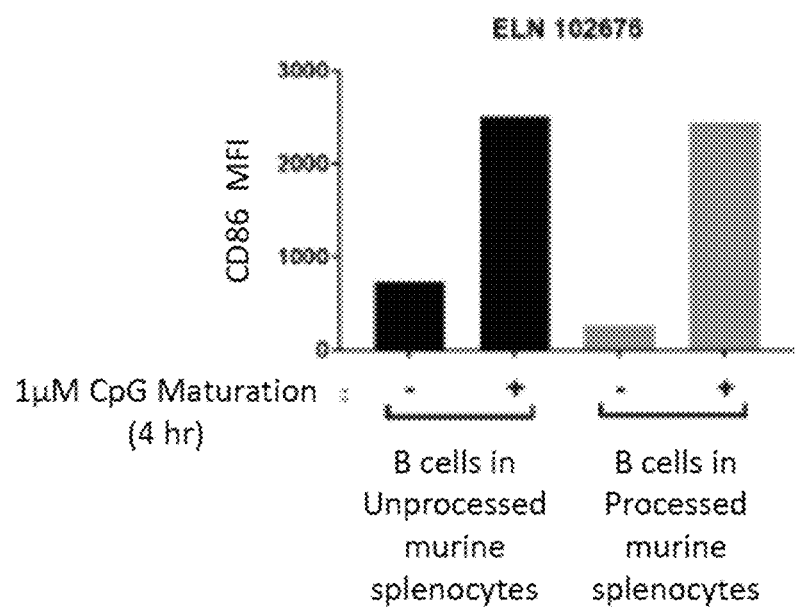
Figure 23D:
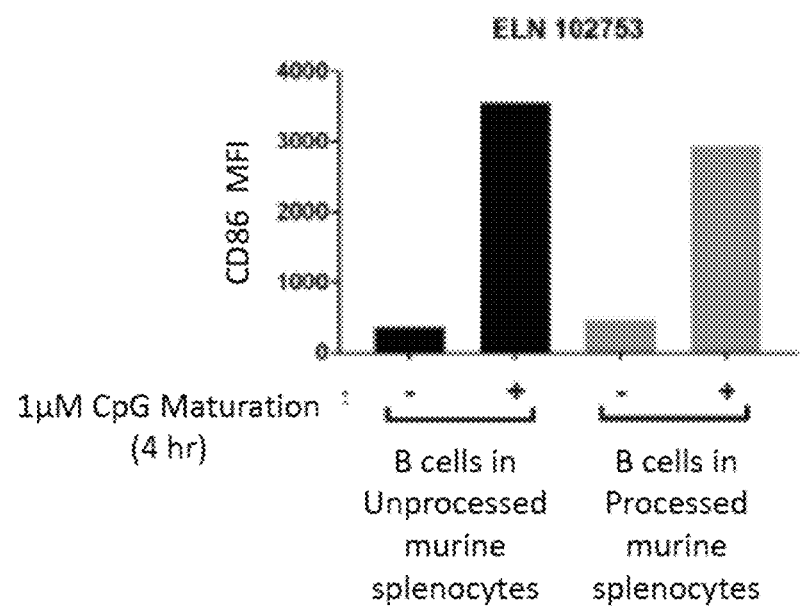
Figure 23E:
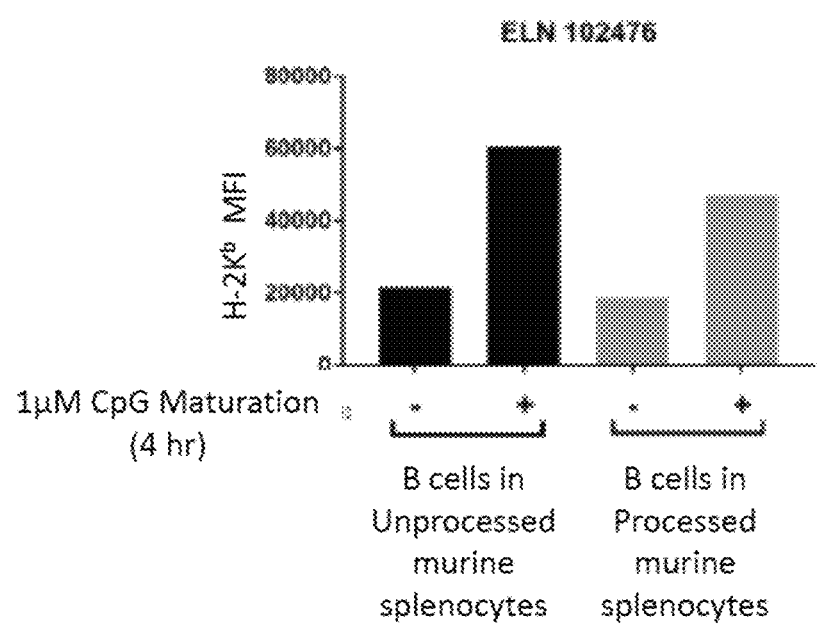
Figure 23F:
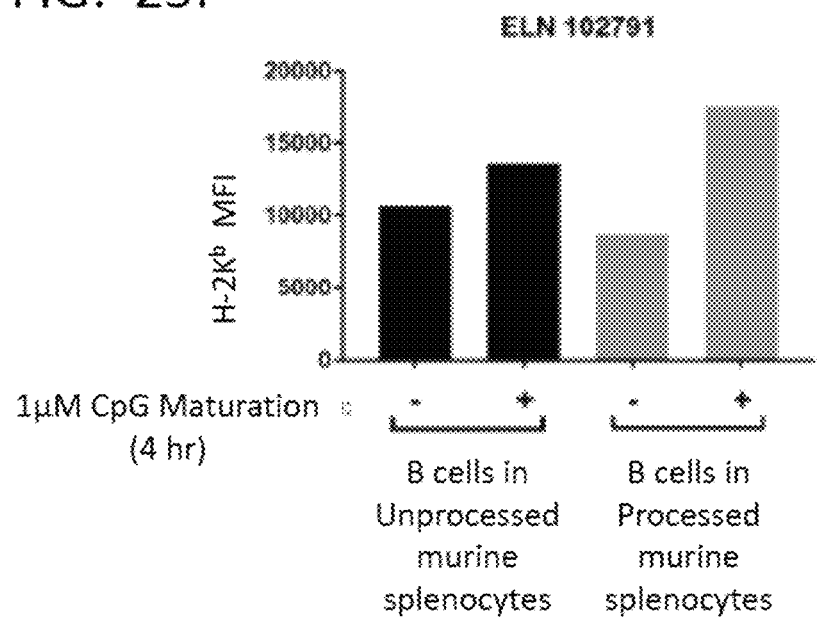
Figure 23G:
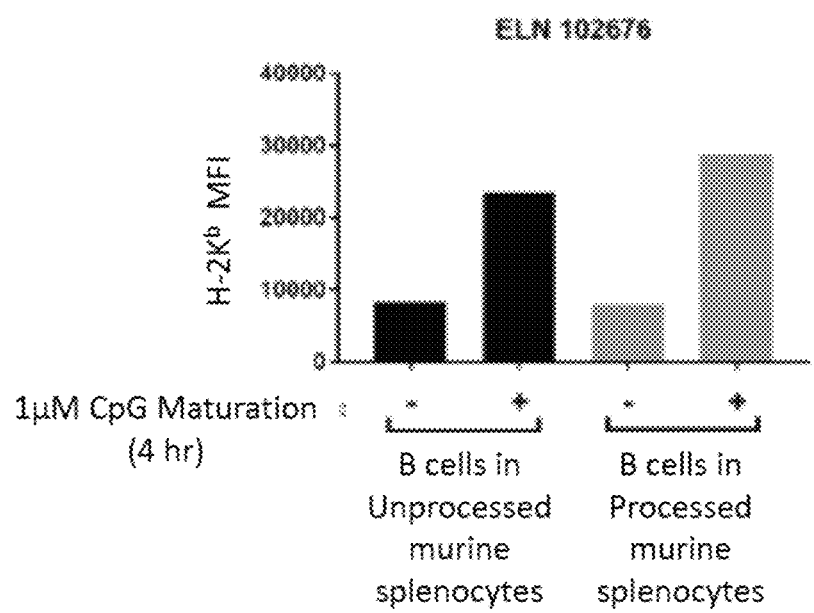
Figure 23H:
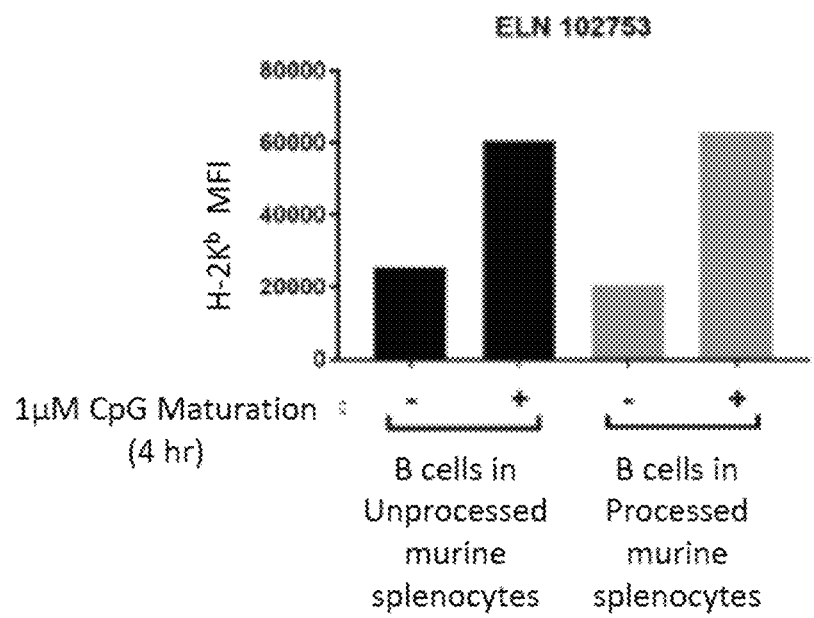
Figure 24A:
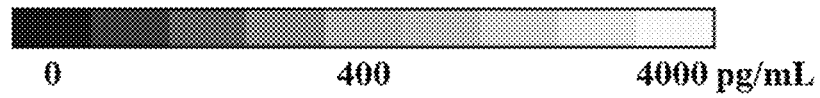
FIGS. 24A-24D show the levels of circulating cytokines in untreated mice (FIG. 24A), mice injected with 1 μg CpG 1826 IV only (FIG. 24B), mice immunized with crafted murine splenocytes SQZ-loaded with E7 SLP (FIG. 24C), or mice co-injected with crafted murine splenocytes SQZ-loaded with E7 SLP and co-injected with 1 μg CpG 1826 IV (FIG. 24D).
Figure 24B:
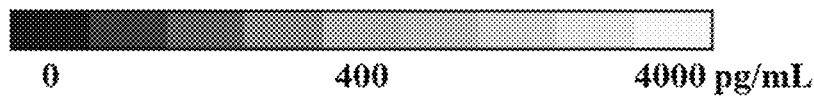
Figure 24C:
Figure 24D:

As shown in FIG. 22, the percentage of IFN-γ+CD8+ T cells for mice treated with Ova-loaded splenocytes was highest when splenocytes were matured with CpG for 4 h with or without co-injection of CpG, with a significant increase when compared to untreated ($P<0.0001$), unmatured splenocytes ($P<0.005$), as well as unmatured splenocytes+co-injected CpG ($P<0.05$). While there was a slight increase in the percentage of IFN-γ+CD8+ T cells, there was no significant benefit to unmatured splenocytes co-injected with CpG or matured splenocytes co-injecting with IFN-α relative to untreated. These data show that there is a requirement for CpG maturation for a significant increase in inflammatory cytokine production in antigen-specific CD8+ T cells, and that co-injection of CpG was slightly better than co-injection of IFN-α.

Example 23

In order to assess the upregulation of B cell maturation markers in PBMCs after maturation with CpG 1826 following SQZ processing, the upregulation of B cell maturation markers was measured by flow cytometry after SQZ-processed murine splenocytes were incubated with CpG1826.

Methods

Splenocytes were obtained from spleens of female C57BL/6J donor mice, and combined with splenocytes that have had their B cells depleted by negative immunomagnetic separation, leading to a splenocyte composition more representative of human PBMCs (i.e., crafted splenocytes). The crafted murine splenocytes were then SQZ-processed without payload and the levels of CD86 and H-2Kb were measured by flow cytometry.

Results

As shown by the mean fluorescence intensity (MFI) in FIGS. 23A-G, four independent experiments demonstrated increased CD86 and murine MHC-I (H-2Kb) expression on B220+ cells (B cells) within the crafted murine splenocytes following CpG 1826 maturation. The increase in CD86 and H-2Kb expression for B220+ cell subsets (B cells) subsequent to maturation with CpG1826 was similar for both SQZ-processed crafted murine splenocytes (gray bars) and unprocessed crafted murine splenocytes (black bars). These data indicate that SQZ-processing did not alter the effects of CpG on the maturation of B220+ cells (B cells) within crafted murine splenocytes.

Example 24

In order to determine if antigen-loaded PBMCs co-injected with adjuvants will elicit systemic effects in serum cytokine levels, murine splenocytes were loaded with an HPV antigen and matured with CpG, and introduced into mice with or without CpG co-injection, and the circulating cytokines in mice were measured by multiplexed cytokine assays.

Methods

Splenocytes were obtained from spleens of female C57BL/6J donor mice, and combined with splenocytes that have had their B cells depleted by negative immunomagnetic separation, leading to a splenocyte composition more representative of human PBMCs (i.e., crafted splenocytes). The crafted murine splenocytes were SQZ-loaded with 20 µM E7 SLP (GQAEPDRAHYNIVTFSSKSDSTLRLSVQSTHVDIR (SEQ ID NO: 25)), followed by incubation with CpG 1826 (1 µM in R10) for 4 hours at 37° C. Female C57BL/6J recipient mice were either injected with the crafted murine splenocytes SQZ-loaded with E7 SLP (M-SQZ-Spleno-HPV), or injected with 1 µg of CpG 1826 IV (No cells), or with a combination of both (M-SQZ-Spleno-HPV+1 µg co-injected CpG), and the levels of circulating cytokines were measured from blood via a murine multiplex (25-plex) cytokine/chemokine assay.
Results As shown in FIGS. 24A-24D, the ranges of serum cytokine concentrations in mice immunized with SQZ-loaded crafted murine splenocytes (FIG. 24C, 24D) were comparable to the ranges of serum cytokine concentrations measured in the no treatment control mice (FIG. 24A) and in mice injected with 1 µg CpG 1826 IV (No cells) (FIG. 24B) at all timepoints. These results indicate that immunization with M-SQZ-Spleno-HPV with or without CpG 1826 co-injection did not lead to changes in either the production or serum concentrations of pro-inflammatory cytokines relative to no treatment or CpG (No Cells) controls. The presence of serum cytokines in all conditions further demonstrated immunization with M-SQZ-Spleno-HPV had no systemic effects in serum cytokine production or secretion.

Example 25

Figure 25:
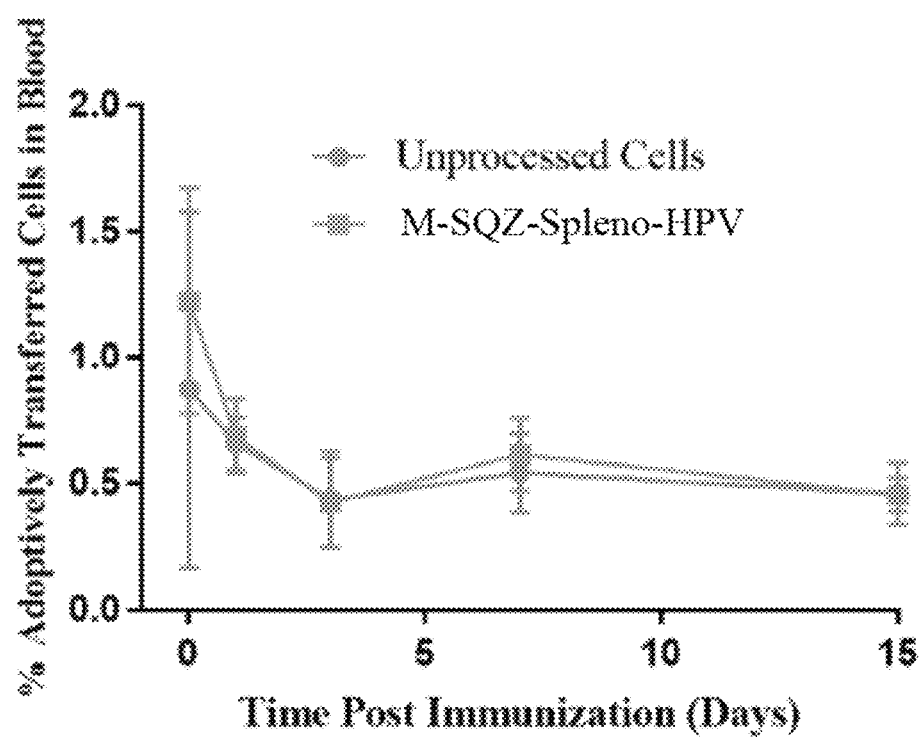
FIG. 25 shows the circulation kinetics of crafted murine splenocytes SQZ-loaded with E7 SLP (M-SQZ-Spleno-HPV) and unprocessed crafted murine splenocytes.

To investigate the impact of SQZ-mediated processing of PBMCs on circulation kinetics upon adoptive transfer, murine splenocytes SQZ-loaded with E7 SLP (M-SQZ-Spleno-HPV) and unprocessed murine splenocytes were respectively administered to mice via intravenous injection and the number of circulating donor murine splenocytes in blood over time was determined by flow cytometry.
Methods Splenocytes were obtained from spleens of female C57BL/6J (CD45.1) donor mice, and combined with splenocytes that have had their B cells depleted by negative immunomagnetic separation, leading to a splenocyte composition more representative of human PBMCs (i.e., crafted splenocytes). The crafted murine splenocytes were then SQZ-loaded with 20 µM E7 SLP (GQAE-PDRAHYNIVTFSSKSDSTLRLSVQSTHVDIR (SEQ ID NO: 25)), followed by incubation with CpG 1826 (1 µM in R10) for 4 hours at 37° C., and the loaded crafted murine splenocytes were injected retro-orbitally into female CD45.2 B6.SJL-Ptprca Pepcb/BoyJ recipient mice (5-7 mice/group), with blood (100 uL) collected from recipient mice over the course of two weeks post-administration at the following timepoints: 30 minutes post-administration, Day 1, Day 3, Day 7, and Day 15. The number of circulating crafted murine splenocytes over time were assessed by flow cytometry.
Results As shown in FIG. 25, upon adoptive transfer, M-SQZ-Spleno-HPV and the unprocessed crafted murine splenocytes exhibited similar persistence in the host blood over the course of two weeks post-immunization (cumulative data displayed from 4 independent experiments). By one-way ANOVA and Tukey post-hoc tests, there is no statistical difference between the two groups at any timepoint. These studies demonstrate that the circulation kinetics of M-SQZ-Spleno-HPV is not statistically different from unprocessed crafted murine splenocytes.

Example 26

Figure 26A:
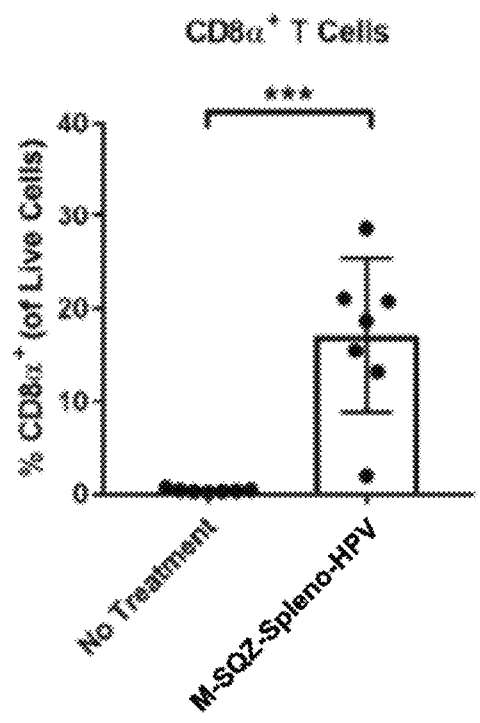
FIGS. 26A-26E show the amount of E7-specific T cell infiltration and FIG. 26F shows the tumor volume over time after immunization with crafted murine splenocytes SQZ-loaded with E7 SLP or unprocessed crafted murine splenocytes. The percentage of CD8+ T cells per live cells in tumor environment, and the number of CD8+ T cells per tumor mass are shown in FIGS. 26A and 26D respectively. The percentage of E7-specific T cells per live cells in tumor environment, and the number of E7-specific T cells per tumor mass are shown in FIGS. 26C and 26E respectively. The percentage of E7-specific T cells per CD8+ T cells in the tumor environment is shown in FIG. 26B.
Figure 26B:
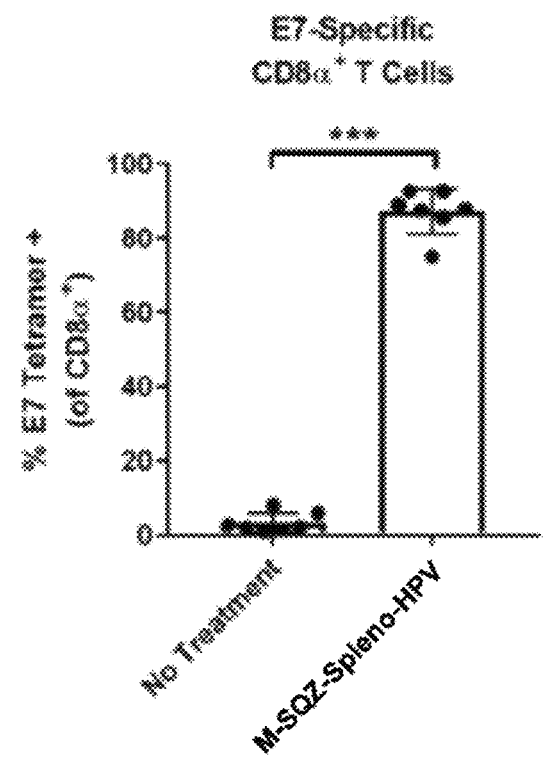
Figure 26C:
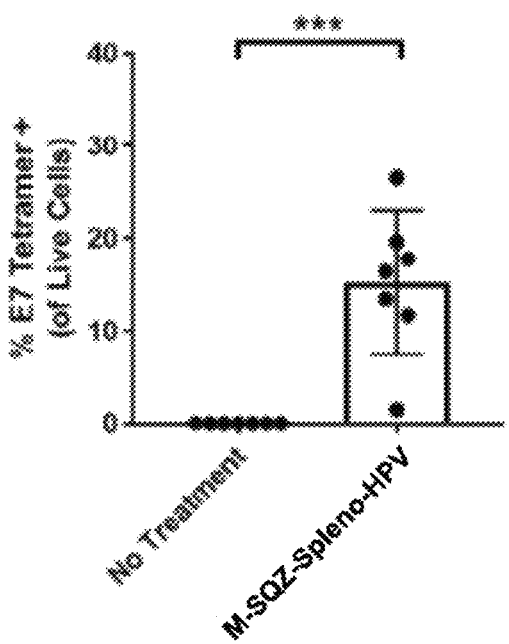
Figure 26D:
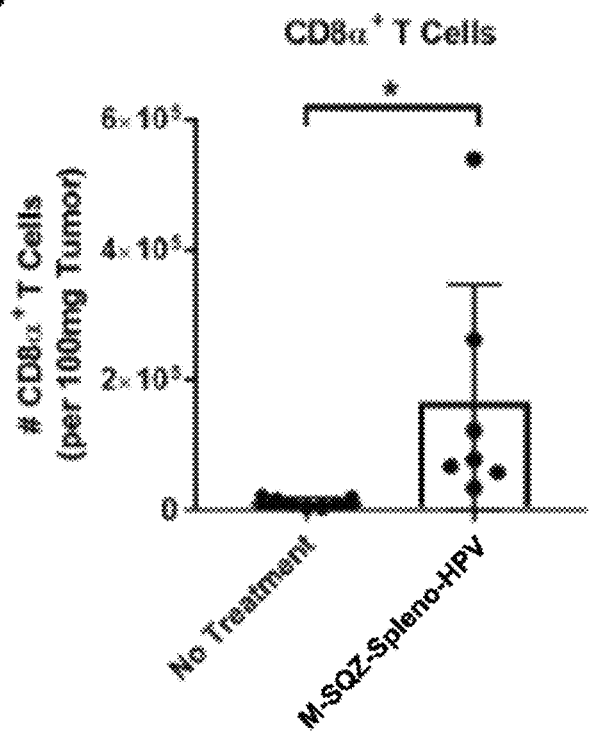
Figure 26E:
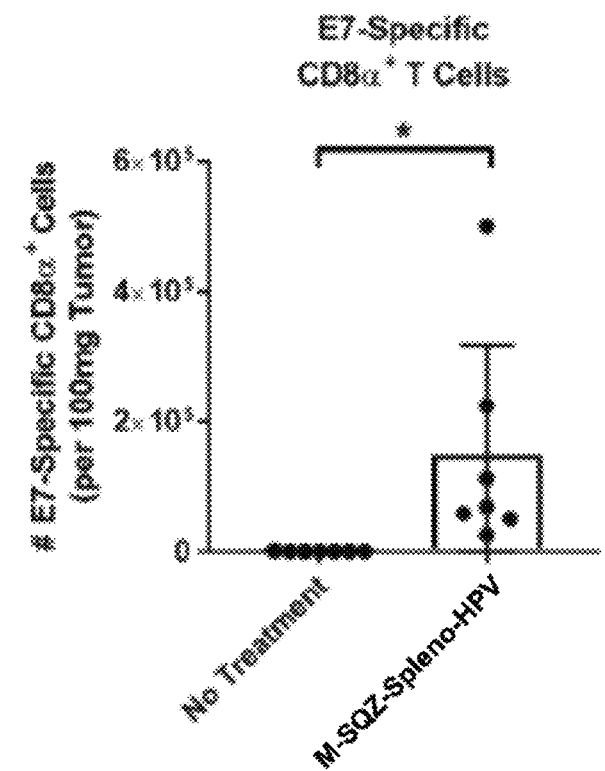
Figure 26F:
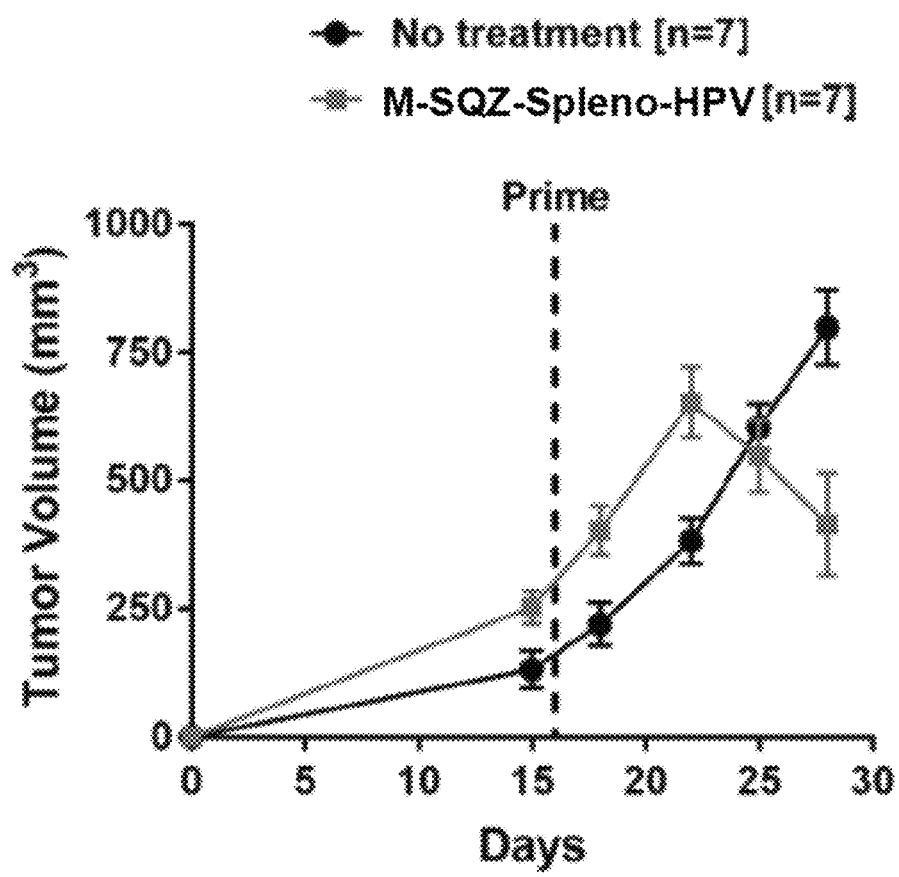
Figure 27A:
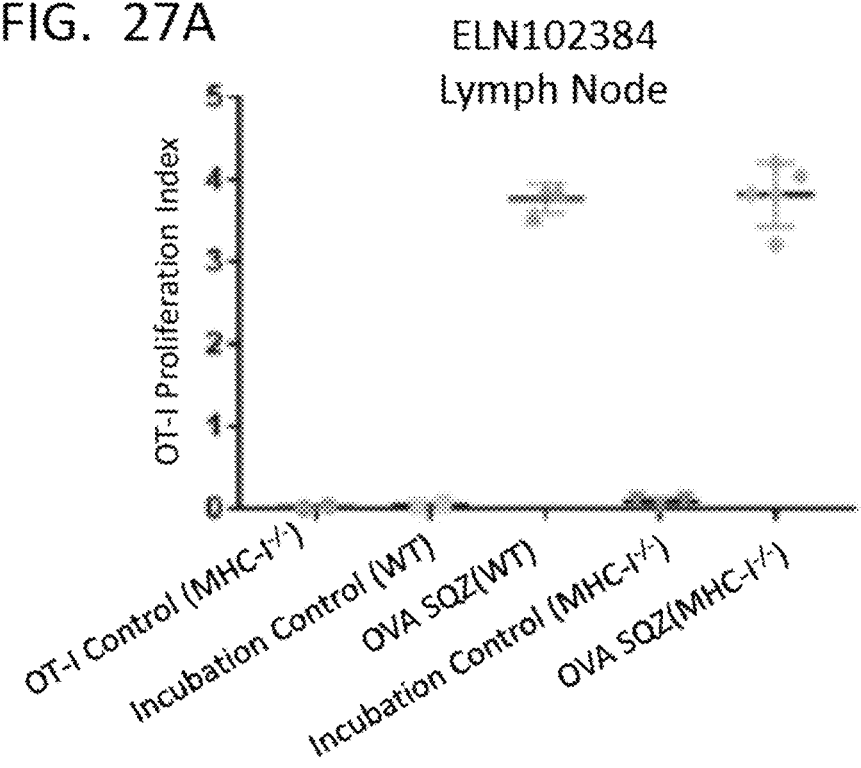
Figure 27B:
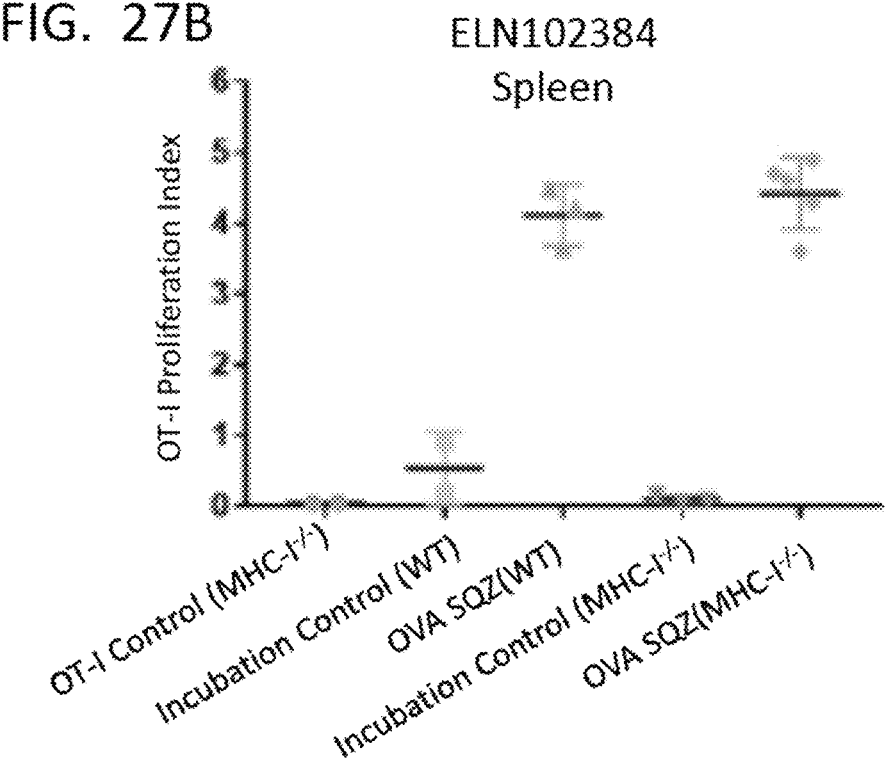
Figure 28A:
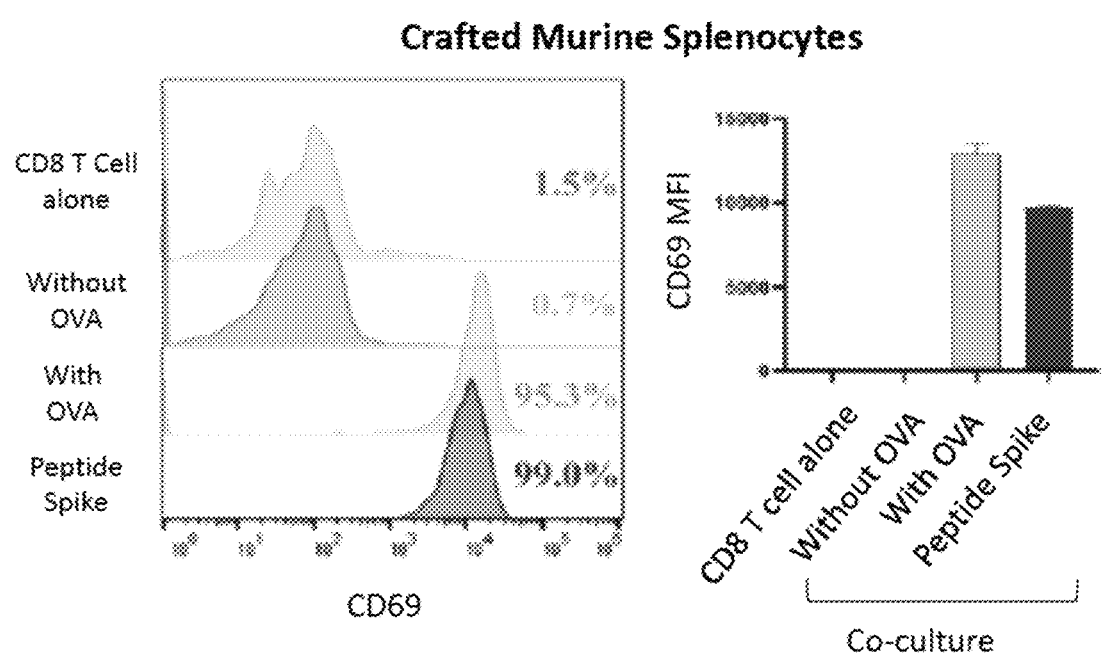
FIGS. 28A-28E show the proliferation and expression of activation marker CD69 in OT-I CD8+ T cell after co-culturing with crafted murine splenocytes SQZ-loaded with OVA (FIG. 28A), or with the indicated subsets of crafted murine splenocytes SQZ-loaded with OVA (subsets of B cells, T cells, monocytes, NK cells for FIGS. 28B, 28C, 28D, 28E respectively).
Figure 28B:
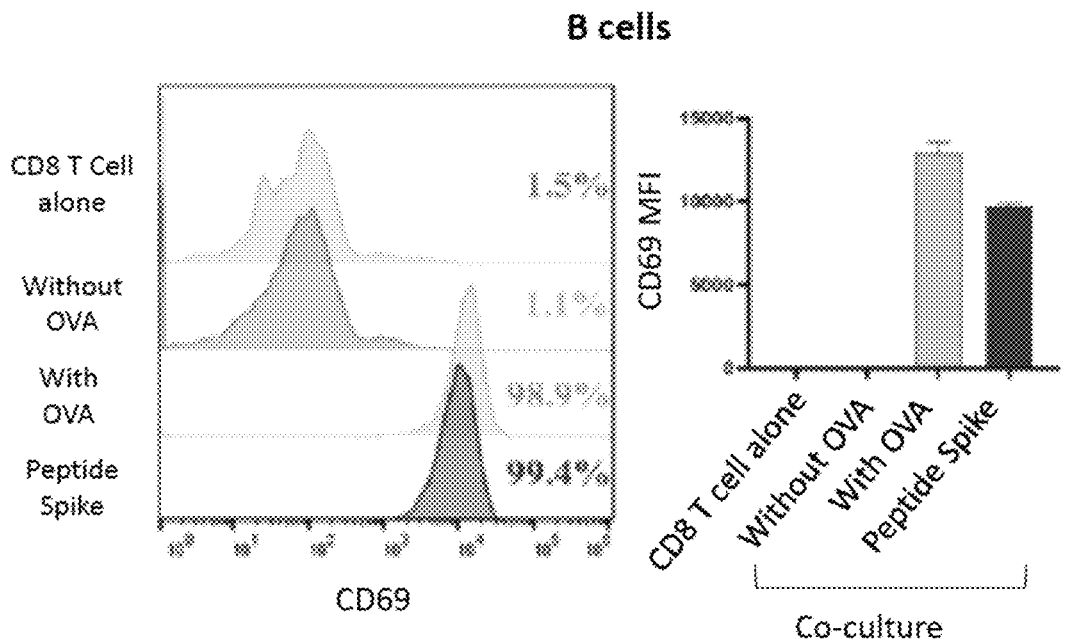
Figure 28C:
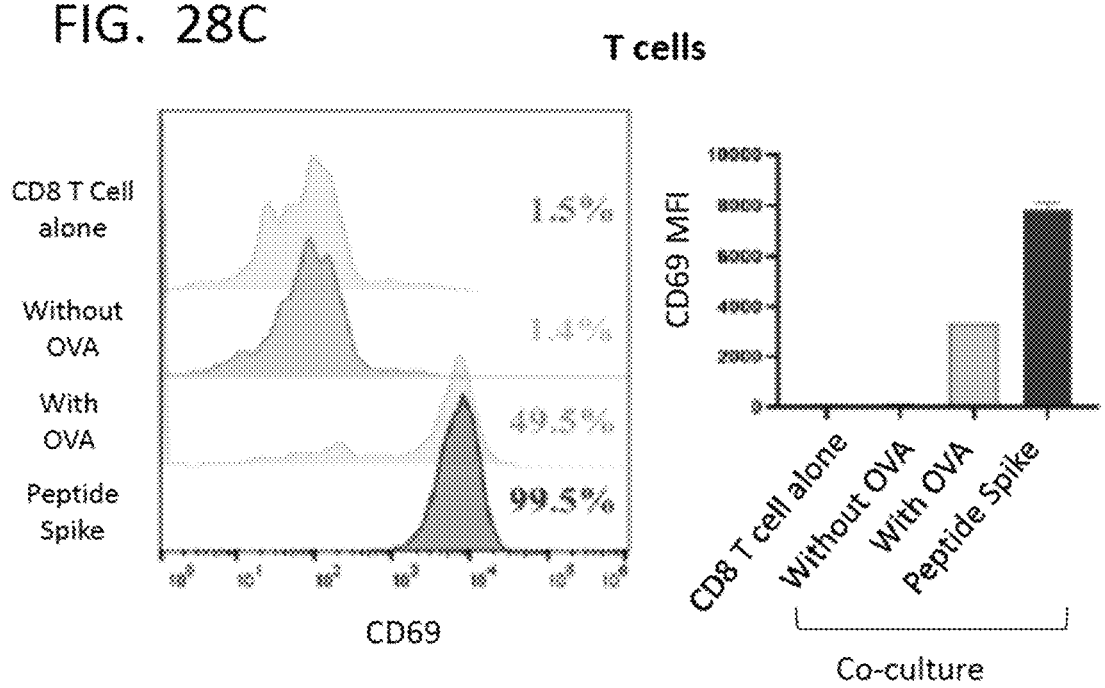
Figure 28D:
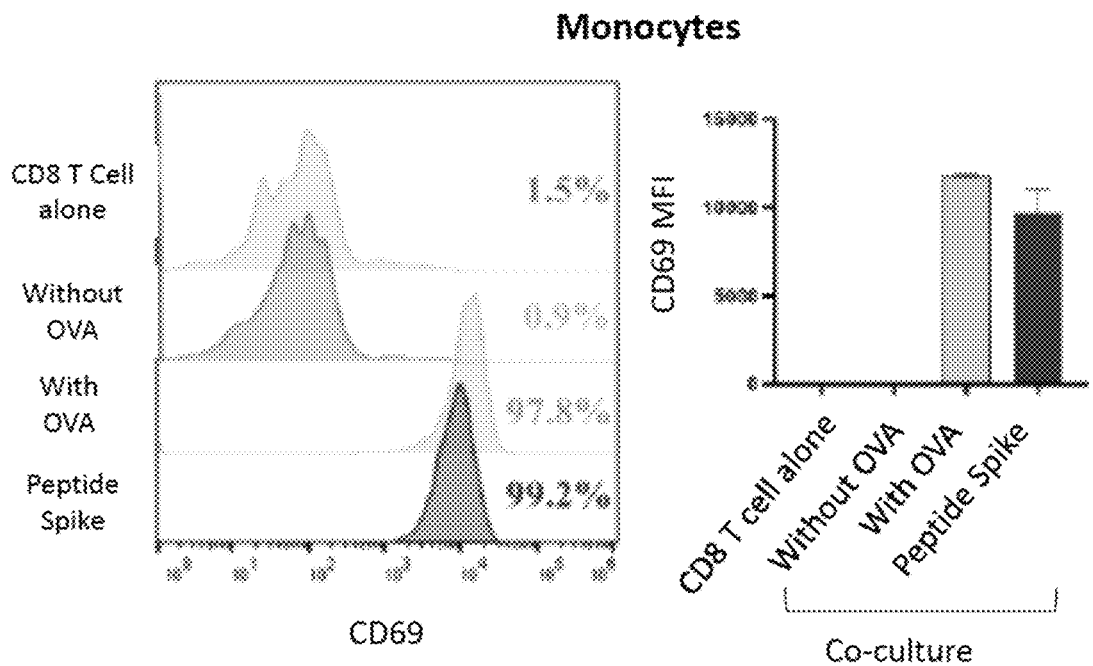
Figure 28E:
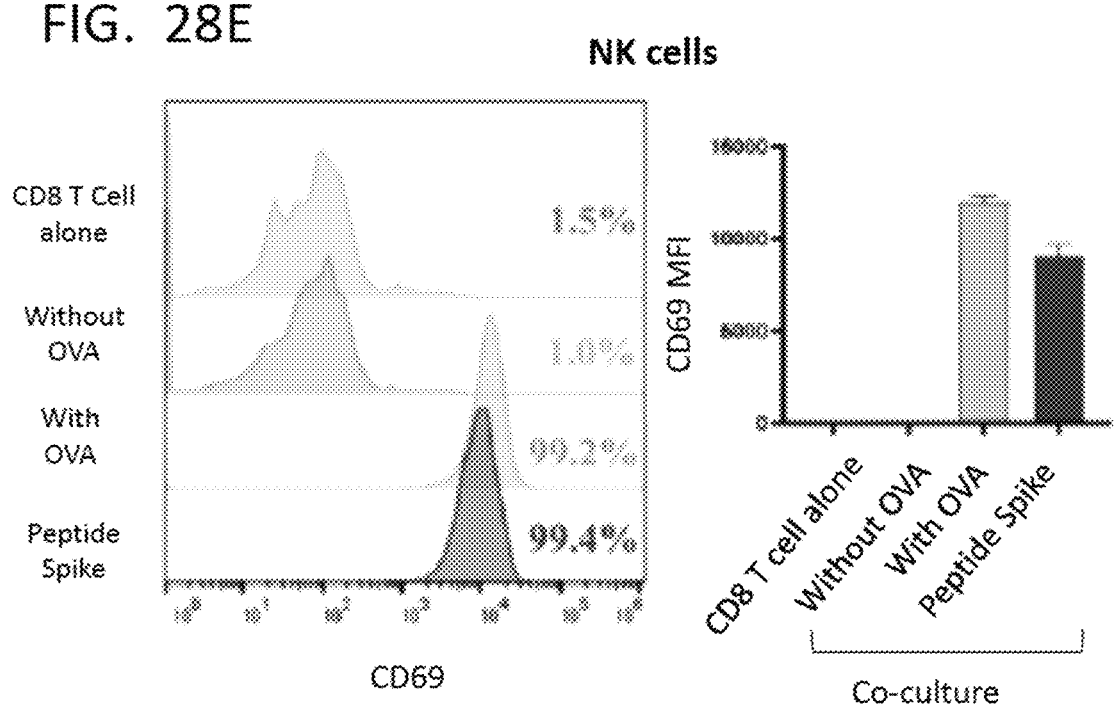

The objective of this study was to quantify E7-specific CD8+ T cells in the tumor microenvironment of TC-1 tumors 12 days post immunization with M-SQZ-Spleno-HPV, compared to control cells, and to correlate the E7-specific CD8+ T cells with tumor clearance in a tumor growth model.
Methods On Day 0, TC-1 cells (50 k/mouse in 100 µL of PBS) were injected subcutaneously in the right rear flank of female C57BL/6J mice (7/group). On Day 16, splenocytes were obtained from spleens of female C57BL/6J donor mice, and combined with splenocytes that have had their B cells depleted by negative immunomagnetic separation, leading to a splenocyte composition more representative of human PBMCs (i.e., crafted splenocytes). The crafted murine splenocytes were SQZ-loaded with 20 µM E7 SLP (GQAE-PDRAHYNIVTFSSKSDSTLRLSVQSTHVDIR (SEQ ID NO: 25)), incubated with CpG 1826 (1 µM in R10) for 4 hours at 37° C. and the loaded crafted murine splenocytes were injected retro-orbitally into the tumor bearing mice. On Day 28 (12 days post-immunization), tumors were excised and from which a single-cell suspension was generated. The single-cell suspension was assessed for tumor-infiltrating lymphocytes (TILs) by flow cytometry.
Results As seen in FIG. 26A, mice immunized with M-SQZ-Spleno-HPV had a 44.7-fold increase in the percentage of CD8+ T cells in the tumor compared to control mice (no treatment) 12 days after immunization (i.e. 28th day post tumor implant). In M-SQZ-Spleno-HPV treated animals, the majority of these CD8+ T cells were specific for the E7 antigen as determined by tetramer staining (87.2±6.0% of the CD8α+ population) (FIG. 26B). The percentage of cells positive for E-7 tetramer staining in the tumor was also quantified (FIG. 26C). This demonstrates that immunization with M-SQZ-Spleno-HPV significantly increased the presence of E7-specific CD8+ T cells in the tumor microenvironment 12 days post immunization in comparison to the no treatment group (765-fold increase). As shown in FIGS. 26D and 26E, this increase in E7 specific CD8+ T cells was also observed when normalized to tumor mass. These data demonstrate that immunization with M-SQZ-Spleno-HPV in the TC-1 mouse tumor model led to a significant increase in E7-specific CD8+ T cells infiltrating the tumor. The increase in E7-specific CD8+ T cells (FIGS. 26A-E) coupled with the decrease in tumor volume (FIG. 26F) supported that M-SQZ-Spleno-HPV reduced tumor burden by expanding E7-specific effector CD8+ T cells.

Example 27

In order to demonstrate whether the murine splenocytes processed with a model antigen (Ova) stimulates OT-I CD8+ T cell proliferation in vivo through direct presentation of SIINFEKL (SEQ ID NO: 54) (the CD8-restricted epitope of ovalbumin), MHC-I −/− mice were used as recipients to decouple antigen hand-off to professional APCs in recipient mice to allow examination of direct presentation by murine splenocytes SQZ-processed with OVA.
Methods
On Day 0, OT-I T cells were isolated from the splenocytes of female OT-I mice by immunomagnetic separation. Isolated OT-I T cells were stained with CFSE prior to injection into female recipient mice (WT or MHC-I −/−) retro-orbitally (2.5*10$^6$ cells/mouse). Next, splenocytes were obtained from spleens of female CD45.1 C57BL/6J donor mice, and combined with splenocytes that have had their B cells depleted by negative immunomagnetic separation, leading to a splenocyte composition more representative of human PBMCs (i.e., crafted splenocytes). The crafted murine splenocytes were SQZ-loaded with Ova (400 µg/mL), incubated with CpG 1826 (1 µM in R10) for 4 hours at 37° C. and the loaded crafted murine splenocytes were injected retro-orbitally into recipient mice (5*10$^6$ cells/mouse). On Day 3, lymph nodes and spleens were excised from the recipient mice and assessed for proliferation using flow cytometry and CFSE staining.
Results As shown in FIGS. 27A-D, both C57BL/6J (WT) and MHC-I−/− mice that received the crafted murine splenocytes SQZ-loaded with ovalbumin exhibited robust OT-I CD8+ T cell proliferation, with a proliferation index ranging from 4-6 in both spleen and lymph node. WT and MHC-I−/− mice that received the crafted murine splenocytes incubated with ovalbumin (incubation control, without SQZ processing) had little to no OT-I CD8+ T cell proliferation, demonstrating that the SQZ process is required to introduce antigen into crafted murine splenocytes for direct presentation to CD8+ T cells in vivo. Mice that received OT-I T cells only (control for unstimulated adoptively transferred OT-I CD8+ T cells) induced no proliferation of CD8+ T cell. These results demonstrate that MHC-I presentation is restricted to the transferred crafted murine splenocytes processed with ovalbumin, ruling out the possibility for antigen handoff to recipient antigen presenting cells (APCs) playing a role in the subsequent CD8+ T cell response. Proliferation of OT-I CD8+ T cells in MHC-I−/− recipients demonstrates that the SQZ-processed crafted murine splenocytes directly presents antigen.

Example 28

This study examined the antigen presentation ability of four cell types within crafted murine splenocytes (B cells, T cells, NK cells, and monocytes) by assessing activation of antigen-specific T cells upon co-culture.
Methods On Day 0, splenocytes were obtained from spleens of female CD45.1 C57BL/6J donor mice, and combined with splenocytes that have had their B cells depleted by negative immunomagnetic separation, leading to a splenocyte composition more representative of human PBMCs (i.e., crafted splenocytes). Crafted murine splenocytes were then SQZ-processed with or without Ova (400 µg/mL), and incubated with CpG 1826 (1 µM in R10) for 4 hours at 37° C. After 4 hours, aliquots of the SQZ-loaded crafted murine splenocytes (5*10$^6$ cells/mouse) were subjected to various immunomagnetic separations to obtain purified subsets of monocytes, B cells, T cells and NK cells. Next, OT-I T cells were isolated from the splenocytes of female OT-I mice by immunomagnetic separation. OT-I (1*10$^5$ cells/well) were co-cultured with either the crafted murine splenocytes or the respective individual cell subsets (SQZ-processed with or without OVA) and incubated for 24 h at 37° C. For positive control (Peptide Spike), SIINFEKL (SEQ ID NO: 54) peptide (OVA257-264-1 µg/mL) was added into the suspension with OT-I and unprocessed crafted murine splenocytes and kept for the entire duration of the co-culture. The T cell activation marker CD69 was then assessed by flow cytometry.
Results Cell surface CD69 expression was used as a readout of OT-I CD8+ T cell activation, because the surface expression of this marker increases following engagement of the T cell receptor by peptide antigen presented in the context of MHC-I. As shown in FIGS. 28A-28E, all four major cell types within the crafted murine splenocytes (B cells, T cells, NK cells, and monocytes) were capable of directly presenting antigen to OT-I CD8+ T cells. These data indicate that each of these cell types can function as antigen presenting cells. All cell types SQZ-processed with Ova and matured with CpG 1826 presented antigen to the OT-I CD8+ T cells and induced activation of OT-I T cells at levels comparable to the positive control (Peptide Spike).

Example 29

This study determined if fluorescently labeled HPV E6 or E7 SLPs, or the combination thereof, can be delivered intracellularly through SQZ processing and whether any delivered SLPs are localized in the cytosol of human PBMCs.
Methods Human PBMCs from 3 different HLA-A*02+ donors were SQZ-loaded with 50 µM FAM-labeled E6, E7 or the combination of E6+E7 on ice and the cells were co-stained with an AF647-conjugated anti-CD45 antibody (plasma membrane marker) stain and Hoechst 33342 staining (nuclear staining). Human PBMCs SQZ processed with RPMI only served as the negative control. The localization of the peptides was determined by confocal imaging. Specifically, localization of any FAM-E6 and/or FAM-E7 SLP was visualized on a scanning disk confocal microscope. Z-stack analysis was performed on the cells to determine the precise localization of FAM-E6 and/or FAM-E7 SLP. Line scan traces were performed on confocal slices from the middle of a Z-stack for each sample (i.e. the image of such a slice depicted the middle of the cell) and these slices were analyzed to confirm any intracellular delivery of SLPs following SQZ processing. For the line scan traces, cells with a clear FAM signal were selected for analysis, where the line scan was traced through the center of the cell (white circle), along the white lines displayed on the fluorescent images (FIGS. 29A-29F, top panels).
Results Following SQZ processing, the FAM fluorescent signal was observed to be encircled by the plasma membrane within the optical slices examined (FIGS. 29B, 29D, 29F, top three panels), whereas no FAM signals were detected in negative controls (FIGS. 29A, 29C, 29E, top three panels). Most SQZ-loaded cells displayed visible intracellular SLP of varying intensities in the widefield images; however, dimmer signals could be difficult to visualize due to the dynamic range of the microscope. Line scan traces showed that the majority of the FAM fluorescent signal was detected within the confines of the plasma membrane signal (FIGS. 29B, 29D, 29F, bottom panels) when comparing to traces of negative controls which only showed the plasma membrane signal (FIGS. 29A, 29C, 29E, bottom panels), indicating that the FAM-E6 and FAM-E7 SLPs were intracellular following SQZ processing. This indicates that the SQZ process loaded the respective SLPs into the cytosol, though some signal was detected to colocalize with the nucleus (not shown). Of note, FAM molecules are typically cleaved from immunogenic epitopes during the proteasomal processing of SLPs for presentation on MHC-I. Thus, in live systems, the FAM signals from FAM-labeled SLPs will be uncoupled from SLP as it is processed and presented on MHC-I. However, in these experiments human PBMCs were fixed and then stained immediately after SQZ processing to minimize such processing of the FAM-labelled SLPs. This confocal imaging study confirms the intracellular delivery of fluorescently labeled E6 and E7 SLPs (FAM-E6 and FAM-E7) into human PBMCs by the SQZ process.

Example 30

In order to determine if a disease-relevant antigen loaded into murine B cells can lead to proliferation of antigen-specific T cells, gp100 was loaded into B cells by SQZ-processing, and the proliferation of gp100-specific T cells (pmel CD8+ T cell) was analyzed by flow cytometry.
Methods
Murine B cells were left untreated (NC), incubated at room temperature with gp100 synthetic long peptide (SLP) (Incub. ctrl), SQZ-processed in the presence of the gp100 SLP (Squeeze), or pulsed with short peptide for 1 h at 37° C. (PP). B cells ($5\times10^6$ cells/mouse) were co-injected with 3 µg LPS to immunize mice that had also received $2.5\times10^6$ CFSE labeled pmel CD8+ T cells. To measure for proliferation, CFSE dilution in the pmel CD8+ T cells was assessed 3 days after immunization (n=5 mice per group).
Results
Murine B cells loaded with gp100 by SQZ-processing led to significant increases in gp100-specific T cell proliferation, as shown by the increased CFSE dilution (FIG. 30 left panel) and subsequent quantification of proliferation index (FIG. 30 right panel). SQZ-loaded B cells had a near 5-fold increase in proliferation relative to untreated controls, peptide pulse control or endocytosis control (FIG. 30 right panel). These data show that SQZ-loading of antigen into B cells leads to significantly more efficient stimulation of antigen-specific T cell proliferation than incubating B cells with SLP or the minimal epitope.

Example 31

In order to determine if splenocytes SQZ-loaded with a synthetic long peptide (SLP) can prime a protective immune response, crafted splenocytes were SQZ-processed in the presence of E7 synthetic long peptide (E7 SLP) and subsequently administered to mice, at both 14 days and 7 days prior to implantation of HPV16 E6/E7 expressing tumor cell line TC-1.
Methods
Splenocytes were obtained from spleens of female CD45.1 C57BL/6J donor mice, and combined with splenocytes that have had their B cells depleted by negative immunomagnetic separation, leading to a splenocyte composition more representative of human PBMCs (i.e., crafted splenocytes). The crafted splenocytes were then SQZ-processed in the presence of a SLP containing a CD8 epitope for HPV16 E7. Mice were primed on day −14 and boosted on day −7 with crafted splenocytes SQZ-loaded with the E7 SLP. On day 0, mice were subcutaneously implanted on the right flank with the HPV16 E6/E7-positive TC-1 tumor cell line. Tumor growth, as measured by the formula ((length×width2)/2), was compared between mice from the untreated groups (Cohort I and Cohort II) and a group treated with HPV E7-loaded crafted splenocytes. All immunized mice remained tumor free for 60 days and were subsequently rechallenged with TC-1 tumor cells subcutaneously implanted on the left flank, and compared to a different cohort of untreated animals implanted with tumor cells on the left flank.
Results
As shown in FIG. 31, all mice treated with SQZ-loaded crafted splenocytes (15/15) were protected from the primary tumor challenge while untreated animals invariably developed tumors. Upon rechallenge, 11/15 mice treated with SQZ-loaded crafted splenocytes were fully protected from tumor growth which was consistent with the formation of protective immunological memory.

Example 32

To examine the effect of boosting using varying doses of E7 SLP-loaded crafted splenocytes, squeezed with E7 synthetic long peptide. Mice were administered with the indicated doses of squeezed splenocytes SQZ-loaded with E7 SLP, either as a prime only immunization on day 10 post implant, or as a prime/boost/boost regimen administered on days 10, 17, and 24.
Methods
At Day 0, C57BL/6J female mice were injected in the right rear flank with TC1 tumor cells (50 k cells/mouse). On Day 10 (prime), splenocytes were obtained from spleens of female C57BL/6J donor mice, and combined with splenocytes that have had their B cells depleted by negative immunomagnetic separation to better mimic human PBMCs, leading to a splenocyte composition more representative of human PBMCs (i.e., crafted splenocytes). The crafted plenocytes were loaded with pre-complexed 20 µM E7 SLP (GQAEPDRAHYNIVTFSSKSD-STLRLSVQSTHVDIR (SEQ ID NO: 25))+20 µM mouse serum albumin (MSA) via SQZ (60 psi; 4 µm constriction, room temperature) and incubated with CpG 1826 (1 µM in R10) for 4 hours. Female C57BL/6J recipient mice (10/group) were injected retro-orbitally on Day 10 with 100 µL of either vehicle (PBS), splenocytes (1M cells/mouse) or splenocytes (1M cells/mouse)+CpG (1 µg/mouse).

To examine the effect of booster immunizations, a cohort of the therapeutically immunized mice received additional doses of SQZ-loaded splenocytes on days 17 and 24 (Prime/boost/boost). Tumor growth, as measured by the formula ((length×width2)/2), was compared between untreated mice and the indicated treatment groups until Day 50.
Results
As shown in FIG. 32, a single dose of $0.1\times10^6$ SQZ-loaded splenocytes administered on Day 10 had modest efficacy in priming immune response; however, boosting with additional doses of $0.1\times10^6$ cells enhanced therapeutic efficacy significantly. On the other hand, dosage(s) of $1.0\times10^6$ cells delayed tumor growth when administered as either a single priming dose prime or under a prime and boost regimen.

Example 33

In order to determine the impact the maturation+/−co-injection of adjuvant on the ability of antigen-loaded splenocytes to lead to tumor growth inhibition in a therapeutic setting, splenocytes were either matured with, co-injected with or matured and co-injected with adjuvant and tested in the HPV E7-expressing TC1 tumor model, with the area of the tumors and survival plotted against time.
Methods
At Day 0, C57BL/6J female mice were injected in the right rear flank with TC1 tumor cells (50 k cells/mouse). On Day 10 (prime), splenocytes were obtained from spleens of female C57BL/6J donor mice, and combined with splenocytes that have had their B cells depleted by negative immunomagnetic separation to better mimic human PBMCs, leading to a splenocyte composition more representative of human PBMCs (i.e., crafted splenocytes).

Crafted splenocytes were loaded with pre-complexed 20 µM E7 SLP (GQAEPDRAHYNIVTFSSKSD-STLRLSVQSTHVDIR (SEQ ID NO: 25))+20 µM mouse serum albumin (MSA) via SQZ (60 psi; 4 µm constriction, room temperature) and incubated with CpG 1826 (1 µM in R10) for 4 hours. Female C57BL/6J recipient mice (10/group) were injected retro-orbitally on Day 10 with 100 µL of either vehicle (PBS), splenocytes (1M cells/mouse) or splenocytes+CpG (1 µg/mouse). TC-1 tumor growth was measured beginning 1 week post-tumor implantation two times per week and compared to tumor growth in untreated mice for 60 days.
Results Tumor growth, as measured by the formula ((length× width²)/2), was compared between mice from the untreated group (no splenocytes) and groups treated with adjuvant alone (CpG), splenocytes or splenocytes+co-injected adjuvant. As shown in FIGS. 33A and B, while there was no observable difference between the tumor growth of untreated animals and those treated with CpG alone (median survival of 28 and 32 days, respectively), there was a slight inhibition in the rate of tumor growth for un-matured splenocytes loaded with E7 (median survival of 35 days). However, the groups that received matured, loaded splenocytes, either with or without co-injection of CpG, led to tumor regression, with tumors not reaching their initial maximum over the course of the study (median survival of 53 and 56 days, respectively). These data show that splenocytes loaded by SQZ and matured with adjuvant (with or without adjuvant co-injection) can induce tumor regression in a therapeutic model of HPV-associated cancer.

Example 34

To assess MHC-I presentation of SQZ-delivered antigens by major cell subsets contained within mouse splenocytes, crafted murine splenocytes were SQZ-loaded with OVA and subsequently the presentation in subsets were analyzed via flow cytometry using 25-D1.16 antibody. The 25-D1.16 antibody specifically binds to H-2Kb (MHC-I) on the surface of mouse cells only when it presents the immunodominant CD8+ T cell epitope from ovalbumin (SIINFEKL (SEQ ID NO: 54)).
Methods Splenocytes were obtained from spleens of female CD45.1 C57BL/6J donor mice, and combined with splenocytes that have had their B cells depleted by negative immunomagnetic separation, leading to a splenocyte composition more representative of human PBMCs (i.e., crafted splenocytes). The crafted splenocytes were then SQZ-processed without cargo (SQZ only) or SQZ-processed in the presence of ovalbumin protein (SQZ+OVA). At the indicated time points, cells were stained with an antibody panel that included the 25-D1.16 antibody to assess SIINFEKL (SEQ ID NO: 54) presentation on H-2Kb for each indicated cell type, and analyzed by flow cytometry (T cells, B cells, NK cells, and monocytes).
Results As shown in FIG. 34, for cells SQZ-processed in the presence of OVA, antigen presentation was detectable at the 2- and 4-hour time points for monocytes, T cells, B cells, and NK cells. This was evident from the increased signal from the 25-D1.16 antibody staining relative to cells that were not SQZ-processed with OVA (SQZ only). At 2 and 4 hours after SQZ-processing, an increase in fluorescence intensity of >40% was detectable for T cells, B cells, and NK cells. For monocytes, the increase in fluorescence intensity was >10% at 2 and 4 hours after SQZ-processing.

Example 35

In order to demonstrate whether murine splenocytes processed with a tumor antigen (HPV16 E7) stimulates E7-specific T cell proliferation, mice were immunized with crafted murine splenocytes were SQZ-loaded with E7 SLP, and endogenous T cell response upon antigen re-stimulation was measured by intracellular cytokine staining.
Methods Splenocytes were obtained from spleens of female CD45.1 C57BL/6J donor mice, and combined with splenocytes that have had their B cells depleted by negative immunomagnetic separation, leading to a splenocyte composition more representative of human PBMCs (i.e., crafted splenocytes). The crafted murine splenocytes were SQZ-loaded with E7 SLP (20 µM), incubated with CpG 1826 (1 µM in R10) for 4 hours at 37° C. and the loaded crafted murine splenocytes were injected retro-orbitally into C57BL/6J recipient mice at 1 million, 0.25 million or 0.1 million cells per mouse. Control mice were left untreated. 7 days after immunization, spleens were harvested from the recipient mice and re-stimulated with the E7 minimal epitope ex vivo. Intracellular cytokine staining was performed to determine the percentage of endogenous CD8 T-cells that produced interferon-γ in response to E7 recognition.
Results As shown in FIG. 35, mice that received 1 million crafted murine splenocytes SQZ-loaded with E7 SLP exhibited robust E7-specific CD8+ T cell proliferation in the spleen, as illustrated by the significant induction of IFN-γ secretion when recipient mouse spleen was stimulated with the E7 minimal epitope ex vivo. Mice that received 0.25 million crafted murine splenocytes SQZ-loaded with E7 SLP also exhibited E7-specific CD8+ T cell proliferation in the spleen, as illustrated by the observable induction of IFN-γ when recipient mouse spleen was stimulated with the E7 minimal epitope ex vivo. In contrast, untreated animals did not exhibit any observable E7-specific CD8+ T cell proliferation, as illustrated by the lack of IFN-γ secretion when spleen was stimulated with the E7 minimal epitope ex vivo.

Example 36

The objective of this study was to quantify E7-specific CD8+ T cells in the tumor microenvironment of TC-1 tumors 12 days post immunization with M-SQZ-Spleno-HPV, or with a peptide vaccine (E7 SLP+CpG), compared to control cells, and to correlate the E7-specific CD8+ T cells with tumor clearance in a tumor growth model.
Methods On Day 0, TC-1 cells (50 k/mouse in 100 µL of PBS) were injected subcutaneously in the right rear flank of female C57BL/6J mice (7/group). On Day 16, splenocytes were obtained from spleens of female C57BL/6J donor mice, and combined with splenocytes that have had their B cells depleted by negative immunomagnetic separation, leading to a splenocyte composition more representative of human PBMCs (i.e., crafted splenocytes). The crafted murine splenocytes were SQZ-loaded with 20 µM E7 SLP (GQAE-PDRAHYNIVTFSSKSDSTLRLSVQSTHVDIR (SEQ ID NO: 25)), incubated with CpG 1826 (1 µM in R10) for 4 hours at 37° C. and the loaded crafted murine splenocytes were injected IV (retro-orbitally) into the tumor bearing mice. For mice receiving a peptide vaccine, 150 µg of E7 SLP and 50 µg of CpG were injected subcutaneous (per mouse) to the recipient mice on Day 16. Control mice were left untreated.

On Day 28 (12 days post-immunization), tumors were excised and from which a single-cell suspension was generated. The single-cell suspension was assessed for tumor-infiltrating lymphocytes (TILs) by flow cytometry.
Results As seen in FIG. 36A, mice immunized with M-SQZ-Spleno-HPV had a significant increase in CD45+ leukocytes among live cells within the tumor microenvironment, compared to mice receiving peptide vaccine or control mice at 12 days after immunization (i.e. 28th day post tumor implant). Of these leukocytes in the tumor, mice immunized with M-SQZ-Spleno-HPV had a significantly higher percentage of CD8+ T cells (>30%), compared to control mice (<5%) and mice receiving peptide vaccine (<20%) (FIG. 36B). Furthermore, in M-SQZ-Spleno-HPV treated animals, the majority of these CD8+ T cells (>80%) were specific for the E7 antigen as determined by tetramer staining compared to control mice (<5%) and mice receiving peptide vaccine (<40%) (FIG. 36C). As seen in FIG. 36D, administration of M-SQZ-Spleno-HPV led to regression of tumor volume beginning 4 days post-immunization, as compared to untreated mice or mice treated with a peptide vaccine, where the tumor growth was not inhibited. Taken together, these data demonstrate that immunization with M-SQZ-Spleno-HPV in the TC-1 mouse tumor model led to a significant increase in E7-specific CD8+ T cells infiltrating the tumor. The increase in E7-specific CD8+ T cells (FIGS. 36A-C) coupled with the decrease in tumor volume (FIG. 36D) supported that M-SQZ-Spleno-HPV reduced tumor burden by expanding E7-specific effector CD8+ T cells.

Example 37

The objective of this study is to demonstrate the scalability of SQZ-loading of human PBMCs. Human PBMCs were subjected to SQZ-processing in the presence of Dextran at a manufacturing scale, and the payload delivery and PBMC viability was assessed.
Methods Leukopaks (HEMACARE®) containing peripheral blood of healthy HLA-A2+ donors were obtained and PBMCs were isolated via elutriation. The resulting PBMCs were resuspended in 120 mL RPMI to obtain a PBMC suspension with a concentration of $7.20 \times 10^7$ cells/mL. The RBC suspension was then either (i) incubated, or (ii) subjected to SQZ-processing (50 psi, 4 µm diameter constriction, 2-8° C.), in the presence of fluorescent Dextran (3 kDa Dextra AF680). SQZ-processing was subsequently quenched with placing the SQZ-processed cells into 1000 mLs of RPMI. 2 hours subsequent to incubation or SQZ-processing, the viability as well as fluorescent Dextran delivery were measured via flow cytometry for PBMC, and for each cell type within: B cells (CD20+), T cells (CD3+), NK cells (CD56+) and monocytes (CD14+).
Results FIG. 37A shows the number of cells SQZ-processed in the manufacturing setting described in this example is more than 3 orders of magnitude higher the number of cells SQZ-processed in an experimental setting. As shown in FIG. 37B, there was no significant difference in viability between the incubation control and the SQZ-processed PBMCs, with both registering above 80% viability. As shown in FIG. 37C, 3 kDa Dextran was delivered via SQZ-processing into about 80% of all PBMCs, and at least into 60% of each cell type. Over 90% of CD14+ monocytes were loaded with Dextran after SQZ-processing. In contrast, less than 10% of PBMCs incubated with Dextran showed any delivery. Taken together, the results show that SQZ-mediated delivery can be used at a manufacturing scale to deliver payloads efficiently into all component cell types in the PBMC without any significant loss of viability.

Example 38

In order to determine whether mRNA introduced by SQZ delivery could be translated and expressed in PBMC subsets, human PBMCs were subjected to SQZ-processing in the presence of mRNA encoding CD86 or IFNα2 and the protein expression of CD86 or IFNα2 was assessed by flow cytometry or intracellular staining.
Methods Human PBMCs were either left untreated (NC), or subjected to SQZ-processing in the presence of mRNA encoding CD86 or IFNα2 (SQZ) or an empty payload (Empty SQZ). Subsequent to SQZ-loading, the PBMCs loaded with CD86-encoding mRNA were analyzed for CD86 surface expression by flow cytometry in component cell types of B cells (CD19+), T cells (CD3+), NK cells (CD56+) and monocytes (CD14+). For PBMCs SQZ-processed with IFNα2-encoding mRNA, the loaded PBMCs were incubated with GOLGIPLUG/GOLGISTOP for 4 hours to stop secretion, and subsequently analyzed for IFNα2 expression by intracellular staining in in component cell types of B cells (CD19+), T cells (CD3+), NK cells (CD56+) and monocytes (CD14+).
Results As shown in FIGS. 38A and 38B, all PBMC subset populations demonstrated expression of CD86 or IFNα2, in at least about 40% of the respective cells, following delivery of the respective encoding mRNAs, as compared to untreated PBMCs, or control PBMCs SQZ-processed with empty payload. CD14+ monocytes inherently express CD86. The results indicated mRNAs can be introduced by SQZ delivery into PBMCs for efficient expression of the encoded protein.

Example 39

In order to determine the variation in degree and duration in expression of candidate mRNAs introduced by SQZ delivery, human PBMCs were SQZ-loaded with mRNA encoding CD86 or 4-1BBL and the corresponding protein expression of CD86 or 4-1BBL was assessed by flow cytometry.
Methods Human PBMCs were subjected to SQZ-processing in the presence of mRNA encoding CD86 or IFNα2 (SQZ) or an empty payload (Empty SQZ). Subsequent to SQZ-loading, the PBMCs loaded with the respective mRNAs were incubated for 4 hours at 37° C., and the expression of the respective encoded protein was measured every 24 hours by flow cytometry in component cell types of B cells (CD19+), T cells (CD3+), NK cells (CD56+) and monocytes (CD14+).
Results FIGS. 39A and 39B shows the expression of CD86 and 4-1BBL in the T cell subset populations within the PBMCs SQZ-loaded with the respective mRNAs. As shown in FIG. 39A, The T cell subset within PBMCs loaded with CD86-encoding mRNA showed a significant increase in the percentage of CD86+ cells compared to control, at 4 hours to 48 hours post SQZ-processing, and the percentage of CD86+ cells slightly decreased only at 72 hours post SQZ processing. As shown in FIG. 39B, The T cell subset within PBMCs loaded with 4-1BBL-encoding mRNA showed a moderate increase in the percentage of 4-1BBL+ cells at 4 hours post SQZ-processing, and the percentage of 4-1BBL+-positive cells noticeably decreased after only 24 hours of incubation. The results indicated that SQZ-delivery of different candidate mRNAs can result in different degrees and durations in the expression of encoded protein.

Example 40

In order to determine whether translation-enhancing modifications of mRNA will affect expression of candidate mRNAs introduced by SQZ delivery, human PBMCs were SQZ-loaded with an unmodified eGFP-encoding mRNA or a GFP-endocing mRNA with 5-metoxyuridine backbone (5moU), and the corresponding eGFP expression was assessed by flow cytometry.
Methods
Human PBMCs were subjected to SQZ-processing in the presence of 0 to 200 µg/mL of an unmodified eGFP-encoding mRNA or a GFP-endocing mRNA with 5moU backbone. Subsequent to SQZ-loading, the PBMCs loaded with the respective mRNAs were incubated for 4 hours at 37° C., and the eGFP expression was measured by mean fluorescence intensity (MFI) via flow cytometry in component cell types of B cells (CD19+), T cells (CD3+), NK cells (CD56+) and monocytes (CD14+).
Results
FIG. 40 shows the expression of eGFP in the T cell subset populations within the PBMCs SQZ-loaded with the unmodified eGFP mRNA or the 5moU-modified eGFP mRNA. As shown in FIG. 40, The T cell subset within PBMCs loaded with unmodified eGFP mRNA showed a higher MFI compared to that loaded with 5moU-modified eGFP mRNA. The results indicated that 5moU RNA modification did not result in enhanced translation of mRNAs delivered by SQZ processing.

Example 41

In order to determine whether cytokines encoded by mRNAs introduced by SQZ delivery could be translated, expressed and secreted in PBMC subsets, human PBMCs were SQZ-loaded with mRNA encoding IL-12, IFNα or IL-2 respectively and the corresponding secretion of IL-12, IFNα or IL-2 was assessed by ELISA.
Methods
Human PBMCs were either left untreated (NC), or subjected to SQZ-processing in the presence of mRNA encoding IL-12 (50 µg/mL IL-12a and 50 µg/mL IL-12b mRNA), mRNA encoding IFNα (100 µg/mL) or mRNA encoding IL-2 (SQZ) (100 µg/mL), or an empty payload (Empty SQZ). After SQZ-loading, the respective PBMCs loaded with the cytokine-encoding mRNAs were then incubated for 4 hours at 37° C., and subsequently the supernatant was assayed by ELISA to determine the expression and secretion of the respective cytokines.
Results
As shown in FIG. 41, PBMCs SQZ-loaded with cytokine-encoding mRNAs exhibited significant expression and secretion of IL-12, IFNα or IL-2 respectively. The results indicated mRNAs can be introduced by SQZ delivery into PBMCs for efficient expression and secretion of encoded cytokines.

Example 42

As illustrated in FIG. 42A, in addition to T cell receptor engagement by antigen presenting cells (Signal 1), the activation of an immune response is enhanced by additional signals such as co-stimulatory receptor activation (Signal 2) and cytokine receptor binding (Signal 3). In order to determine whether mRNAs introduced by SQZ delivery could be translated and expressed into protein effectors for these enhancing signals, human PBMCs were SQZ-loaded with mRNA encoding CD70 or 4-1BBL (for Signal 2) and/or with mRNA encoding IFNα2 or IL-2 (Signal 3) respectively. The corresponding expression of CD70 or 4-1BBL was measured by flow cytometry, while the corresponding secretion of IFNα2 or IL-2 was measured from culture supernatant via ELISA.
Methods
Human PBMCs were either left untreated (NC), or subjected to SQZ-processing in the presence of respective mRNA encoding CD70, 4-1BBL, IFNα2 or IL-2. Subsequent to SQZ-processing with mRNA encoding CD70 or 4-1BBL, the PBMCs loaded with the respective mRNAs were incubated for 4 hours at 37° C., and the expression of the respective encoded protein CD70 or 4-1BBL was measured every 24 hours by flow cytometry in component cell types of B cells (CD19+), T cells (CD3+), NK cells (CD56+) and monocytes (CD14+). After SQZ-loading with mRNA encoding IFNα2 or IL-2, the PBMCs loaded with the respective mRNAs were then incubated for 4 hours at 37° C., and subsequently the supernatants were collected at time points up to 24 hours, and assayed by ELISA to determine the expression and secretion of the respective cytokines IFNα2 or IL-2.
Results
As shown in FIG. 42B, all loaded PBMC subset populations exhibited expression of CD70 or 4-1BBL respectively, following delivery of the respective encoding mRNAs, as shown by the increased in mean fluorescence intensity assayed by flow cytometry. The respective expression of CD70 or 4-1BBL was maintained for at least 48 hours. Among the PBMC subsets, monocytes exhibited higher expression of the SQZ-delivered mRNA encoding CD70 or 4-1BBL. As shown in FIG. 42C, PBMCs SQZ-loaded with cytokine-encoding mRNAs exhibited significant expression and secretion of IFNα2 or IL-2 respectively, and the expression and secretion was maintained for at least 24 hours post-SQZ processing. The results indicated mRNAs can be introduced by SQZ delivery into PBMCs for efficient expression and secretion of the molecules providing enhancing signals in immune activation.

Example 43

As illustrated in FIG. 42A, in addition to T cell receptor engagement by antigen presenting cell (Signal 1), the activation of an immune response is enhanced by additional signals such as co-stimulatory receptor activation (Signal 2) and cytokine receptor binding (Signal 3). In order to determine whether Signal 1 activation will affect translation and expression of mRNAs introduced by SQZ delivery, crafted mouse splenocytes were SQZ-loaded with candidate mRNA (eGFP or CD86) with or without stimulation of Concanavalin A (ConA), an antigen-independent mitogen inducing Signal 1. The corresponding eGFP and CD86 expression was then measured by flow cytometry.

Methods

Splenocytes were obtained from spleens of female C57BL/6J donor mice, and combined with splenocytes that have had their B cells depleted by negative immunomagnetic separation, leading to a splenocyte composition more representative of human PBMCs (i.e., crafted splenocytes). The crafted murine splenocytes were either left unstimulated (No ConA) or stimulated with ConA before or after SQZ processing (pre-SQZ stim or post-SQZ stim). For SQZ-mediated delivery, the crafted murine splenocytes were subjected to SQZ-processing in the presence of respective mRNA encoding eGFP or CD86 (at 100 µg/mL) or an empty payload (Empty SQZ). Subsequent to SQZ-processing with mRNA encoding eGFP or CD86, the crafted murine splenocytes loaded with the respective mRNAs were incubated for 4 hours at 37° C., and the expression of the respective encoded protein eGFP or CD86 was measured by flow cytometry in component cell types of B cells (CD19+), T cells (CD3+), NK cells (CD56+) and monocytes (CD14+).

Results

As shown in FIG. 43A, crafted murine splenocytes without ConA stimulation or stimulated by ConA after SQZ-loading showed moderate eGFP translation and expression, with 15.3% to 17.0% of the T cell subset being GFP+ in flow analysis. Stimulation of crafted murine splenocytes with ConA prior to SQZ-loading dramatically increased eGFP translation and expression, with 91.1% of the T cell subset being GFP+ in flow analysis. Similarly, as shown in FIG. 43B, crafted murine splenocytes without ConA stimulation showed moderate CD86 translation and expression, as demonstrated by the small increase in CD86 MFI in the T cell subset population compared to control, whereas stimulation of crafted murine splenocytes with ConA prior to SQZ-loading dramatically increased CD86 translation and expression, as demonstrated by the significant increase in CD86 MFI in the T cell subset population compared to control. These results indicated that ConA stimulation enhances translation of candidate mRNAs delivered by SQZ processing.

Example 44

As illustrated in FIG. 42A, in addition to T cell receptor engagement by antigen presenting cell (Signal 1), the activation of an immune response is enhanced by additional signals such as co-stimulatory receptor activation (Signal 2) and cytokine receptor binding (Signal 3). In order to determine the expression efficacy and kinetics of mRNAs encoding Signal 2 and Signal 3 effectors in murine cells, crafted murine splenocytes were SQZ-loaded with candidate mRNAs (CD70, CD80, CD86 and OX40L for Signal 2; IL-12, IL-2 and IFNα2 for Signal 3). The corresponding expression of CD70, CD80, CD86 or OX40L was measured by flow cytometry, while the corresponding secretion of IL-12, IL-2 and IFNα2 was measured from culture supernatant via ELISA.

Methods

Splenocytes were obtained from spleens of female C57BL/6J donor mice, and combined with splenocytes that have had their B cells depleted by negative immunomagnetic separation, leading to a splenocyte composition more representative of human PBMCs (i.e., crafted splenocytes). For SQZ-mediated delivery, the crafted murine splenocytes were subjected to SQZ-processing in the presence of respective mRNA encoding CD70, CD80, CD86 or OX40L, or mRNA encoding IL-12, IL-2 and IFNα2 (all at 100 µg/mL); or an empty payload (Empty SQZ). Subsequent to SQZ-processing with mRNA encoding Signal 2 effectors, the crafted murine splenocytes loaded with the respective mRNAs were incubated for 4 hours at 37° C., and the expression of the respective encoded protein CD70, CD80, CD86 or OX40L was measured by flow cytometry for 48 hours in component cell types of B cells (CD19+), T cells (CD3+), NK cells (CD56+) and monocytes (CD14+). Subsequent to SQZ-processing with mRNA encoding Signal 2 effectors, the crafted murine splenocytes loaded with the respective mRNAs were incubated for 4 hours at 37° C., and the expression of the respective encoded protein CD70, CD80, CD86 or OX40L was measured by flow cytometry for 48 hours in component cell types of B cells (CD19+), T cells (CD3+), NK cells (CD56+) and monocytes (CD14+). After SQZ-processing with mRNA encoding Signal 3 effectors (cytokines), the crafted murine splenocytes loaded with the respective mRNAs were then incubated for 4 hours at 37° C., and subsequently the supernatants were collected at time points up to 48 hours, and assayed to determine the expression and secretion of the respective cytokines IL-12, IL-2 and IFNα2 (FIG. 44A).

Results

As shown in FIG. 44B, crafted murine splenocytes SQZ-loaded with Signal 2 effectors (CD70, CD80, CD86 or OX40L) showed significant translation and expression of the respective proteins, as illustrated by the appreciable increase in MFI respectively. CD86 expression was observed to persist up to at least 48 hours post-SQZ, CD70 expression dissipated at 48 hours post-SQZ, whereas CD80 and OX40K dissipated at 24 hours post-SQZ. As shown in FIG. 44C, crafted murine splenocytes SQZ-loaded with Signal 3 effectors (IL-12, IL-2 or IFNα2) showed significant expression and secretion of the respective cytokines, as illustrated by the appreciable increase in signal detected in ELISA assay. IL-12 and IL-2 secretion was significantly induced at 4 hours post-SQZ, increased slightly at 24 hours post-SQZ and slightly tapered off at 48 hours. In contrast, IFNα2 secretion significantly increased from 4 hours post-SQZ to 24 hours post-SQZ and further increased at 48 hours post-SQZ. These results indicated that mRNAs encoding Signal 2 and Signal 3 effectors were effectively translated and expressed following SQZ-mediated intracellular delivery. However, the duration and magnitude of expression of these effectors varied by the effector molecule.

Example 45

In order to determine whether mRNAs encoding Signal 2 and Signal 3 effectors in murine cells can enhance antigen-specific immune response in vitro, ConA-activated crafted murine splenocytes were SQZ-loaded with OVA antigen as well as candidate mRNAs (CD70, CD80, CD86 for Signal 2; IL-2 for Signal 3). The SQZ-loaded crafted splenocytes were subsequently co-cultured with OVA-specific OT-I CD8+ T cells, and the activation of OT-I T cells was measured via ELISA of IFN-γ secretion.

Methods

Splenocytes were obtained from spleens of female C57BL/6J donor mice, and combined with splenocytes that have had their B cells depleted by negative immunomagnetic separation, leading to a splenocyte composition more representative of human PBMCs (i.e., crafted splenocytes), and subsequently activated with ConA. For SQZ-mediated delivery, the crafted murine splenocytes were subjected to SQZ-processing in the presence of (i) OVA (5 µg/mL) as well as (ii) respective mRNA encoding CD70, CD80, or CD86, or mRNA encoding IL-12 (all at 100 µg/mL); or without mRNA. Subsequent to SQZ-processing with mRNA encoding Signal 2 or Signal 3 effectors, the crafted murine splenocytes loaded with the respective mRNAs were incubated for 4 hours at 37° C., and the co-cultured for 24 hours with OT-I CD8+ T cells at a 1:2 or 1:4 ratio. To assay T cell activation, supernatant was collected from the co-culture and subjected to IFN-γ ELISA assay (FIG. 45A).
Results As shown in FIGS. 45B and 45C, ConA-activated, crafted murine splenocytes SQZ-loaded with OVA combined with Signal 2 effectors (CD70, CD80, or CD86) or Signal 3 effector (IL-12) showed significant increase in activation of OVA-specific OT-I CD8+ T cells. The increase in OVA-specific T cell response was particularly significant when CD86 mRNA or IL-12 mRNA was co-delivered with OVA into the crafted murine splenocytes. These results indicated that in addition to being capable of being translated and expressed, the mRNAs encoding Signal 2 and Signal 3 effectors could enhance the ability of murine splenocytes' function as antigen presenting cells in activating antigen-specific T cell response.

Example 46

In order to determine whether mRNAs encoding antigens in human PBMCs can enhance antigen-specific immune response in vitro, human PBMCs were SQZ-loaded with a variety of available antigens, and subsequently co-cultured with the respective antigen-specific ASTARTE responder T cells, where the activation of responder T cells was measured via ELISA of IFN-γ secretion.
Methods Human PBMCs were either (i) left untreated (NC), (ii) pulsed with 1 μg/mL of respective peptide antigen (PP, positive control) or (iii) subjected to SQZ-processing in the presence of 100 μg/mL mRNA encoding respective antigen (E7, HSV GF1, MART-1, pp65 or Influenza M1), or (iv) SQZ-processed with an empty payload (Empty SQZ). Western blot was used to analyze translation of the loaded mRNAs at 4 hours and 24 hours after SQZ-processing. For assaying immune activation, after SQZ-loading, the PBMCs loaded with the respective antigen-encoding mRNAs were incubated for 4 hours at 37° C., and co-cultured for 24 hours with respective antigen-specific ASTARTE responder T cells. To measure for T cell activation, supernatant was collected from the co-culture and subjected to IFN-γ ELISA.
Results As shown in FIGS. 46B and 46C, subsequent to SQZ-mediated delivery of mRNAs encoding HPV16-E7 and Influenza M1, the respective antigens were translated and expressed, as indicated by the clear bands on Western blots. For T cell activation assays (FIG. 46A), PBMCs SQZ-loaded with mRNAs encoding E7, HSV GD1, MART-1 or pp65 antigens did not induce observable responder T cell activation compared to PBMCs subjected to peptide pulse (PP), as demonstrated by lack of IFN-γ secretion after co-culture; but PBMCs SQZ-loaded with mRNA encoding Influenza M1 strongly induced M1-specific T cell activation, as observed by significant induction of IFN-γ secretion after co-culture as compared to PBMC subjected to peptide pulse (PP). These results indicated that, using current protocols, antigen-encoding mRNAs could be employed in SQZ-mediated delivery to facilitate antigen presentation and stimulate antigen-specific T cell response for some but not all antigens.

Example 47

In order to compare the efficacy of SQZ-delivered antigen encoding mRNAs and peptide antigens in facilitating murine immune cells to activate an antigen-specific response in vitro, whole murine splenocytes were SQZ-loaded with OVA proteins or OVA-encoding mRNA and subsequently co-cultured with the OVA-specific OT-I CD8+ T cells, where the activation of OT-I T cells was measured via CD69 expression.
Methods Splenocytes were obtained from spleens of female C57BL/6J donor mice, and were subjected SQZ-processing using a 3.5 μm width, 30 μm height constriction at 60 psi under room temperature, in the presence of (i) mRNA encoding OVA (0 to 250 nM), or OVA protein (0 to 1250 nM). Western blot was used to analyze translation of the loaded mRNAs at 4 hours and 24 hours after SQZ-processing. For assaying immune activation, after SQZ-loading, the splenocytes loaded with the respective OVA-encoding mRNA or with OVA protein were incubated for 4 hours at 37° C., and co-cultured for 24 hours with OT-I CD8+ T cells. To measure for T cell activation, CD69 expression on OT-I CD8+ T cells was measured via flow cytometry (FIG. 47A).
Results As shown in FIG. 47B, when SQZ-loaded at the same respective molarity in murine splenocytes, OVA-encoding mRNA was much more potent (~20 fold more potent) than OVA proteins in facilitating the activation of OT-I CD8+ T cells. Splenocytes SQZ-processed in the presence of <50 nM OVA mRNA led to a significant percentage of OT-I CD8+ T cells expressing CD69 upon co-culture. In comparison, splenocytes SQZ-processed in the presence of at least 1000 nM OVA protein led to achieve similar percentages of CD69-expressing OT-I CD8+ T cells upon co-culture. These results indicated that at least for OVA antigen, splenocyte loading of antigen-encoding mRNAs was more effective than that of protein in facilitating in vitro activation of antigen-specific T cell response.

Example 48

In order to determine the effect of combination with immune checkpoint inhibitors on the ability of antigen-loaded splenocytes on tumor growth inhibition in a therapeutic setting, mice implanted with HPV E7-expressing TC1 tumor model were either administered with anti-CTLA4 injections, with crafted murine splenocytes SQZ-loaded with E7 SLP (M-SQZ-Spleno-HPV), or administered with a combination of both, and the tumor volumes and survival were plotted against time.
Methods At Day 0, C57BL/6J female mice were injected in the right rear flank with TC1 tumor cells (50 k cells/mouse). On Day 10 (prime), splenocytes were obtained from spleens of female C57BL/6J donor mice, and combined with splenocytes that have had their B cells depleted by negative immunomagnetic separation to better mimic human PBMCs, leading to a splenocyte composition more representative of human PBMCs (i.e., crafted splenocytes). Crafted splenocytes were SQZ-loaded with 20 μM E7 SLP (GQAEPDRAHYNIVTFSSKSDSTLRLSVQSTHVDIR (SEQ ID NO: 25)), incubated with CpG 1826 (1 μM in R10) for 4 hours at 37° C. and the loaded crafted murine splenocytes were injected IV (retro-orbitally) into the tumor bearing mice (M-SQZ-PBMC-HPV) (1×10$^6$ cells per mice). Cohorts of mice having received the loaded splenocytes and mice without the loaded splenocytes were then administered with anti-CTLA4 injections at the indicated schedules (Sch. 1: Day 11, 14, 17; Sch. 2: Day 17, 20, 24; Sch. 3: Day 24, 28, 31 after TC-1 implantation). Control mice were left untreated. (10 mice per group) (FIGS. 48A, 48B). TC-1 tumor growth was measured beginning 1 week post-tumor implantation two times per week and compared to tumor growth in untreated mice for 60 days.

Results

Figure 48C:
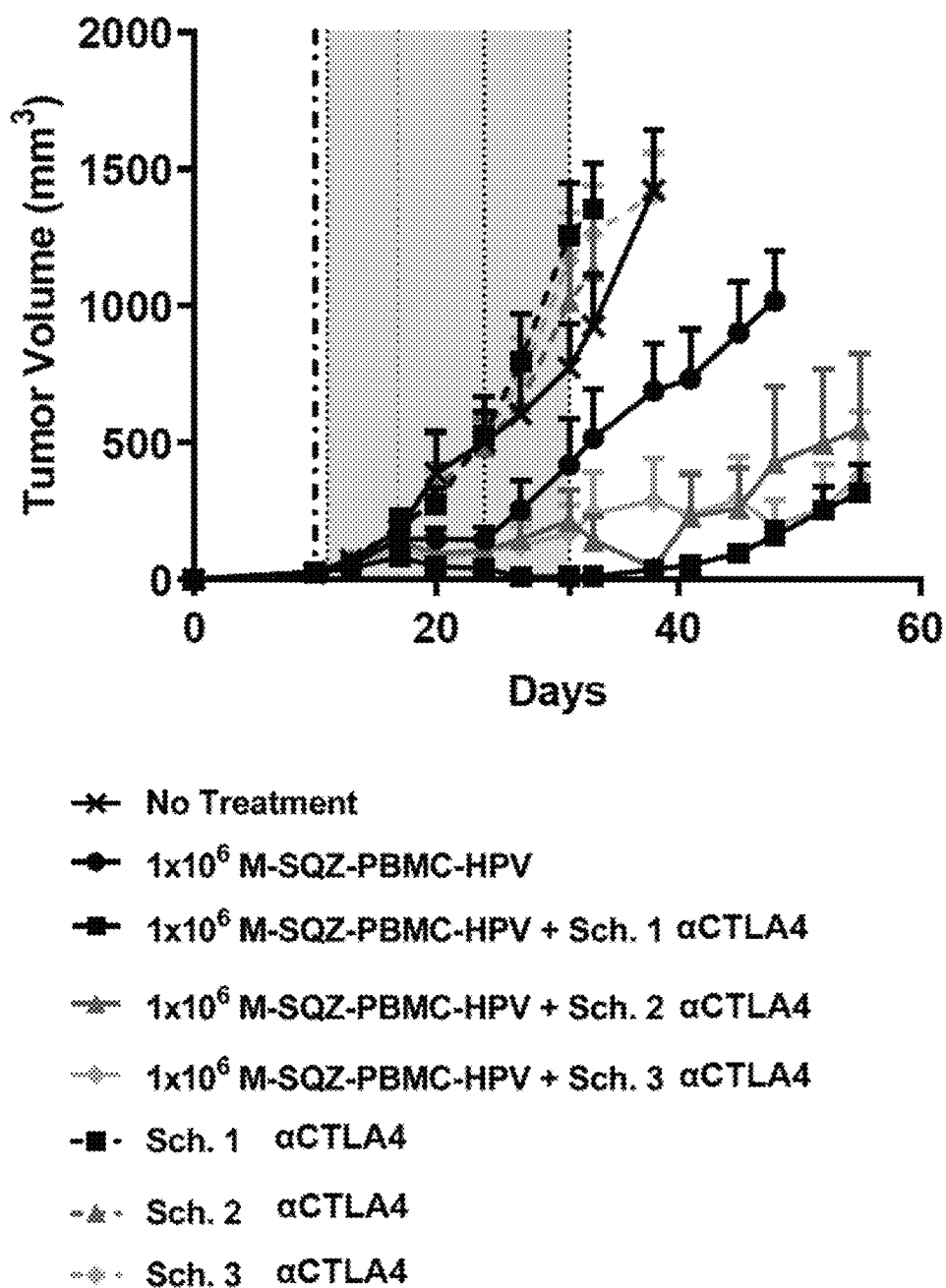

Tumor growth, as measured by the formula ((length× width$^2$)/2), was compared between control mice (Untreated) and groups treated with crafted E7-loaded splenoytces (M-SQZ-PBMC-HPV), groups treated with anti-CTLA4 (α-CTLA4) and groups treated with a combination of both (M-SQZ-PBMC-HPV+α-CTLA4). As shown in FIG. 48C, while there was no observable difference between the tumor growth in control mice and in mice treated with anti-CTLA4 alone (Sch. 1 α-CTLA4; Sch. 2 α-CTLA4; Sch. 3 α-CTLA4), there was an appreciable inhibition in the rate of tumor growth for mice primed with E7-loaded splenocytes (M-SQZ-PBMC-HPV). Noticeably, the combination of E7-loaded splenocytes and anti-CTLA4 administration showed a significant additive effect in inhibiting TC-1 tumor growth (M-SQZ-PBMC-HPV+α-CTLA4) (FIG. 48C).

Figure 48D:
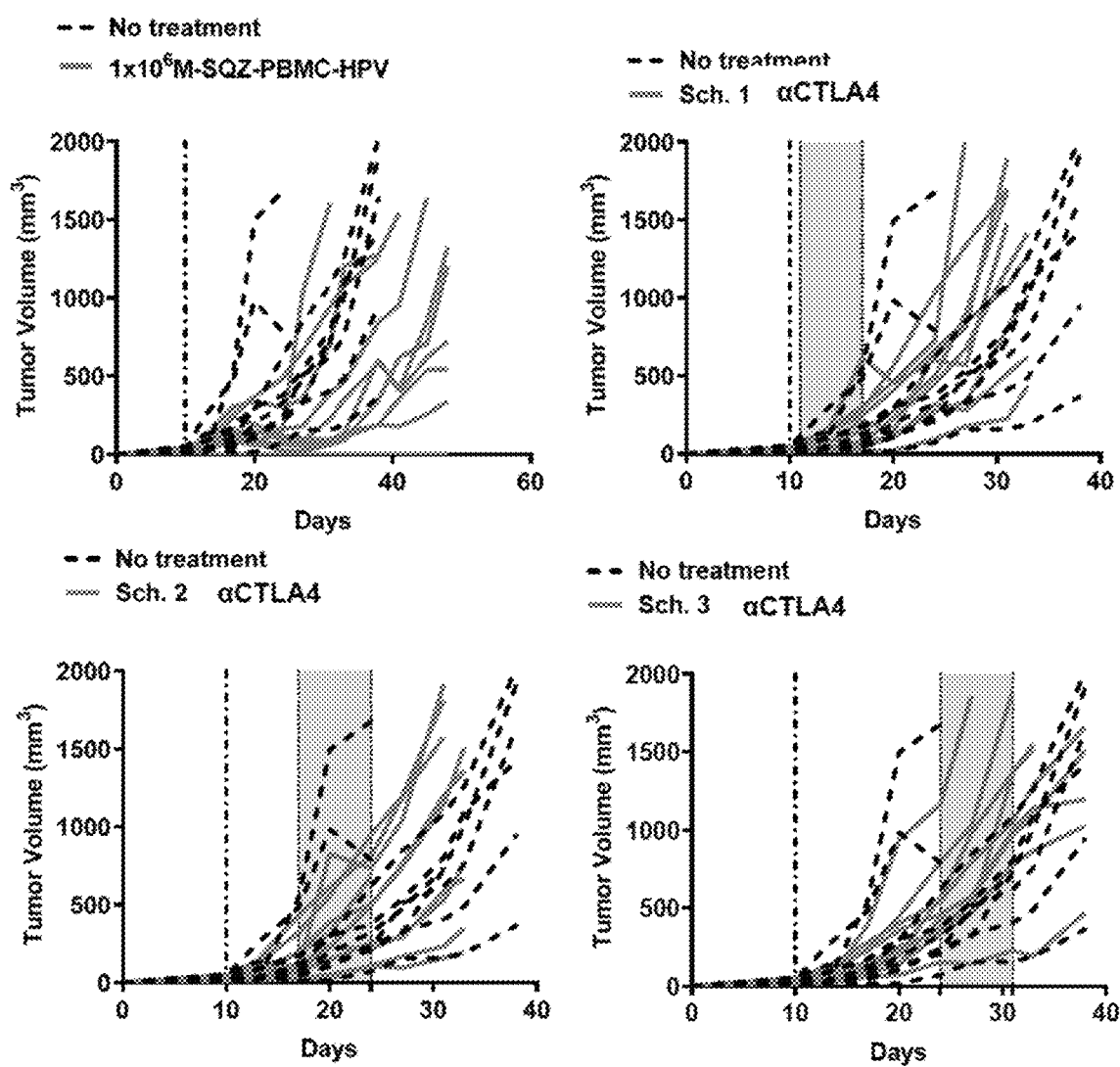
Figure 48E:
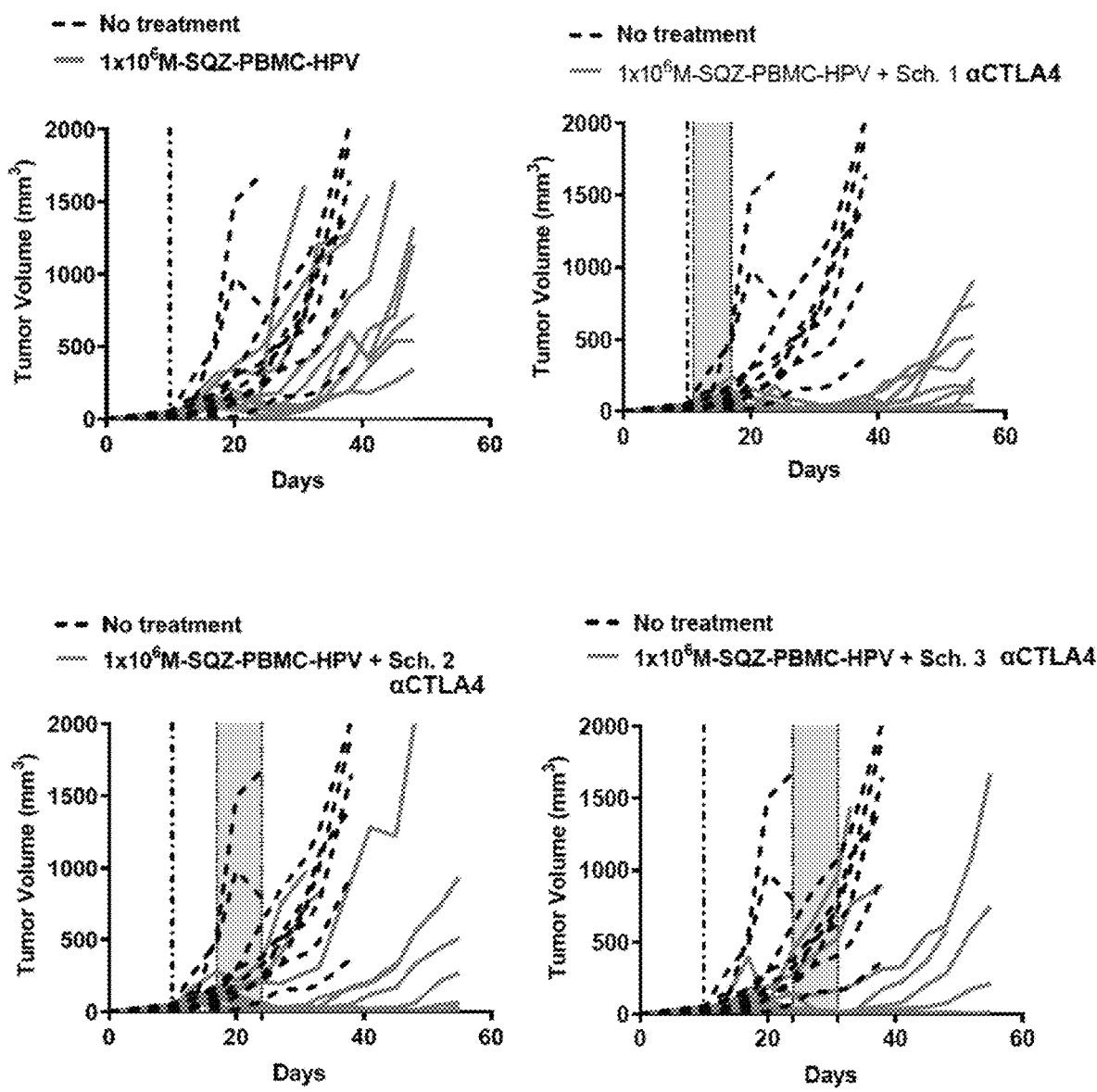

Untreated mice, mice treated with anti-CTLA4 alone (Sch. 1 α-CTLA4; Sch. 2 α-CTLA4; Sch. 3 α-CTLA4) or mice primed with E7-loaded splenocytes (M-SQZ-PBMC-HPV) all developed tumor at Day 40 or earlier (FIG. 48D). In comparison, mice receiving combination of E7-loaded splenocytes and anti-CTLA4 administration (M-SQZ-PBMC-HPV+α-CTLA4) showed inhibited or delayed tumor development, with 2, 1, and 3 mice being tumor free at Day 60 for M-SQZ-PBMC-HPV+Sch. 1 α-CTLA4, M-SQZ-PBMC-HPV+Sch. 2 α-CTLA4 and M-SQZ-PBMC-HPV+Sch. 3 α-CTLA4 respectively (FIG. 48E).

Figure 48F:
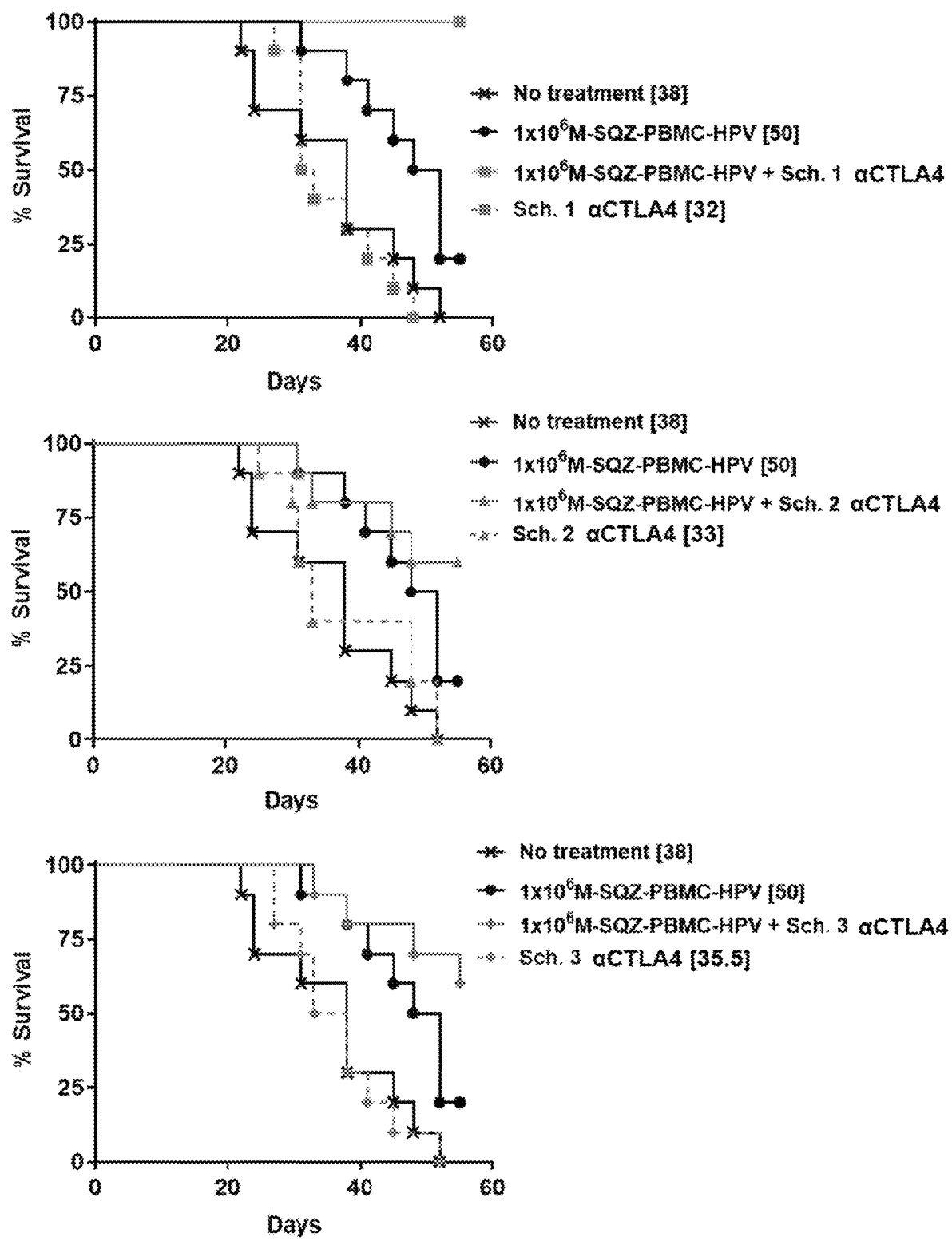

Consistent with the results in tumor growth inhibition, the combination of E7-loaded splenocytes and anti-CTLA4 administration also showed an additive effect in improving survival of TC-1 carrying mice. Untreated mice showed a median survival of 38 days, whereas mice treated with anti-CTLA4 alone (Sch. 1 α-CTLA4; Sch. 2 α-CTLA4; Sch. 3 α-CTLA4) showed median survival of 32, 33 and 35.5 days respectively. Mice primed with E7-loaded splenocytes (M-SQZ-PBMC-HPV) showed slightly improved median survival at 50 days. Noticeably, median survival has not been reached for mice receiving combinations of E7-loaded splenocytes and anti-CTLA4 administration (M-SQZ-PBMC-HPV+α-CTLA4) at Day 60 subsequent to TC-1 implantation (FIG. 48F).

These results indicated that therapeutic combination of antigen-loaded splenocytes and immune checkpoint inhibitor afforded additive benefits in inhibiting tumor growth and in improving survival.

Sequence Listing

| SEQ ID NO | Sequence | Description |
| --- | --- | --- |
| 1 | TIHDIILECV | HPV16-E6 (29-38), human epitope |
| 2 | EVYDFAFRDL | HPV16-E6 (48-57), murine epitope |
| 3 | YMLDLQPETT | HPV16-E7 (11-20), human epitope |
| 4 | RAHYNIVTF | HPV16-E7 (49-57), murine epitope |
| 5 | LPQLSTELQT | HPV16-E6 (19-28) N-terminal polypeptide, human |
| 6 | QLCTELQT | HPV16-E6 (21-28) N-terminal polypeptide, human |
| 7 | KQQLLRR | HPV16-E6 (41-47) N-terminal polypeptide, native murine |
| 8 | VYSKQQLLRR | HPV16-E6 (38-47) N-terminal polypeptide, classic murine |
| 9 | MHGDTPTLHE | HPV16-E7 (1-10) N-terminal polypeptide, human |
| 10 | GQAEPD | HPV16-E7 (43-48) N-terminal polypeptide, murine |

Sequence Listing

| SEQ ID NO | Sequence | Description |
|---|---|---|
| 11 | YSKQQLLRREVYDFAF | HPV16-E6 (39-54) C-terminal polypeptide, human |
| 12 | YCKQQLL | HPV16-E6 (39-45) C-terminal polypeptide, human |
| 13 | CIVYRDGN | HPV16-E6 (58-65) C-terminal polypeptide, native murine |
| 14 | SIVYRDGNPYAVSDK | HPV16-E6 (58-72) C-terminal polypeptide, classic murine |
| 15 | DLYCYEQLNDSSEEE | HPV16-E7 (21-35) C-terminal polypeptide, human |
| 16 | CCKCDSTLRLCVQSTHVDIR | HPV16-E7 (58-77) C-terminal polypeptide, native murine |
| 17 | SSKSDSTLRLSVQSTHVDIR | HPV16-E7 (58-77) C-terminal polypeptide, classic murine |
| 18 | LPQLSTELQTTIHDIILECVYSKQQLLRREVYDFAF | HPV16-E6 (19-54) SLP, human |
| 19 | QLCTELQTTIHDIILECVYCKQQLL | HPV16-E6 (21-45) SLP, human |
| 20 | KQQLLRREVYDFAFRDLCIVYRDGN | HPV16-E6 (41-65) SLP, native murine |
| 21 | VYSKQQLLRREVYDFAFRDLSIVYRDGNPYAVSDK | HPV16-E6 (38-72) SLP, classic murine |
| 22 | MHGDTPTLHEYMLDLQPETTDLYCYEQLNDSSEEE | HPV16-E7 (1-35) SLP, human |
| 23 | QLCTELQTYMLDLQPETTYCKQQLL | HPV16-E7.6 SLP, human |
| 24 | GQAEPDRAHYNIVTFCCKCDSTLRLCVQSTHVDIR | HPV16-E7 (43-77) SLP, native murine |
| 25 | GQAEPDRAHYNIVTFSSKSDSTLRLSVQSTHVDIR | HPV16-E7 (43-77) SLP, classic murine |
| 26 | ggGGTCAACGTTGAgggggg<br>Bases shown in capital letters are phosphodiester, and those in lower case are phosphorothioate | ODN 1585 (Class A, mouse-specific) |
| 27 | ggGGGACGA:TCGTCgggggg<br>Bases shown in capital letters are phosphodiester, and those in lower case are phosphorothioate | ODN 2216 (Class A, human-selective) |

Sequence Listing

| SEQ ID NO | Sequence | Description |
|---|---|---|
| 28 | gggGACGAC:GTCGTGgggggg<br>Bases shown in capital letters are phosphodiester, and those in lower case are phosphorothioate | ODN 2336<br>(Class A, human preferred) |
| 29 | tccatgacgttcctgatgct<br>Bases shown in capital letters are phosphodiester, and those in lower case are phosphorothioate | ODN 1668<br>(Class B, mouse specific) |
| 30 | tccatgacgttcctgacgtt<br>Bases are phosphorothioate | ODN 1826<br>(Class B, mouse specific) |
| 31 | tcgtcgttttgtcgttttgtcgtt<br>Bases are phosphorothioate | ODN 2006<br>(Class B, human selective) |
| 32 | tcg tcg ttg tcg ttt tgt cgt t<br>Bases are phosphorothioate | ODN 2007<br>(Class B, bovine/porcine) |
| 33 | tcg acg ttc gtc gtt cgt cgt tc<br>Bases are phosphorothioate | ODN BW006<br>(Class B, human & mouse) |
| 34 | tcg cga cgt tcg ccc gac gtt cgg ta<br>Bases are phosphorothioate | ODN D-SL01<br>(Class B, multispecies) |
| 35 | tcgtcgttttcggcgc:gcgccg<br>Bases are phosphorothioate | ODN 2395<br>(Class C, human/mouse) |
| 36 | tcgtcgtcgttc:gaacgacgttgat<br>Bases are phosphorothioate | ODN M362<br>(Class C, human/mouse) |
| 37 | tcg cga acg ttc gcc gcg ttc gaa cgc gg<br>Bases are phosphorothioate | ODN D-SL03<br>(Class C, multispecies) |
| 38 | MHGDTPTLHEYMLDLQPETTDLYCYEQLNDSSEEE | E7 |
| 39 | LYCYEQLNDSSEEEDEIDGPAGQAEPDRAHYNIVT | E7 |
| 40 | GQAEPDRAHYNIVTFCCKCDSTLRLCVQSTHVDIR | E7 |
| 41 | TLRLCVQSTHVDIRTLEDLLMGTLGIVCPICSQKP | E7 |
| 42 | MHQKRTAMFQDPQERPRKLPQLCTELQTTIHD | E6 |
| 43 | LPQLCTELQTTIHDIILECVYCKQQLLRREVY | E6 |
| 44 | KQQLLRREVYDFAFRDLCIVYRDGN | E6 |
| 45 | RDLCIVYRDGNPYAVCDKCLKFYSKI | E6 |
| 46 | DKCLKFYSKISEYRHYCYSLYGTTL | E6 |
| 47 | HYCYSLYGTTLEQQYNKPLCDLLIR | E6 |
| 48 | YGTTLEQQYNKPLCDLLIRCINCQKPLCPEEK | E6 |
| 49 | RCINCQKPLCPEEKQRHLDKKQRFHNIRGRWT | E6 |
| 50 | DKKQRFHNIRGRWTGRCMSCCRSSRTRRETQL | E6 |

| SEQ ID NO | Sequence | Description |
|---|---|---|
| 51 | PPWQAGILARNLVPMVATVQGQNLKYQEFFWDAND | pp65 SLP, human |
| 52 | PPWQAGILAR | pp65 N-terminal polypeptide, human |
| 53 | QGQNLKYQEFFWDAND | pp65 C-terminal polypeptide, human |

What is claimed is:

1. A conditioned plurality of modified PBMCs comprising an antigen intracellularly, wherein the antigen is exogenous to the modified PBMCs, and wherein the plurality of modified PBMCs have been incubated with an adjuvant for about 4 hours to less than 24 hours to condition the plurality of modified PBMCs such that the conditioned plurality of modified PBMCs are capable of inducing an in vivo T cell immune response, and wherein the in vivo T cell immune response is at least about 2-fold greater than that induced by corresponding non-conditioned plurality of modified PBMCs.

2. A conditioned plurality of modified PBMCs comprising an antigen and a first adjuvant intracellularly, wherein the antigen and the first adjuvant are exogenous to the modified PBMCs, wherein the plurality of modified PBMCs have been incubated with a second adjuvant for about 4 hours to less than 24 hours to condition the plurality of modified PBMCs such that the conditioned plurality of modified PBMCs are capable of inducing an in vivo T cell immune response, wherein the in vivo T cell immune response is at least about 2-fold greater than that induced by corresponding non-conditioned plurality of modified PBMCs, and wherein the first adjuvant and the second adjuvant are not the same.

3. The conditioned plurality of modified PBMCs of claim 1, wherein the antigen was intracellularly delivered to a plurality of input PBMCs to produce the plurality of modified PBMCs, by passing a cell suspension comprising the plurality of input PBMCs through a cell-deforming constriction, thereby causing perturbations of the input PBMCs such that the antigen enters the input PBMCs through the perturbations when contacted with the input PBMCs.

4. The conditioned plurality of modified PBMCs of claim 2, wherein the antigen and/or the first adjuvant was intracellularly delivered to a plurality of input PBMCs to produce the plurality of modified PBMCs by passing a cell suspension comprising the plurality of input PBMCs through a cell-deforming constriction, thereby causing perturbations of the input PBMCs such that the antigen and/or the first adjuvant enters the input PBMCs through the perturbations when contacted with the input PBMCs.

5. The conditioned plurality of modified PBMCs of claim 2, which have been further incubated with an agent that enhances the viability and/or function of the modified PBMCs as compared to corresponding modified PBMCs that have not been further incubated with the agent that enhances the viability and/or function of the modified PBMCs.

6. The conditioned plurality of modified PBMCs of claim 3, wherein the diameter of the cell-deforming constriction is about 10% to about 99% of the mean diameter of the plurality of input PBMCs.

7. The conditioned plurality of modified PBMCs of claim 3, wherein the diameter of the cell-deforming constriction is: (a) about 4.2 μm to about 6 μm; (b) about 4.2 μm to about 4.8 μm; or (c) about 4.5 μm.

8. The conditioned plurality of modified PBMCs of claim 3, wherein the cell suspension comprising the plurality of input PBMCs is passed through multiple cell-deforming constrictions wherein the multiple cell-deforming constrictions are arranged in series and/or in parallel.

9. The conditioned plurality of modified PBMCs of claim 1, wherein the plurality of modified PBMCs have been incubated with the adjuvant for about 4 hours to about 10 hours; or for about 4 hours to about 6 hours; or for about 4 hours.

10. The conditioned plurality of modified PBMCs of claim 2, wherein the first adjuvant and/or second adjuvant comprises a CpG oligodeoxynucleotide (ODN), LPS, IFN-α, STING agonists, RIG-I agonists, poly I:C, R837, R848, a TLR3 agonist, a TLR4 agonist, or a TLR 9 agonist.

11. The conditioned plurality of modified PBMCs of claim 10, wherein the first and/or second adjuvant is a CpG oligodeoxynucleotide (ODN).

12. The conditioned plurality of modified PBMCs of claim 2, wherein the antigen comprises a disease-associated antigen, an infectious disease antigen, or a cancer antigen.

13. The conditioned plurality of modified PBMCs of claim 12, wherein: (i) the disease-associated antigen is a human papillomavirus (HPV) antigen or (ii) the infectious disease antigen is a hepatitis B virus (HBV) antigen.

14. The conditioned plurality of modified PBMCs of claim 2, which exhibit increased expression of:
(a) one or more co-stimulatory molecules; and/or
(b) one or more cytokines;
as compared to a corresponding plurality of non-conditioned modified PBMCs.

15. The conditioned plurality of modified PBMCs of claim 14, wherein:
(a) the one or more co-stimulatory molecules comprise B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112; and/or
(b) the one or more cytokines comprise IL-15, IL-12, IL-2, IFN-α, IFN-γ, IL-6, MCP-1, MIP-1β, IP-10, TNF-α, or IL-21.

16. A composition comprising the conditioned plurality of modified PBMCs of claim 2.

17. A method for stimulating an immune response in an individual in need thereof, comprising administering to the individual the conditioned plurality of modified PBMCs of claim 1, and wherein after the administration, an immune response against the antigen is stimulated in the individual.

18. A method for stimulating an immune response in an individual in need thereof, comprising administering to the individual the conditioned plurality of modified PBMCs of claim 2, and wherein after the administration, an immune response against the antigen is stimulated in the individual.

19. The method of claim 17, further comprising administering an additional agent to the individual.

20. The method of claim 18, further comprising administering an additional agent to the individual.

21. The method of claim 19, wherein the additional agent comprises:

(a) a cytokine;
(b) an immune checkpoint inhibitor; and/or
(c) a therapeutic agent.

22. The method of claim 21, wherein:
(a) the cytokine is IL-2;
(b) the immune checkpoint inhibitor is targeted to any one of PD-1, PD-L1, CTLA-4, LAG3, VISTA, and TIM-3; and/or
(c) the therapeutic agent is a chemotherapeutic agent.

23. A method for generating a conditioned plurality of PBMCs comprising an antigen intracellularly, comprising incubating a plurality of PBMCs with an adjuvant for about 4 hours to less than 24 hours to condition the plurality of PBMCs such that the conditioned plurality of PBMCs are capable of inducing an in vivo T cell immune response, wherein the in vivo T cell immune response is at least about 2-fold greater than that induced by corresponding non-conditioned plurality of PBMCs, and wherein the antigen is intracellularly delivered to the plurality of PBMCs before or after the incubating.

24. The method of claim 23, wherein the antigen is intracellularly delivered to the plurality of PBMCs by passing a cell suspension comprising the plurality of PBMCs through a cell-deforming constriction, thereby causing perturbations of the PBMCs such that the antigen enters the PBMCs through the perturbations when contacted with the PBMCs.

25. The method of claim 23, wherein the adjuvant comprises a CpG oligodeoxynucleotide (ODN), LPS, IFN-α, STING agonists, RIG-I agonists, poly I:C, R837, R848, a TLR3 agonist, a TLR4 agonist, or a TLR 9 agonist.

26. The method of claim 23, wherein the antigen comprises a disease-associated antigen, an infectious disease antigen, or a cancer antigen.

27. The method of claim 26, wherein: (i) the disease-associated antigen is a human papillomavirus (HPV) antigen or (ii) the infectious disease antigen is hepatitis B virus (HBV) antigen.

28. The method of claim 23, wherein after the incubating, the conditioned plurality of PBMCs exhibit increased expression of: (a) one or more co-stimulatory molecules; and/or (b) one or more cytokines; as compared to a corresponding plurality of non-conditioned modified PBMCs.

29. The method of claim 28, wherein: (a) the one or more co-stimulatory molecules comprise B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112; and/or (b) the one or more cytokines comprise IL-15, IL-12, IL-2, IFN-α, IFN-γ, IL-6, MCP-1, MIP-1β, IP-10, TNF-α, or IL-21.

30. The method of claim 24, wherein the diameter of the cell-deforming constriction is about 10% to about 99% of the mean diameter of the plurality of PBMCs.

31. A composition comprising the conditioned plurality of modified PBMCs of claim 1.

32. A method of treating a disease or disorder in an individual in need thereof, comprising administering to the individual the conditioned plurality of modified PBMCs of claim 1.

33. The method of claim 32, wherein the disease or disorder comprises a cancer, infectious disease, or viral-associated disease.

34. A method of treating a disease or disorder in an individual in need thereof, comprising administering to the individual the conditioned plurality of modified PBMCs of claim 2.

35. The method of claim 34, wherein the disease or disorder comprises a cancer, infectious disease, or viral-associated disease.

36. The conditioned plurality of modified PBMCs of claim 4, wherein the diameter of the cell-deforming constriction is about 10% to about 99% of the mean diameter of the plurality of input PBMCs.

37. The conditioned plurality of modified PBMCs of claim 4, wherein the diameter of the cell-deforming constriction is: (a) about 4.2 μm to about 6 μm; (b) about 4.2 μm to about 4.8 μm; or (c) about 4.5 μm.

38. The conditioned plurality of modified PBMCs of claim 2, wherein the plurality of modified PBMCs have been incubated with the adjuvant for about 4 hours to about 10 hours; or for about 4 hours to about 6 hours; or for about 4 hours.

\* \* \* \* \*